(12) United States Patent
Geuijen et al.

(10) Patent No.: US 11,667,714 B2
(45) Date of Patent: Jun. 6, 2023

(54) BINDING MOLECULES THAT MODULATE A BIOLOGICAL ACTIVITY EXPRESSED BY A CELL

(71) Applicant: Merus N.V., Utrecht (NL)

(72) Inventors: Cecilia Anna Wilhelmina Geuijen, Utrecht (NL); Rinse Klooster, Utrecht (NL); Cornelis Adriaan De Kruif, Utrecht (NL); Paulus Johannes Tacken, Utrecht (NL); Mark Throsby, Utrecht (NL); Ton Logtenberg, Utrecht (NL)

(73) Assignee: Merus N.V., Utrecht (NL)

( * ) Notice: Subject to any disclaimer, the term of this patent is extended or adjusted under 35 U.S.C. 154(b) by 97 days.

(21) Appl. No.: 16/628,547

(22) PCT Filed: Jul. 6, 2018

(86) PCT No.: PCT/NL2018/050449
§ 371 (c)(1),
(2) Date: Jan. 3, 2020

(87) PCT Pub. No.: WO2019/009726
PCT Pub. Date: Jan. 10, 2019

(65) Prior Publication Data
US 2020/0325227 A1    Oct. 15, 2020

(30) Foreign Application Priority Data
Jul. 6, 2017 (EP) ..................................... 17180064

(51) Int. Cl.
| | |
|---|---|
| *C07K 16/28* | (2006.01) |
| *A61P 35/00* | (2006.01) |
| *C07K 16/30* | (2006.01) |
| *C07K 16/46* | (2006.01) |
| *A61K 39/00* | (2006.01) |

(52) U.S. Cl.
CPC .......... *C07K 16/2818* (2013.01); *A61P 35/00* (2018.01); *C07K 16/2827* (2013.01); *C07K 16/30* (2013.01); *C07K 16/468* (2013.01); *A61K 2039/505* (2013.01); *C07K 2317/31* (2013.01); *C07K 2317/526* (2013.01); *C07K 2317/55* (2013.01); *C07K 2317/565* (2013.01); *C07K 2317/74* (2013.01); *C07K 2317/92* (2013.01)

(58) Field of Classification Search
None
See application file for complete search history.

(56) References Cited

U.S. PATENT DOCUMENTS
| | | | |
|---|---|---|---|
| 9,248,181 B2 | 2/2016 | De Kruif et al. | |
| 9,358,286 B2 | 6/2016 | De Kruif et al. | |

FOREIGN PATENT DOCUMENTS
| | | | |
|---|---|---|---|
| WO | WO-2004/009618 A2 | 1/2004 | |
| WO | WO-2006121168 A1 | 11/2006 | |
| WO | WO-2009126920 A3 | 10/2009 | |
| WO | WO-2009157771 A2 | 12/2009 | |
| WO | WO-2010077634 A1 | 7/2010 | |
| WO | WO-2013157953 A1 | 10/2013 | |
| WO | WO-2013157954 A1 | 10/2013 | |
| WO | WO 2015/112900 * | 7/2015 | ............. C07K 16/28 |
| WO | WO-2015112900 A1 | 7/2015 | |

OTHER PUBLICATIONS

Kijanka et al. (EurJ Nucl Med Mol Imaging, 40: 1718-1729, 2013).*
Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79): 18294-18302, 2011).*
Almagro, J.C. and Fransson, J., "Humanization of antibodies," *Frontiers in Bioscience* 13:1619-1633, Frontiers in Bioscience, United States (2008).
Armour, K.L. et al., "Recombinant human IgG molecules lacking Fc gamma receptor I binding and monocyte triggering activities," *Eur. J. Immunol.* 29(8):2613-24, Wiley-VCH Verlag, Germany (1999).
Brandt, C.S. et al., "The B7 family member B7-H6 is a tumor cell ligand for the activating natural killer cell receptor NKp30 in humans," *J Exp Med*. 206(7): 1495-503, Rockefeller University Press, United States (2009).
Butte, M.J., et al., "Interaction of human PD-L1 and B7-1," *Mol Immunol*. 45(13):3567-72, Elsevier Ltd., Great Britain (2008).
De Haard, H.J. et al., "A large non-immunized human Fab fragment phage library that permits rapid isolation and kinetic analysis of high affinity antibodies," *J. Biol. Chem*. 274(26):18218-30, American Society for Biochemistry and Molecular Biology, Inc., United States (1999).
Del Bano, J., et al., "Taking up Cancer Immunotherapy Challenges: Bispecific Antibodies, the Path Forward?" *Antibodies* 5(1), 23 pages, MDPI AG, Switzerland (2016).

(Continued)

*Primary Examiner* — Nelson B Moseley, II

(74) *Attorney, Agent, or Firm* — Sterne, Kessler, Goldstein & Fox P.L.L.C.

(57) ABSTRACT

The invention provides means and methods for inhibiting a biological activity of cells. In one embodiment the invention is concerned with a method of inhibiting a biological activity in a first or second cell mediated by the binding of two membrane proteins that are binding partners for each other. The mentioned biological activity is inhibited by providing the cells with an antibody or antibody like molecule that can bind to each of the mentioned binding partners and the binding blocks the binding of the two binding partners thereby inhibiting the mentioned biological activity.

48 Claims, 52 Drawing Sheets

Specification includes a Sequence Listing.

(56) References Cited

OTHER PUBLICATIONS

Hofmeyer, K.A., et al. "The contrasting role of B7-H3," *Proceedings of the National Academy of Sciences of the United States of America*, 705(30): 10277-10278, National Academy of Sciences, United States (2008).

Idusogie, E.E., et al., "Mapping of the C1q Binding Site on Rituxan, a chimeric Antibody with a Human IgG1 Fc," *J Immunol.* American Association of Immunologists, United States (2000).

International Search Report and Written Opinion for International Application No. PCT/NL2018/050449, dated Jan. 10, 2018, European Patent Office, Rijswijk, 13 pages.

Janakiram, M., et al., "Expression, Clinical Significance, and Receptor Identification of the Newest B7 Family Member HHLA2 Protein." *Clin Cancer Res.* 21(10):2359-66, American Association for Cancer Research Inc., United States (2015).

Kraan, J., et al., "Endothelial CD276 (B7-H3) expression is increased in human malignancies and distinguishes between normal and tumour-derived circulating endothelial cells," *Br J Cancer* 777(1): 149-156, Nature Publishing Group, Great Britain (2014).

Labrijn, A., et al., "Therapeutic IgG4 antibodies engage in Fab-arm exchange with endogenous human IgG4 in vivo," *Nat Biotechnol.* 27(8):767-71, Nature Publishing Group, Great Britain (2009).

Marks, J.D., et al., "By-passing immunization. Human antibodies from V-gene libraries displayed on phage," *J Mol Biol.* 222(3):581-97, Academic Press Limited, United States (1991).

Merchant, A.M., et al., "An efficient route to human bispecific IgG," *Nature Biotechnol.* 16(7):677-81, Nature Publishing Group, Great Britain (1998).

Moon, E.K., et al., "Blockade of Programmed Death 1 Augments the Ability of Human T cells Engineered to Target NY-ESO-1 to Control Tumor Growth after Adoptive Transfer," *Clinical Cancer Research* 22(2):436-447, American Association for Cancer Research, United States (2016).

Morrison, S.L. "Two heads are better than one," *Nature Biotechnol.* 25(11): 1233-1234, Nature Publishing Group, Great Britain (2007).

Nissim, A., et al., "Antibody fragments from a 'single pot' phage display library as immunochemical reagents," *The EMBO J.* 75(3):692-8, Oxford University Press, Great Britain (1994).

Sharpe, A.H., et al., "The B7-CD28 Superfamily", *Nat Rev Immunol.* 2(2):116-126, Nature Pub. Group, Great Britain, (2002).

Shields, R.L., et al., "High resolution mapping of the binding site on human IgG1 for Fc gamma RI, Fc gamma RII, Fc gamma RIII, and FcRn and design of IgGl variants with improved binding to the Fc gamma R," *J Biol Chem.* 276(9) :6591-604, The American Society for Biochemistry and Molecular Biology, Inc., United States (2001).

Xu, L., et al., "Stimulation of B7-H3 (CD276) directs the differentiation of human marrow stromal cells to osteoblasts," *Immunobiology* 276(12): 1311-1317, Elsevier GmbH, Germany (2011).

Zhou, G., et al., "Antibodies Against Immune Checkpoint Molecules Restore Functions of Tumor-infiltrating T cells in Hepatocellular Carcinomas," *Gastroenterology* 153(4):1107-1119, American Gastroenterological Association Institute, United States (2017).

\* cited by examiner

DIQMTQSPSSLSASVGDRVTITCRASQSISSYLNWYQQKPGKAPKLLIYAASSLQSGVP
SRFSGSGSGTDFTLTISSLQPEDFATYYCQQSYSTPPTFGQGTKVEIK
RTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

Figure 1B

```
gacatccagatgacccagtctccatcctccctgtctgcatctgtaggagacagagtcacc
 D   I   Q   M   T   Q   S   P   S   S   L   S   A   S   V   G   D   R   V   T
atcacttgccgggcaagtcagagcattagcagctacttaaattggtatcagcagaaacca
 I   T   C   R   A   S   Q   S   I   S   S   Y   L   N   W   Y   Q   Q   K   P
gggaaagcccctaagctcctgatctatgctgcatccagtttgcaaagtggggtcccatca
 G   K   A   P   K   L   L   I   Y   A   A   S   S   L   Q   S   G   V   P   S
aggttcagtggcagtggatctgggacagatttcactctcaccatcagcagtctgcaacct
 R   F   S   G   S   G   S   G   T   D   F   T   L   T   I   S   S   L   Q   P
gaagattttgcaacttactactgtcaacagagttacagtacccctccaacgttcggccaa
 E   D   F   A   T   Y   Y   C   Q   Q   S   Y   S   T   P   P   T   F   G   Q
gggaccaaggtggagatcaaa
 G   T   K   V   E   I   K
```

Figure 1C

```
cgaactgtggctgcaccatctgtcttcatcttcccgccatctgatgagcagttgaaatct
 R   T   V   A   A   P   S   V   F   I   F   P   P   S   D   E   Q   L   K   S
ggaactgcctctgttgtgtgcctgctgaataacttctatcccagagaggccaaagtacag
 G   T   A   S   V   V   C   L   L   N   N   F   Y   P   R   E   A   K   V   Q
tggaaggtggataacgccctccaatcgggtaactcccaggagagtgtcacagagcaggac
 W   K   V   D   N   A   L   Q   S   G   N   S   Q   E   S   V   T   E   Q   D
agcaaggacagcacctacagcctcagcagcaccctgacgctgagcaaagcagactacgag
 S   K   D   S   T   Y   S   L   S   S   T   L   T   L   S   K   A   D   Y   E
aaacacaaagtctacgcctgcgaagtcacccatcagggcctgagctcgcccgtcacaaag
 K   H   K   V   Y   A   C   E   V   T   H   Q   G   L   S   S   P   V   T   K
agcttcaacaggggagagtgttag
 S   F   N   R   G   E   C   -
```

Figure 1D

DIQMTQSPSSLSASVGDRVTITCRASQSISSYLNWYQQKPGKAPKLLIYAASSLQSGVPSRFSGSGSG
TDFTLTISSLQPEDFATYYCQQSYSTPPITFGQGTRLEIK

Figure 1E

DIQMTQSPSSLSASVGDRVTITCRASQSISSYLNWYQQKPGKAPKLLIYAASSLQSGVPSRFSGSGSG
TDFTLTISSLQPEDFATYYCQQSYSTP

VH: dependent on the MF (target): Figure 3.

Figure 2B gctagcaccaagggcccatcggtcttcccctggcaccctcctccaagagcacctctggg
 A   S   T   K   G   P   S   V   F   P   L   A   P   S   S   K   S   T   S   G
ggcacagcggccctgggctgcctggtcaaggactacttccccgaaccggtgacggtgtcg
 G   T   A   A   L   G   C   L   V   K   D   Y   F   P   E   P   V   T   V   S
tggaactcaggcgccctgaccagcggcgtgcacaccttcccggctgtcctacagtcctca
 W   N   S   G   A   L   T   S   G   V   H   T   F   P   A   V   L   Q   S   S
ggactctactccctcagcagcgtcgtgaccgtgcctccagcagcttgggcacccagacc
 G   L   Y   S   L   S   S   V   V   T   V   P   S   S   S   L   G   T   Q   T
tacatctgcaacgtgaatcacaagcccagcaacaccaaggtggacaagagagtt
 Y   I   C   N   V   N   H   K   P   S   N   T   K   V   D   K   R   V

Figure 2C gagcccaaatcttgtgacaaaactcacacatgcccaccgtgccca
 E   P   K   S   C   D   K   T   H   T   C   P   P   C   P

Figure 2D gcacctgaactcctggggggaccgtcagtcttcctcttccccccaaaacccaaggacacc
 A   P   E   L   L   G   G   P   S   V   F   L   F   P   P   K   P   K   D   T
ctcatgatctcccggacccctgaggtcacatgcgtggtggtggacgtgagccacgaagac
 L   M   I   S   R   T   P   E   V   T   C   V   V   V   D   V   S   H   E   D
cctgaggtcaagttcaactggtacgtggacggcgtggaggtgcataatgccaagacaaag
 P   E   V   K   F   N   W   Y   V   D   G   V   E   V   H   N   A   K   T   K
ccgcgggaggagcagtacaacagcacgtaccgtgtggtcagcgtcctcaccgtcctgcac
 P   R   E   E   Q   Y   N   S   T   Y   R   V   V   S   V   L   T   V   L   H
caggactggctgaatggcaaggagtacaagtgcaaggtctccaacaaagccctcccagcc
 Q   D   W   L   N   G   K   E   Y   K   C   K   V   S   N   K   A   L   P   A
cccatcgagaaaaccatctccaaagccaaa
 P   I   E   K   T   I   S   K   A   K

Figure 2E

```
gcacctgaactcggcaggggaccgtcagtcttcctcttccccccaaaacccaaggacacc
 A  P  E  L  G  R  G  P  S  V  F  L  F  P  P  K  P  K  D  T
ctcatgatctcccggacccctgaggtcacatgcgtggtggtggacgtgagccacgaagac
 L  M  I  S  R  T  P  E  V  T  C  V  V  V  D  V  S  H  E  D
cctgaggtcaagttcaactggtacgtggacggcgtggaggtgcataatgccaagacaaag
 P  E  V  K  F  N  W  Y  V  D  G  V  E  V  H  N  A  K  T  K
ccgcgggaggagcagtacaacagcacgtaccgtgtggtcagcgtcctcaccgtcctgcac
 P  R  E  E  Q  Y  N  S  T  Y  R  V  V  S  V  L  T  V  L  H
caggactggctgaatggcaaggagtacaagtgcaaggtctccaacaaagccctcccagcc
 Q  D  W  L  N  G  K  E  Y  K  C  K  V  S  N  K  A  L  P  A
cccatcgagaaaaccatctccaaagccaaa
 P  I  E  K  T  I  S  K  A  K
```

Figure 2F

```
gggcagccccgagaaccacaggtgtacaccaagcccccatcccgggaggagatgaccaag
 G  Q  P  R  E  P  Q  V  Y  T  K  P  P  S  R  E  E  M  T  K
aaccaggtcagcctgaagtgcctggtcaaaggcttctatcccagcgacatcgccgtggag
 N  Q  V  S  L  K  C  L  V  K  G  F  Y  P  S  D  I  A  V  E
tgggagagcaatgggcagccggagaacaactacaagaccacgcctcccgtgctggactcc
 W  E  S  N  G  Q  P  E  N  N  Y  K  T  T  P  P  V  L  D  S
gacggctccttcttcctctatagcaagctcaccgtggacaagagcaggtggcagcagggg
 D  G  S  F  F  L  Y  S  K  L  T  V  D  K  S  R  W  Q  Q  G
aacgtcttctcatgctccgtgatgcatgaggctctgcacaaccactacacgcagaagagc
 N  V  F  S  C  S  V  M  H  E  A  L  H  N  H  Y  T  Q  K  S
ctctccctgtctccgggttga
 L  S  L  S  P  G  -
```

Figure 2G

```
gggcagccccgagaaccacaggtgtacaccgaccccccatcccgggaggagatgaccaag
 G  Q  P  R  E  P  Q  V  Y  T  D  P  P  S  R  E  E  M  T  K
aaccaggtcagcctgacctgcgaggtcaaaggcttctatcccagcgacatcgccgtggag
 N  Q  V  S  L  T  C  E  V  K  G  F  Y  P  S  D  I  A  V  E
tgggagagcaatgggcagccggagaacaactacaagaccacgcctcccgtgctggactcc
 W  E  S  N  G  Q  P  E  N  N  Y  K  T  T  P  P  V  L  D  S
gacggctccttcttcctctatagcaagctcaccgtggacaagagcaggtggcagcagggg
 D  G  S  F  F  L  Y  S  K  L  T  V  D  K  S  R  W  Q  Q  G
aacgtcttctcatgctccgtgatgcatgaggctctgcacaaccactacacgcagaagagc
 N  V  F  S  C  S  V  M  H  E  A  L  H  N  H  Y  T  Q  K  S
ctctccctgtctccgggttga
 L  S  L  S  P  G  -
```

QVQLVQSGAEVKKPGSSVKVSCKASGDTFR<u>SYGIT</u>WVRQAPGQGLEWMG<u>GIIPVFGT
TNYAQKFQG</u>RVTITADKSTSTVFMELNSLRSEDTAVYYCAR<u>RRGYSNPHWLDP</u>WGQ
GTLVTVSS

Figure 3b. MF5594

EVQLVQSGAEVKKPGSSVKVSCKASGGTFS<u>TYAIS</u>WVRQAPGQGLEWMG<u>WIIPIFDT
GNYAQKIQG</u>RVTITADKSTSTAYMELTSLRSEDTAVYYCAR<u>HDYTNTVDAFDI</u>WGQG
TMVTVSS

Figure 3c. MF5576

QVQLVQSGSELKKPGASVKVSCKASGYTFT<u>SHAMN</u>WVRQAPGQGLEWMG<u>WINPNT
GNPTYAQGFTG</u>RFVFSLDTSVSTAYLQISSLKAEDTAVYYCAI<u>DRGYMSNWVFAEYFP
H</u>WGQGTLVTVSS

Figure 3d. MF5561

QVQLVQSGAEVKKPGSSVKVSCKASGGTFN<u>TYAIN</u>WVRQAPGQGLEWMG<u>GIIPIFDT
ANYAQRFQG</u>RVTITADKSTSTAYMELSSLRSEDTAVYFCAK<u>DQTGYSSTLFDY</u>WGQG
TLVTVSS

Figure 3e. MF5557

QVQLVQSGAEVKRPGSSVKVSCKASGGTFN<u>TYSIT</u>WVRQAPGQGLEWMG<u>GIIPVFGT
SKYAQKFQD</u>RVTITADKSTNTAYMELSSLRSEDTAVYYCAR<u>DPSFSSSSGWFDP</u>WGQ
GTLVTVSS

Figure 3f. MF5553

QVQLVQSGSELKKPGASVKVSCKASGYTFT<u>NYAIN</u>WVRQAPGQGLEWMG<u>WINPNTG
NPTYAQGFTG</u>RFVFSLDTSVSTAYLQISSLKAEDTAVYYCAR<u>DRKYVTNWVFAEDFQ
H</u>WGQGTLVTVSS

Figure 3g. MF5442

EVQLVQSGAEVKKPGSSVRVSCKASGGTFN<u>TYAIN</u>WVRQAPGQGLEWVG<u>RIIPIFDTA
NYAQKFQG</u>RVTISADKSTTTAYMELSSLRSEDTAVFYCAK<u>DETGYSSSNFQH</u>WGQGT
LVTVSS

Figure 3h. MF5439

QVQLVQSGAEVKKPGSSVKVSCKASGGTFS<u>TYGIL</u>WVRQAPGQGLEWMG<u>GIIPIFGT ANYAQKFQG</u>RVTITADISTSTAYMELSSLRSEDTAVYYCAR<u>GGGNYYEFVY</u>WGQGTL VTVSS

Figure 3i. MF5426

QVQLVQSGAEVKKPGSSVKVSCKASGDTFR<u>SYGIT</u>WVRQAPGQGLEWMG<u>GIIPIFGT TNYAQKFQG</u>RVTITADKSTSTVYMELSSLRSEDTAVYYCAR<u>RRGYSNPHWLDP</u>WGQ GTLVTVSS

Figure 3j. MF5424

EVQLVQSGAEVMRPGSSVKVSCKASGGIFN<u>TYTII</u>WVRQAPGQGLEWMG<u>GIIPIFDTP NFAQKFQG</u>RLTITADKSTNTAYMELTSLRSEDTAVYYCAR<u>EGCNHGVCYPY</u>WGQGT LVTVSS

Figure 3k. MF5382

EVQLVQSGAEVKNPGSSVKVSCKATGGTFN<u>TYGTN</u>WVRQAPGQGLEWMG<u>GIIPIFGT ANYAQKFQG</u>RVTITADKSTTTAYMEVSSLRSEDTAVYYCAR<u>GGADMGTLDY</u>WGQGT LVTVSS

Figure 3l. MF5377

EVQLVQSGAEVKKPGSSVKVSCKASGGIFS<u>TYAIS</u>WVRQAPGQGLEWMG<u>GIIPIFDTP NYAQKFQG</u>RVTITADKSTSTAYMDLSSLRSEDTAVYYCAK<u>NVRGYSAYDLDY</u>WGQGT LVTVSS

Figure 3m. MF5359

EVQLVQSGAEVKKPGSSVKVSCKASGDTFN<u>TYSIT</u>WVRQAPGQGLEWMG<u>SIVPIFGTI NNAQKFQG</u>RVTITADKSANTAYMELSSLRSEDTAVYYCAR<u>DNTMVRGVDYYYMDV</u>W GKGTMVTVSS

Figure 3n. MF5361

QVQLVQSGSELKKPGASVKVSCKASGYTFT<u>SYSLN</u>WVRQAPGQGLEWMG<u>WINTNTG NPTYAQGF</u>TGRFVFSLDSSVTTAYLQISSLKAEDTAVYYCTR<u>DHDFRRGRSLDV</u>WGK GTTVTVSS

Figure 3o. MF6982

EVQLVESGGDLVQPGGSLRLSCAASGFTFS<u>SYAMS</u>WVRQAPGKGLEWVS<u>TISGGGTN IYYADSVKG</u>RFTISRDNSKNTLFLQMNSLRAGDTAVYYCAS<u>PYGSGYLDV</u>WGQGTLV TVSS

Figure 3p. MF6974

EVQLVESGGDLVQPGGSLRLSCAASGFTFN<u>SYAMS</u>WVRQAPGKGLEWVS<u>TISGGGA
NIYYADSVKG</u>RFTISRDNSKSTLYLQMNSLRAEDTAVYFCAS<u>PYGSGYFDV</u>WGQGTL
VTVSS

Figure 3q. MF6972

EVQLQESGPGLVKPSETLSLTCTVSGGSIS<u>TYFWS</u>WIRQPPGKGLEWIG<u>YIYYSGSTNY
NPSLKS</u>RVTISVDTSKNQFSLKLSSVTAADTAVYYCAR<u>GGYSGYGGDDFDI</u>WGQGTM
VTVSS

Figure 3r. MF6936

EVQLVQSGAEVKKPGSSVKVSCKASGDTFS<u>NYVIN</u>WVRQAPGQGLEWMG<u>MIIPVFDT
TSYERKFQG</u>RVTITADKSTSTAYMELTSLRSEDTAVYYCAR<u>GTVGATLLFDN</u>WGQGT
LVTVSS

Figure 3s. MF6935

QVQLVQSGAEVKKPGSSVKVSCKASGGTFS<u>SYVIS</u>WVRQAPGQGLEWMG<u>MIIPIFDT
ANYAQKFQG</u>RVTITADKSTSTASMELRSLRSEDTAVYYCAR<u>GTVSGTLVFDY</u>WGQGT
LVTVSS

Figure 3t. MF6932

QVQLVQSGAEVKKPGSSVKVSCKASGGTFS<u>SYAIS</u>WVRQAPGQGLEWMG<u>MIIPFFDT
ANYAQKFQG</u>RVTITADKSTSTASMELRSLRSEDTAVYYCAR<u>GTVSATLVFDY</u>WGQGT
LVTVSS

Figure 3u. MF6076

QVQLQESGPGLVKPSETLSLTCTVSTDSLG<u>FYFWS</u>WIRQPPGKGLEWIG<u>YIYYSGSAN
FNPSLKS</u>RVTMSIDTSNNQFSLKLRSVTAADTAVYFCAR<u>GGYTGYGGDWFDP</u>WGQG
TLVTVSS

Figure 3v. MF6236

QVQLQESGPGLVKPSETLSLTCTVSGGSIG<u>YYFWS</u>WIRQPPGKGLEWIG<u>YIYYSGSTN
FNPSLKS</u>RVTMSVDTSKNQFSLNLRSVTTADTAVYYCAR<u>GGYTGHGGDWFDP</u>WGQG
TLVTVSS

Figure 3w. MF6256

EVQLVQSGAEVKKPGSSMKVSCKASGGTFS<u>SYVIS</u>WVRQAPGQGLEWMG<u>MIIPVFDT
SSYEKKFQG</u>RITIIADKSTSTVYLELSSLRSEDAAVYYCAR<u>GTVEATLLFDF</u>WGQGTLV
TVSS

Figure 3x. MF6930

EVQLVQSGAEVKKPGSSMKVSCKASGGTFS<u>NYVIS</u>WVRQAPGQGLEWMG<u>MIIPVFET ATYEKKFQG</u>RVTIIADKSTSTVYMELSSLRSEDAAVYYCAR<u>GTVEATLLFDY</u>WGQGTL VTVSS

Figure 3y. MF6226

QVQLQESGPGLVKPSETLSLTCTVSGDSIG<u>YYFWS</u>WIRQPPGKGLEWIG<u>YVYYSGSNN LNPSLKS</u>RVTLSVDTSKNQFSLRLNSMTAADTAVYYCAR<u>GGYSGYGGDSFDL</u>WGQGT TVTVSS

EVQLVETGAEVKKPGASVKVSCKASDYIFT<u>KYDIN</u>WVRQAPGQGLEWMG<u>WMSANTGNTGYAQKFQG</u>RVTMTRDTS
INTAYMELSSLTSGDTAVYFCAR<u>SSLFKTETAPYYHFALD</u>VWGQGTTVTVSS

Figure 10
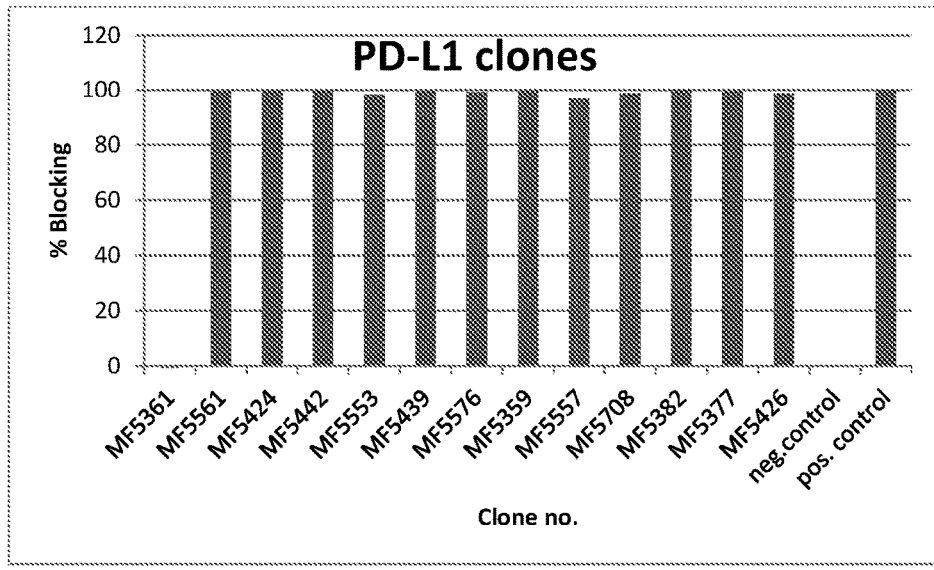
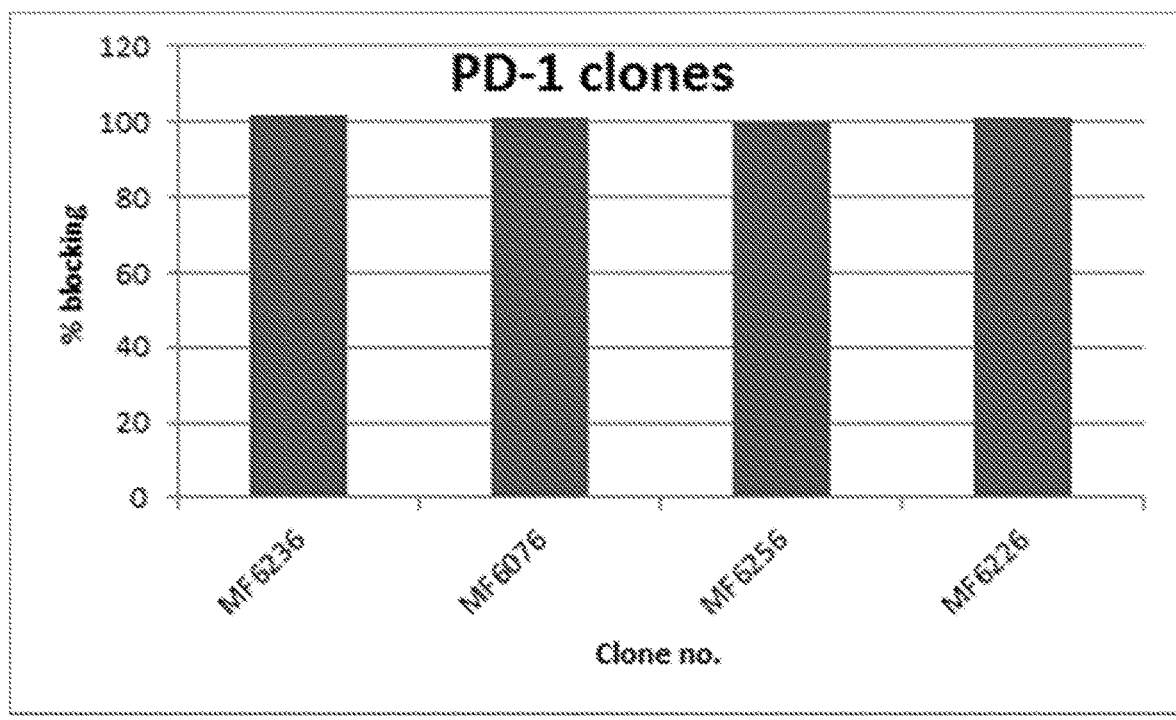

Figure 12
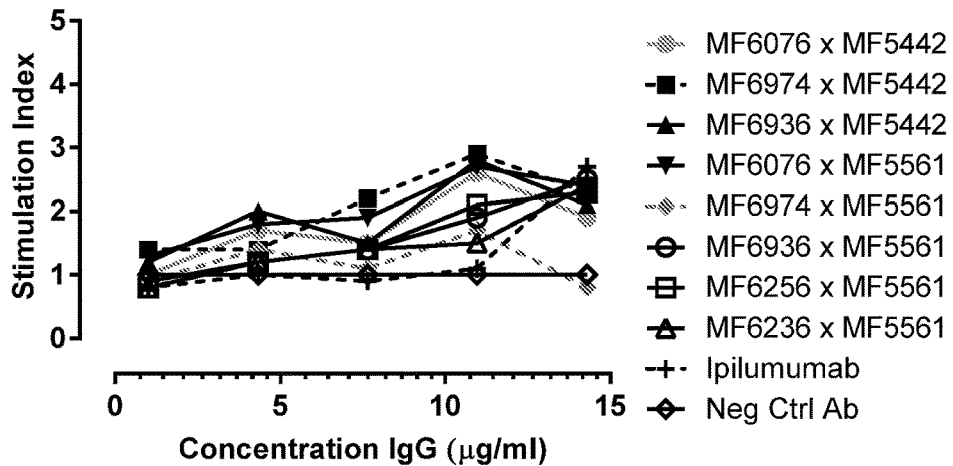
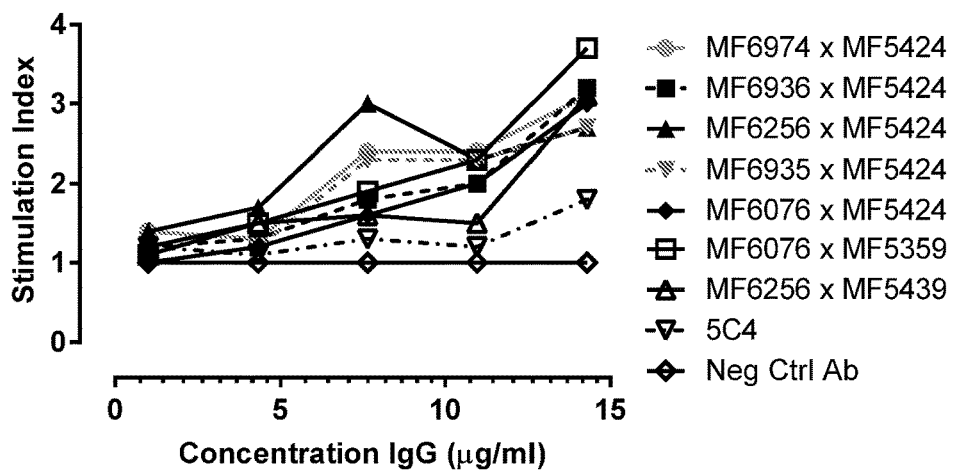
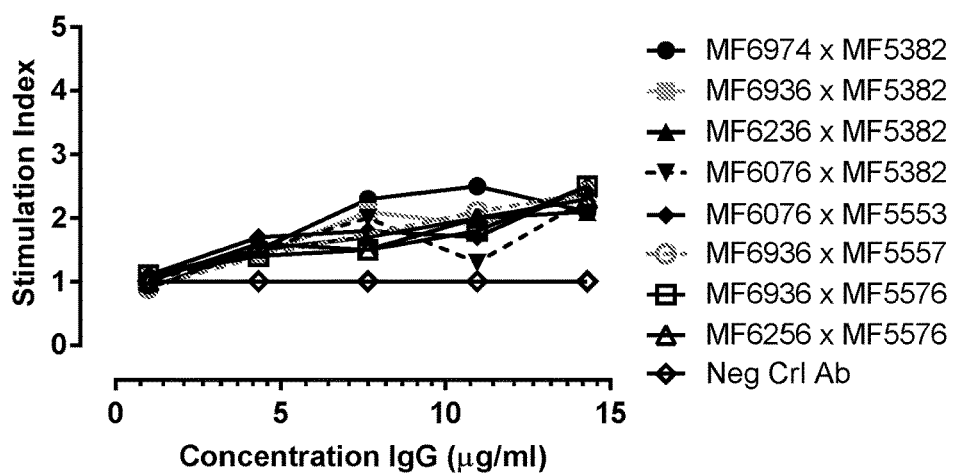

QVQLQESGPGLVKPSETLSLTCTVSTDSLG<u>FYFWS</u>WIRQPPGKGLEWIG<u>YIYYSGSANFNPSLKS</u>RVTMS
IDTSNNQFSLKLRSVTAADTAVYFCAR<u>GGYTGYGGDWFDP</u>WGQGTLVTVSS (SEQ ID NO: 44)

MF7699

QVQLQESGPGLVKPSETLSLTCTVSTDSLG<u>FYFWS</u>WIRQPPGKGLEWIG<u>YIYYSGSANFNPSLKS</u>RVTMS
IDTSNNQFSLKLSSVTAADT<u>AVYFCARGGYTGYGGDWFDPWGQGTL</u>VTVSS (SEQ ID NO: 50)

MF7698

EVQLQESGPGLVKPSETLSLTCTVSTDSLG<u>FYFWS</u>WIRQPPGKGLEWIG<u>YIYYSGSANFNPSLKS</u>RVTMS
IDTSNNQFSLKLRSVTAADTAVYFCAR<u>GGYTGYGGDWFDP</u>WGQGTLVTVSS (SEQ ID NO: 51)

MF6256

EVQLVQSGAEVKKPGSSMKVSCKASGGTFS<u>SYVIS</u>WVRQAPGQGLEWMG<u>MIIPVFDTSSYEKKFQG</u>RITI
IADKSTSTVYLELSSLRSEDAAVYYCAR<u>GTVEATLLFDF</u>WGQGTLVTVSS (SEQ ID NO: 46)

MF6935

QVQLVQSGAEVKKPGSSVKVSCKASGGTFS<u>SYVIS</u>WVRQAPGQGLEWM<u>GMIIPIFDTANYAQKFQG</u>RVTI
TADKSTSTASMELRSLRSEDTAVYYCAR<u>GTVSGTLVFDY</u>WGQGTLVTVSS (SEQ ID NO: 42)

MF7687

QVQLVQSGAEVKKPGSSMKVSCKASGGSFS<u>SAVIS</u>WVRQAPGQGLEWM<u>GMIIPVFDTASYAKKFQG</u>RVTI
TADKSTNTVYMELSRLRSEDAAVYYCAR<u>GTVEATLLFDY</u>WGLGTLVTVSS (SEQ ID NO: 52)

MF7686

QVQLVQSGAEVKKPGSSMKVSCKASGGSFS<u>SAVIS</u>WVRQAPGQGLEWM<u>GMIIPVFDTASYAKKFQG</u>RVTI
TADKSTNTVYMELSRLRSEDAAVYYCAR<u>GTVEATLLFDY</u>WGRGTLVTVSS (SEQ ID NO: 53)

QVQLVQSGAEVKKPGSSMKVSCKASGGSFS<u>SAVIS</u>WVRQAPGQGLEWM<u>GMIIPVFDTASYEKKFQG</u>RVTI
TADKSTNTVYMELSRLRSEDAAVYYCAR<u>GTVEATLLFDY</u>WGRGTLVTVSS  (SEQ ID NO: 54)

MF7684

QVQLVQSGAEVKKPGSSVKVSCKASGGTFS<u>SYVIS</u>WVRQAPGQGLEWM<u>GMIIPIFDTANYAQKFQG</u>RVTI
TADKSTSTASMELRSLRSEDTAVYYCAR<u>GTVEATLLFDY</u>WGRGTLVTVSS  (SEQ ID NO: 55)

MF6936

EVQLVQSGAEVKKPGSSVKVSCKASGDTFS<u>NYVIN</u>WVRQAPGQGLEWM<u>GMIIPVFDTTSYERKFQG</u>RVTI
TADKSTSTAYMELTSLRSEDTAVYYCAR<u>GTVGATLLFDN</u>WGQGTLVTVSS  (SEQ ID NO: 41)

MF6929

EVQLVQSGAEVKKPGSSVKVSCKASGGTFS<u>SYVIS</u>WVRQAPGQGLEWM<u>GMIIPVFETVSYEQKFQG</u>RVTI
TADKSTSTAYMELSSLRSEDTAVYYCAR<u>GTVEATLLFDY</u>WGQGTLVTVSS  (SEQ ID NO: 56)

MF6974

EVQLVESGGDLVQPGGSLRLSCAASGFTFN<u>SYAMS</u>WVRQAPGKG<u>LEWVSTISGGGANIYYADSVKG</u>RFTI
SRDNSKSTLYLQMNSLRAEDTAVYFCAS<u>PYGSGYFDV</u>WGQGTLVTVSS  (SEQ ID NO: 39)

PD-L1

MF5442

EVQLVQSGAEVKKPGSSVRVSCKASGGTFN<u>TYAIN</u>WVRQAPGQGLEWV<u>GRIIPIFDTANYAQKFQG</u>RVTI
SADKSTTTAYMELSSLRSEDTAVFYCAK<u>DETGYSSSNFQH</u>WGQGTLVTVSS  (SEQ ID NO: 30)

MF7691

QVQLVQSGAEVKKPGSSVRVSCKASGGTFN<u>TYAIN</u>WVRQAPGQGLEWV<u>GRIIPIFDTANYAQKFQG</u>RVTI
SADKSTTTAYMELSSLRSEDTAVFYCAK<u>DETGYSSSNFQH</u>WGQGTLVTVSS  (SEQ ID NO: 57)

QVQLVQSGAEVKKPGSSVRVSCKASGGTFN<u>TYAIN</u>WVRQAPGQGLEWVGR<u>IIPIFGTANYAQKFQG</u>RVTI SADKSTTTAYMELSSLRSEDTAVFYCAK<u>DETGYSSSNFQH</u>WGQGTLVTVSS (SEQ ID NO: 58)

MF7689

QVQLVQSGAEVKKPGSSVRVSCKASGGTFN<u>TYAIN</u>WVRQAPGQGLEWVGR<u>IIPIFGTANYAQKFQG</u>RVTI SADKSTTTAYMELSSLRSEDTAVFYCAK<u>DETGYSSSNFQH</u>WGRGTLVTVSS (SEQ ID NO: 59)

MF7688

QVQLVQSGAEVKKPGSSVRVSCKASGGTFN<u>TYAIN</u>WVRQAPGQGLEWVGR<u>IIPIFDTANYAQKFQG</u>RVTI SADKSTTTAYMELSSLRSEDTAVFYCAK<u>DETGYSSSNFQH</u>WGRGTLVTVSS (SEQ ID NO: 60)

MF5553

QVQLVQSGSELKKPGASVKVSCKASGYTFT<u>NYAIN</u>WVRQAPGQGLEWMG<u>WINPNTGNPTYAQGFTG</u> RFVF SLDTSVSTAYLQISSLKAEDTAVY<u>YCARDRKYVTNWVFAED</u>FQHWGQGTLVTVSS (SEQ ID NO: 29)

MF5439

QVQLVQSGAEVKKPGSSVKVSCKASGGTFS<u>TYGIL</u>WVRQAPGQGLEWMG<u>GIIPIFGTANYAQKFQG</u>RVTI TADISTSTAYMELSSLRSEDTAVYYCAR<u>GGGNYYEFVY</u>WGQGTLVTVSS (SEQ ID NO: 31)

MF7700

QVQLVQSGAEVKKPGSSVKVSCKASGGTFS<u>TYGIL</u>WVRQAPGQGLEWMG<u>GIIPIFGTANYAQKFQG</u>RVTI TADKSTSTAYMELSSLRSEDTAVYYCAR<u>GGGNYYEFVY</u>WGQGTLVTVSS (SEQ ID NO: 61)

MF7701

QVQLVQSGAEVKKPGSSVKVSCKASGGTFS<u>TYGIL</u>WVRQAPGQGLEWMG<u>GIIPIFGTANYAQKFQG</u>RVTI TADKSTSTAYMELSSLRSEDTAVYYCAR<u>GGGNYYEFVY</u>WGRGTLVTVSS (SEQ ID NO: 62)

MF5424

EVQLVQSGAEVMRPGSSVKVSCKASGGIFN<u>TYTII</u>WVRQAPGQGLEWMG<u>GIIPIFDTPNFAQKFQG</u>RLTI TADKSTNTAYMELTSLRSEDTAVYYCAR<u>EGCNHGVCYPY</u>WGQGTLVTVSS (SEQ ID NO: 33)

EVQLVQSGAEVMRPGSSVKVSCKASGGIFN<u>TYTII</u>WVRQAPGQGLEWMG<u>GIIPIFDTPNFAQKFQD</u>RLTI
TADKSTNTAYMELTSLRSEDTAVYYCAR<u>EGCNHGVCYPY</u>WGQGTLVTVSS  (SEQ ID NO: 63)

MF5442

EVQLVQSGAEVKKPGSSVRVSCKASGGTFN<u>TYAIN</u>WVRQAPGQGLEWVG<u>RIIPIFDTANYAQKFQG</u>RVTI
SADKSTTTAYMELSSLRSEDTAVFYCAK<u>DETGYSSSNFQH</u>WGQGTLVTVSS  (SEQ ID NO: 30)

MF5557

QVQLVQSGAEVKRPGSSVKVSCKASGGTFN<u>TYSIT</u>WVRQAPGQGLEWMG<u>GIIPVFGTSKYAQKFQD</u>RVTI
TADKSTNTAYMELSSLRSEDTAVYYCAR<u>DPSFSSSSGWFDP</u>WGQGTLVTVSS  (SEQ ID NO: 28)

MF7694

QVQLVQSGAEVKRPGSSVKVSCKASGGTFN<u>TYSIT</u>WVRQAPGQGLEWMG<u>GIIPVFGTSKYAQKFQG</u>RVTI
TADKSTNTAYMELSSLRSEDTAVYYCAR<u>DPSFSSSSGWFDP</u>WGQGTLVTVSS   (SEQ ID NO: 64)

MF7693

QVQLVQSGAEVKRPGSSVKVSCKASGGTFN<u>TYSIT</u>WVRQAPGQGLEWMG<u>GIIPVFGTSKYAQKFQG</u>RVTI
TADKSTNTAYMELSSLRSEDTAVYYCAR<u>DPSFSSSSGWFDP</u>WGRGTLVTVSS  (SEQ ID NO: 65)

MF7692

QVQLVQSGAEVKRPGSSVKVSCKASGGTFN<u>TYSIT</u>WVRQAPGQGLEWMG<u>GIIPVFGTSKYAQKFQD</u>RVTI
TADKSTNTAYMELSSLRSEDTAVYYCAR<u>DPSFSSSSGWFDP</u>WGRGTLVTVSS   (SEQ ID NO: 66)

MF7697

QVQLVQSGAEVKKPGSSVKVSCKASGGTFS<u>SYAIS</u>WVRQAPGQGLEWMG<u>GIIPIFGTANYAQKFQG</u>RVTI
TADKSTSTAYMELSSLRSEDTAVYYCAR<u>AKTWYGFGDALDY</u>WGQGTLVTVSS   (SEQ ID NO: 67)

MF7696

QVQLVQSGAEVKKPGSSVKVSCKASGGTFS<u>SYAIS</u>WVRQAPGQGLEWMG<u>GIIPIFGTANYAQKFQG</u>RVTI
TADKSTSTAYMELSSLRSEDTAVYYCAR<u>AKTWYGFGDALDY</u>WGRGTLVTVSS   (SEQ ID NO: 68)

QVQLVQSGAEVKKPGSSVKVSCKASGGTFS<u>SYAIS</u>WVRQAPGQGLEWM<u>GGIIPIFGTANYAQKFQG</u>
RVTITADESTSTAYMELSSLRSEDTAVYY<u>CARAKTWYGFG</u>DALDYWGRGTLVTVSS (SEQ ID NO: 69)

Figure 14
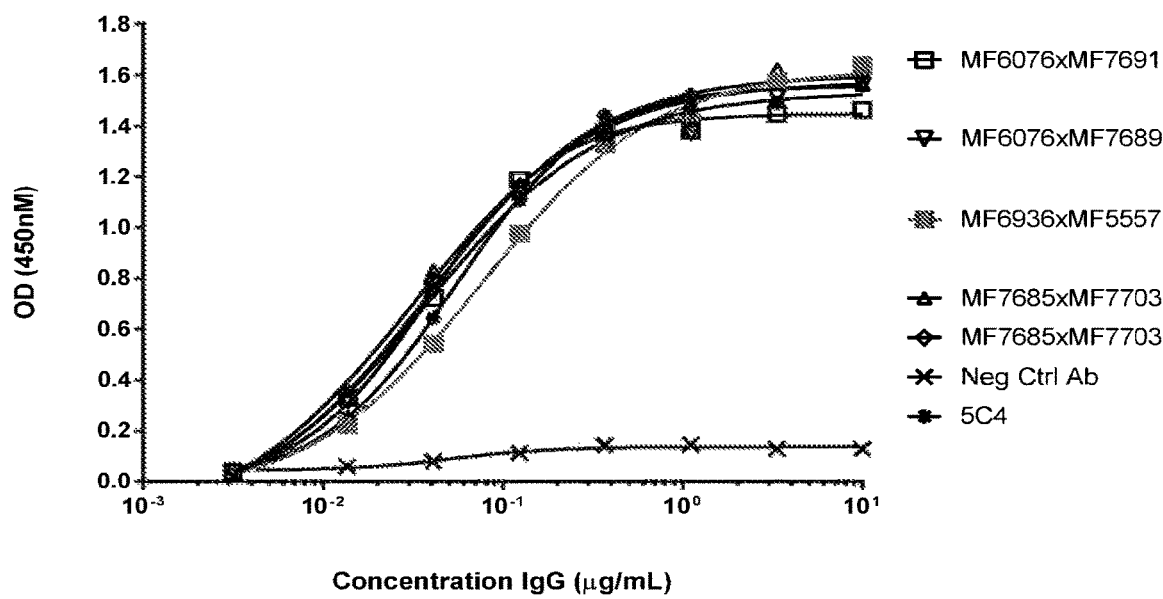
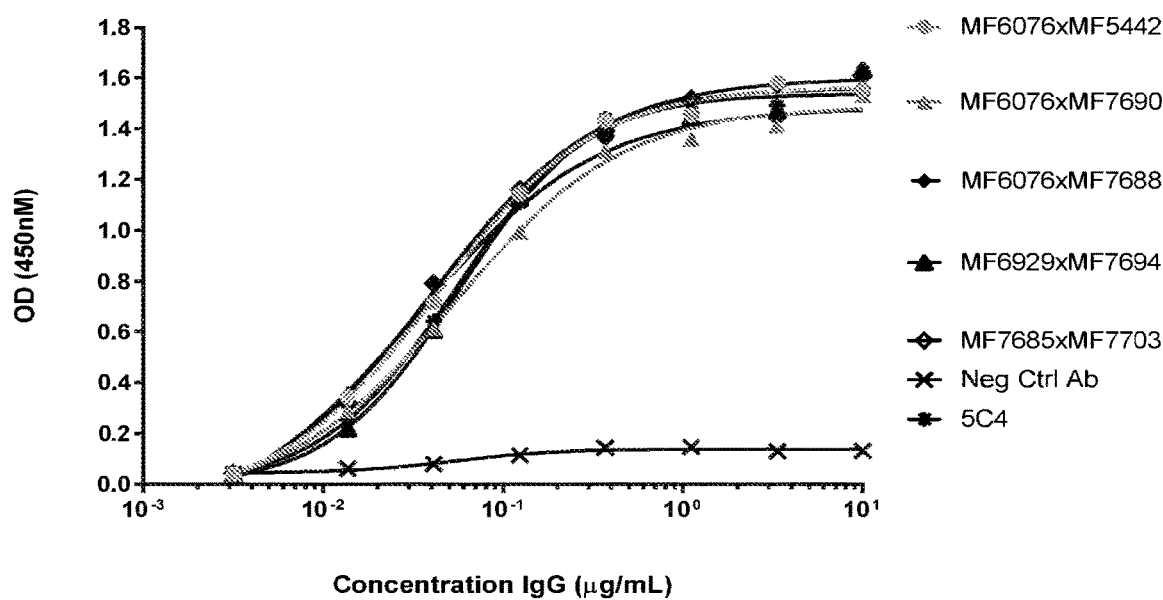

Figure 14 Cont'd
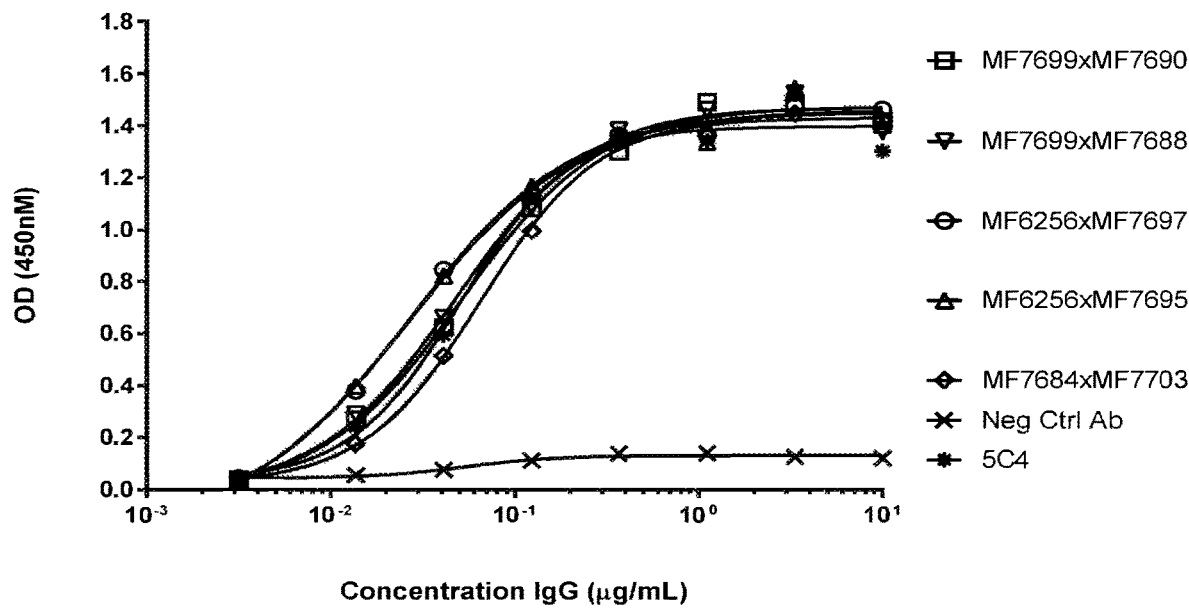
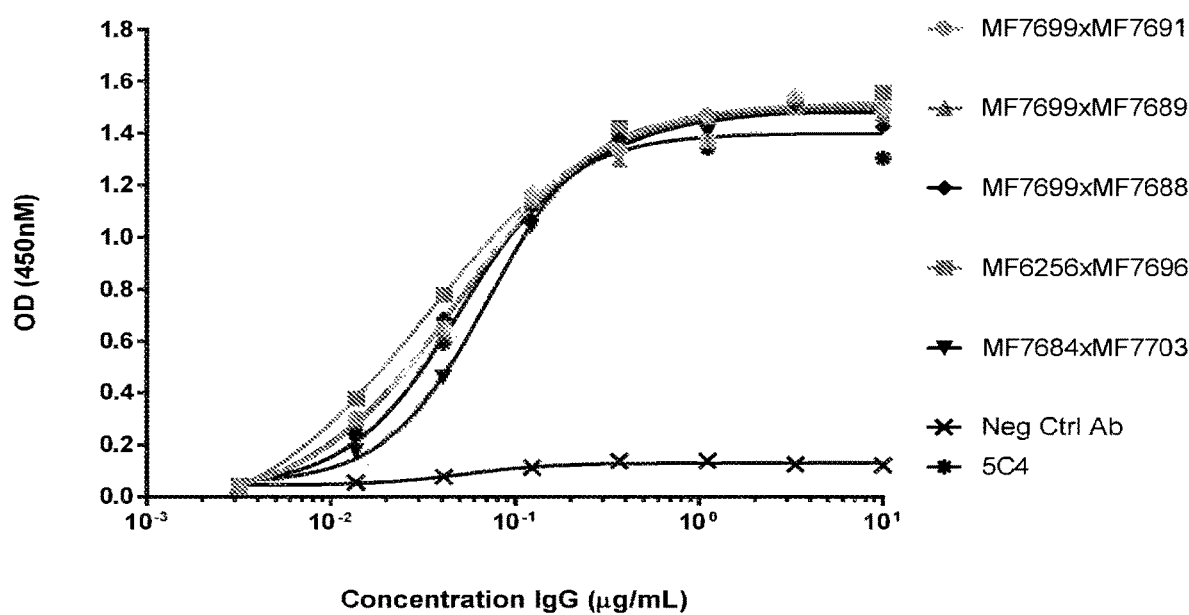

Figure 14 Cont'd
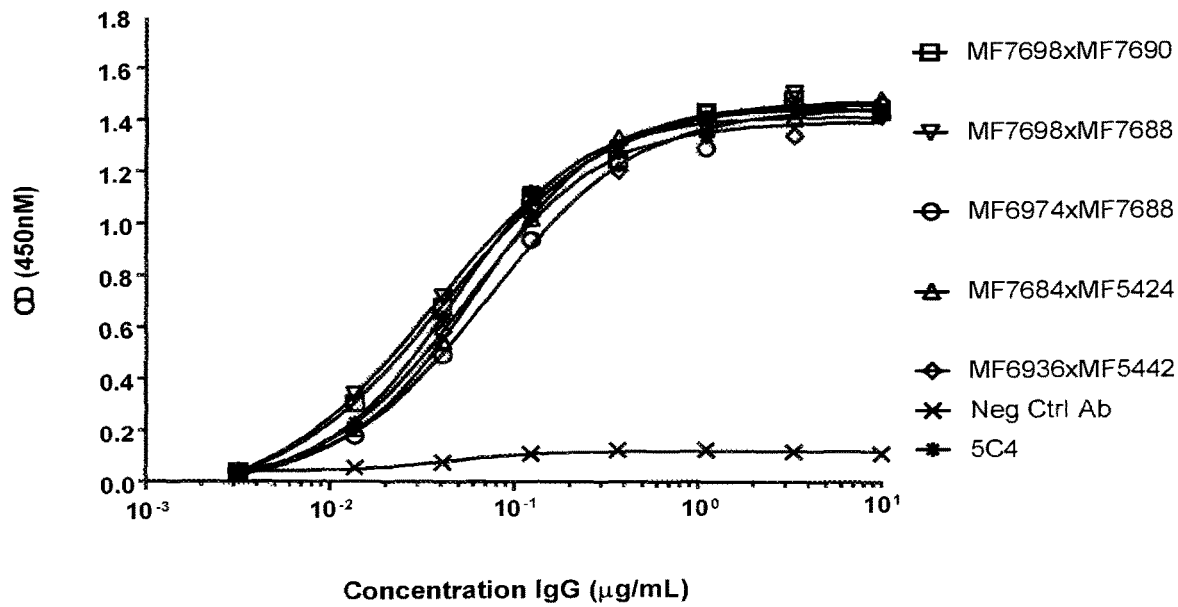
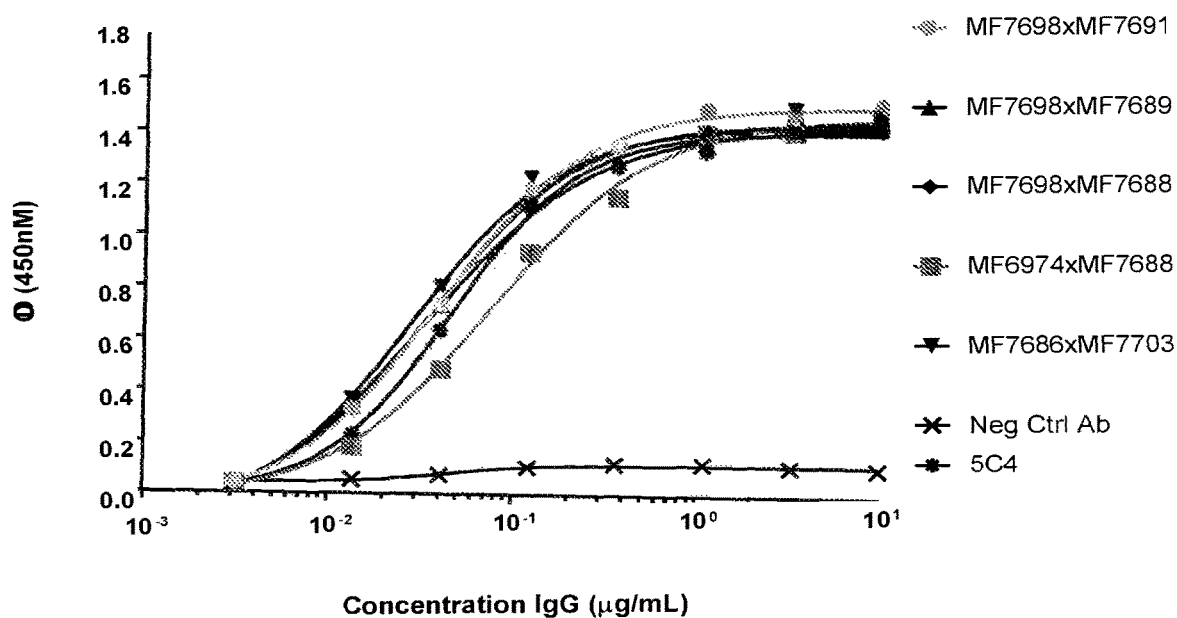

Figure 14 Cont'd
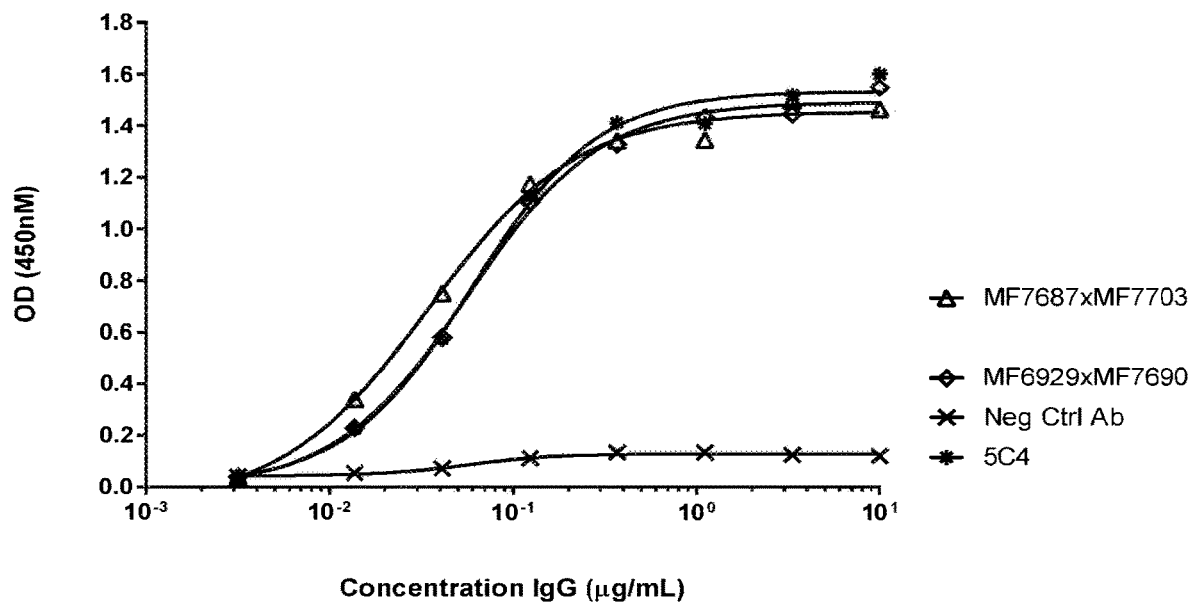
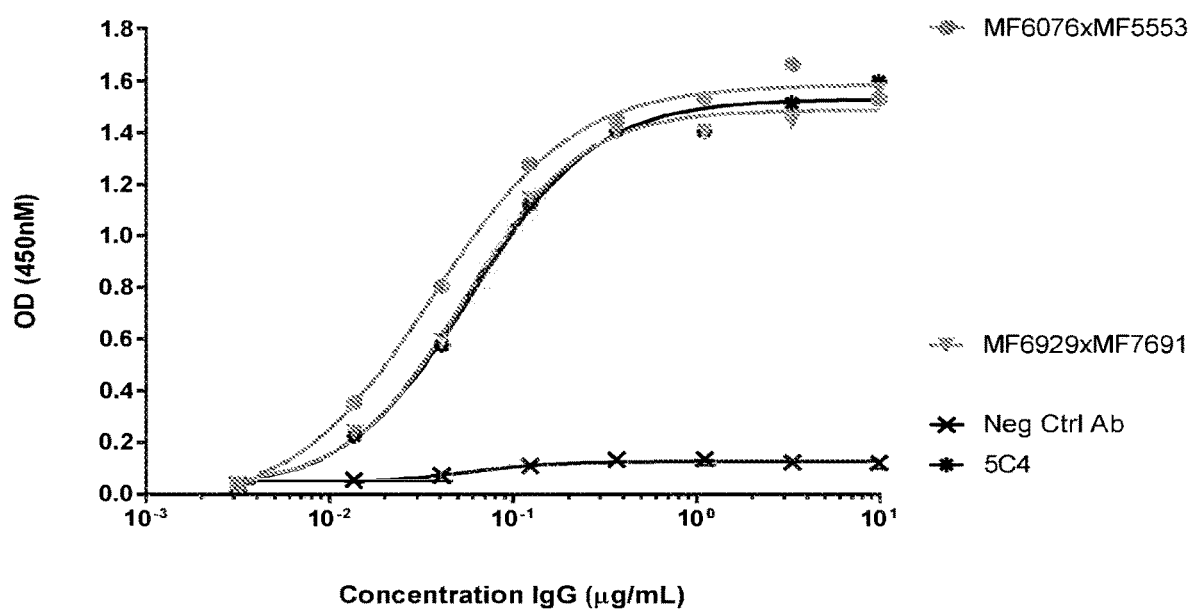

Figure 14 Cont'd
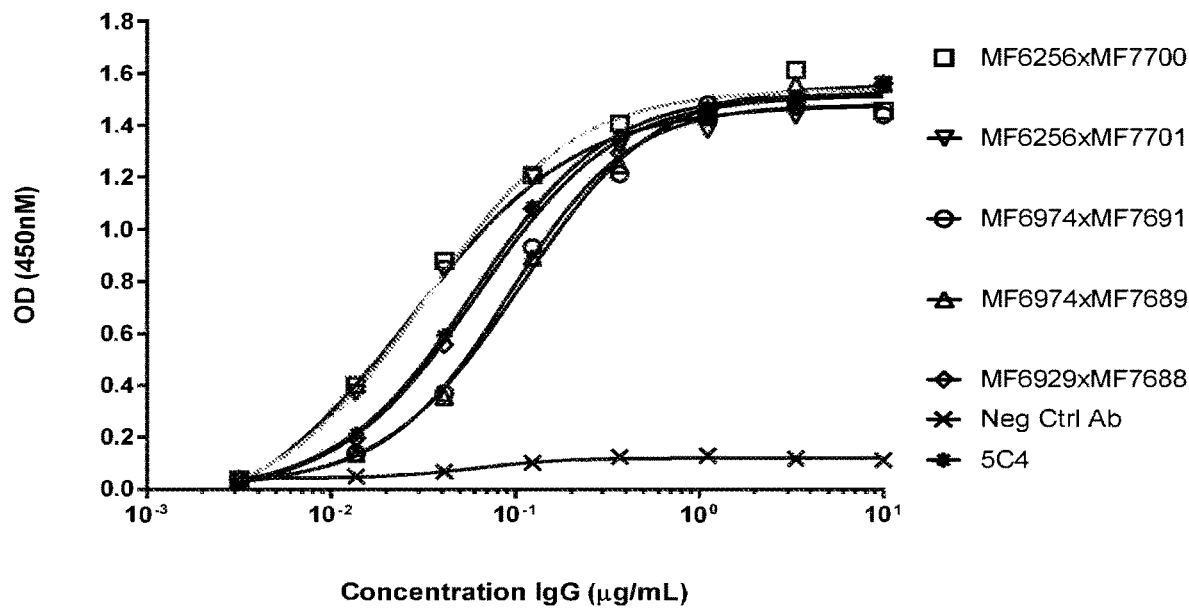
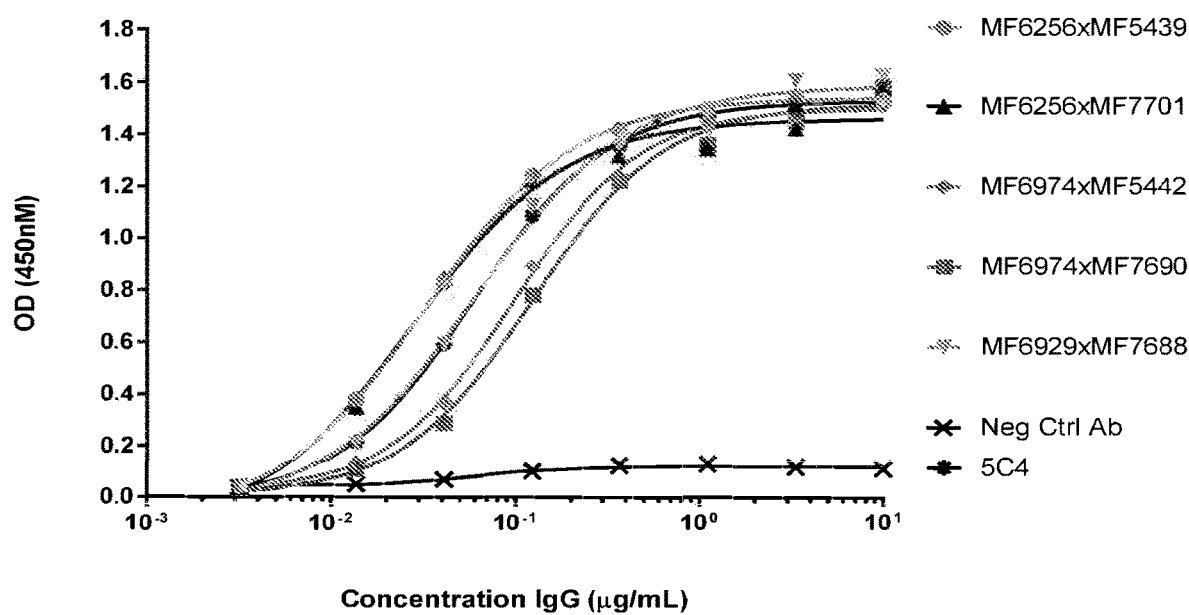

Figure 14 Cont'd
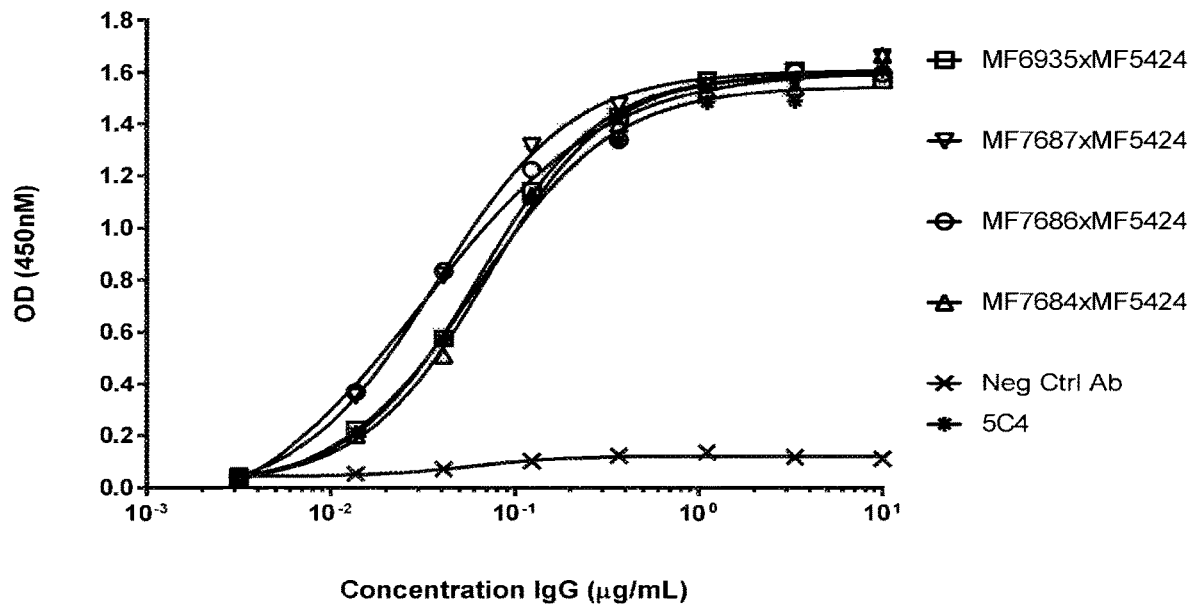
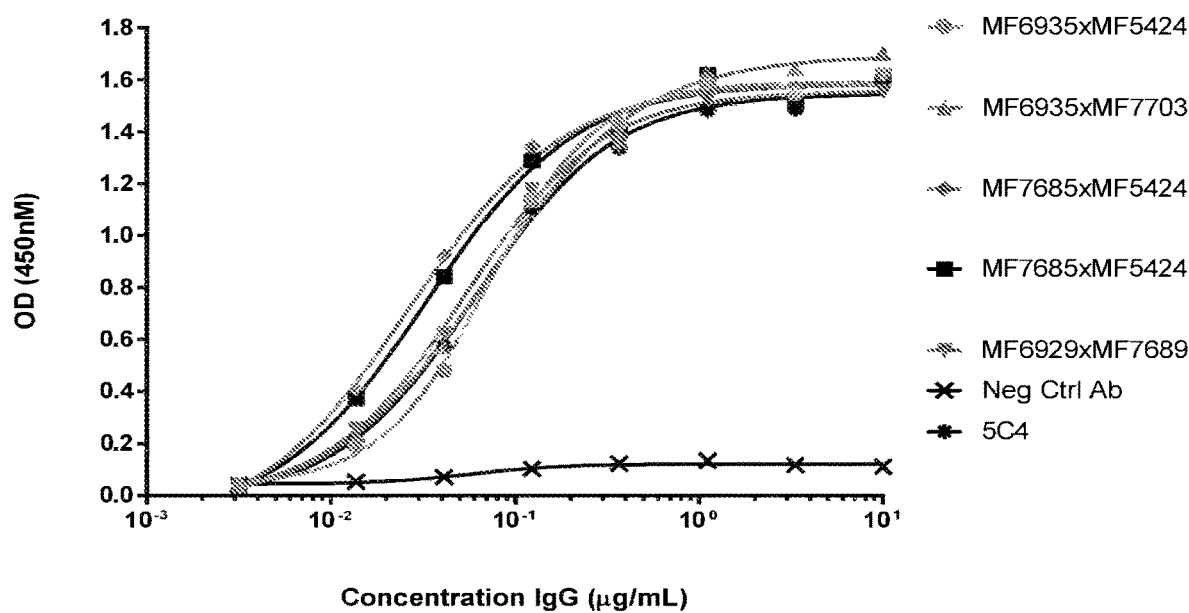

Figure 14 Cont'd
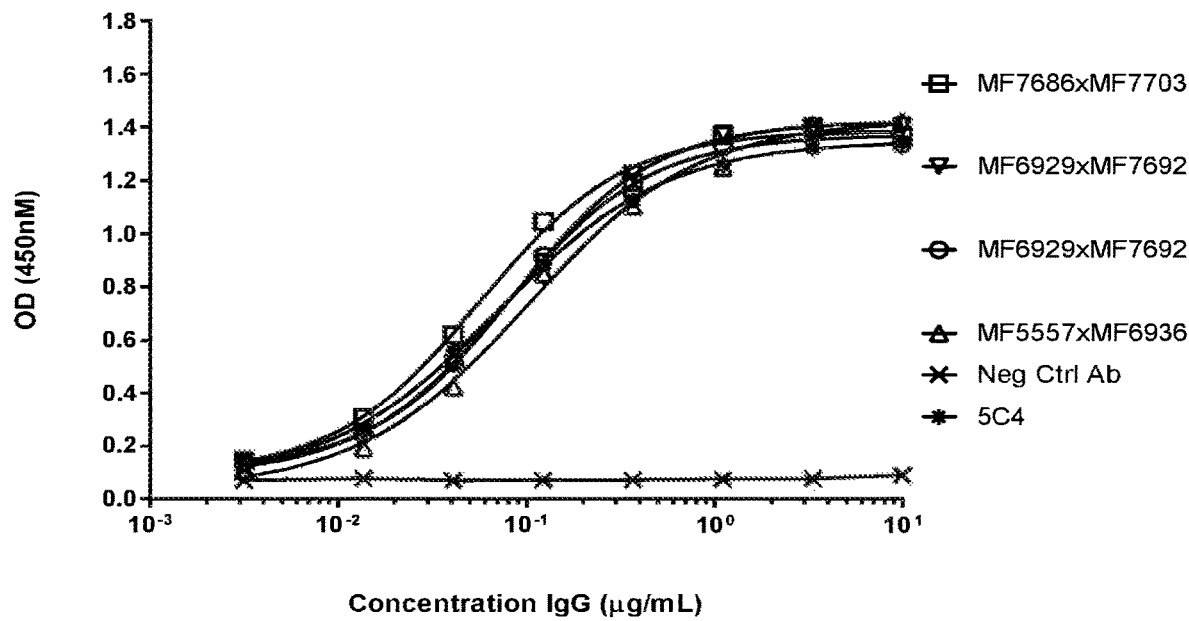
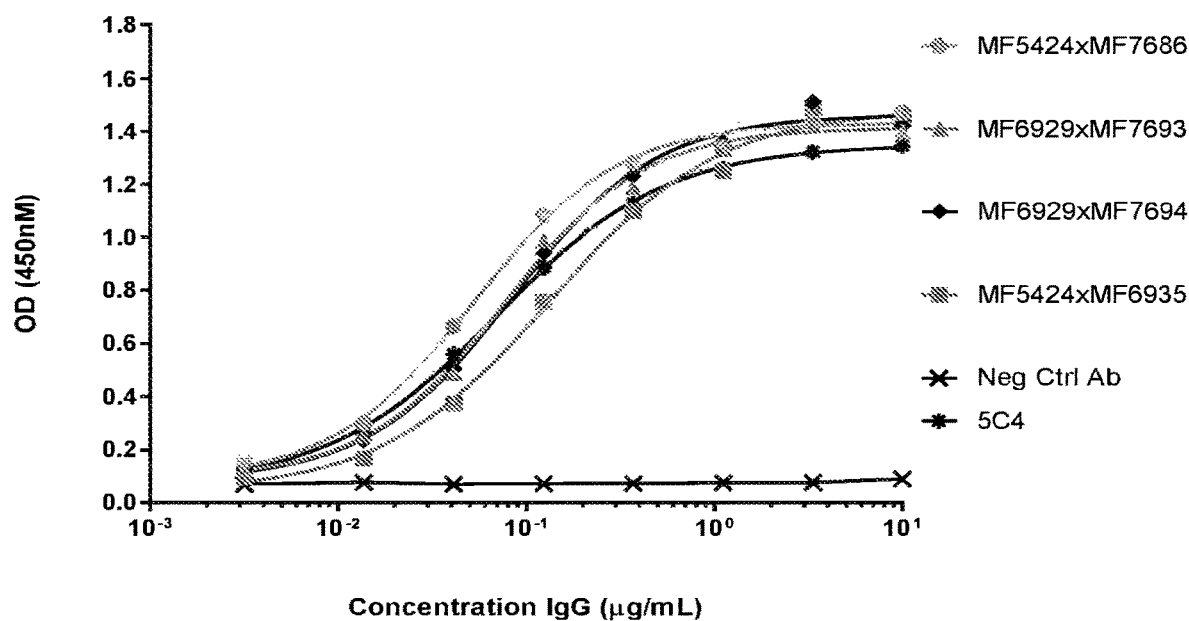

Figure 15 Cont'd
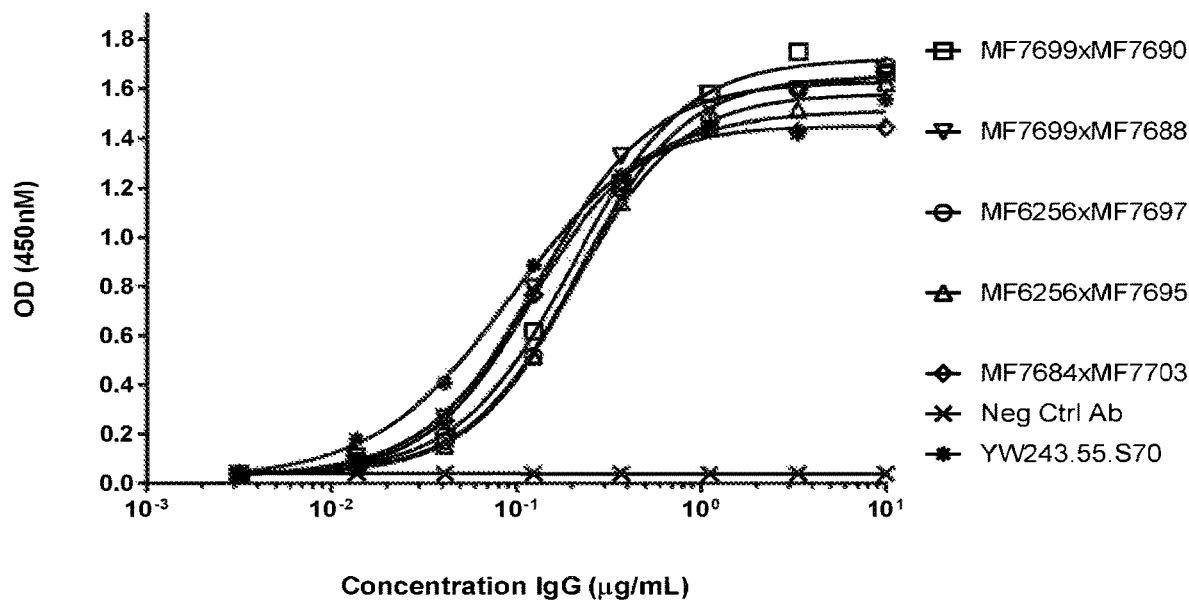
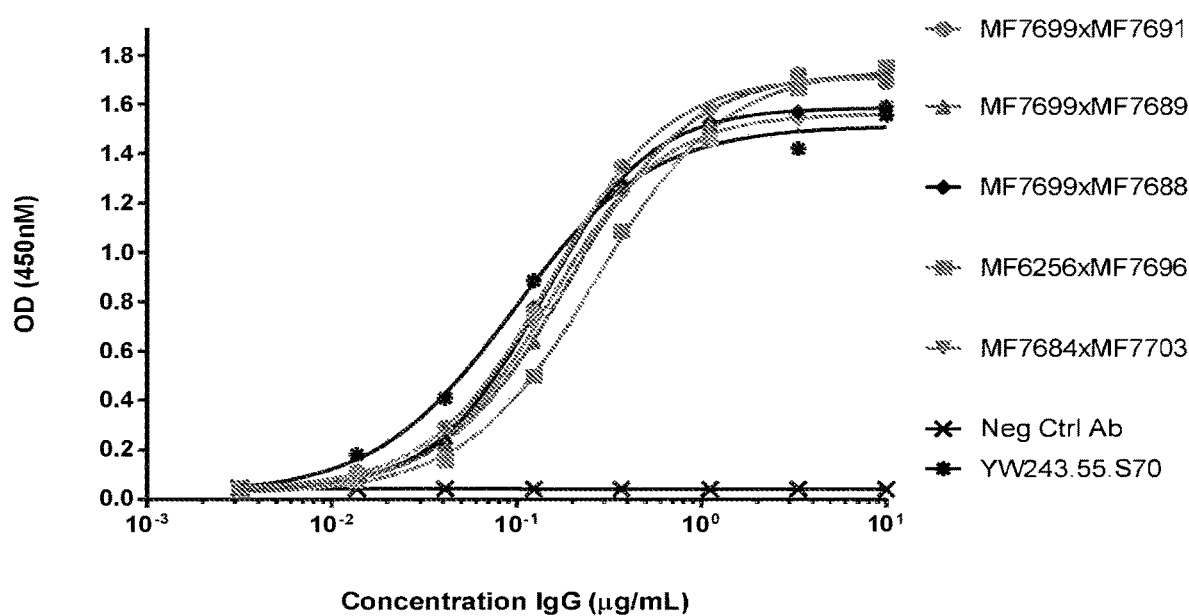

Figure 15 Cont'd
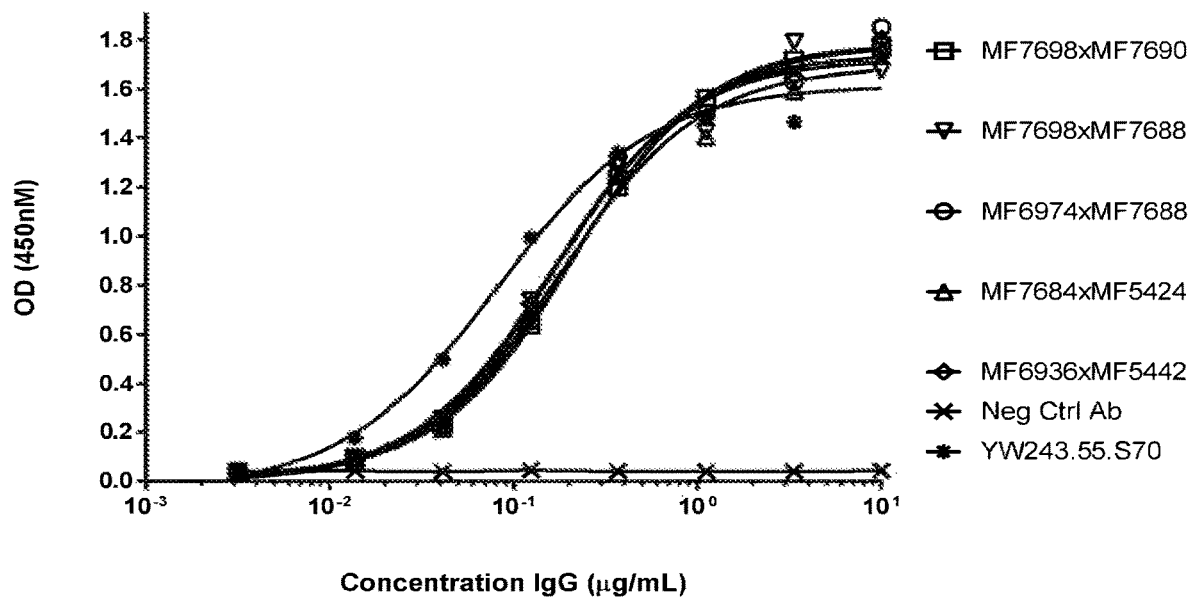
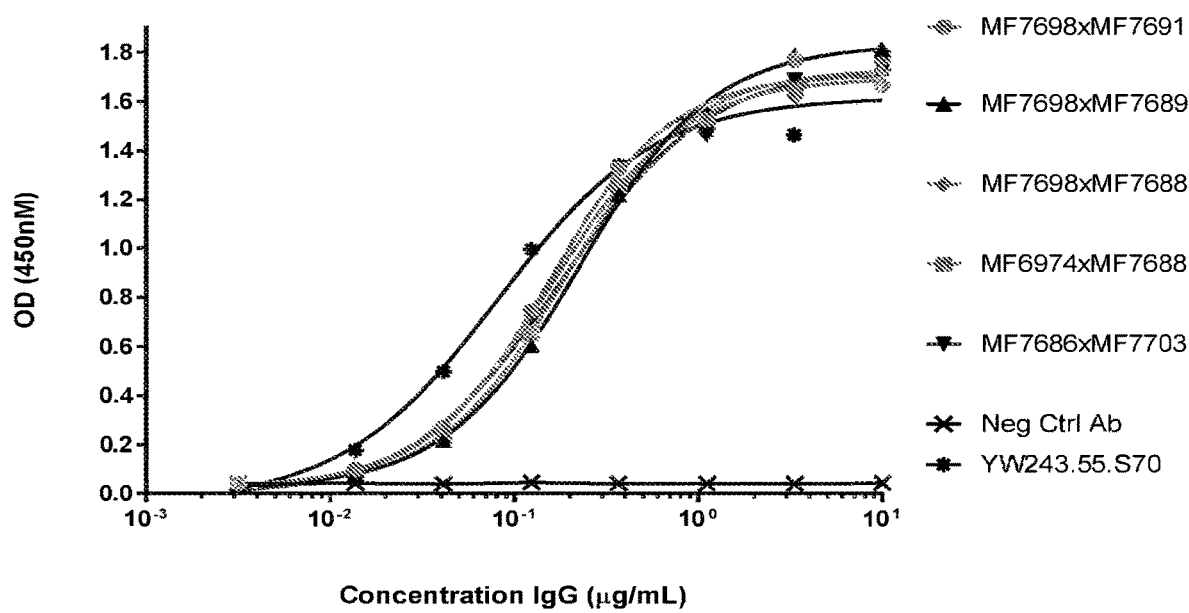

Figure 15 Cont'd
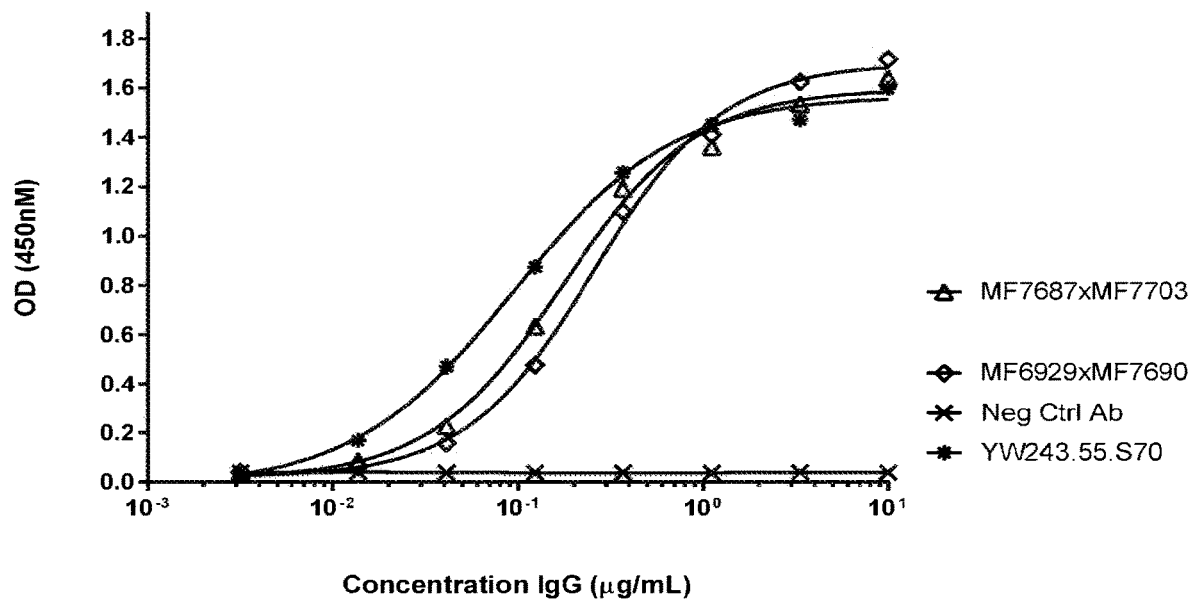
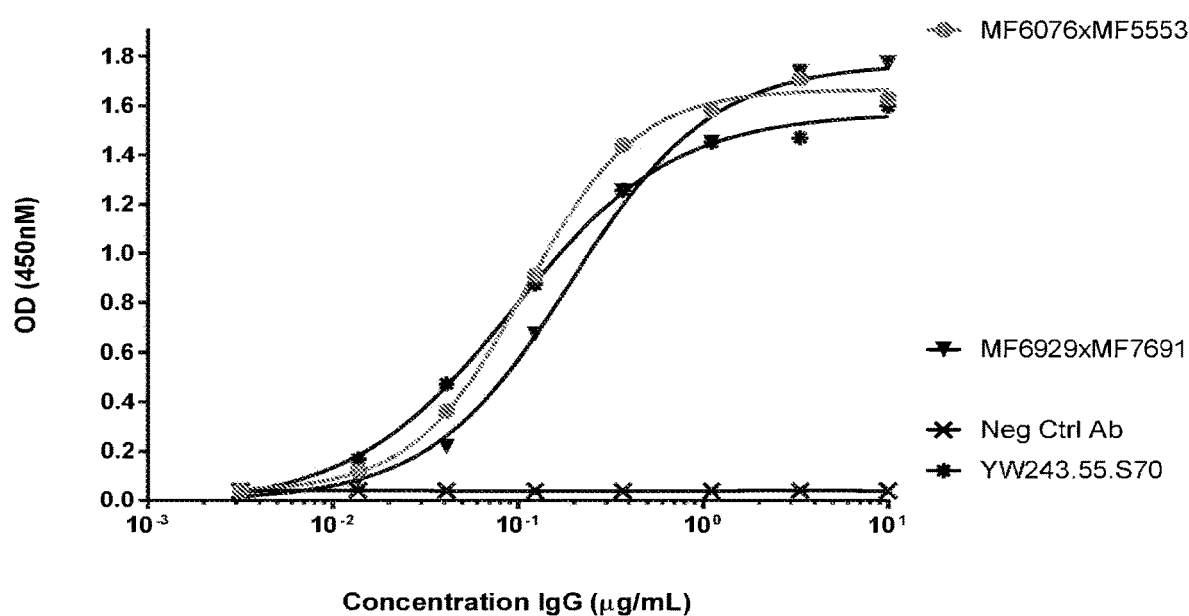

Figure 15 Cont'd
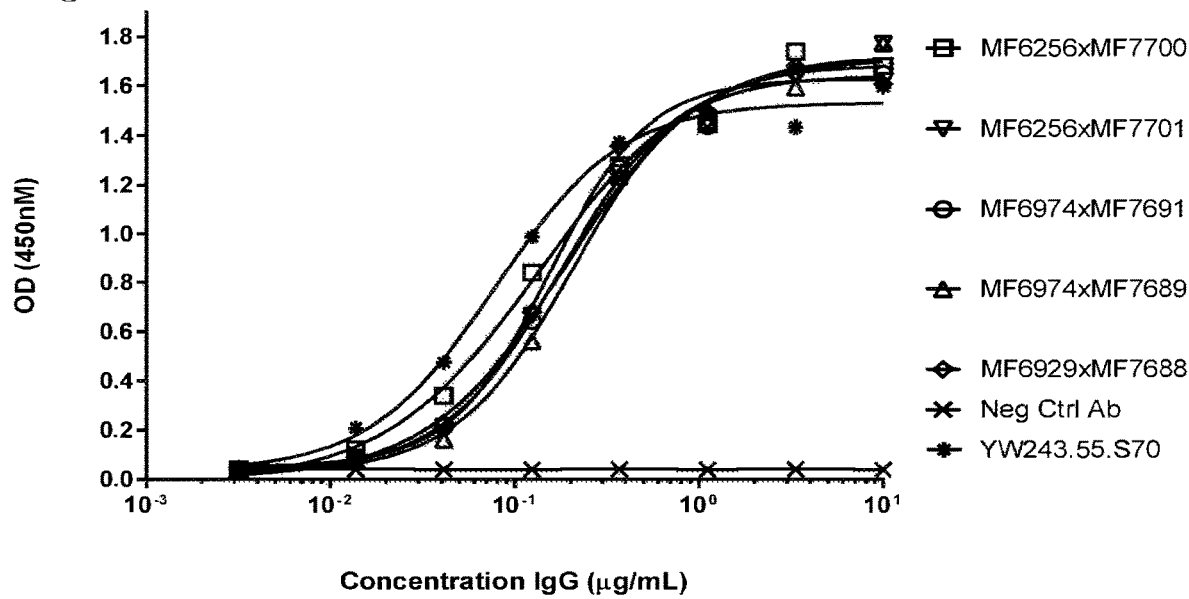
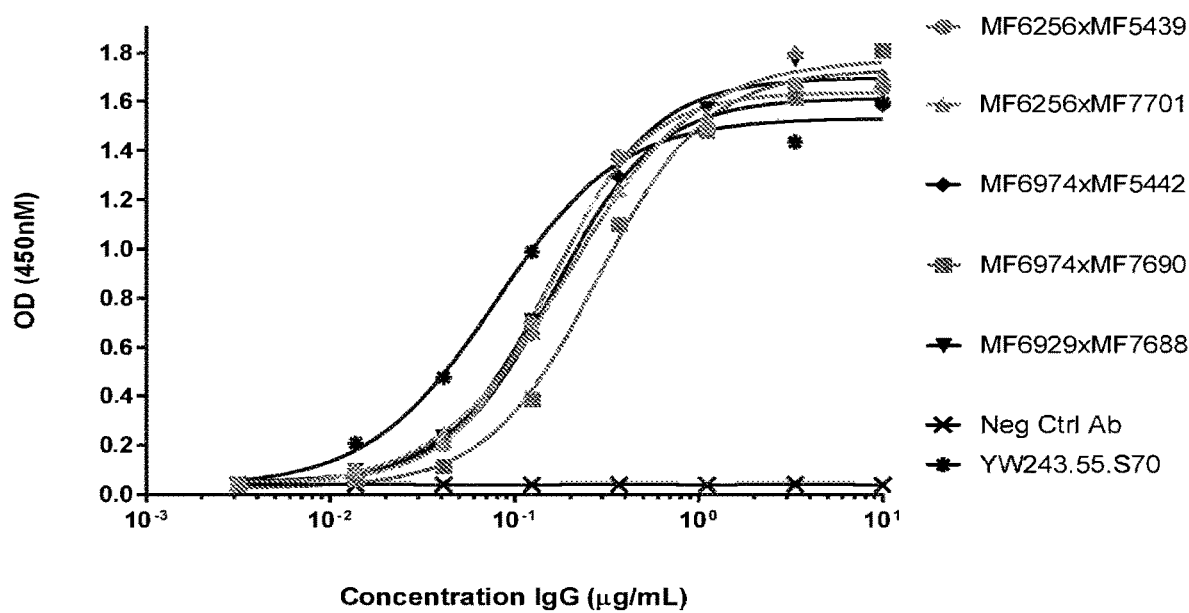

Figure 15 Cont'd
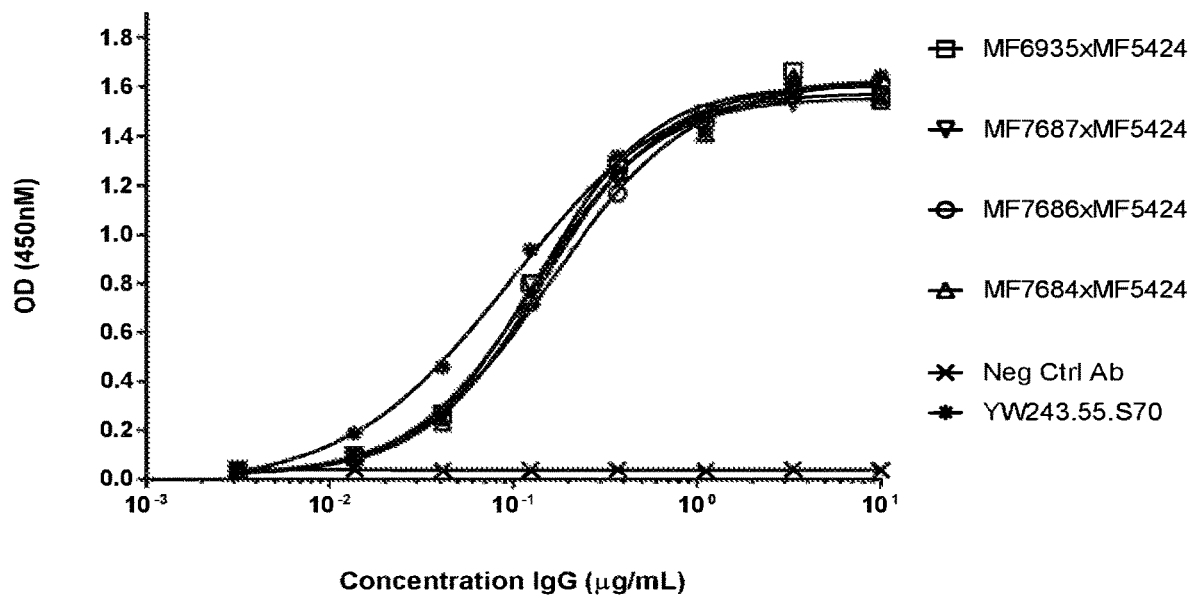
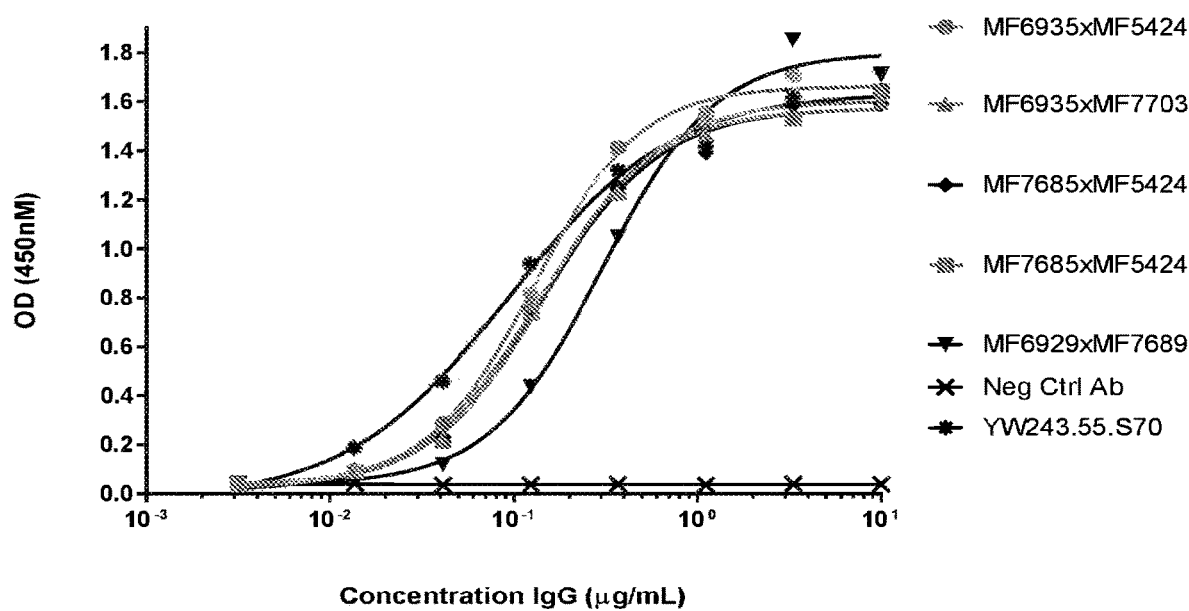

Figure 15 Cont'd
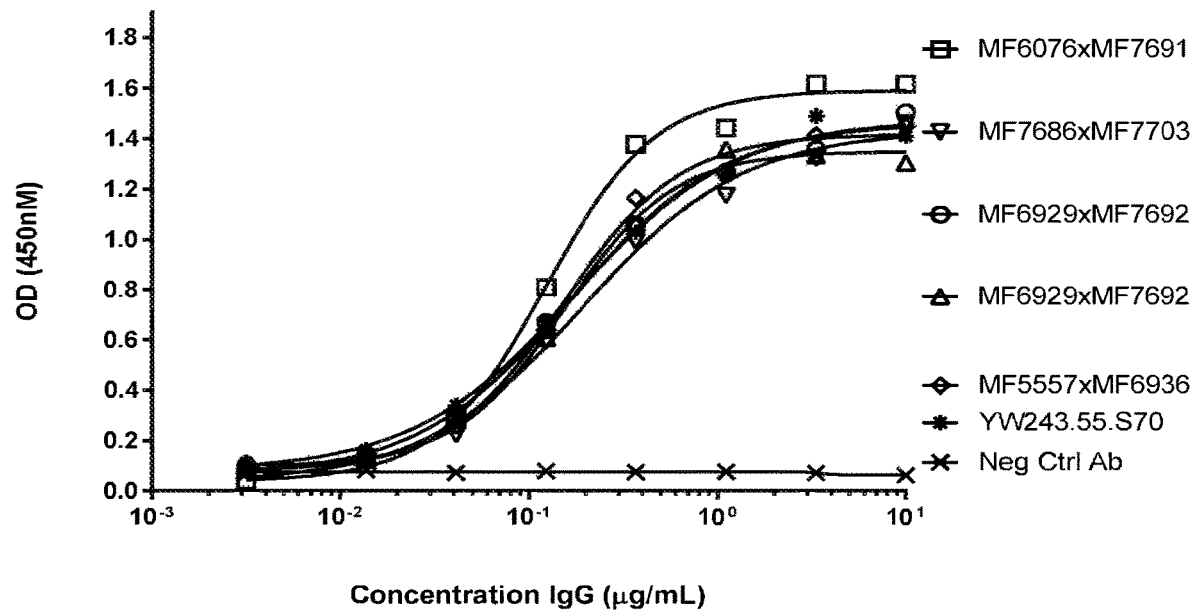
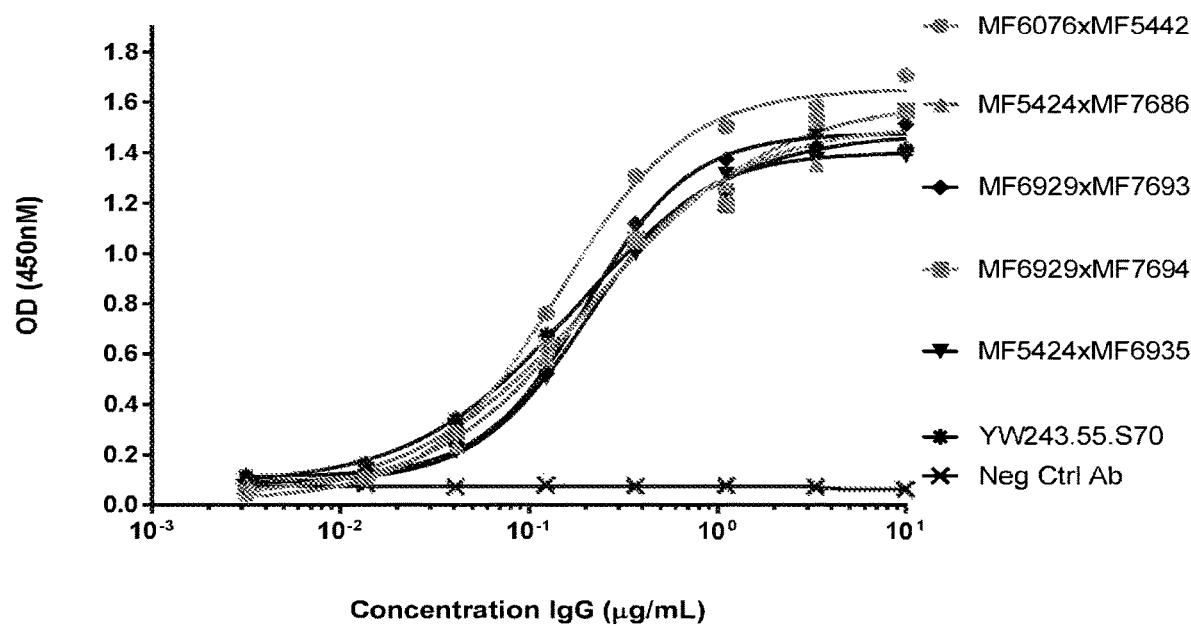

Figure 16
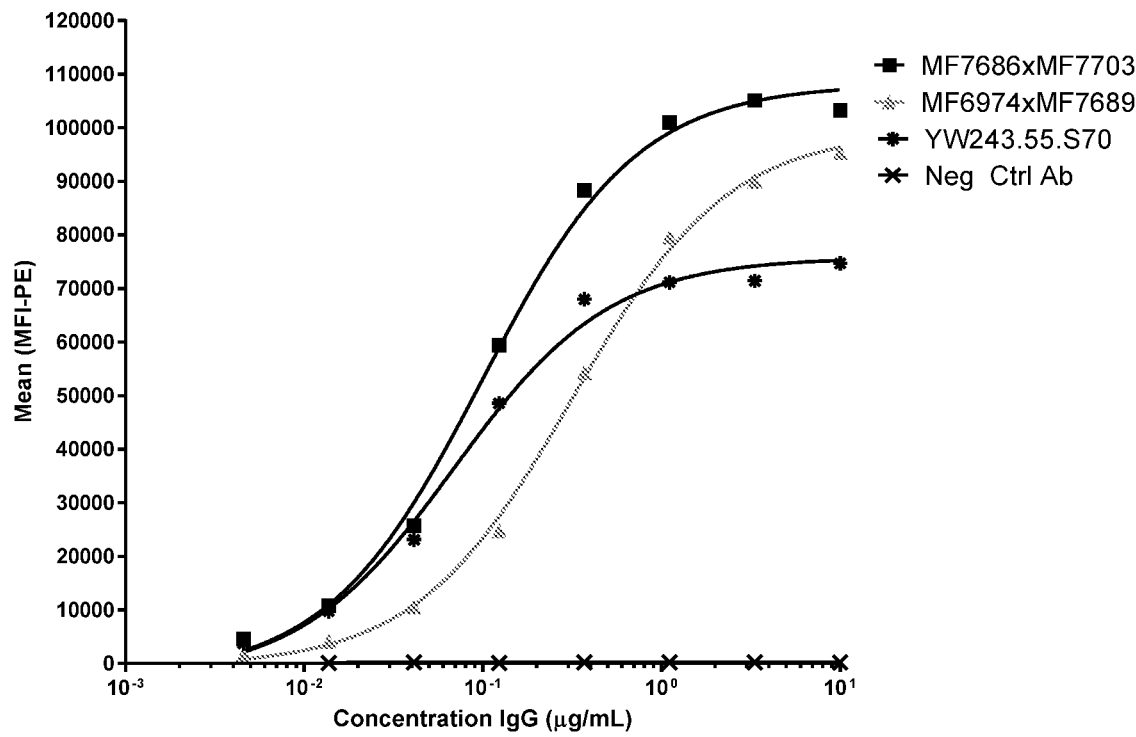
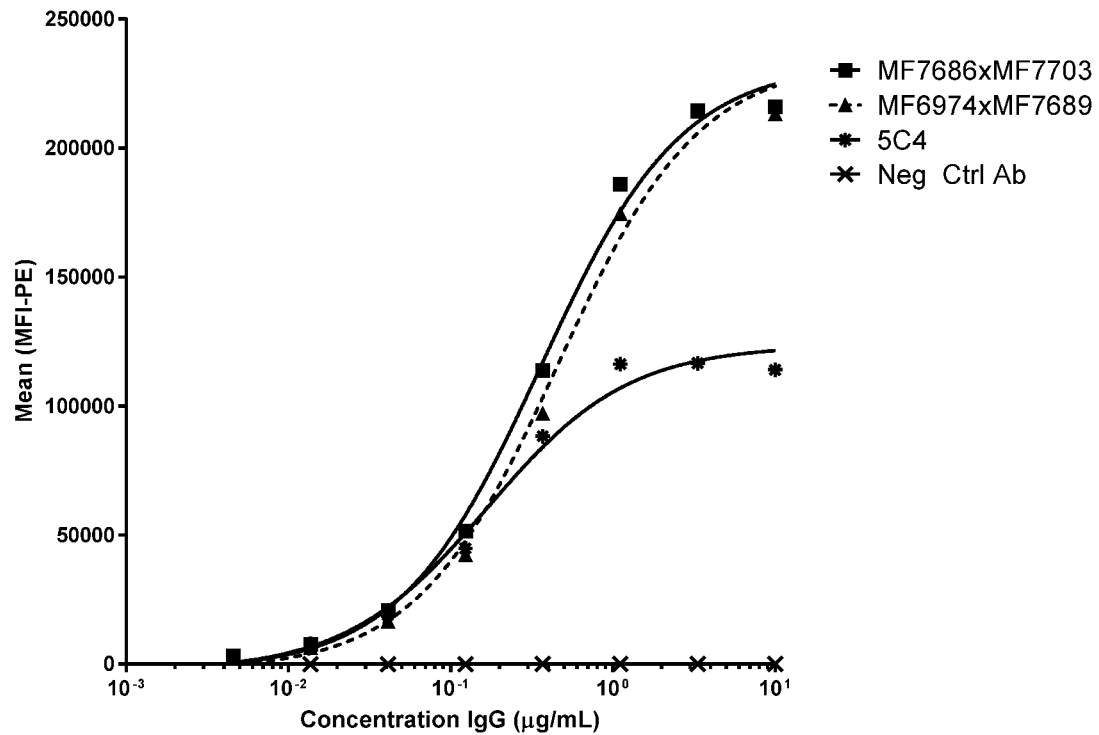

Figure 17
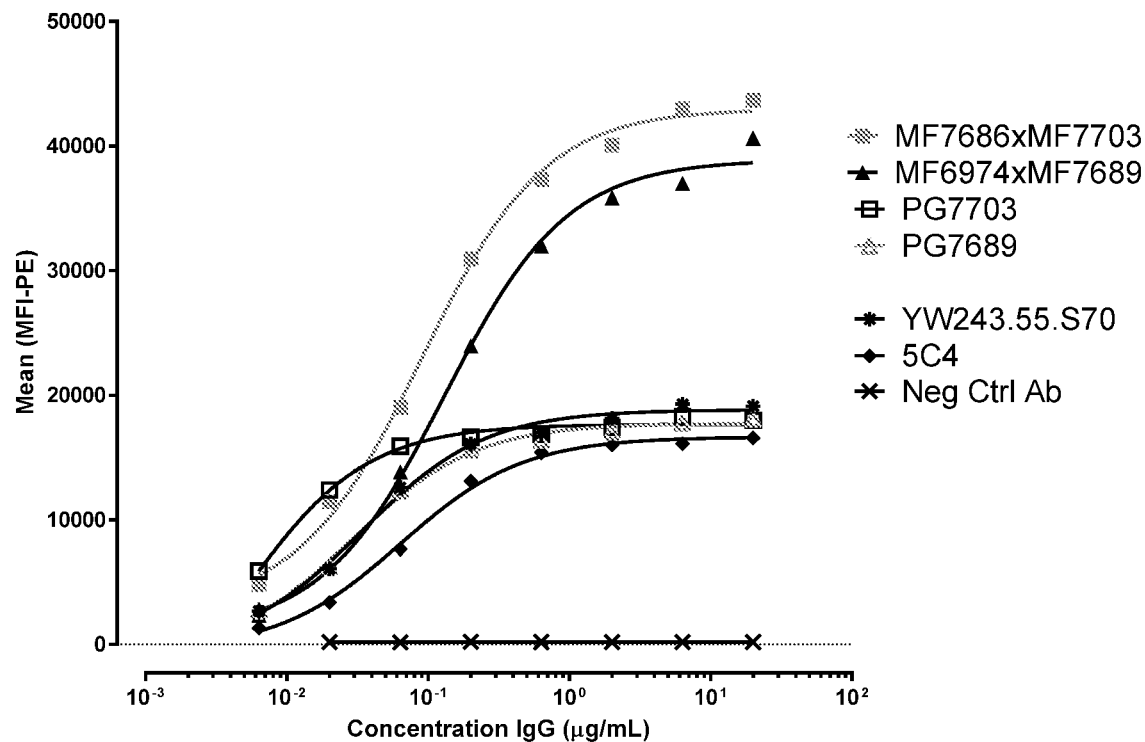
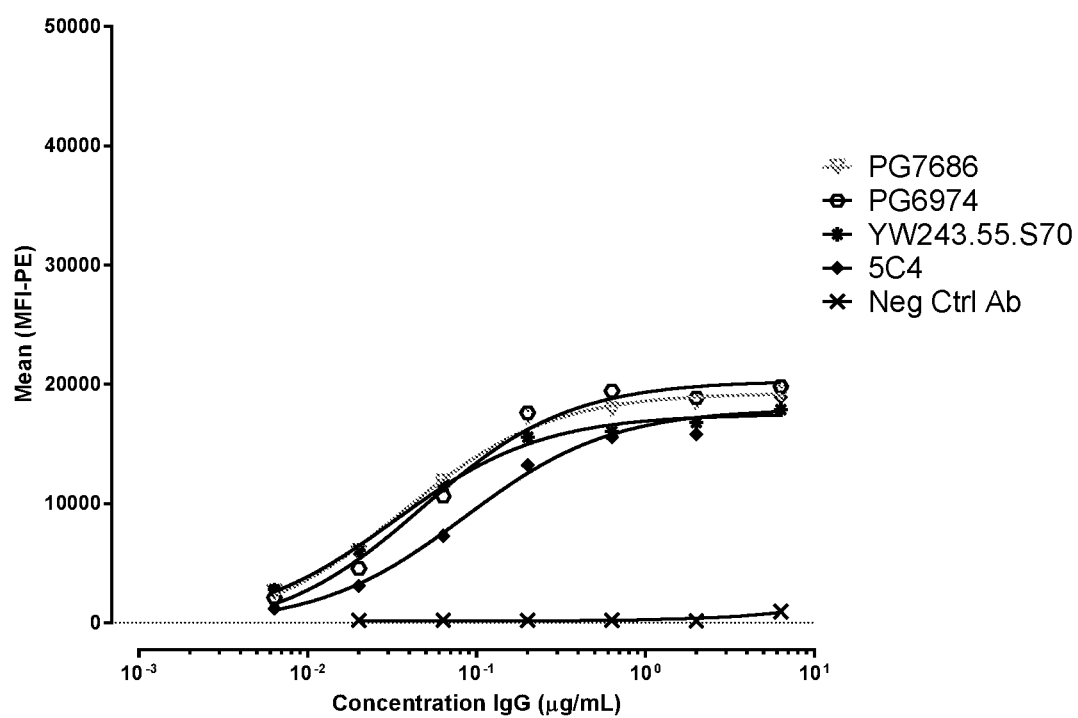

Figure 20
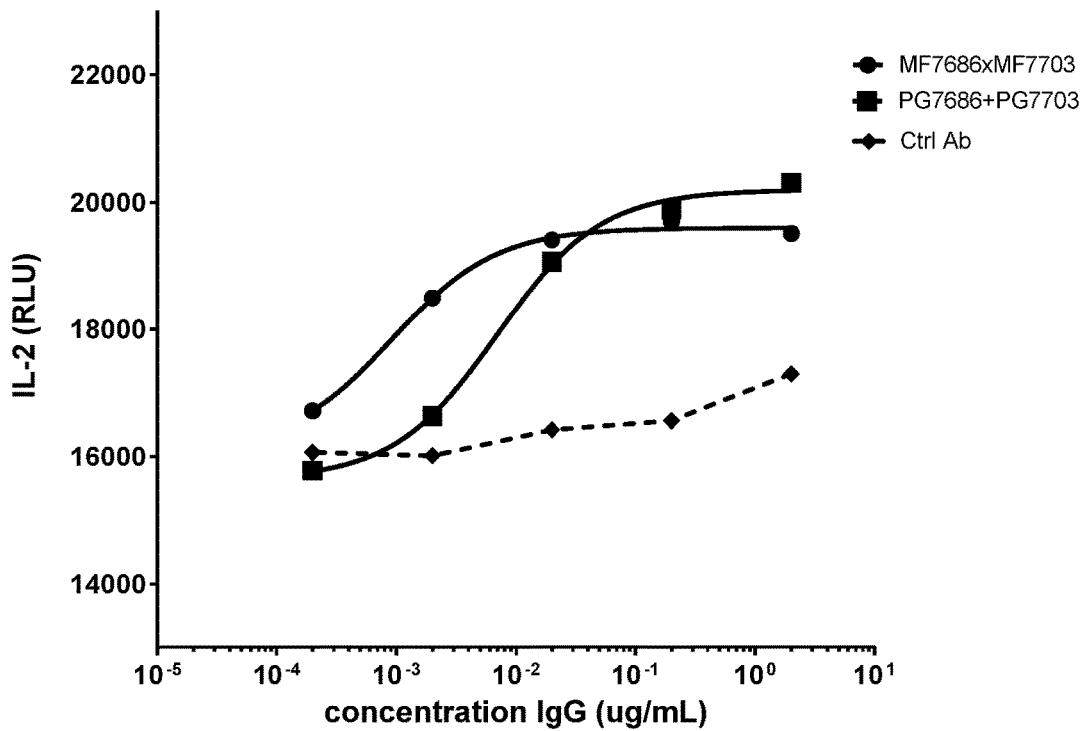
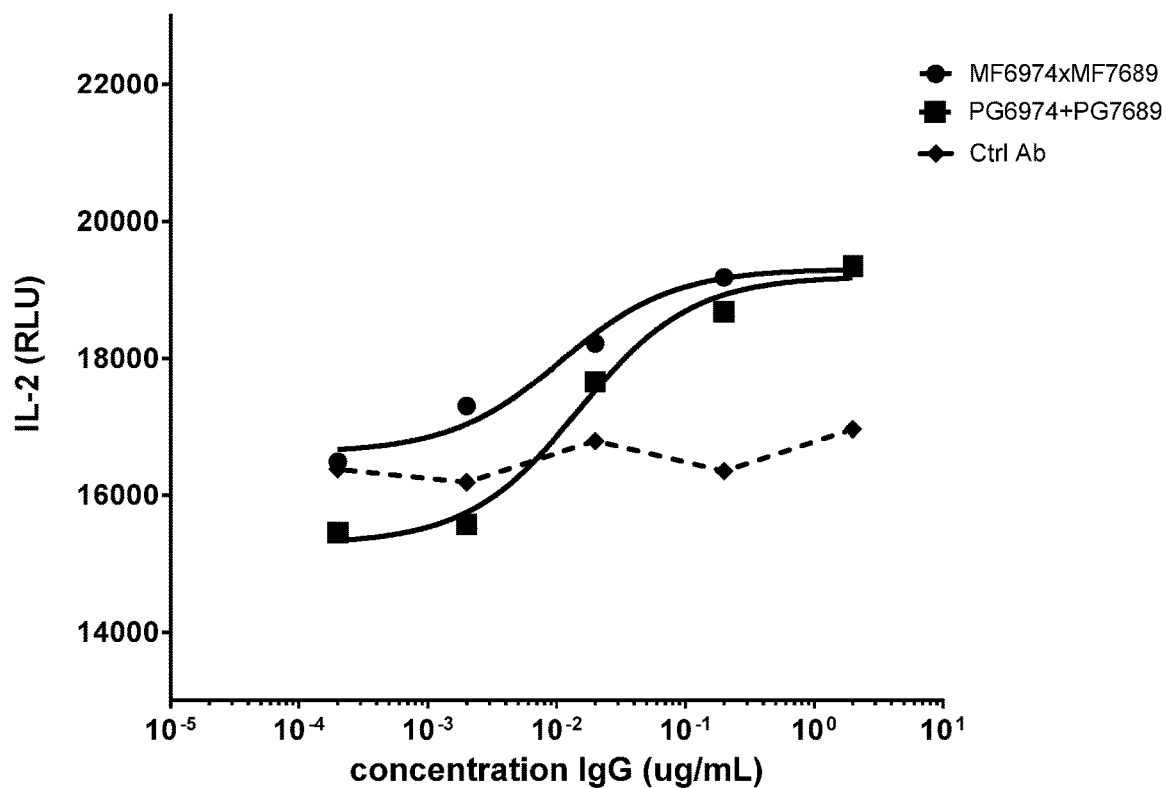

SEQUENCE LISTING

```
<160> NUMBER OF SEQ ID NOS: 71

<210> SEQ ID NO 1
<211> LENGTH: 288
<212> TYPE: PRT
<213> ORGANISM: Homo sapiens
<220> FEATURE:
<221> NAME/KEY: SIGNAL
<222> LOCATION: (1)..(20)
<220> FEATURE:
<221> NAME/KEY: DOMAIN
<222> LOCATION: (21)..(170)
<223> OTHER INFORMATION: ECD
<220> FEATURE:
<221> NAME/KEY: DOMAIN
<222> LOCATION: (171)..(191)
<223> OTHER INFORMATION: transmembrane domain
<220> FEATURE:
<221> NAME/KEY: DOMAIN
<222> LOCATION: (192)..(288)
<223> OTHER INFORMATION: Intracellular tail

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45
```

```
Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 2
<211> LENGTH: 288
<212> TYPE: PRT
<213> ORGANISM: Macaca fascicularis
<220> FEATURE:
<221> NAME/KEY: SIGNAL
<222> LOCATION: (1)..(20)
<220> FEATURE:
<221> NAME/KEY: DOMAIN
<222> LOCATION: (21)..(170)
<223> OTHER INFORMATION: ECD
<220> FEATURE:
<221> NAME/KEY: DOMAIN
<222> LOCATION: (171)..(191)
<223> OTHER INFORMATION: TM
<220> FEATURE:
<221> NAME/KEY: DOMAIN
<222> LOCATION: (192)..(288)
<223> OTHER INFORMATION: Intracellular tail

<400> SEQUENCE: 2

Met Gln Ile Pro Gln Ala Pro Trp Pro Val Val Trp Ala Val Leu Gln
1               5                   10                  15

Leu Gly Trp Arg Pro Gly Trp Phe Leu Glu Ser Pro Asp Arg Pro Trp
            20                  25                  30

Asn Ala Pro Thr Phe Ser Pro Ala Leu Leu Leu Val Thr Glu Gly Asp
        35                  40                  45

Asn Ala Thr Phe Thr Cys Ser Phe Ser Asn Ala Ser Glu Ser Phe Val
    50                  55                  60
```

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Arg Leu Pro Asn Gly Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Ala Leu Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Gln Gly Thr Ile Glu Ala Arg Arg Thr Gly Gln Pro
                195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
                245                 250                 255

Leu Gly Thr Ser Ser Pro Ala Arg Arg Gly Ser Ala Asp Gly Pro Arg
                260                 265                 270

Ser Pro Arg Pro Leu Arg Pro Glu Asp Gly His Cys Ser Trp Pro Leu
                275                 280                 285

```
<210> SEQ ID NO 3
<211> LENGTH: 290
<212> TYPE: PRT
<213> ORGANISM: Homo sapiens
<220> FEATURE:
<221> NAME/KEY: SIGNAL
<222> LOCATION: (1)..(18)
<220> FEATURE:
<221> NAME/KEY: DOMAIN
<222> LOCATION: (19)..(238)
<223> OTHER INFORMATION: ECD
<220> FEATURE:
<221> NAME/KEY: DOMAIN
<222> LOCATION: (239)..(259)
<223> OTHER INFORMATION: TM
<220> FEATURE:
<221> NAME/KEY: DOMAIN
<222> LOCATION: (260)..(290)
<223> OTHER INFORMATION: Intracellular tail

<400> SEQUENCE: 3
```

Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
 50                 55                  60

Ile Gln Phe Val His Gly Glu Glu Asp Leu Lys Val Gln His Ser Ser

```
                65                  70                  75                  80
Tyr Arg Gln Arg Ala Arg Leu Leu Lys Asp Gln Leu Ser Leu Gly Asn
                    85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
                115                 120                 125

Lys Val Asn Ala Pro Tyr Asn Lys Ile Asn Gln Arg Ile Leu Val Val
                130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
                195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290

<210> SEQ ID NO 4
<211> LENGTH: 290
<212> TYPE: PRT
<213> ORGANISM: Macaca mulatta
<220> FEATURE:
<221> NAME/KEY: SIGNAL
<222> LOCATION: (1)..(18)
<220> FEATURE:
<221> NAME/KEY: DOMAIN
<222> LOCATION: (19)..(237)
<223> OTHER INFORMATION: ECD
<220> FEATURE:
<221> NAME/KEY: DOMAIN
<222> LOCATION: (238)..(259)
<223> OTHER INFORMATION: TM
<220> FEATURE:
<221> NAME/KEY: DOMAIN
<222> LOCATION: (260)..(290)
<223> OTHER INFORMATION: Intracellular tail

<400> SEQUENCE: 4

Met Arg Ile Phe Ala Val Phe Ile Phe Thr Ile Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Arg Phe Pro Val Glu Lys Gln Leu
                35                  40                  45

Gly Leu Thr Ser Leu Ile Val Tyr Trp Glu Met Glu Asp Lys Asn Ile
            50                  55                  60
```

```
Ile Gln Phe Val His Gly Glu Glu Asp Leu Lys Val Gln His Ser Asn
 65                  70                  75                  80

Tyr Arg Gln Arg Ala Gln Leu Leu Lys Asp Gln Leu Ser Leu Gly Asn
                 85                  90                  95

Ala Ala Leu Arg Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Leu Asn
            180                 185                 190

Val Thr Ser Thr Leu Arg Ile Asn Thr Thr Ala Asn Glu Ile Phe Tyr
        195                 200                 205

Cys Ile Phe Arg Arg Leu Gly Pro Glu Glu Asn His Thr Ala Glu Leu
    210                 215                 220

Val Ile Pro Glu Leu Pro Leu Ala Leu Pro Pro Asn Glu Arg Thr His
225                 230                 235                 240

Leu Val Ile Leu Gly Ala Ile Phe Leu Leu Leu Gly Val Ala Leu Thr
                245                 250                 255

Phe Ile Phe Tyr Leu Arg Lys Gly Arg Met Met Asp Met Lys Lys Ser
            260                 265                 270

Gly Ile Arg Val Thr Asn Ser Lys Lys Gln Arg Asp Thr Gln Leu Glu
        275                 280                 285

Glu Thr
    290

<210> SEQ ID NO 5
<211> LENGTH: 214
<212> TYPE: PRT
<213> ORGANISM: Artificial Sequence
<220> FEATURE:
<223> OTHER INFORMATION: common light chain

<400> SEQUENCE: 5

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 6
<211> LENGTH: 321
<212> TYPE: DNA
<213> ORGANISM: Artificial Sequence
<220> FEATURE:
<223> OTHER INFORMATION: common light chain variable domain (IGKV1-
      39/jk1)
<220> FEATURE:
<221> NAME/KEY: CDS
<222> LOCATION: (1)..(321)

<400> SEQUENCE: 6 gac atc cag atg acc cag tct cca tcc tcc ctg tct gca tct gta gga       48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tac       96
Asp Arg Val Thr Ile Thr Cys Arg Ala Ser Gln Ser Ile Ser Ser Tyr
            20                  25                  30 tta aat tgg tat cag cag aaa cca ggg aaa gcc cct aag ctc ctg atc      144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt ggc      192
Tyr Ala Ala Ser Ser Leu Gln Ser Gly Val Pro Ser Arg Phe Ser Gly
    50                  55                  60 agt gga tct ggg aca gat ttc act ctc acc atc agc agt ctg caa cct      240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt acc cct cca      288
Glu Asp Phe Ala Thr Tyr Tyr Cys Gln Gln Ser Tyr Ser Thr Pro Pro
                85                  90                  95 acg ttc ggc caa ggg acc aag gtg gag atc aaa                          321
Thr Phe Gly Gln Gly Thr Lys Val Glu Ile Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: Synthetic Construct

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 8
<211> LENGTH: 324
<212> TYPE: DNA
<213> ORGANISM: Artificial Sequence
<220> FEATURE:
<223> OTHER INFORMATION: common light chain constant region
<220> FEATURE:
<221> NAME/KEY: CDS
<222> LOCATION: (1)..(324)

<400> SEQUENCE: 8 cga act gtg gct gca cca tct gtc ttc atc ttc ccg cca tct gat gag        48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc       96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa       144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc       192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag       240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg       288
Lys His Lys Val Tyr Ala Cys Glu Val Thr His Gln Gly Leu Ser Ser
                85                  90                  95 ccc gtc aca aag agc ttc aac agg gga gag tgt tag                       324
Pro Val Thr Lys Ser Phe Asn Arg Gly Glu Cys
            100                 105

<210> SEQ ID NO 9
<211> LENGTH: 107
<212> TYPE: PRT
<213> ORGANISM: Artificial Sequence
<220> FEATURE:
<223> OTHER INFORMATION: Synthetic Construct

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
```

```
                    85                  90                  95

Pro Val Thr Lys Ser Phe Asn Arg Gly Glu Cys
                100                 105

<210> SEQ ID NO 10
<211> LENGTH: 108
<212> TYPE: PRT
<213> ORGANISM: Artificial Sequence
<220> FEATURE:
<223> OTHER INFORMATION: IGKV1-39/jk5 common light chain variable domain

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
                100                 105

<210> SEQ ID NO 11
<211> LENGTH: 95
<212> TYPE: PRT
<213> ORGANISM: Artificial Sequence
<220> FEATURE:
<223> OTHER INFORMATION: V-region IGKV1-39A

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 12
<211> LENGTH: 294
<212> TYPE: DNA
<213> ORGANISM: Artificial Sequence
<220> FEATURE:
<223> OTHER INFORMATION: heavy chain CH1 region
<220> FEATURE:
<221> NAME/KEY: CDS
<222> LOCATION: (1)..(294)

<400> SEQUENCE: 12 gct agc acc aag ggc cca tcg gtc ttc ccc ctg gca ccc tcc tcc aag      48
Ala Ser Thr Lys Gly Pro Ser Val Phe Pro Leu Ala Pro Ser Ser Lys
```

```
1               5                   10                  15
agc acc tct ggg ggc aca gcg gcc ctg ggc tgc ctg gtc aag gac tac        96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc       144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc       192
Gly Val His Thr Phe Pro Ala Val Leu Gln Ser Ser Gly Leu Tyr Ser
    50                  55                  60 ctc agc agc gtc gtg acc gtg ccc tcc agc agc ttg ggc acc cag acc       240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag       288
Tyr Ile Cys Asn Val Asn His Lys Pro Ser Asn Thr Lys Val Asp Lys
                85                  90                  95 aga gtt                                                                294
Arg Val <210> SEQ ID NO 13
<211> LENGTH: 98
<212> TYPE: PRT
<213> ORGANISM: Artificial Sequence
<220> FEATURE:
<223> OTHER INFORMATION: Synthetic Construct

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 14
<211> LENGTH: 45
<212> TYPE: DNA
<213> ORGANISM: Artificial Sequence
<220> FEATURE:
<223> OTHER INFORMATION: heavy chain hinge region
<220> FEATURE:
<221> NAME/KEY: CDS
<222> LOCATION: (1)..(45)

<400> SEQUENCE: 14 gag ccc aaa tct tgt gac aaa act cac aca tgc cca ccg tgc cca            45
Glu Pro Lys Ser Cys Asp Lys Thr His Thr Cys Pro Pro Cys Pro
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic Construct
```

<400> SEQUENCE: 15

Glu Pro Lys Ser Cys Asp Lys Thr His Thr Cys Pro Pro Cys Pro
1               5                   10                  15

<210> SEQ ID NO 16
<211> LENGTH: 330
<212> TYPE: DNA
<213> ORGANISM: Artificial Sequence
<220> FEATURE:
<223> OTHER INFORMATION: heavy chain CH2 region
<220> FEATURE:
<221> NAME/KEY: CDS
<222> LOCATION: (1)..(330)

<400> SEQUENCE: 16

| gca cct gaa ctc ctg ggg gga ccg tca gtc ttc ctc ttc ccc cca aaa | 48 |
| Ala Pro Glu Leu Leu Gly Gly Pro Ser Val Phe Leu Phe Pro Pro Lys | |
| 1               5                   10                  15 | |

| ccc aag gac acc ctc atg atc tcc cgg acc cct gag gtc aca tgc gtg | 96 |
| Pro Lys Asp Thr Leu Met Ile Ser Arg Thr Pro Glu Val Thr Cys Val | |
|                 20                  25                  30 | |

| gtg gtg gac gtg agc cac gaa gac cct gag gtc aag ttc aac tgg tac | 144 |
| Val Val Asp Val Ser His Glu Asp Pro Glu Val Lys Phe Asn Trp Tyr | |
|         35                  40                  45 | |

| gtg gac ggc gtg gag gtg cat aat gcc aag aca aag ccg cgg gag gag | 192 |
| Val Asp Gly Val Glu Val His Asn Ala Lys Thr Lys Pro Arg Glu Glu | |
| 50                  55                  60 | |

| cag tac aac agc acg tac cgt gtg gtc agc gtc ctc acc gtc ctg cac | 240 |
| Gln Tyr Asn Ser Thr Tyr Arg Val Val Ser Val Leu Thr Val Leu His | |
| 65                  70                  75                  80 | |

| cag gac tgg ctg aat ggc aag gag tac aag tgc aag gtc tcc aac aaa | 288 |
| Gln Asp Trp Leu Asn Gly Lys Glu Tyr Lys Cys Lys Val Ser Asn Lys | |
|             85                  90                  95 | |

| gcc ctc cca gcc ccc atc gag aaa acc atc tcc aaa gcc aaa | 330 |
| Ala Leu Pro Ala Pro Ile Glu Lys Thr Ile Ser Lys Ala Lys | |
|         100                 105                 110 | |

<210> SEQ ID NO 17
<211> LENGTH: 110
<212> TYPE: PRT
<213> ORGANISM: Artificial Sequence
<220> FEATURE:
<223> OTHER INFORMATION: Synthetic Construct

<400> SEQUENCE: 17

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

-continued

```
<210> SEQ ID NO 18
<211> LENGTH: 330
<212> TYPE: DNA
<213> ORGANISM: Artificial Sequence
<220> FEATURE:
<223> OTHER INFORMATION: CH2 containing L235G and G238R silencing
      substitutions
<220> FEATURE:
<221> NAME/KEY: CDS
<222> LOCATION: (1)..(330)

<400> SEQUENCE: 18 gca cct gaa ctc ggc agg gga ccg tca gtc ttc ctc ttc ccc cca aaa     48
Ala Pro Glu Leu Gly Arg Gly Pro Ser Val Phe Leu Phe Pro Pro Lys
1               5                  10                  15 ccc aag gac acc ctc atg atc tcc cgg acc cct gag gtc aca tgc gtg     96
Pro Lys Asp Thr Leu Met Ile Ser Arg Thr Pro Glu Val Thr Cys Val
            20                  25                  30 gtg gtg gac gtg agc cac gaa gac cct gag gtc aag ttc aac tgg tac    144
Val Val Asp Val Ser His Glu Asp Pro Glu Val Lys Phe Asn Trp Tyr
        35                  40                  45 gtg gac ggc gtg gag gtg cat aat gcc aag aca aag ccg cgg gag gag    192
Val Asp Gly Val Glu Val His Asn Ala Lys Thr Lys Pro Arg Glu Glu
    50                  55                  60 cag tac aac agc acg tac cgt gtg gtc agc gtc ctc acc gtc ctg cac    240
Gln Tyr Asn Ser Thr Tyr Arg Val Val Ser Val Leu Thr Val Leu His
65                  70                  75                  80 cag gac tgg ctg aat ggc aag gag tac aag tgc aag gtc tcc aac aaa    288
Gln Asp Trp Leu Asn Gly Lys Glu Tyr Lys Cys Lys Val Ser Asn Lys
                85                  90                  95 gcc ctc cca gcc ccc atc gag aaa acc atc tcc aaa gcc aaa              330
Ala Leu Pro Ala Pro Ile Glu Lys Thr Ile Ser Lys Ala Lys
            100                 105                 110

<210> SEQ ID NO 19
<211> LENGTH: 110
<212> TYPE: PRT
<213> ORGANISM: Artificial Sequence
<220> FEATURE:
<223> OTHER INFORMATION: Synthetic Construct

<400> SEQUENCE: 19

Ala Pro Glu Leu Gly Arg Gly Pro Ser Val Phe Leu Phe Pro Pro Lys
1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 20
<211> LENGTH: 321
<212> TYPE: DNA
<213> ORGANISM: Artificial Sequence
<220> FEATURE:
<223> OTHER INFORMATION: CH3 domain containing substitutions L351K and
```

```
                                      T366K (KK))
<220> FEATURE:
<221> NAME/KEY: CDS
<222> LOCATION: (1)..(321)

<400> SEQUENCE: 20 ggg cag ccc cga gaa cca cag gtg tac acc aag ccc cca tcc cgg gag      48
Gly Gln Pro Arg Glu Pro Gln Val Tyr Thr Lys Pro Pro Ser Arg Glu
1               5                   10                  15 gag atg acc aag aac cag gtc agc ctg aag tgc ctg gtc aaa ggc ttc      96
Glu Met Thr Lys Asn Gln Val Ser Leu Lys Cys Leu Val Lys Gly Phe
                20                  25                  30 tat ccc agc gac atc gcc gtg gag tgg gag agc aat ggg cag ccg gag     144
Tyr Pro Ser Asp Ile Ala Val Glu Trp Glu Ser Asn Gly Gln Pro Glu
            35                  40                  45 aac aac tac aag acc acg cct ccc gtg ctg gac tcc gac ggc tcc ttc     192
Asn Asn Tyr Lys Thr Thr Pro Pro Val Leu Asp Ser Asp Gly Ser Phe
    50                  55                  60 ttc ctc tat agc aag ctc acc gtg gac aag agc agg tgg cag cag ggg     240
Phe Leu Tyr Ser Lys Leu Thr Val Asp Lys Ser Arg Trp Gln Gln Gly
65              70                  75                  80 aac gtc ttc tca tgc tcc gtg atg cat gag gct ctg cac aac cac tac     288
Asn Val Phe Ser Cys Ser Val Met His Glu Ala Leu His Asn His Tyr
                85                  90                  95 acg cag aag agc ctc tcc ctg tct ccg ggt tga                         321
Thr Gln Lys Ser Leu Ser Leu Ser Pro Gly
            100                 105

<210> SEQ ID NO 21
<211> LENGTH: 106
<212> TYPE: PRT
<213> ORGANISM: Artificial Sequence
<220> FEATURE:
<223> OTHER INFORMATION: Synthetic Construct

<400> SEQUENCE: 21

Gly Gln Pro Arg Glu Pro Gln Val Tyr Thr Lys Pro Pro Ser Arg Glu
1               5                   10                  15

Glu Met Thr Lys Asn Gln Val Ser Leu Lys Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65              70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 22
<211> LENGTH: 321
<212> TYPE: DNA
<213> ORGANISM: Artificial Sequence
<220> FEATURE:
<223> OTHER INFORMATION: CH3 domain containing substitutions L351D and
      L368E (DE))
<220> FEATURE:
<221> NAME/KEY: CDS
<222> LOCATION: (1)..(321)

<400> SEQUENCE: 22
```

```
ggg cag ccc cga gaa cca cag gtg tac acc gac ccc cca tcc cgg gag       48
Gly Gln Pro Arg Glu Pro Gln Val Tyr Thr Asp Pro Pro Ser Arg Glu
1               5                   10                  15 gag atg acc aag aac cag gtc agc ctg acc tgc gag gtc aaa ggc ttc       96
Glu Met Thr Lys Asn Gln Val Ser Leu Thr Cys Glu Val Lys Gly Phe
            20                  25                  30 tat ccc agc gac atc gcc gtg gag tgg gag agc aat ggg cag ccg gag      144
Tyr Pro Ser Asp Ile Ala Val Glu Trp Glu Ser Asn Gly Gln Pro Glu
        35                  40                  45 aac aac tac aag acc acg cct ccc gtg ctg gac tcc gac ggc tcc ttc      192
Asn Asn Tyr Lys Thr Thr Pro Pro Val Leu Asp Ser Asp Gly Ser Phe
    50                  55                  60 ttc ctc tat agc aag ctc acc gtg gac aag agc agg tgg cag cag ggg      240
Phe Leu Tyr Ser Lys Leu Thr Val Asp Lys Ser Arg Trp Gln Gln Gly
65              70                  75                  80 aac gtc ttc tca tgc tcc gtg atg cat gag gct ctg cac aac cac tac      288
Asn Val Phe Ser Cys Ser Val Met His Glu Ala Leu His Asn His Tyr
                85                  90                  95 acg cag aag agc ctc tcc ctg tct ccg ggt tga                          321
Thr Gln Lys Ser Leu Ser Leu Ser Pro Gly
            100                 105

<210> SEQ ID NO 23
<211> LENGTH: 106
<212> TYPE: PRT
<213> ORGANISM: Artificial Sequence
<220> FEATURE:
<223> OTHER INFORMATION: Synthetic Construct

<400> SEQUENCE: 23

Gly Gln Pro Arg Glu Pro Gln Val Tyr Thr Asp Pro Pro Ser Arg Glu
1               5                   10                  15

Glu Met Thr Lys Asn Gln Val Ser Leu Thr Cys Glu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65              70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 24
<211> LENGTH: 121
<212> TYPE: PRT
<213> ORGANISM: Artificial Sequence
<220> FEATURE:
<223> OTHER INFORMATION: MF5708

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Arg Ser Tyr
            20                  25                  30

Gly Ile Thr Trp Val Arg Gln Ala Pro Gly Gln Gly Leu Glu Trp Met
        35                  40                  45
```

-continued

Gly Gly Ile Ile Pro Val Phe Gly Thr Thr Asn Tyr Ala Gln Lys Phe
        50                  55                  60

Gln Gly Arg Val Thr Ile Thr Ala Asp Lys Ser Thr Ser Thr Val Phe
65                  70                  75                  80

Met Glu Leu Asn Ser Leu Arg Ser Glu Asp Thr Ala Val Tyr Tyr Cys
                85                  90                  95

Ala Arg Arg Gly Tyr Ser Asn Pro His Trp Leu Asp Pro Trp Gly
            100                 105                 110

Gln Gly Thr Leu Val Thr Val Ser Ser
            115                 120

<210> SEQ ID NO 25
<211> LENGTH: 121
<212> TYPE: PRT
<213> ORGANISM: Artificial Sequence
<220> FEATURE:
<223> OTHER INFORMATION: MF5594

<400> SEQUENCE: 25

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
                20                  25                  30

Ala Ile Ser Trp Val Arg Gln Ala Pro Gly Gln Gly Leu Glu Trp Met
            35                  40                  45

Gly Trp Ile Ile Pro Ile Phe Asp Thr Gly Asn Tyr Ala Gln Lys Ile
        50                  55                  60

Gln Gly Arg Val Thr Ile Thr Ala Asp Lys Ser Thr Ser Thr Ala Tyr
65                  70                  75                  80

Met Glu Leu Thr Ser Leu Arg Ser Glu Asp Thr Ala Val Tyr Tyr Cys
                85                  90                  95

Ala Arg His Asp Tyr Thr Asn Thr Val Asp Ala Phe Asp Ile Trp Gly
            100                 105                 110

Gln Gly Thr Met Val Thr Val Ser Ser
            115                 120

<210> SEQ ID NO 26
<211> LENGTH: 125
<212> TYPE: PRT
<213> ORGANISM: Artificial Sequence
<220> FEATURE:
<223> OTHER INFORMATION: MF5576

<400> SEQUENCE: 26

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser His
                20                  25                  30

Ala Met Asn Trp Val Arg Gln Ala Pro Gly Gln Gly Leu Glu Trp Met
            35                  40                  45

Gly Trp Ile Asn Pro Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Ile Asp Arg Gly Tyr Met Ser Asn Trp Val Phe Ala Glu Tyr Phe
            100                 105                 110

-continued

Pro His Trp Gly Gln Gly Thr Leu Val Thr Val Ser Ser
            115                 120                 125

<210> SEQ ID NO 27
<211> LENGTH: 121
<212> TYPE: PRT
<213> ORGANISM: Artificial Sequence
<220> FEATURE:
<223> OTHER INFORMATION: MF5561

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Thr Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Asp Thr Ala Asn Tyr Ala Gln Arg Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Lys Asp Gln Thr Gly Tyr Ser Ser Thr Leu Phe Asp Tyr Trp Gly
            100                 105                 110

Gln Gly Thr Leu Val Thr Val Ser Ser
        115                 120

<210> SEQ ID NO 28
<211> LENGTH: 122
<212> TYPE: PRT
<213> ORGANISM: Artificial Sequence
<220> FEATURE:
<223> OTHER INFORMATION: MF5557

<400> SEQUENCE: 28

Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Asn Thr Tyr
            20                  25                  30

Ser Ile Thr Trp Val Arg Gln Ala Pro Gly Gln Gly Leu Glu Trp Met
        35                  40                  45

Gly Gly Ile Ile Pro Val Phe Gly Thr Ser Lys Tyr Ala Gln Lys Phe
    50                  55                  60

Gln Asp Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Phe Ser Ser Ser Gly Trp Phe Asp Pro Trp
            100                 105                 110

Gly Gln Gly Thr Leu Val Thr Val Ser Ser
        115                 120

<210> SEQ ID NO 29
<211> LENGTH: 125
<212> TYPE: PRT
<213> ORGANISM: Artificial Sequence
<220> FEATURE:
<223> OTHER INFORMATION: MF5553

-continued

<400> SEQUENCE: 29

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Ala Ile Asn Trp Val Arg Gln Ala Pro Gly Gln Gly Leu Glu Trp Met
        35                  40                  45

Gly Trp Ile Asn Pro Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Arg Lys Tyr Val Thr Asn Trp Val Phe Ala Glu Asp Phe
            100                 105                 110

Gln His Trp Gly Gln Gly Thr Leu Val Thr Val Ser Ser
        115                 120                 125

<210> SEQ ID NO 30
<211> LENGTH: 121
<212> TYPE: PRT
<213> ORGANISM: Artificial Sequence
<220> FEATURE:
<223> OTHER INFORMATION: MF5442

<400> SEQUENCE: 30

Glu Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Asn Thr Tyr
            20                  25                  30

Ala Ile Asn Trp Val Arg Gln Ala Pro Gly Gln Gly Leu Glu Trp Val
        35                  40                  45

Gly Arg Ile Ile Pro Ile Phe Asp Thr Ala Asn Tyr Ala Gln Lys Phe
    50                  55                  60

Gln Gly Arg Val Thr Ile Ser Ala Asp Lys Ser Thr Thr Thr Ala Tyr
65                  70                  75                  80

Met Glu Leu Ser Ser Leu Arg Ser Glu Asp Thr Ala Val Phe Tyr Cys
                85                  90                  95

Ala Lys Asp Glu Thr Gly Tyr Ser Ser Ser Asn Phe Gln His Trp Gly
            100                 105                 110

Gln Gly Thr Leu Val Thr Val Ser Ser
        115                 120

<210> SEQ ID NO 31
<211> LENGTH: 119
<212> TYPE: PRT
<213> ORGANISM: Artificial Sequence
<220> FEATURE:
<223> OTHER INFORMATION: MF5439

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Leu Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
            50                  55                  60

Gln Gly Arg Val Thr Ile Thr Ala Asp Ile Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Asn Tyr Tyr Glu Phe Val Tyr Trp Gly Gln Gly
                100                 105                 110

Thr Leu Val Thr Val Ser Ser
        115

<210> SEQ ID NO 32
<211> LENGTH: 121
<212> TYPE: PRT
<213> ORGANISM: Artificial Sequence
<220> FEATURE:
<223> OTHER INFORMATION: MF5426

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Arg Ser Tyr
                20                  25                  30

Gly Ile Thr Trp Val Arg Gln Ala Pro Gly Gln Gly Leu Glu Trp Met
            35                  40                  45

Gly Gly Ile Ile Pro Ile Phe Gly Thr Thr Asn Tyr Ala Gln Lys Phe
        50                  55                  60

Gln Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Arg Gly Tyr Ser Asn Pro His Trp Leu Asp Pro Trp Gly
                100                 105                 110

Gln Gly Thr Leu Val Thr Val Ser Ser
        115                 120

<210> SEQ ID NO 33
<211> LENGTH: 120
<212> TYPE: PRT
<213> ORGANISM: Artificial Sequence
<220> FEATURE:
<223> OTHER INFORMATION: MF5424

<400> SEQUENCE: 33

Glu Val Gln Leu Val Gln Ser Gly Ala Glu Val Met Arg Pro Gly Ser
1               5                   10                  15

Ser Val Lys Val Ser Cys Lys Ala Ser Gly Gly Ile Phe Asn Thr Tyr
                20                  25                  30

Thr Ile Ile Trp Val Arg Gln Ala Pro Gly Gln Gly Leu Glu Trp Met
            35                  40                  45

Gly Gly Ile Ile Pro Ile Phe Asp Thr Pro Asn Phe Ala Gln Lys Phe
        50                  55                  60

Gln Gly Arg Leu Thr Ile Thr Ala Asp Lys Ser Thr Asn Thr Ala Tyr
65                  70                  75                  80

Met Glu Leu Thr Ser Leu Arg Ser Glu Asp Thr Ala Val Tyr Tyr Cys
                85                  90                  95

Ala Arg Glu Gly Cys Asn His Gly Val Cys Tyr Pro Tyr Trp Gly Gln

```
              100                 105                 110

Gly Thr Leu Val Thr Val Ser Ser
        115                 120

<210> SEQ ID NO 34
<211> LENGTH: 119
<212> TYPE: PRT
<213> ORGANISM: Artificial Sequence
<220> FEATURE:
<223> OTHER INFORMATION: MF5382

<400> SEQUENCE: 34

Glu Val Gln Leu Val Gln Ser Gly Ala Glu Val Lys Asn Pro Gly Ser
1               5                   10                  15

Ser Val Lys Val Ser Cys Lys Ala Thr Gly Gly Thr Phe Asn Thr Tyr
            20                  25                  30

Gly Thr Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Thr Thr Ala Tyr
65                  70                  75                  80

Met Glu Val Ser Ser Leu Arg Ser Glu Asp Thr Ala Val Tyr Tyr Cys
                85                  90                  95

Ala Arg Gly Gly Ala Asp Met Gly Thr Leu Asp Tyr Trp Gly Gln Gly
            100                 105                 110

Thr Leu Val Thr Val Ser Ser
        115

<210> SEQ ID NO 35
<211> LENGTH: 121
<212> TYPE: PRT
<213> ORGANISM: Artificial Sequence
<220> FEATURE:
<223> OTHER INFORMATION: MF5377

<400> SEQUENCE: 35

Glu Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Asp Thr Pro Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Lys Asn Val Arg Gly Tyr Ser Ala Tyr Asp Leu Asp Tyr Trp Gly
            100                 105                 110

Gln Gly Thr Leu Val Thr Val Ser Ser
        115                 120

<210> SEQ ID NO 36
<211> LENGTH: 124
<212> TYPE: PRT
<213> ORGANISM: Artificial Sequence
<220> FEATURE:
```

<223> OTHER INFORMATION: MF5359

<400> SEQUENCE: 36

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Asn Thr Tyr
            20                  25                  30

Ser Ile Thr Trp Val Arg Gln Ala Pro Gly Gln Gly Leu Glu Trp Met
        35                  40                  45

Gly Ser Ile Val Pro Ile Phe Gly Thr Ile Asn Asn Ala Gln Lys Phe
    50                  55                  60

Gln Gly Arg Val Thr Ile Thr Ala Asp Lys Ser Ala Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asn Thr Met Val Arg Gly Val Tyr Tyr Tyr Met Asp
            100                 105                 110

Val Trp Gly Lys Gly Thr Met Val Thr Val Ser Ser
        115                 120

<210> SEQ ID NO 37
<211> LENGTH: 121
<212> TYPE: PRT
<213> ORGANISM: Artificial Sequence
<220> FEATURE:
<223> OTHER INFORMATION: MF5361

<400> SEQUENCE: 37

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ser Leu Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Ser Ser Val Thr Thr Ala Tyr
65                  70                  75                  80

Leu Gln Ile Ser Ser Leu Lys Ala Glu Asp Thr Ala Val Tyr Tyr Cys
                85                  90                  95

Thr Arg Asp His Asp Phe Arg Arg Gly Arg Ser Leu Asp Val Trp Gly
            100                 105                 110

Lys Gly Thr Thr Val Thr Val Ser Ser
        115                 120

<210> SEQ ID NO 38
<211> LENGTH: 118
<212> TYPE: PRT
<213> ORGANISM: Artificial Sequence
<220> FEATURE:
<223> OTHER INFORMATION: MF6982

<400> SEQUENCE: 38

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
                        35                  40                  45

Ser Thr Ile Ser Gly Gly Thr Asn Ile Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Gly Asp Thr Ala Val Tyr Tyr Cys
                 85                  90                  95

Ala Ser Pro Tyr Gly Ser Gly Tyr Leu Asp Val Trp Gly Gln Gly Thr
                100                 105                 110

Leu Val Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: MF6974

<400> SEQUENCE: 39

Glu Val Gln Leu Val Glu Ser Gly Gly Asp Leu Val Gln Pro Gly Gly
 1               5                  10                  15

Ser Leu Arg Leu Ser Cys Ala Ala Ser Gly Phe Thr Phe Asn Ser Tyr
                20                  25                  30

Ala Met Ser Trp Val Arg Gln Ala Pro Gly Lys Gly Leu Glu Trp Val
                35                  40                  45

Ser Thr Ile Ser Gly Gly Gly Ala Asn Ile Tyr Tyr Ala Asp Ser Val
 50                  55                  60

Lys Gly Arg Phe Thr Ile Ser Arg Asp Asn Ser Lys Ser Thr Leu Tyr
 65                  70                  75                  80

Leu Gln Met Asn Ser Leu Arg Ala Glu Asp Thr Ala Val Tyr Phe Cys
                 85                  90                  95

Ala Ser Pro Tyr Gly Ser Gly Tyr Phe Asp Val Trp Gly Gln Gly Thr
                100                 105                 110

Leu Val Thr Val Ser Ser
        115

<210> SEQ ID NO 40
<211> LENGTH: 121
<212> TYPE: PRT
<213> ORGANISM: Artificial Sequence
<220> FEATURE:
<223> OTHER INFORMATION: MF6972

<400> SEQUENCE: 40

Glu Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Thr Tyr
                20                  25                  30

Phe Trp Ser Trp Ile Arg Gln Pro Pro Gly Lys Gly Leu Glu Trp Ile
                35                  40                  45

Gly Tyr Ile Ile Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95
```

-continued

Arg Gly Gly Tyr Ser Gly Tyr Gly Gly Asp Asp Phe Asp Ile Trp Gly
                100                 105                 110

Gln Gly Thr Met Val Thr Val Ser Ser
        115                 120

<210> SEQ ID NO 41
<211> LENGTH: 120
<212> TYPE: PRT
<213> ORGANISM: Artificial Sequence
<220> FEATURE:
<223> OTHER INFORMATION: MF6936

<400> SEQUENCE: 41

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Asn Tyr
            20                  25                  30

Val Ile Asn Trp Val Arg Gln Ala Pro Gly Gln Gly Leu Glu Trp Met
        35                  40                  45

Gly Met Ile Ile Pro Val Phe Asp Thr Thr Ser Tyr Glu Arg Lys Phe
    50                  55                  60

Gln Gly Arg Val Thr Ile Thr Ala Asp Lys Ser Thr Ser Thr Ala Tyr
65                  70                  75                  80

Met Glu Leu Thr Ser Leu Arg Ser Glu Asp Thr Ala Val Tyr Tyr Cys
                85                  90                  95

Ala Arg Gly Thr Val Gly Ala Thr Leu Leu Phe Asp Asn Trp Gly Gln
                100                 105                 110

Gly Thr Leu Val Thr Val Ser Ser
        115                 120

<210> SEQ ID NO 42
<211> LENGTH: 120
<212> TYPE: PRT
<213> ORGANISM: Artificial Sequence
<220> FEATURE:
<223> OTHER INFORMATION: MF6935

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Val Ile Ser Trp Val Arg Gln Ala Pro Gly Gln Gly Leu Glu Trp Met
        35                  40                  45

Gly Met Ile Ile Pro Ile Phe Asp Thr Ala Asn Tyr Ala Gln Lys Phe
    50                  55                  60

Gln Gly Arg Val Thr Ile Thr Ala Asp Lys Ser Thr Ser Thr Ala Ser
65                  70                  75                  80

Met Glu Leu Arg Ser Leu Arg Ser Glu Asp Thr Ala Val Tyr Tyr Cys
                85                  90                  95

Ala Arg Gly Thr Val Ser Gly Thr Leu Val Phe Asp Tyr Trp Gly Gln
                100                 105                 110

Gly Thr Leu Val Thr Val Ser Ser
        115                 120

<210> SEQ ID NO 43
<211> LENGTH: 120
<212> TYPE: PRT
<213> ORGANISM: Artificial Sequence

```
<220> FEATURE:
<223> OTHER INFORMATION: MF6932

<400> SEQUENCE: 43

Gln Val Gln Leu Val Gln Ser Gly Ala Glu Val Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Met Ile Ile Pro Phe Phe Asp Thr Ala Asn Tyr Ala Gln Lys Phe
50                  55                  60

Gln Gly Arg Val Thr Ile Thr Ala Asp Lys Ser Thr Ser Thr Ala Ser
65                  70                  75                  80

Met Glu Leu Arg Ser Leu Arg Ser Glu Asp Thr Ala Val Tyr Tyr Cys
                85                  90                  95

Ala Arg Gly Thr Val Ser Ala Thr Leu Val Phe Asp Tyr Trp Gly Gln
            100                 105                 110

Gly Thr Leu Val Thr Val Ser Ser
        115                 120

<210> SEQ ID NO 44
<211> LENGTH: 121
<212> TYPE: PRT
<213> ORGANISM: Artificial Sequence
<220> FEATURE:
<223> OTHER INFORMATION: MF6076

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Thr Val Ser Thr Asp Ser Leu Gly Phe Tyr
                20                  25                  30

Phe Trp Ser Trp Ile Arg Gln Pro Pro Gly Lys Gly Leu Glu Trp Ile
            35                  40                  45

Gly Tyr Ile Tyr Tyr Ser Gly Ser Ala Asn Phe Asn Pro Ser Leu Lys
50                  55                  60

Ser Arg Val Thr Met Ser Ile Asp Thr Ser Asn Asn Gln Phe Ser Leu
65                  70                  75                  80

Lys Leu Arg Ser Val Thr Ala Ala Asp Thr Ala Val Tyr Phe Cys Ala
                85                  90                  95

Arg Gly Gly Tyr Thr Gly Tyr Gly Gly Asp Trp Phe Asp Pro Trp Gly
            100                 105                 110

Gln Gly Thr Leu Val Thr Val Ser Ser
        115                 120

<210> SEQ ID NO 45
<211> LENGTH: 121
<212> TYPE: PRT
<213> ORGANISM: Artificial Sequence
<220> FEATURE:
<223> OTHER INFORMATION: MF6236

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Tyr Tyr
                20                  25                  30
```

```
Phe Trp Ser Trp Ile Arg Gln Pro Pro Gly Lys Gly Leu Glu Trp Ile
            35                  40                  45

Gly Tyr Ile Tyr Tyr Ser Gly Ser Thr Asn Phe Asn Pro Ser Leu Lys
 50                  55                  60

Ser Arg Val Thr Met Ser Val Asp Thr Ser Lys Asn Gln Phe Ser Leu
 65                  70                  75                  80

Asn Leu Arg Ser Val Thr Thr Ala Asp Thr Ala Val Tyr Tyr Cys Ala
                85                  90                  95

Arg Gly Gly Tyr Thr Gly His Gly Gly Asp Trp Phe Asp Pro Trp Gly
                100                 105                 110

Gln Gly Thr Leu Val Thr Val Ser Ser
            115                 120

<210> SEQ ID NO 46
<211> LENGTH: 120
<212> TYPE: PRT
<213> ORGANISM: Artificial Sequence
<220> FEATURE:
<223> OTHER INFORMATION: MF6256

<400> SEQUENCE: 46

Glu Val Gln Leu Val Gln Ser Gly Ala Glu Val Lys Lys Pro Gly Ser
 1               5                  10                  15

Ser Met Lys Val Ser Cys Lys Ala Ser Gly Gly Thr Phe Ser Ser Tyr
                20                  25                  30

Val Ile Ser Trp Val Arg Gln Ala Pro Gly Gln Gly Leu Glu Trp Met
            35                  40                  45

Gly Met Ile Ile Pro Val Phe Asp Thr Ser Ser Tyr Glu Lys Lys Phe
 50                  55                  60

Gln Gly Arg Ile Thr Ile Ile Ala Asp Lys Ser Thr Ser Thr Val Tyr
 65                  70                  75                  80

Leu Glu Leu Ser Ser Leu Arg Ser Glu Asp Ala Ala Val Tyr Tyr Cys
                85                  90                  95

Ala Arg Gly Thr Val Glu Ala Thr Leu Leu Phe Asp Phe Trp Gly Gln
                100                 105                 110

Gly Thr Leu Val Thr Val Ser Ser
            115                 120

<210> SEQ ID NO 47
<211> LENGTH: 120
<212> TYPE: PRT
<213> ORGANISM: Artificial Sequence
<220> FEATURE:
<223> OTHER INFORMATION: MF6930

<400> SEQUENCE: 47

Glu Val Gln Leu Val Gln Ser Gly Ala Glu Val Lys Lys Pro Gly Ser
 1               5                  10                  15

Ser Met Lys Val Ser Cys Lys Ala Ser Gly Gly Thr Phe Ser Asn Tyr
                20                  25                  30

Val Ile Ser Trp Val Arg Gln Ala Pro Gly Gln Gly Leu Glu Trp Met
            35                  40                  45

Gly Met Ile Ile Pro Val Phe Gly Thr Ala Thr Tyr Glu Lys Lys Phe
 50                  55                  60

Gln Gly Arg Val Thr Ile Ile Ala Asp Lys Ser Thr Ser Thr Val Tyr
 65                  70                  75                  80

Met Glu Leu Ser Ser Leu Arg Ser Glu Asp Ala Ala Val Tyr Tyr Cys
                85                  90                  95
```

```
Ala Arg Gly Thr Val Glu Ala Thr Leu Leu Phe Asp Tyr Trp Gly Gln
            100                 105                 110

Gly Thr Leu Val Thr Val Ser Ser
        115                 120

<210> SEQ ID NO 48
<211> LENGTH: 121
<212> TYPE: PRT
<213> ORGANISM: Artificial Sequence
<220> FEATURE:
<223> OTHER INFORMATION: MF6226

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Gly Tyr Tyr
            20                  25                  30

Phe Trp Ser Trp Ile Arg Gln Pro Pro Gly Lys Gly Leu Glu Trp Ile
        35                  40                  45

Gly Tyr Val Tyr Tyr Ser Gly Ser Asn Asn Leu Asn Pro Ser Leu Lys
    50                  55                  60

Ser Arg Val Thr Leu Ser Val Asp Thr Ser Lys Asn Gln Phe Ser Leu
65                  70                  75                  80

Arg Leu Asn Ser Met Thr Ala Ala Asp Thr Ala Val Tyr Tyr Cys Ala
                85                  90                  95

Arg Gly Gly Tyr Ser Gly Tyr Gly Gly Asp Ser Phe Asp Leu Trp Gly
            100                 105                 110

Gln Gly Thr Thr Val Thr Val Ser Ser
        115                 120

<210> SEQ ID NO 49
<211> LENGTH: 127
<212> TYPE: PRT
<213> ORGANISM: Artificial Sequence
<220> FEATURE:
<223> OTHER INFORMATION: tetanus toxin specific VH

<400> SEQUENCE: 49

Glu Val Gln Leu Val Glu Thr Gly Ala Glu Val Lys Lys Pro Gly Ala
1               5                   10                  15

Ser Val Lys Val Ser Cys Lys Ala Ser Asp Tyr Ile Phe Thr Lys Tyr
            20                  25                  30

Asp Ile Asn Trp Val Arg Gln Ala Pro Gly Gln Gly Leu Glu Trp Met
        35                  40                  45

Gly Trp Met Ser Ala Asn Thr Gly Asn Thr Gly Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Ser Leu Thr Ser Gly Asp Thr Ala Val Tyr Phe Cys
                85                  90                  95

Ala Arg Ser Ser Leu Phe Lys Thr Glu Thr Ala Pro Tyr Tyr His Phe
            100                 105                 110

Ala Leu Asp Val Trp Gly Gln Gly Thr Thr Val Thr Val Ser Ser
        115                 120                 125

<210> SEQ ID NO 50
<211> LENGTH: 121
<212> TYPE: PRT
```

```
<213> ORGANISM: Artificial Sequence
<220> FEATURE:
<223> OTHER INFORMATION: MF7699

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Thr Val Ser Thr Asp Ser Leu Gly Phe Tyr
            20                  25                  30

Phe Trp Ser Trp Ile Arg Gln Pro Pro Gly Lys Gly Leu Glu Trp Ile
        35                  40                  45

Gly Tyr Ile Tyr Tyr Ser Gly Ser Ala Asn Phe Asn Pro Ser Leu Lys
    50                  55                  60

Ser Arg Val Thr Met Ser Ile Asp Thr Ser Asn Asn Gln Phe Ser Leu
65                  70                  75                  80

Lys Leu Ser Ser Val Thr Ala Ala Asp Thr Ala Val Tyr Phe Cys Ala
                85                  90                  95

Arg Gly Gly Tyr Thr Gly Tyr Gly Gly Asp Trp Phe Asp Pro Trp Gly
            100                 105                 110

Gln Gly Thr Leu Val Thr Val Ser Ser
        115                 120

<210> SEQ ID NO 51
<211> LENGTH: 121
<212> TYPE: PRT
<213> ORGANISM: Artificial Sequence
<220> FEATURE:
<223> OTHER INFORMATION: MF7698

<400> SEQUENCE: 51

Glu Val Gln Leu Gln Glu Ser Gly Pro Gly Leu Val Lys Pro Ser Glu
1               5                   10                  15

Thr Leu Ser Leu Thr Cys Thr Val Ser Thr Asp Ser Leu Gly Phe Tyr
            20                  25                  30

Phe Trp Ser Trp Ile Arg Gln Pro Pro Gly Lys Gly Leu Glu Trp Ile
        35                  40                  45

Gly Tyr Ile Tyr Tyr Ser Gly Ser Ala Asn Phe Asn Pro Ser Leu Lys
    50                  55                  60

Ser Arg Val Thr Met Ser Ile Asp Thr Ser Asn Asn Gln Phe Ser Leu
65                  70                  75                  80

Lys Leu Arg Ser Val Thr Ala Ala Asp Thr Ala Val Tyr Phe Cys Ala
                85                  90                  95

Arg Gly Gly Tyr Thr Gly Tyr Gly Gly Asp Trp Phe Asp Pro Trp Gly
            100                 105                 110

Gln Gly Thr Leu Val Thr Val Ser Ser
        115                 120

<210> SEQ ID NO 52
<211> LENGTH: 120
<212> TYPE: PRT
<213> ORGANISM: Artificial Sequence
<220> FEATURE:
<223> OTHER INFORMATION: MF7687

<400> SEQUENCE: 52

Gln Val Gln Leu Val Gln Ser Gly Ala Glu Val Lys Lys Pro Gly Ser
1               5                   10                  15

Ser Met Lys Val Ser Cys Lys Ala Ser Gly Gly Ser Phe Ser Ser Ala
            20                  25                  30
```

```
Val Ile Ser Trp Val Arg Gln Ala Pro Gly Gln Gly Leu Glu Trp Met
            35                  40                  45

Gly Met Ile Ile Pro Val Phe Asp Thr Ala Ser Tyr Ala Lys Lys Phe
     50                  55                  60

Gln Gly Arg Val Thr Ile Thr Ala Asp Lys Ser Thr Asn Thr Val Tyr
 65                  70                  75                  80

Met Glu Leu Ser Arg Leu Arg Ser Glu Asp Ala Ala Val Tyr Tyr Cys
                 85                  90                  95

Ala Arg Gly Thr Val Glu Ala Thr Leu Leu Phe Asp Tyr Trp Gly Leu
            100                 105                 110

Gly Thr Leu Val Thr Val Ser Ser
            115                 120

<210> SEQ ID NO 53
<211> LENGTH: 120
<212> TYPE: PRT
<213> ORGANISM: Artificial Sequence
<220> FEATURE:
<223> OTHER INFORMATION: MF7686

<400> SEQUENCE: 53

Gln Val Gln Leu Val Gln Ser Gly Ala Glu Val Lys Lys Pro Gly Ser
 1               5                  10                  15

Ser Met Lys Val Ser Cys Lys Ala Ser Gly Gly Ser Phe Ser Ser Ala
             20                  25                  30

Val Ile Ser Trp Val Arg Gln Ala Pro Gly Gln Gly Leu Glu Trp Met
            35                  40                  45

Gly Met Ile Ile Pro Val Phe Asp Thr Ala Ser Tyr Ala Lys Lys Phe
     50                  55                  60

Gln Gly Arg Val Thr Ile Thr Ala Asp Lys Ser Thr Asn Thr Val Tyr
 65                  70                  75                  80

Met Glu Leu Ser Arg Leu Arg Ser Glu Asp Ala Ala Val Tyr Tyr Cys
                 85                  90                  95

Ala Arg Gly Thr Val Glu Ala Thr Leu Leu Phe Asp Tyr Trp Gly Arg
            100                 105                 110

Gly Thr Leu Val Thr Val Ser Ser
            115                 120

<210> SEQ ID NO 54
<211> LENGTH: 120
<212> TYPE: PRT
<213> ORGANISM: Artificial Sequence
<220> FEATURE:
<223> OTHER INFORMATION: MF7685

<400> SEQUENCE: 54

Gln Val Gln Leu Val Gln Ser Gly Ala Glu Val Lys Lys Pro Gly Ser
 1               5                  10                  15

Ser Met Lys Val Ser Cys Lys Ala Ser Gly Gly Ser Phe Ser Ser Ala
             20                  25                  30

Val Ile Ser Trp Val Arg Gln Ala Pro Gly Gln Gly Leu Glu Trp Met
            35                  40                  45

Gly Met Ile Ile Pro Val Phe Asp Thr Ala Ser Tyr Glu Lys Lys Phe
     50                  55                  60

Gln Gly Arg Val Thr Ile Thr Ala Asp Lys Ser Thr Asn Thr Val Tyr
 65                  70                  75                  80

Met Glu Leu Ser Arg Leu Arg Ser Glu Asp Ala Ala Val Tyr Tyr Cys
```

```
                    85                  90                  95

Ala Arg Gly Thr Val Glu Ala Thr Leu Leu Phe Asp Tyr Trp Gly Arg
                100                 105                 110

Gly Thr Leu Val Thr Val Ser Ser
        115                 120

<210> SEQ ID NO 55
<211> LENGTH: 120
<212> TYPE: PRT
<213> ORGANISM: Artificial Sequence
<220> FEATURE:
<223> OTHER INFORMATION: MF7684

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Val Ile Ser Trp Val Arg Gln Ala Pro Gly Gln Gly Leu Glu Trp Met
            35                  40                  45

Gly Met Ile Ile Pro Ile Phe Asp Thr Ala Asn Tyr Ala Gln Lys Phe
        50                  55                  60

Gln Gly Arg Val Thr Ile Thr Ala Asp Lys Ser Thr Ser Thr Ala Ser
65                  70                  75                  80

Met Glu Leu Arg Ser Leu Arg Ser Glu Asp Thr Ala Val Tyr Tyr Cys
                85                  90                  95

Ala Arg Gly Thr Val Glu Ala Thr Leu Leu Phe Asp Tyr Trp Gly Arg
                100                 105                 110

Gly Thr Leu Val Thr Val Ser Ser
        115                 120

<210> SEQ ID NO 56
<211> LENGTH: 120
<212> TYPE: PRT
<213> ORGANISM: Artificial Sequence
<220> FEATURE:
<223> OTHER INFORMATION: MF6929

<400> SEQUENCE: 56

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Val Ile Ser Trp Val Arg Gln Ala Pro Gly Gln Gly Leu Glu Trp Met
            35                  40                  45

Gly Met Ile Ile Pro Val Phe Glu Thr Val Ser Tyr Glu Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Val Glu Ala Thr Leu Leu Phe Asp Tyr Trp Gly Gln
                100                 105                 110

Gly Thr Leu Val Thr Val Ser Ser
        115                 120

<210> SEQ ID NO 57
<211> LENGTH: 121
```

<212> TYPE: PRT
<213> ORGANISM: Artificial Sequence
<220> FEATURE:
<223> OTHER INFORMATION: MF7691

<400> SEQUENCE: 57

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Asn Thr Tyr
            20                  25                  30

Ala Ile Asn Trp Val Arg Gln Ala Pro Gly Gln Gly Leu Glu Trp Val
        35                  40                  45

Gly Arg Ile Ile Pro Ile Phe Asp Thr Ala Asn Tyr Ala Gln Lys Phe
50                  55                  60

Gln Gly Arg Val Thr Ile Ser Ala Asp Lys Ser Thr Thr Thr Ala Tyr
65                  70                  75                  80

Met Glu Leu Ser Ser Leu Arg Ser Glu Asp Thr Ala Val Phe Tyr Cys
                85                  90                  95

Ala Lys Asp Glu Thr Gly Tyr Ser Ser Ser Asn Phe Gln His Trp Gly
            100                 105                 110

Gln Gly Thr Leu Val Thr Val Ser Ser
        115                 120

<210> SEQ ID NO 58
<211> LENGTH: 121
<212> TYPE: PRT
<213> ORGANISM: Artificial Sequence
<220> FEATURE:
<223> OTHER INFORMATION: MF7690

<400> SEQUENCE: 58

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Asn Thr Tyr
            20                  25                  30

Ala Ile Asn Trp Val Arg Gln Ala Pro Gly Gln Gly Leu Glu Trp Val
        35                  40                  45

Gly Arg Ile Ile Pro Ile Phe Gly Thr Ala Asn Tyr Ala Gln Lys Phe
50                  55                  60

Gln Gly Arg Val Thr Ile Ser Ala Asp Lys Ser Thr Thr Thr Ala Tyr
65                  70                  75                  80

Met Glu Leu Ser Ser Leu Arg Ser Glu Asp Thr Ala Val Phe Tyr Cys
                85                  90                  95

Ala Lys Asp Glu Thr Gly Tyr Ser Ser Ser Asn Phe Gln His Trp Gly
            100                 105                 110

Gln Gly Thr Leu Val Thr Val Ser Ser
        115                 120

<210> SEQ ID NO 59
<211> LENGTH: 121
<212> TYPE: PRT
<213> ORGANISM: Artificial Sequence
<220> FEATURE:
<223> OTHER INFORMATION: MF7689

<400> SEQUENCE: 59

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Asn Thr Tyr

```
                20                  25                  30
Ala Ile Asn Trp Val Arg Gln Ala Pro Gly Gln Gly Leu Glu Trp Val
            35                  40                  45

Gly Arg Ile Ile Pro Ile Phe Gly Thr Ala Asn Tyr Ala Gln Lys Phe
        50                  55                  60

Gln Gly Arg Val Thr Ile Ser Ala Asp Lys Ser Thr Thr Thr Ala Tyr
65                  70                  75                  80

Met Glu Leu Ser Ser Leu Arg Ser Glu Asp Thr Ala Val Phe Tyr Cys
                85                  90                  95

Ala Lys Asp Glu Thr Gly Tyr Ser Ser Ser Asn Phe Gln His Trp Gly
            100                 105                 110

Arg Gly Thr Leu Val Thr Val Ser Ser
        115                 120

<210> SEQ ID NO 60
<211> LENGTH: 121
<212> TYPE: PRT
<213> ORGANISM: Artificial Sequence
<220> FEATURE:
<223> OTHER INFORMATION: MF7688

<400> SEQUENCE: 60

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Asn Thr Tyr
            20                  25                  30

Ala Ile Asn Trp Val Arg Gln Ala Pro Gly Gln Gly Leu Glu Trp Val
            35                  40                  45

Gly Arg Ile Ile Pro Ile Phe Asp Thr Ala Asn Tyr Ala Gln Lys Phe
        50                  55                  60

Gln Gly Arg Val Thr Ile Ser Ala Asp Lys Ser Thr Thr Thr Ala Tyr
65                  70                  75                  80

Met Glu Leu Ser Ser Leu Arg Ser Glu Asp Thr Ala Val Phe Tyr Cys
                85                  90                  95

Ala Lys Asp Glu Thr Gly Tyr Ser Ser Ser Asn Phe Gln His Trp Gly
            100                 105                 110

Arg Gly Thr Leu Val Thr Val Ser Ser
        115                 120

<210> SEQ ID NO 61
<211> LENGTH: 119
<212> TYPE: PRT
<213> ORGANISM: Artificial Sequence
<220> FEATURE:
<223> OTHER INFORMATION: MF7700

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Leu Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gly Gly Gly Asn Tyr Tyr Glu Phe Val Tyr Trp Gly Gln Gly
            100                 105                 110

Thr Leu Val Thr Val Ser Ser
        115
```

<210> SEQ ID NO 62
<211> LENGTH: 119
<212> TYPE: PRT
<213> ORGANISM: Artificial Sequence
<220> FEATURE:
<223> OTHER INFORMATION: MF7701

<400> SEQUENCE: 62

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Leu Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Asn Tyr Tyr Glu Phe Val Tyr Trp Gly Arg Gly
            100                 105                 110

Thr Leu Val Thr Val Ser Ser
        115
```

<210> SEQ ID NO 63
<211> LENGTH: 120
<212> TYPE: PRT
<213> ORGANISM: Artificial Sequence
<220> FEATURE:
<223> OTHER INFORMATION: MF7703

<400> SEQUENCE: 63

```
Glu Val Gln Leu Val Gln Ser Gly Ala Glu Val Met Arg Pro Gly Ser
1               5                   10                  15

Ser Val Lys Val Ser Cys Lys Ala Ser Gly Gly Ile Phe Asn Thr Tyr
            20                  25                  30

Thr Ile Ile Trp Val Arg Gln Ala Pro Gly Gln Gly Leu Glu Trp Met
        35                  40                  45

Gly Gly Ile Ile Pro Ile Phe Asp Thr Pro Asn Phe Ala Gln Lys Phe
    50                  55                  60

Gln Asp Arg Leu Thr Ile Thr Ala Asp Lys Ser Thr Asn Thr Ala Tyr
65                  70                  75                  80

Met Glu Leu Thr Ser Leu Arg Ser Glu Asp Thr Ala Val Tyr Tyr Cys
                85                  90                  95

Ala Arg Glu Gly Cys Asn His Gly Val Cys Tyr Pro Tyr Trp Gly Gln
            100                 105                 110

Gly Thr Leu Val Thr Val Ser Ser
        115                 120
```

<210> SEQ ID NO 64

```
<211> LENGTH: 122
<212> TYPE: PRT
<213> ORGANISM: Artificial Sequence
<220> FEATURE:
<223> OTHER INFORMATION: MF7694

<400> SEQUENCE: 64
```

Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Asn Thr Tyr
            20                  25                  30

Ser Ile Thr Trp Val Arg Gln Ala Pro Gly Gln Gly Leu Glu Trp Met
        35                  40                  45

Gly Gly Ile Ile Pro Val Phe Gly Thr Ser Lys Tyr Ala Gln Lys Phe
    50                  55                  60

Gln Gly Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Phe Ser Ser Ser Ser Gly Trp Phe Asp Pro Trp
            100                 105                 110

Gly Gln Gly Thr Leu Val Thr Val Ser Ser
        115                 120

```
<210> SEQ ID NO 65
<211> LENGTH: 122
<212> TYPE: PRT
<213> ORGANISM: Artificial Sequence
<220> FEATURE:
<223> OTHER INFORMATION: MF7693

<400> SEQUENCE: 65
```

Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Asn Thr Tyr
            20                  25                  30

Ser Ile Thr Trp Val Arg Gln Ala Pro Gly Gln Gly Leu Glu Trp Met
        35                  40                  45

Gly Gly Ile Ile Pro Val Phe Gly Thr Ser Lys Tyr Ala Gln Lys Phe
    50                  55                  60

Gln Gly Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Phe Ser Ser Ser Ser Gly Trp Phe Asp Pro Trp
            100                 105                 110

Gly Arg Gly Thr Leu Val Thr Val Ser Ser
        115                 120

```
<210> SEQ ID NO 66
<211> LENGTH: 122
<212> TYPE: PRT
<213> ORGANISM: Artificial Sequence
<220> FEATURE:
<223> OTHER INFORMATION: MF7692

<400> SEQUENCE: 66
```

Gln Val Gln Leu Val Gln Ser Gly Ala Glu Val Lys Arg Pro Gly Ser
1               5                   10                  15

```
Ser Val Lys Val Ser Cys Lys Ala Ser Gly Gly Thr Phe Asn Thr Tyr
            20                  25                  30

Ser Ile Thr Trp Val Arg Gln Ala Pro Gly Gln Gly Leu Glu Trp Met
        35                  40                  45

Gly Gly Ile Ile Pro Val Phe Gly Thr Ser Lys Tyr Ala Gln Lys Phe
    50                  55                  60

Gln Asp Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Phe Ser Ser Ser Gly Trp Phe Asp Pro Trp
                100                 105                 110

Gly Arg Gly Thr Leu Val Thr Val Ser Ser
        115                 120

<210> SEQ ID NO 67
<211> LENGTH: 122
<212> TYPE: PRT
<213> ORGANISM: Artificial Sequence
<220> FEATURE:
<223> OTHER INFORMATION: MF7697

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Thr Trp Tyr Gly Phe Gly Asp Ala Leu Asp Tyr Trp
                100                 105                 110

Gly Gln Gly Thr Leu Val Thr Val Ser Ser
        115                 120

<210> SEQ ID NO 68
<211> LENGTH: 122
<212> TYPE: PRT
<213> ORGANISM: Artificial Sequence
<220> FEATURE:
<223> OTHER INFORMATION: MF7696

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80
```

Met Glu Leu Ser Ser Leu Arg Ser Glu Asp Thr Ala Val Tyr Tyr Cys
            85                  90                  95

Ala Arg Ala Lys Thr Trp Tyr Gly Phe Gly Asp Ala Leu Asp Tyr Trp
        100                 105                 110

Gly Arg Gly Thr Leu Val Thr Val Ser Ser
    115                 120

<210> SEQ ID NO 69
<211> LENGTH: 122
<212> TYPE: PRT
<213> ORGANISM: Artificial Sequence
<220> FEATURE:
<223> OTHER INFORMATION: MF7695

<400> SEQUENCE: 69

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ala Lys Thr Trp Tyr Gly Phe Gly Asp Ala Leu Asp Tyr Trp
        100                 105                 110

Gly Arg Gly Thr Leu Val Thr Val Ser Ser
    115                 120

<210> SEQ ID NO 70
<211> LENGTH: 6
<212> TYPE: PRT
<213> ORGANISM: Artificial Sequence
<220> FEATURE:
<223> OTHER INFORMATION: light chain CDR1

<400> SEQUENCE: 70

Gln Ser Ile Ser Ser Tyr
1               5

<210> SEQ ID NO 71
<211> LENGTH: 9
<212> TYPE: PRT
<213> ORGANISM: Artificial Sequence
<220> FEATURE:
<223> OTHER INFORMATION: light chain CDR3

<400> SEQUENCE: 71

Gln Gln Ser Tyr Ser Thr Pro Pro Thr
1               5

BINDING MOLECULES THAT MODULATE A BIOLOGICAL ACTIVITY EXPRESSED BY A CELL

CROSS-REFERENCE TO RELATED APPLICATIONS

This application is a U.S. national stage filing of International Application No. PCT/NL2018/050449, filed Jul. 6, 2018; which claims priority to EP Application No. 17180064.2, filed Jul. 6, 2017. The entire contents of International Application No. PCT/NL2018/050449 are hereby incorporated herein by reference.

REFERENCE TO A SEQUENCE LISTING SUBMITTED ELECTRONICALLY VIA EFS-WEB

This application includes a Sequence Listing submitted electronically via EFS-Web (Name: "4096_0280001_Seq-listing_ST25"; Size: 99,851 bytes; and Date of Creation: Nov. 28, 2022), which is hereby incorporated by reference in its entirety.

Cancer is still a major cause of death in the world, in spite of the many advances that have been made in the treatment of the disease and the increased knowledge of the molecular events that lead to cancer. Colorectal cancer (CRC), for instance, is the third most common cancer worldwide. In 2008, 1.23 million people were diagnosed with the disease. It is the second most common cancer in Europe, with around 447,000 new cases diagnosed in 2012 (13% of the total). Colorectal cancer is the fourth most common cause of cancer death, estimated to be responsible for 608,000 (EU 148,000) deaths per annum. While some new treatments have been advanced in CRC many have failed clinical testing; metastatic CRC is still largely incurable with conventional treatments. Melanoma is another example of a cancer that occurs very frequently. When detection is not early enough the cancer is likely to metastasize at which stage it is very hard to treatment. Immune-intervention treatments have been shown to be effective to at least some of the patients with metastasized melanoma. Non-small cell lung cancer is a cancer type that is rarely discovered at an early enough stage for surgery. Also these types of cancers have been successfully treatment with immune-intervention treatments.

Traditionally, most cancer drug discovery has focused on agents that block essential cell functions and kill dividing cells. However, in cases of advanced cancer, no matter how aggressively applied, even to the point where patients suffer life-threatening side-effects from the treatment, chemotherapy rarely results in a complete cure. In most cases the tumors in the patients stop growing or temporarily shrink (referred to as remission) only to start proliferating again, some times more rapidly (referred to as relapse), and become increasingly more difficult to treat. More recently the focus of cancer drug development has moved away from broadly cytotoxic chemotherapy to targeted cytostatic therapies with less toxicity. Treatment of advanced cancer has been validated clinically in leukemia and some other cancers. However, in a majority of carcinomas, targeted approaches are still proving not effective enough to completely abolish cancer in the majority of the patients.

Targeting of cancers has been achieved using a variety of different methods including for instance small molecules directed towards signaling proteins on which the cancer depends for survival and/or growth; vaccines with tumor specific proteins; cell therapies with immune cells that actively kill tumor cells and antibodies that target cytotoxic molecules to the tumor; interfere with signaling and/or that (re)direct the immune system of the host to the tumor cells. Monoclonal antibodies that block CTLA-4 or PD-1 have been shown to induce a durable clinical response in subjects that had melanoma, NSCLC, renal cell carcinoma and urothelial carcinoma patients.

The present invention provides novel means and methods for (re)directing immune system components. The invention also relates to means and methods for modulating a biological activity expressed by cells.

SUMMARY OF THE INVENTION

In one aspect the invention provides a method of inhibiting a biological activity in a first or second cell mediated by the binding of a first membrane protein on a first cell to a second membrane protein on a second cell, wherein said first and second membrane proteins are binding partners (i.e. a ligand and receptor pair), the method comprising providing a system comprising said first and second cell with an antibody or a variant of said antibody that maintains the binding specificity of the antibody comprising a variable domain that can bind to an extracellular part of said first membrane protein and a variable domain that can bind to an extracellular part of said second membrane protein; and incubating said system under conditions that are permissive for the first or second cell to express said biological activity mediated by the binding of said first membrane protein to said second membrane protein in the absence of said antibody or variant thereof;

wherein the binding of the variable domain that can bind to an extracellular part of said first membrane protein blocks the binding of said first membrane protein to said second membrane protein and/or the binding of the variable domain that can bind to an extracellular part of said second membrane protein blocks the binding of said first membrane protein to said second membrane protein.

In some embodiments, the said method may be an in vitro or ex vivo method.

The binding of the antibody or variant thereof preferably reduces an activity of the binding of the receptor-ligand pair in said first cell. The binding preferably reduces an inhibitory activity of the binding of the receptor-ligand pair in said first cell. Receptor-ligand pairs of the CD28 family and the B7 family that exhibit inhibitory activity are also so-called coinhibitory receptor-ligand pairs.

The invention also provides a method of inhibiting a biological activity in a first or second cell mediated by the binding of a member of the CD28 family (first membrane protein) on a first cell to a member of the B7 family (second membrane protein) on a second cell, wherein said first and second membrane protein are binding partners (i.e. a ligand and receptor pair), the method comprising providing a system comprising said first and second cell with an antibody or a variant of said antibody that maintains the binding specificity of the antibody comprising a variable domain that can bind to an extracellular part of said first membrane protein and a variable domain that can bind to an extracellular part of said second membrane protein; and incubating said system under conditions that are permissive for the first or second cell to express said biological activity mediated by the binding of said first membrane protein to said second membrane protein in the absence of said antibody or variant thereof;

wherein the binding of the variable domain that can bind to an extracellular part of said first membrane protein blocks the binding of said first membrane protein to said second membrane protein and/or the binding of the variable domain that can bind to an extracellular part of said second membrane protein blocks the binding of said first membrane protein to said second membrane protein.

In some embodiments, the said method is an in vitro or ex vivo method.

The binding of the antibody or variant thereof preferably reduces an activity of the binding of the receptor-ligand pair in said first cell. The binding preferably reduces an inhibitory activity of the binding of the receptor-ligand pair in said first cell. Receptor-ligand pairs that exhibit inhibitory activity are so-called coinhibitory receptor-ligand pairs.

Also provided is a method of enhancing a biological activity in a first or second cell mediated by the binding of a first membrane protein on a first cell to a second membrane protein on a second cell, the method comprising providing a system comprising said first and second cell with an antibody or a variant of said antibody that maintains the binding specificity of the antibody, that comprises a variable domain that can bind to an extracellular part of said first membrane protein and a variable domain that can bind to an extracellular part of said second membrane protein; and incubating said system under conditions that are permissive for the first or second cell to express said biological activity mediated by the binding of said first membrane protein to said second membrane protein in the absence of said antibody or variant thereof;

wherein the binding of the variable domain that can bind to an extracellular part, of said first membrane protein does not block the binding of said first membrane protein to said second membrane protein and the binding of the variable domain that can bind to an extracellular part of said second membrane protein does not block the binding of said first membrane protein to said second membrane protein.

In some embodiments, said method is an in vitro or ex vivo method.

The first membrane protein is preferably Programmed Cell Death 1 protein (PD-1); cytotoxic T-lymphocyte-associated protein 4 (CTLA-4); B- and T-lymphocyte attenuator (BTLA); or Transmembrane And Immunoglobulin Domain Containing 2 (TMIGD2).

The second membrane protein is preferably Programmed Cell Death 1 Ligand 1 protein (PD-L1); Programmed Cell Death 1 Ligand 2 protein (PD-L2); ICOSL; CD80; CD86; B7-H3; B7-H4; TNFRSF14; B7-H6 or B7-H7. In a preferred embodiment the second membrane protein is PD-L1; PD-L2; CD80; CD86; B7-H4; TNFRSF14; or B7-H7. In a particularly preferred embodiment the second membrane protein is PD-L1; or PD-L2, preferably PD-L1. In a particularly preferred embodiment the first membrane protein is PD-1 and the second membrane protein is PD-L1. A molecule of the present invention is preferably a bispecific antibody capable of blocking the interaction of PD-1 with PD-L1 and/or PD-L2 and PD-L1 with PD-1 and/or CD80. Preferably a molecule of the present invention is capable of blockade of the full PD-1 axis, including PD-1 with PD-L1 or PD-L2, and PD-L1 with PD-1 and CD80. See FIG. 33.

The invention also provides an antibody or a variant of said antibody that maintains the binding specificity of the antibody, that comprises a variable domain that can bind to an extracellular part of a first membrane protein and a variable domain that can bind to an extracellular part of a second membrane protein, wherein said first and second membrane protein are binding partners (i.e. a ligand and receptor pair) and wherein the binding of the variable domain that can bind to an extracellular part of said first membrane protein blocks the binding of said first membrane protein to said second membrane protein and/or the binding of the variable domain that can bind to an extracellular part of said second membrane protein blocks the binding of said first membrane protein to said second membrane protein.

The invention also provides an antibody or a variant of said antibody that maintains the binding specificity of the antibody, that comprises a variable domain that can bind to an extracellular part of a protein of the CD28 family (first membrane protein) and a variable domain that can bind to an extracellular part of a protein of the B7 family (second membrane protein);

wherein said first and second membrane protein are binding partners (i.e. a ligand and receptor pair) and wherein the binding of the variable domain that can bind to an extracellular part of said first membrane protein blocks the binding of said first membrane protein to said second membrane protein and/or the binding of the variable domain that can bind to an extracellular part of said second membrane protein blocks the binding of said first membrane protein to said second membrane protein. The binding of the antibody or variant thereof preferably reduces an activity of the binding of the receptor-ligand pair in said first cell. The binding preferably reduces an inhibitory activity of the binding of the receptor-ligand pair in said first cell. Receptor-ligand pairs that exhibit inhibitory activity are so-called coinhibitory receptor-ligand pairs.

The antibody or variant thereof is preferably a bispecific antibody.

In a preferred embodiment the antibody or a variant of said antibody that maintains the binding specificity of the antibody comprises a variable domain that can bind to an extracellular part of PD-1; CTLA-4; BTLA; or TMIGD2; and a variable domain that can bind to an extracellular part of PD-L1; PD-L2; CD80, CD86, B7-H4, TNFRSF14, or B7-H7.

In a preferred embodiment the antibody or a variant of said antibody that maintains the binding specificity of the antibody comprises a variable domain that can bind to an extracellular part of PD-1; and a variable domain that can bind to an extracellular part of PD-L1 or PD-L2.

Preferably the binding of a variable domain that can bind PD-1 blocks the binding of PD-1 to PD-L1.

Preferably the binding of a variable domain that can bind PD-1 also blocks the binding of PD-1 to PD-L2.

Preferably the binding of a variable domain that can bind PD-1 also blocks the binding of PD-1 to PD-L1 and PD-L2.

The binding of a variable domain that can bind PD-L1 may block the binding of PD-L1 to PD-1.

The binding of a variable domain that can hind PD-L1 may block the binding of PD-L1 to CD80.

Binding of the variable domain that can bind PD-L1 may block the binding of PD-L1 to PD-1 and also may block the binding of PD-L1 to CD80.

Further provided is a composition or a kit of parts or a pharmaceutical composition that comprises one or more antibodies or variants thereof of the invention.

Also provided is a nucleic acid molecule that codes for an at least one CDR region, preferably for a heavy chain variable region, of an antibody of the invention or a variant of said antibody that maintains the binding specificity of the antibody. Also provided is a nucleic acid molecule or a collection of nucleic acid molecules that codes for an antibody of the invention or a variant of said antibody that maintains the binding specificity of the antibody. Further provided is a vector comprising a nucleic acid molecule of the invention.

Also provided is a cell or non-human animal comprising one or more nucleic acid molecules that alone or together code for an antibody or a variant of said antibody that maintains the binding specificity of the antibody, of the invention. Also provided are methods of producing an antibody or a variant of said antibody that maintains the binding specificity of the antibody, of the invention using a cell as described, preferably together with the harvesting of the antibody or variant thereof from a culture of the cells.

Further provided is a cell system that comprises an antibody or a variant of said antibody that maintains the binding specificity of the antibody of the invention.

Also provided is a method for the treatment of an individual that has a disease that involves aberrant cells such as cancer or has a chronic infection, such as with a virus or parasite, the method comprising administering an antibody of the invention or a variant of said antibody that maintains the binding specificity of the antibody of the invention to the individual in need thereof. The antibody or variant thereof can preferably bind to PD-1 and PD-L1. The variable domain that binds PD-1 preferably blocks the binding of PD-1 to PD-L1. The variable domain that binds PD-L1 preferably blocks the binding of PD-1 to PD-L1. The antibody or variant thereof is preferably a bispecific antibody capable of blocking the interaction of PD-1 with PD-L1 and/or PD-L2 and PD-L1 with PD-1 and/or CD80. Preferably a molecule of the present invention is capable of blockade of the full PD-1 axis, including PD-1 with PD-L1 or PD-L2, and PD-L1 with PD-1 and CD80.

Further provided is an antibody of the invention, or a variant thereof or a nucleic acid molecule for use as a medicament.

The invention further provides an antibody of the invention or a variant of said antibody that maintains the binding specificity of the antibody of the invention, for use in the treatment of an individual that has a disease that involves aberrant cells such as cancer, or that has an infection, such as an infection with a virus or parasite.

Further provided is a use of an antibody or variant according to the invention for the preparation of a medicament for the treatment or prevention of cancer and/or an infection, such as an infection with a virus or parasite.

The parasite may be an intracellular parasite.

Further provided is a method of inducing and/or stimulating an immune response in an individual against an aberrant cell in said individual, the method comprising providing said individual with an antibody or a variant of said antibody that maintains the binding specificity of the antibody of the invention. The aberrant cell is preferably a cancer cell, a virus-infected cell, a parasite or a parasite infected cell. In a preferred embodiment the cell is a cancer cell or a neoplastic cell.

DETAILED DESCRIPTION OF THE INVENTION

The CD28 family of receptors plays a role in controlling the adaptive immune response. Members of the CD28 family include PD-1; CTLA-4; BTLA; TMIGD2; ICOS; CD28; and NKp30. Where some members of this family such as CD28 and ICOS induce co-stimulatory signals upon binding to the corresponding B7 family member (ligand), other members, of note CTLA4 and PD-1 induce inhibitory signals upon binding of the B-7 family member (CD80; CD86; PD-L1 or PD-L2).

Programmed Cell Death 1 protein (PD-1) is a cell surface receptor that belongs to the CD28 family of receptors and is expressed on T cells and pro-B cells. PD-1 is presently known to bind two ligands, PD-L1 and PD-L2. PD-1, functioning as an immune checkpoint, plays an important role in down regulating the immune system by inhibiting the activation of T-cells, which in turn reduces autoimmunity and promotes self-tolerance. The inhibitory effect of PD-1 is thought to be accomplished through a dual mechanism of promoting apoptosis (programmed cell death) in antigen specific T-cells in lymph nodes while simultaneously reducing apoptosis in regulatory T cells (suppressor T cells). PD-1 is also known under a number of different aliases such as PDCD1; Programmed Cell Death 1; Systemic Lupus Erythematosus Susceptibility 2; Protein PD-1; HPD-1; PD1; Programmed Cell Death 1 Protein; CD279 Antigen; CD279; HPD-L; HSLE1; SLEB2; and PD-1. External Ids for PD-1 are HGNC: 8760; Entrez Gene: 5133; Ensembl: ENSG00000188389; OMIM: 600244; and UniProtKB: Q15116. New classes of drugs that block the activity of PD-1, the PD-1 inhibitors, activate the immune system to attack tumors and are therefore used with success to treat some types of cancer.

Cytotoxic T-lymphocyte-associated protein 4 (CTLA-4) is a protein receptor that functions as an immune checkpoint. The member of the CD28 family of receptors is involved in downregulating immune responses in an animal. The protein acts as an "off" switch when bound to CD80 or CD86 on the surface of antigen-presenting cells. CTLA4 is known under a number of other names such as Cytotoxic T-Lymphocyte Associated Protein 4; Insulin-Dependent Diabetes Mellitus 12; Celiac Disease 3; CD152; Ligand And Transmembrane Spliced Cytotoxic T Lymphocyte Associated Antigen 4; Cytotoxic T-Lymphocyte-Associated Antigen 4; CD152 Antigen; CELIAC3; IDDM12; ALPS5; GRD4; CSE; and CD. External Ids for CTLA4 are HGNC: 2505; Entrez Gene: 1493; Ensembl: ENSG00000163599; OMIM: 123890; and UniProtKB: P16410.

B- and T-lymphocyte attenuator (BTLA) is another member of the CD28 family of proteins. It is induced during activation of T cells. BTLA is expressed on Th1 cells but not Th2 cells. BTLA is a binding partner of B7-H4. Unlike other members of this family, BTLA can interact with non-B7 family members. BTLA displays T-Cell inhibition via interaction with tumor necrosis family receptors (TNF-R). BTLA is a ligand for tumor necrosis factor (receptor) superfamily, member 14 (TNFRSF14), also known as herpes virus entry mediator (HVEM). BTLA-HVEM complexes negatively regulate T-cell immune responses. Other names for BTLA are B And T Lymphocyte Associated Protein; CD272 Antigen; BTLA1; and CD272. External Ids for BTLA are HGNC: 21087; Entrez Gene: 151888; Ensembl: ENSG00000186265; OMIM: 607925; and UniProtKB: Q7Z6A9.

Transmembrane And Immunoglobulin Domain Containing 2 (TMIGD2) is a member of the CD28 family of proteins. The protein can be detected in cells of epithelial and endothelial origins, and is able to enhance angiogenesis in vitro when overexpressed by endothelial cell lines. TGMID2 is reported to be a stimulatory receptor expressed on naïve T-cells. A ligand for the receptor is HHLA2 (B7-H7). The latter is expressed on a wide variety of cancer cells. TMIGD2 is known under a number of other names such as Transmembrane And Immunoglobulin Domain Containing 2; Immunoglobulin-Containing And Proline-Rich Receptor-1; CD28 Homologue 2; CD28 Homolog; IGPR-1; CD28H; and IGPR1. External Ids for TMIGD2 are HGNC: 28324; Entrez Gene: 126259; Ensembl: ENSG00000167664; OMIM: 614715; and UniProtKB: Q96BF3.

ICOS (Inducible T-cell Costimulator) or CD278 is a CD28 family costimulatory molecule that is expressed on activated T cells. It is thought to be important for Th2 cells in particular. The protein forms homodimers and plays an important role in cell-cell signaling, immune responses, and regulation of cell proliferation. Compared to wild-type naïve T cells, ICOS knock-out T cells activated with plate-bound anti-CD3 have reduced proliferation and IL-2 secretion. Patients that were treated with Ipilimumab (a monoclonal antibody that binds CTLA-4) have increased ICOS+ T cells in tumor tissues and blood. The increase served as a pharmacodynamic biomarker of anti-CTLA-4 treatment. ICOS is known under a number of different names such as Activation-Inducible Lymphocyte Immunomediatory Molecule; AILIM; Inducible Costimulator; CD278 Antigen; CD278; and CVID1. External Ids for ICOS are HGNC: 5351; Entrez Gene: 29851; Ensembl: ENSG00000163600; OMIM: 604558 and UniProtKB: Q9Y6W8.

CD28 (Cluster of Differentiation 28) is one of the proteins expressed on T cells that provide co-stimulatory signals required for T cell activation and survival. T cell stimulation through CD28 in addition to the T-cell receptor (TCR) can provide a potent signal for the production of various interleukins (IL-G in particular). CD28 is the receptor for CD80 (B7.1) and CD86 (B7.2) proteins. When activated by Toll-like receptor ligands, the CD80 expression is upregulated in antigen presenting cells (APCs). The CD86 expression on antigen presenting cells is constitutive (expression is independent of environmental factors). CD28 is a B7 receptor that is constitutively expressed on naïve T cells. Association of the TCR of a naive T cell with MHC:antigen complex without CD28:B7 interaction is thought to result in a T cell that is allergic. CD28 is known under a number of different names such as CD28 Molecule; CD28 Antigen; Tp44; T-Cell-Specific Surface Glycoprotein; and CD28 Antigen (Tp44). External Ids for CD28 are HGNC: 1653; Entrez Gene: 940; Ensembl: ENSG00000178562; OMIM: 186760 and UniProtKB: P10747.

NKp30 is a member of the CD28 family. It is a member of the natural cytotoxicity receptors (NCRs) which include NKp30, NKp44 and NKp46. Natural Killer (NK) cells recognize and destroy tumors and virus-infected cells in an antibody-independent manner. The regulation of NK cells is mediated by activating and inhibiting receptors on the NK cell surface. One family of activating receptors is the NCR family. The NCRs initiate tumor targeting by recognition of heparan sulfate on cancer cells. NKp30 interacts with highly charged HS/heparin structures. One of the ligands of NKp30 is B7-H6. B7-H6 is a co-stimulatory molecule. B7-HG is not normally expressed on normal cells, but can be highly expressed on tumor cells. It can also be expressed on antigen presenting cells (APC) by the induction. NK cells can be activated to release TNFα and IFNγ as a result of the interaction of NKp30 with B7-H6. NKp30 is known under a number of different names such as Natural Cytotoxicity Triggering Receptor 3 (NCR3); Natural Killer Cell P30-Related Protein; Activating Natural Killer Receptor P30; Lymphocyte Antigen 117; NK-P30; LY117; 1C7; Activating NK-A1 Receptor; CD337 Antigen; CD337; or MALS. External Ids for NKp30 are HGNC: 19077; Entrez Gene: 259197; Ensembl: ENSG00000204475; OMIM: 611550; and UniProtKB: O14931.

The B7 family comprises a number of structurally related, cell-surface proteins, which bind to receptors on lymphocytes that regulate immune responses. Activation of lymphocytes is initiated by engagement of cell-surface, antigen-specific T-cell receptors or B-cell receptors. Additional signals delivered simultaneously by B7 ligands further determine the immune response of these cells. These so-called 'costimulatory' or 'coinhibitory' signals are delivered by B7 family members through the CD28 family of receptors on lymphocytes. Binding of B7-family members with costimulatory receptors augments immune responses, and binding with coinhibitory receptors attenuates immune responses. Presently seven members of the family or known: B7.1 (CD80), B7.2 (CD86), inducible costimulator ligand (ICOS-L), programmed death-1 ligand (PD-L1), programmed death-2 ligand (PD-L2), B7-H3, and B7-H4. B7 family members are expressed in lymphoid and non-lymphoid tissues. Effects of members on regulating immune responses are shown in the development of immunodeficiency and autoimmune diseases in mice with mutations in B7-family genes. Manipulation of the signals delivered by B7 ligands has shown potential in the treatment of autoimmunity, inflammatory diseases and cancer.

CD80 is a protein found on activated B cells and monocytes that provides a costimulatory signal necessary for T cell activation and survival. It is the ligand for two different proteins on the T cell surface: CD28 and CTLA-4. When bound to CD28 it is associated with co-stimulation whereas binding to CTLA4 is associated with attenuation of an immune response. CD80 works in tandem with CD86 to activate T cells. CD80 is reported to also bind PD-L1. CD80 is known under a number of other names such as CD80 Molecule; CD80 Antigen; CD28 Antigen Ligand 1; B7-1 Antigen; B-Lymphocyte Activation Antigen B7; CTLA-4 Counter-Receptor B7.1; Activation B7-1 Antigen; CD28LG1; CD28LG; LAB7; BB1; B7; Costimulatory Factor CD80; CD80 Antigen; and B7-1. External Ids for CD80 are HGNC: 1700; Entrez Gene: 941; Ensembl: ENSG00000121594; OMIM: 112203; and UniProtKB: P33681.

CD86 is a protein expressed on antigen-presenting cells. It can provide costimulatory signals for T cell activation and survival. It is the ligand for two different proteins on the T cell surface: It is the ligand for two different proteins on the T cell surface: CD28 and CTLA-4. When bound to CD28 it is associated with co-stimulation whereas binding to CTLA4 is associated with attenuation of an immune response. CD8G works in tandem with CD80 to activate T cells. It is known under a number of different names such as CD8G Molecule; CD8G Antigen; CD28 Antigen Ligand 2; B7-2 Antigen; CTLA-4 Counter-Receptor B7.2; CD28LG2; FUN-1; BU63; B70; B-Lymphocyte Activation Antigen B7-2; B-Lymphocyte Antigen B7-2; Activation B7-2 Antigen; CD86 Antigen; LAB72; and B7-2. External Ids for CD86 are HGNC: 1705; Entrez Gene: 942; Ensembl: ENSG00000114013; OMIM: 601020; and UniProtKB: P42081.

PD-L1 is a type 1 transmembrane protein that plays a role in suppressing an immune response during particular events such as pregnancy, tissue allografts, autoimmune disease and other disease states such as hepatitis. PD-L1 is expressed in various types of cancers, including NSCLC, melanoma, renal cell carcinoma, gastric cancer, hepatocellular as well as various leukemias and multiple myeloma. PD-L1 is present in the cytoplasm and plasma membrane of cancer cells, but not all cancers or all cells within a tumor express PD-L1. Multiple tumor microenvironment cells contribute to immune suppression by upregulating PD-L1 expression. This effect is called "adaptive immune resistance", because the tumor protects itself by inducing PD-L1 in response to IFN-γ produced by activated T cells. PD-L1 can also be regulated by oncogenes, this mechanism is known as inherent, immune resistance. Within the tumor microenvironment, PD-L1 is also expressed on myeloid cells and activated T cells. The expression of PD-L1 is induced by multiple proinflammatory molecules, including types 1 and 111FN-γ, TNF-α, LPS, GM-CSF and VEGF, as well as the cytokines IL-10 and IL-4. The binding of PD-L1 to PD-1 or B7.1 (CD80) transmits an inhibitory signal which reduces the proliferation of the PD-1 expressing T cells. PD-1 is thought to be able to control the accumulation of foreign antigen specific T cells through apoptosis. PD-L1 is expressed by a variety of cancer cells and the expression thereof is thought to be at least in part responsible for a dampening of an immune response against the cancer cell. PD-L1 is a member of the B7-family of protein and is known under a variety of other names such as CD274 Molecule; CD274 Antigen; B7 Homolog 1; PDCD1 Ligand 1; PDCD1LG1; PDCD1L1; B7H1; PDL1; Programmed Cell Death 1 Ligand 1; Programmed Death Ligand 1; B7-H1; and B7-H. External Ids for CD274 are HGNC: 17635; Entrez Gene: 29126; Ensembl: ENSG00000120217; OMIM: 605402; UniProtKB: Q9NZQ7.

PD-L2 is a second ligand for PD-1. Engagement of PD-1 by PD-L2 inhibits T cell receptor (TCR)-mediated proliferation and cytokine production by T cells. At low antigen concentrations, PD-L2/PD-1 binding inhibits B7-CD28 signals. At high antigen concentrations, PD-L2/PD-1 binding reduces cytokine production. PD-L1 expression is up-regulated on antigen-presenting cells by interferon gamma treatment. It is expressed in some normal tissues and a variety of tumors. PD-L1 and PD-L2 are thought to have overlapping functions and regulate T cell responses. The protein PD-L2 is known under a number of other names such as Programmed Cell Death 1 Ligand 2; B7 Dendritic Cell Molecule; Programmed Death Ligand 2; Butyrophilin B7-DC; PDCD1 Ligand 2; PD-1 Ligand 2; PDCD1L2; B7-DC; CD273; B7DC; PDL2; PD-1-Ligand 2; CD273 Antigen; BA574F11.2; and Btdc. External Ids for PD-L2 are HGNC: 18731; Entrez Gene: 80380; Ensembl: ENSG00000197646; OMIM: 605723; and UniProtKB: Q9BQ51.

Inducible T-Cell Co-Stimulator Ligand (ICOSL or CD275) is constitutively expressed by APCs as well as a number of non-hematologic tissues. Expression can be down-regulated with ongoing inflammation. ICOSL is presently known to interact with ICOS, CD28 and CTLA-4 in humans. ICOSL/CD28 interaction appears to co-stimulate human T primary responses to allogeneic antigens and memory recall responses. ICOSL/CTLA-4 is thought to result coinhibitory signals. ICOSL is also known as ICOSLG; B7-Related Protein 1; B7 Homolog 2; B7-Like Protein G150; B7 Homologue 2; B7RP-1; B7-H2; B7RP1; B7H2; Transmembrane Protein B7-H2 ICOS Ligand; CD275 Antigen; KIAA0653; ICOS-L; LICOS; and GL50. External Ids for ICOSL are HGNC: 17087; Entrez Gene: 23308; Ensembl: ENSG00000160223; OMIM: 605717; and UniProtKB: 075144.

CD276 (or B7-H3) expression is increased in various malignancies and distinguishes between normal and tumor-derived circulating endothelial cells (Kraan et al British Journal of Cancer (2014) 111,149-156). Stimulation of the receptor directs the differentiation of human marrow stromal cells to osteoblasts (Xu et al 2011; Immunobiology 216 (2011) 1311-1317). The protein contains 4 Ig-like domains in humans whereas the mouse protein appears to have 2 of such domains. The protein is thought to be the first identified ligand for the triggering receptor expressed on myeloid cells (TREM)-like transcript 2 (TLT-2 or TREMML2). The latter protein binds B7-H3 (4Ig-B7-H3) and costimulates activation of CD8 T-cells (Hofmeyer et al 2009 PNAS 105; 10277-10278). CD276 is broadly expressed. It acts as a T cell costimulator. CD276 is also known under a number of other names such as CD276 Molecule; Costimulatory Molecule; CD276 Antigen; B7 Homolog 3; 41g-B7-H3; B7-H3; B7H3; and B7RP-2. External Ids for CD276 are HGNC: 19137; Entrez Gene: 80381; Ensembl: ENSG00000103855; OMIM: 605715; and UniProtKB: Q5ZPR3.

B7-H4 (VTCNI) mRNA appears to be broadly expressed but only few cells actively express the protein on the membrane. Expression of the protein on the membrane and binding to activated T cells results in inhibition of T-cell effector function via cell cycle arrest, decreased proliferation, and reduced IL-2 production. B7-H4 is up-regulated on the surface of cancer cells and immunosuppressive tumor-associated macrophages (TAMs) in a variety of human cancers. B7-H4 is a binding partner of BTLA. Signaling through B7-H4 pathway leads to the inhibition of TCR-mediated CD4+ and CD8+ T cell proliferation, cell-cycle progression, and IL-2 production. B7-H4 is also known under a number of other names such as V-Set Domain Containing T Cell Activation Inhibitor 1; Immune Costimulatory Protein B7-H4; T-Cell Costimulatory Molecule B7x; B7 Superfamily Member 1; B7 Homolog 4; B7h.5; B7H4; T Cell Costimulatory Molecule B7x; B7 Family Member, H4; Protein B7S1; PRO1291; VCTN1; B7S1; B7X; and H4 2. External Ids for B7-H4 are HGNC: 28873; Entrez Gene: 79679; Ensembl: ENSG00000134258; OMIM: 608162 and UniProtKB: Q7Z7D3.

B7-H6 belongs to the B7 family (see MIM (305402) and is selectively expressed on tumor cells. Binding of B7-1-16 with NKp30 (NCR3; MIM 611550) results in natural killer (NK) cell activation and cytotoxicity (Brandt et al., 2009 J Exp Med. 2009 Jul. 6; 206(7); 1495-503). Natural killer (NK) cells are lymphocytes of the innate immune system that participate in the elimination of tumors. B7-H6 is a tumor cell surface molecule that binds NKp30, a human receptor which triggers antitumor NK cell cytotoxicity and cytokine secretion. Other names for B7-H6 are NCR3LG1; Natural Killer Cell Cytotoxicity Receptor 3 Ligand 1; B7 Homolog 6; B7H6; Putative Ig-Like Domain-Containing Protein DKFZp686O24166/DKFZp686121167; and DKFZp686O24166. External Ids for B7-H6 are HGNC: 42400; Entrez Gene: 374383; Ensembl: ENSG00000188211; OMIM: 613714; and UniProtKB: Q68D85.

B7-H7 (HHLA2) protein was detected in trophoblastic cells of the placenta and the epithelium of gut, kidney, gallbladder, and breast, but not in most other organs.

HHLA2 protein is widely expressed in human cancers from the breast, lung, thyroid, melanoma, pancreas, ovary, liver, bladder, colon, prostate, kidney, and esophagus. High HHLA2 expression is associated with regional lymph node metastasis and stage (Janakiram et al. Clin Cancer Res; 21(10): 2359-66; May 15, 2015). TMIGD2 is identified as one of the receptors for HHLA2. B7-H7 is known under a number of different names such as HERV-H LTR-Associating 2; Human Endogenous Retrovirus-II Long Terminal Repeat-Associating Protein 2; B7117 and B7y. External Ids for B7-H7 are HGNC: 4905; Entrez Gene: 11148; Ensembl: ENSG00000114455; OMIM: 604371 and UniProtKB: Q9UM44.

Tumor Necrosis Factor Receptor Superfamily Member 14 (TNFRSF14) is a human cell surface receptor of the TNF-receptor superfamily. This protein was originally known as herpesvirus entry mediator A (HveA). It is also known as CD270 in the cluster of differentiation classification. TNFRSF14 was identified as a cellular mediator of herpes simplex virus (HSV) entry. Binding of HSV viral envelope glycoprotein D (gD) to this receptor protein has been shown to be part of the viral entry mechanism. The cytoplasmic region of this receptor was found to bind to several TRAF family members, which may mediate the signal transduction pathways that activate the immune response. TNFRSF14 is known under a number of different names such as Tumor Necrosis Factor Receptor Superfamily, Member 14 (Herpesvirus Entry Mediator); Herpes Virus Entry Mediator A; HVEA; HVEM; TR2; Tumor Necrosis Factor Receptor-Like Genet; Tumor Necrosis Factor Receptor-Like 2; Herpesvirus Entry Mediator A; Herpesvirus Entry Mediator; CD40-Like Protein; CD270 Antigen; LIGHTR; CD270; and ATAR. External Ids for TNFRSF14 are: HGNC: 11912; Entrez Gene: 8764; Ensembl: ENSG00000157873; OMIM: 602746; and UniProtKB: Q92956

Reference to sequence identifiers is done to identify which protein is targeted. An antibody or a variant thereof, such as a variant thereof, of the invention typically also recognizes at least some variants thereof such as allelic variants, splice variants and mutant variants thereof as long as the epitope recognized by the respective variable domain has not been affected. Some of the alternative names may or may not have also been used to refer to other proteins. The names are given for reference purposes only. An antibody or a variant thereof, such as a variant thereof, of the invention binds to the protein as expressed on cells. It can also bind to variants of the protein as long as the epitope to which the antibody binds is available. Thus splicing variants or mutant proteins (if any) will also be bound by an antibody or a variant thereof as long as the epitope is available. The fact that the antibody or a variant thereof binds to the indicated protein means that it can bind to protein as a property and does not necessarily imply that the antibody or a variant thereof is actually bound to the target. It also does not necessarily mean that the variable domain cannot bind to other proteins.

The invention provides a method of inhibiting a biological activity in a first or second cell mediated by the binding of a first membrane protein on a first cell to a second membrane protein on a second cell, the method comprising providing a system comprising said first and second cell with an antibody or a variant thereof comprising a variable domain that can bind to an extracellular part of said first membrane protein and a variable domain that can bind to an extracellular part of said second membrane protein; and incubating said system under conditions that are permissive for expression of said biological activity in the absence of said antibody or a variant thereof;

wherein the binding of the variable domain that can bind to an extracellular part of said first membrane protein blocks the binding of said first membrane protein to said second membrane protein and/or the binding of the variable domain that can bind to an extracellular part of said second membrane protein blocks the binding of said first membrane protein to said second membrane protein. In some embodiments, said method is an in nitro method. The antibody used in the method binds two binding partners and blocks the binding of the two to each other. In the method the two cells that express the binding partners are brought and/or kept together in close proximity but at the same time binding of the binding partners is inhibited. This is different than a combination of two monoclonal monospecific antibodies comprising the variable domains. These also block the binding of the two binding partners, but the cells are not brought and/or kept in close proximity. The special activity of an antibody of the invention, particular of a bispecific antibody of the invention is particularly noticeable in complex environments comprising three or more different cell types.

The invention also provides a method of enhancing a biological activity in a first or second cell mediated by the binding of a first membrane protein on a first cell to a second membrane protein on a second cell, the method comprising providing a system comprising said first and second cell with an antibody or a variant thereof that comprises a variable domain that can bind to an extracellular part of said first membrane protein and a variable domain that can bind to an extracellular part of said second membrane protein; and incubating said system under conditions that are permissive for cells expressing said biological activity in the absence of said antibody or a variant thereof;

wherein the binding of the variable domain that can bind to an extracellular part of said first membrane protein does not block the binding of said first membrane protein to said second membrane protein and the binding of the variable domain that can bind to an extracellular part of said second membrane protein does not block the binding of said first membrane protein to said second membrane protein.

In some embodiments, said method is an in vitro or ex vivo method.

The invention further provides an antibody or a variant thereof that comprises a variable domain that can bind to an extracellular part of a first membrane protein and a variable domain that can bind to an extracellular part of a second membrane protein, wherein said first and second membrane protein are binding partners (i.e. members of a binding pair or a ligand and receptor pair) and wherein the binding of the variable domain that can bind to an extracellular part of said first membrane protein blocks the binding of said first membrane protein to said second membrane protein and/or the binding of the variable domain that can bind to all extracellular part of said second membrane protein blocks the binding of said first membrane protein to said second membrane protein. Such an antibody is useful in a method of inhibiting a biological activity mediated by the binding of said first membrane protein and said second membrane protein as described herein.

The invention further provides an antibody or a variant thereof that comprises a variable domain that can bind to an extracellular part of a first membrane protein and a variable domain that can bind to an extracellular part of a second membrane protein, wherein said first and second membrane protein are binding partners (i.e. members of a binding pair or a ligand and receptor pair) and wherein the binding of the variable domain that can bind to an extracellular part of said first membrane protein does not block the binding of said first membrane protein to said second membrane protein and the binding of the variable domain that can bind to an extracellular part of said second membrane protein does not block the binding of said first membrane protein to said second membrane protein. Such an antibody is useful in a method of enhancing a biological activity mediated by the binding of said first membrane protein and said second membrane protein.

The first membrane protein and second membrane protein are cellular membrane proteins that have at least an extracellular part. The binding of the two can result in a biological activity being expressed in the first cell, the second cell or both. In a method of the present invention the first and the second cell are preferably different cells. The different cells can be of the same type of cell, but typically they are different. A biological activity is an activity expressed by a cell that is measurable in the first and/or second cell or medium that surrounded the cell(s), in response to the binding of the first and second membrane protein. If a biological activity is expressed by both cells the activity may be the same but is typically different. Such binding of a first and second protein is often referred to as receptor-ligand binding. In the present invention both the receptor and the ligand are associated with and at least partly accessible on the extra-cellular side of the cell membrane of the respective cells. The term "receptor" is typically used for the protein that elicits a biological activity of the cell when bound to the ligand. The term "ligand" is typically used for the protein that binds to the receptor. The ligand in the present invention is also a membrane protein and binding of the ligand to the receptor can elicit a biological activity of the ligand comprising cell. A non-limiting example of such so-called bidirectional effects is the interaction of the HVEM/BTLA binding pair. Binding of HVEM to BTLA induces a biological activity in the HVEM expressing cell and a biological activity in the BTLA expressing cell. Thus in the present invention, the use of the term 'ligand' does not necessarily mean that the binding of the receptor to the ligand cannot elicit a biological activity in the cell comprising the ligand on the cellular-membrane. A protein is said to be a membrane protein on a cell if it has a transmembrane region that is present in the cell membrane of the cell it is on. The protein can have further transmembrane regions. In such case, all transmembrane regions that are present in a cell membrane are present in the cell membrane of the same cell.

A receptor and ligand are specific binding partners that typically interact (bind) to each other via non-covalent bonds. The binding is specific in that under physiological conditions the receptor and the ligand will typically only bind to each other and not to other proteins. Some receptors and ligands can specifically bind to a limited number of other binding partners. A non-limiting example is the receptor PD-1 which can interact with the binding partners PD-L1 and PD-L2.

The type of biological activity that is elicited depends on the binding partners. Binding can induce growth; change an activation state of a cell; elicit or inhibit the excretion of one or more cytokines; affect cytolytic function of a cell; etc. The biological activity is typically measured by measuring the response to binding by the receiving (receptor expressing) cell. PD-1/PD-L1 binding, for instance, is typically measured by detecting a biological activity of the PD-1 expressing cell. interaction of PD-1 by its ligands PD-L1 or PD-L2 induces biological activities such as inhibition of T-cell proliferation, inhibition of cytokine production, and inhibition of cytolytic function.

A biological activity is inhibited when the biological activity measured in the presence of the antibody or variant thereof is lower than the biological activity measured under otherwise identical conditions in the absence of the antibody or variant. A biological activity can be inhibited by at least 10, 20, 30, 40, 50, or preferably at least 60%. The biological activity is preferably inhibited by at least 70%, preferably at least 80%, preferably at least 90%. The biological activity is inhibited by at least 10, 20, 30, 40, 50, 60, 70, 80, or 90% when the biological activity measured in the presence of the antibody or variant thereof is correspondingly 10, 20, 30, 40, 50, 60, 70, 80, or 90% lower than the biological activity measured under otherwise identical conditions in the absence of the antibody or variant. A biological activity is typically inhibited when one of the variable domains of an antibody of the invention can block the binding of its target to a binding partner of the target. The biological activity is typically further inhibited when the antibody further comprises a variable domain that, hinds the mentioned binding partner of the target and blocks the binding of the binding partner to the target.

A biological activity is elicited and/or enhanced when the biological activity measured in the presence of the antibody or variant thereof is higher than the biological activity measured under otherwise identical conditions in the absence of the antibody or variant. A biological activity can be enhanced by at least 10, 20, 30, 40, 50, or preferably at least 60%. A biological activity is preferably enhanced by at least 70%, preferably at least 80%, preferably at least 90%. A biological activity is enhanced by at least 10, 20, 30, 40, 50, 60, 70, 80, or 90% when the biological activity measured in the presence of the antibody or variant thereof is correspondingly 10, 20, 30, 40, 50, 60, 70, 80, or 90% higher than the biological activity measured under otherwise identical conditions in the absence of the antibody or variant A biological activity is typically enhanced when both variable domains of an antibody of the invention do not block the binding of their targets to each other.

A suitable system is a cell culture wherein the first cell and second cell are provided. Another suitable system is an animal comprising the first cell and second cell. Other suitable systems are ex vivo systems wherein the cells are maintained in active form but wherein growth of the cell is not necessarily facilitated. A first and second cell can be incubated together under, for instance, assay conditions that not necessarily facilitate growth but allow biological activity to be measured.

Incubating said system under conditions that are permissive for cells expressing said biological activity mediated by the binding of said first membrane protein and said second membrane protein means that the system is maintained under conditions wherein the first and second cell can exhibit a biological activity as a result of the binding partners. In vivo incubation does not have to involve more than passing of sufficient time to allow the biological activity to become apparent.

A variable domain that "blocks" the binding of said first membrane protein to said second membrane protein interferes with binding of the first membrane protein to said second membrane protein. Such a variable domain can bind the first membrane or the second membrane protein. A blocking variable domain that binds for instance a first membrane protein can bind an epitope on said first membrane protein and compete with said second membrane protein for binding to the epitope. Such a blocking variable domain and the second membrane protein can also bind to different epitopes on said first membrane protein. In such cases the blocking activity can for instance be due to diminished binding of the second membrane protein, displacement of second membrane protein when it is already bound to said first membrane protein or may prevent binding to the first membrane protein through steric hindrance. All these and other mechanisms can, at least partially, prevent that said second membrane protein can bind to said first membrane protein. Variable domains that bind the first membrane protein or the second membrane protein can block the binding of the binding partners.

A variable domain that blocks the binding of a specific binding pair of membrane proteins as described herein typically reduces binding of the pair when compared to the binding in the absence of the variable domain. This is typically measured with an antibody comprising the variable domain. This is preferably measured in an in nitro assay. Typically this is done by incubating the variable domain with the membrane protein that it can bind to and subsequently incubating the mixture with the other member of the pair. The binding of the pair is then compared with the binding of the pair in the absence of the variable domain. A variable domain can completely prevent the binding of the first membrane protein to the second membrane protein. It can also partially prevent, the binding of the pair. A variable domain that blocks the binding of a specific binding pair of membrane proteins preferably reduces binding of the pair by at least 50%, preferably at least 60%, preferably at least 70%, preferably at least 80%, and more preferably at least 90% when compared to the binding in the absence of the variable domain. Blocking of binding by a variable domain is defined herein as the blocking obtained using a bivalent monoclonal antibody comprising said two of the same of said variable domains. The variable domain of course also blocks the binding when present in an antibody comprising said variable domain and a variable domain that binds a second target, where the second target can be the same or different than the target bound by the first variable domain. Specific variable domains that can bind an extracellular domain of PD-1 and that at least partially block the binding of PD1 to PD-L1 are variable domains that comprise the amino acid sequence of the VH of MF6076; MF6236; MF6256; MF6932; MF6935; MF6936; MF6972; MF6974; MF6982; MF6929; MF7699; MF7698; MF7687; MF7686; MF7685; or MF7684 (FIG. 3 and/or FIG. 13).

Specific variable domains that can bind an extracellular domain of PD-L1 and that block the binding of PD1 to PD-L1 are variable domains that comprise the amino acid sequence of the VH of MF5359; MF5377; MF5382; MF5424; MF5426; MF5439; MF5442; MF5553; MF5557; MF5561; MF5576; MF5594; MF5708; MF5442; MF7691; MF7690; MF7689; MF7688; MF7700; MF7701; MF7703; MF7694; MF7G93; MF7692; MF7697; MF7696; or MF7695 (FIG. 3 and/or FIG. 13).

A variable domain that does not block the binding of a specific binding pair of membrane proteins as described herein typically does not reduce binding of the pair when compared to the binding in the absence of the variable domain. This is typically measured with an antibody comprising the variable domain. This is preferably measured in an in vitro assay. Typically this is done by incubating the variable domain with the membrane protein that it can bind to and subsequently incubating the mixture with the other member of the pair. The binding of the pair is then compared with the binding of the pair in the absence of the variable domain.

Specific variable domains that can bind an extracellular domain of PD-L1 and that do not block the binding of PD1 to PD-L1 are variable domains that comprise the amino acid sequence of the VH of MF5361 (FIG. 3).

Functional aspects of variable domains in kind not necessarily in amount, such as binding to an antigen, blocking capacity of receptor ligand interaction, biological activity of a variable domain, etc. can be can be determined in various ways. Suitable formats are a FAB fragment or an antibody. A suitable antibody format is a monospecific bivalent antibody comprising two of the variable domains. Another suitable format is for instance a bispecific antibody comprising the variable domain to be tested and another variable domain. The other variable domain is preferably a variable domain with a neutral specificity with respect to the assay to be performed. A suitable neutral variable domain is a variable domain that can bind tetanus toxoid.

An antibody or variant thereof of the invention preferably comprises a variable domain that blocks the binding of its target membrane protein to a binding partner thereof. In this preferred embodiment a further variable domain of the antibody or variant thereof binds a binding partner of the target membrane protein. The variable domain that binds this binding partner can block the binding of the binding partner to the target membrane protein or it does not block the binding of the binding partner to the target membrane protein. In a preferred embodiment variable domain that binds this binding partner can block the binding of the binding partner to the target membrane protein.

In another embodiment an antibody or variant thereof of the invention comprises a variable domain that does not block the binding of its target membrane protein a binding partner thereof. In this preferred embodiment a further variable domain of the antibody or variant thereof binds a binding partner of the target membrane protein. The variable domain that binds this binding partner can block the binding of the binding partner to the target membrane protein or it does not block the binding of the binding partner to the target membrane protein. In a preferred embodiment variable domain that binds this binding partner does not block the binding of the binding partner to the target, membrane protein.

The invention further provides a method of inducing or stimulating an immune response of an immune cell, comprising providing an immune cell (first cell) that has a first membrane protein, preferably a member of the CD28 family on the cell membrane;

a second cell that has a second membrane protein, preferably a member of the B7 family or TNFRSF14 on the cell membrane;

providing an antibody or a variant thereof that comprises a variable domain that can hind to an extracellular part of said first membrane protein and a variable domain that can bind to an extracellular part of said second membrane protein, the method further comprising incubating said first cell and said second cell together with said antibody, thereby inducing or stimulating an immune response of said first cell.

The invention further provides a method of inducing or stimulating an immune response of an immune cell, comprising providing
- an immune cell (first cell) that has a first membrane protein, preferably member of the CD28 family on the cell membrane;
- a second cell that has a second membrane protein, preferably a member of the B7 family or TNFRSF14 on the cell membrane;
- providing an antibody or a variant thereof (first antibody) that comprises a variable domain that can bind to an extracellular part of said first membrane protein and a variable domain that can bind to an extracellular part of said second membrane protein;
- providing a further antibody or a variant (second antibody) thereof comprising a variable domain that can bind to an extracellular part of said first membrane protein and a variable domain that can bind to an extracellular part of said second membrane protein;
- wherein the first and second antibody bind
- different epitopes on said first membrane protein;
- different epitopes on said second membrane protein; or
- different epitopes on said first membrane protein and different epitopes on said first, membrane protein;
- the method further comprising incubating said first cell and said second cell together with said first and second antibody, thereby inducing or stimulating an immune response of said first cell.

The invention further provides a method of inducing or stimulating an immune response of an immune cell, comprising providing
- an immune cell (first cell) that has PD-1 on the cell membrane;
- a second cell that has PD-L1 on the cell membrane;
- providing an antibody or a variant thereof that comprises a variable domain that can bind to an extracellular part of PD-1 and a variable domain that can bind to an extracellular part of PD-L1, the method further comprising incubating said first cell and said second cell together with said antibody, thereby inducing or stimulating an immune response of said first cell. In some embodiments, said method is an in vitro or ex vivo method.

The invention further provides a method of inducing or stimulating an immune response of an immune cell, comprising providing
- an immune cell (first cell) that has PD-1 on the cell membrane;
- a second cell that has PD-L1 on the cell membrane;
- providing an antibody or a variant thereof (first antibody) that comprises a variable domain that can bind to an extracellular part of PD-1 and a variable domain that can bind to an extracellular part of PD-L1;
- providing a further antibody or a variant (second antibody) thereof comprising a variable domain that can bind to an extracellular part of PD-1 and a variable domain that can bind to an extracellular part of PD-L1;
- wherein the first and second antibody bind
- different epitopes on PD-1;
- different epitopes on PD-L1; or
- different epitopes on PD-1 and different epitopes on PD-L1;
- the method further comprising incubating said first cell and said second cell together with said first and second antibody, thereby inducing or stimulating an immune response of said first, cell. In some embodiments, said method is an in euro method.

Said immune response can be T-cell receptor (TCR) mediated or not. In a preferred embodiment said immune response is TCR-receptor mediated. Said immune response is preferably measured by measuring pro-inflammatory cytokine release by the immune cell. In a preferred embodiment the cytokine is IL-2. Changes in the level of IL-2 when compared to the absence of the antibodies indicate whether the immune response is affected by the antibodies. An increase indicated that the immune response is stimulated. A change from non-detectable tot detectably IL-2 is indicative for an induced immune response.

The first cell is preferably an immune cell. An immune cell is preferably a T-cell or NK-cell. In one embodiment said immune cell is a T-cell. The second cell is preferably an antigen presenting cell, a neoplastic cell, a virus infected cell, or an intracellular parasite infected cell. The first, cell is a cell that expresses said first, membrane protein on its cell membrane. The second cell is a cell that expresses said second membrane protein on its cell membrane. The cell membrane is also known as the plasma membrane or cytoplasmic membrane and is a biological membrane that separates the interior of a cell from the outside environment.

The invention further provides a composition or kit of parts comprising two or more antibodies or functional parts, derivatives and/or analogues thereof comprising an antibody or a variant thereof (first antibody) that comprises a variable domain that can bind to an extracellular part of a first membrane protein, preferably a member of the CD28 family and a variable domain that can bind to an extracellular part of a second membrane protein, preferably a member of the B7 family or TNFRSF14; and a further antibody or a variant thereof (second antibody) that comprises a variable domain that can bind to an extracellular part of said first membrane protein and a variable domain that can bind to an extracellular part of said second membrane protein,
- wherein the first and second antibody bind
- different epitopes on said first membrane protein;
- different epitopes on said second membrane protein; or
- different epitopes on said first membrane protein and different epitopes on said second membrane protein.

Embodiments comprising a method, a use, a composition or kit of parts comprising two or more antibodies or functional parts, derivatives and/or analogues thereof that have variable domains that bind the same first and second membrane proteins are also referred to as "Oligoclonics" embodiments. Examples of such Oligoclonics embodiments are embodiments with said first and second antibody. 'Oligoclonics' is a registered trademark. General methods for making such Oligoclonics® products are disclosed in WO 2013/157953 and WO2004/009618 and are incorporated here by reference.

In Oligoclonics embodiments the first and second antibody comprise variable domains that bind the same member of the CD28 family, for example PD-land the same member of the B7 family or TNFRSF14, for example PD-L1. Membranes that comprise a member of a family as described herein typically comprise a number and often a great number of individual proteins of the member on the membrane. Antibodies that have variable domains that bind the same member of a family can bind the same individual protein, but this is not necessarily so. An antibody of the invention that binds TNa membrane protein hinds an epitope on said membrane protein. An epitope is the part of an antigen, in this case the membrane protein that is recognized by the antibody. First and second antibodies that bind different epitopes on a membrane protein can bind the same individual protein on the membrane. To this end the different epitopes are preferably non-overlapping epitopes. In other words the different epitopes are sufficiently separated on the membrane protein that two antibodies can bind simultaneously to the same individual protein. It was surprisingly found that Oligoclonics (a combination of a first and second or more antibodies) can be more effective than the same amount of each of the antibodies alone.

A variable domain of the first antibody that can bind the member of the CD28 family preferably blocks the binding of the member to a binding partner thereof in the B7 family or TNFRSF14. The variable domain of the first antibody that can bind the member of the B7 family or TNFRSF14 preferably blocks the binding of the member to a binding partner thereof in the CD28 family. The variable domain of the second antibody that can bind the member of the CD28 family preferably blocks the binding of the member to its binding partner in the B7 family or TNFRSF14. The variable domain of the second antibody that can bind the member of the B7 family or TNFRSF14 preferably blocks the binding of the member to its binding partner in the CD28 family. Preferred combinations of blocking and non-blocking variable domains in said first and second antibody are indicated herein below.

|  |  | First antibody | | Second antibody | |
|---|---|---|---|---|---|
|  |  | CD28 family | B7 or TNFRSF14 | CD28 family | B7 or TNFRSF14 |
| com- | 1 | Blocking | Blocking | Non-blocking | Non-blocking |
| bina- | 2 | Blocking | Blocking | Non-blocking | Blocking |
| tion | 3 | Blocking | Blocking | Blocking | Non-blocking |
|  | 4 | Blocking | Blocking | Blocking | Blocking |

The above combinations are preferred combinations. The combinations specify that the variable domains of the first antibody are variable domains that block the binding of the member of the CD28 family to a binding partner thereof in the B7 family or TNFRSF14. The second antibody can have one or more variable domains that do not block this interaction. When analyzing Oligoclonics embodiments the antibody that comprises two blocking variable domains is assigned the qualification "first antibody". When the Oligoclonics comprises two or more antibodies that have two blocking variable domains then one of them is assigned the qualification "first antibody". Known binding partners for a member of the CD28 family or a member of the B7 family or TNFRSF14 are indicated herein above.

The first membrane protein is preferably a member of the CD28 family. Members of the CD28 family have a single extracellular immunoglobulin variable-like (IgV) domain followed by a short cytoplasmic tail. The members are expressed on cells of the immune system, either constitutively or induced. Members of the family include CD28, CTLA-4, PD-1, ICOS, BTLA, NKp30, and TMIGD2. The first membrane protein is preferably PD-1; CTLA-4; BTLA; or TMIGD2, preferably PD-1.

The second membrane protein is preferably a member of the B7 family, or TNFRSF14. The phrase "said member of the B7 family or TNFRSF14" means a member selected from the group of proteins consisting of the proteins of the B7 family and TNFRSF14. In a preferred embodiment the second membrane protein is a member of the B7 family. The B7 family is a collection of structurally related, cell-surface proteins, which bind to proteins on lymphocytes that regulate immune responses (CD28 family members). B7 family members are typically referred to as ligands, whereas members of the CD28 family are referred to as receptors. Activation of T and B lymphocytes is initiated by engagement of cell-surface, antigen-specific T-cell receptors or B-cell receptors, but, additional signals delivered simultaneously by one or more B7 ligands determine the ultimate immune response. These 'costimulatory' or 'coinhibitory' signals are delivered by B7 ligands through the CD28 family of receptors on lymphocytes. Interaction of B7-family members with costimulatory receptors augments immune responses, and interaction with coinhibitory receptors attenuates immune responses. Preferred members of the B7-family are CD80; CD86; ICOS-L; PD-L1; PD-L2; B7-H3, B7-H4; B7-H6 and B7-H7. B7 ligands are expressed in lymphoid and non-lymphoid tissues. B7-ligands to transmit a co-inhibitory signal are correlated with neoplasms, virus-infected cell and intra-cellular parasite infected cells and provide them with a capacity to evade or at least dampen an immune response against them. Manipulation of the signals delivered by B7 ligands has shown activity in the treatment of autoimmunity, inflammatory diseases and cancer. In a preferred embodiment the second membrane protein is PD-L1; PD-L2; ICOSL, CD80; CD86; B7-H3; B7-H4; TNFRSF14; B7-H6 or B7-H7. In a preferred embodiment the second membrane protein is PD-L1; PD-L2; CD80; CD86; B7-H4; TNFRSF14; or B7-H7. In a particularly preferred embodiment the second membrane protein is PD-L1; or PD-L2, preferably PD-L1.

In a particularly preferred embodiment the first membrane protein is PD-1 and the second membrane protein is PD-L1.

When the first membrane protein is CD28 it is preferred that the second membrane protein is CD80, CD8G or ICOSL, preferably CD80. Accordingly the antibody or a variant thereof is preferably an antibody or a variant thereof comprising a variable domain that can bind to an extracellular part of CD28 and a variable domain that can bind to an extra-cellular part of CD80; an extra-cellular part of CD86; or an extracellular part that binds ICOSL, preferably an extra-cellular part of CD80. CD28 and CD80 are binding partners. CD28 and CD8G are binding partners and CD28 and ICOSL are binding partners When the first membrane protein is CTLA-4 it is preferred that the second membrane protein is CD80, CD8G or ICOSL, preferably CD80. Accordingly the antibody or a variant thereof is preferably an antibody or a variant thereof comprising a variable domain that can bind to an extracellular part of CTLA-4 and a variable domain that can bind to an extra-cellular part of CD80 or an extra-cellular part of CD86, preferably an extra-cellular part of CD80. CTLA-4 and CD80 are binding partners. CTLA-4 and CD86 are binding partners and CTLA-4 and ICOSL are binding partners When the first membrane protein is ICOS it is preferred that the second membrane protein is ICOSL. Accordingly the antibody or a variant thereof is preferably an antibody or a variant thereof comprising a variable domain that can bind to an extra-cellular part of ICOS and a variable domain that can bind to an extra-cellular part of ICOSL. ICOS and ICOSL are binding partners.

When the first membrane protein is BTLA it is preferred that the second membrane protein is B7-H4 or TNFRSF14, preferably TNFRSF14. Accordingly the antibody or a variant thereof is preferably an antibody or a variant thereof comprising a variable domain that can bind to an extra-cellular part of BTLA and a variable domain that can bind to an extra-cellular part of B7-H4 or an extra-cellular part of TNFRSF14, preferably an extra-cellular part of TNFRSF14.

BTLA and B7-H4 are binding partners and BTLA and TNFRSF14 are binding partners.

When the first membrane protein is NKp30 it is preferred that the second membrane protein is B7-HG. Accordingly the antibody or a variant thereof is preferably an antibody or a variant, thereof comprising a variable domain that can bind to an extra-cellular part of NKp30 and a variable domain that can bind to an extra-cellular part of B7-HG. NKp30 and B7-HG are binding partners.

When the first membrane protein is TMIGD2 it is preferred that the second membrane protein is B7-H7 (HHLA2). Accordingly the antibody is preferably an antibody comprising a variable domain that can bind to an extra-cellular part of TMIGD2 and a variable domain that can bind to an extra-cellular part of B7-H7 (HHLA2). TMIGD2 and B7-H7 are binding partners.

When the first membrane protein is PD-1 it is preferred that the second membrane protein is PD-L1 or PD-L2, preferably PD-L1. PD-1 and PD-L1 are binding partners. PD-1 and PD-L2 are binding partners. PD-L1 and CD80 are binding partners. The antibody or a variant preferably comprises a variable domain that can bind to an extracellular part of PD-1 and a variable domain that can bind to an extra-cellular part of PD-L1 or an extracellular part of PD-L2, preferably an extracellular part, of PD-L1. The PD-1/PD-L1 antibody or a variant, thereof and the PD-1/PD-L2 antibody or a variant thereof are preferably antibodies or a variant thereof that have a PD-1 binding variable domain that, when provided as a bivalent monoclonal antibody that comprises two of said variable domains that bind PD-1, inhibits PD-1/PD-L1 mediated inhibition of T cell receptor mediated activation of a Jurkat cell in a range of 20-150% when compared to the inhibition obtained with the antibody Nivolumab on a Jurkat cell. Some embodiments provide an antibody or variant according to the invention, wherein said antibody or variant comprises a PD1-binding variable domain that, when present in a bivalent monospecific antibody format, counteracts PD-1/PD-L1 mediated inhibition of T cell receptor mediated activation of a Jurkat cell to a higher extent as compared to the antibody Nivolumab. The variable domain that binds an extracellular part of PD-1 is defined as a variable domain that when in a bivalent monospecific antibody format that comprises two of said variable domains that bind PD-1, inhibits PD-1/PD-L1 mediated inhibition of T cell receptor mediated activation of a Jurkat cell in a range of 20-150% when compared to the inhibition obtained with the antibody Nivolumab on a Jurkat cell.

The inhibition of PD-1 inhibition of TCR mediated activation of the Jurkat cell is preferably in the range of 50-150%, preferably 80-150%, more preferably 100-150% when compared to the inhibition obtained with the antibody Nivolumab on said Jurkat cell. In a preferred embodiment the inhibition is at least 100% when compared to the inhibition obtained with the antibody Nivolumab on said Jurkat cell. PD-1 inhibition of TCR mediated activation of Jurkat cells is preferably measured by measuring an immune dampening effect of PD-1/PD-L1 binding in Jurkat cells that are incubated under conditions that would, but for the presence of the antibody or variant thereof, be activated via the T-cell receptor. A suitable assay for determining inhibition is described in the examples. A suitable Jurkat cell line is described in the examples.

The variable domain that can bind to an extracellular part of PD-L1 is preferably a variable domain that, when present in a monovalent monoclonal antibody, binds PD-L1 with a $K_D$ of 0.1-14 nM as measured by surface plasmon resonance (SPR), preferably it has a $K_D$ of 0.5-14 nM, preferably a $K_D$ of 1-14 nM, preferably a Ku of 1-12 nM, preferably a $K_D$ of 2-12 nM as measured by SPR. In some preferred embodiments, an antibody or variant according to the invention comprises a variable domain that can bind to an extracellular part of PD-L1, wherein said variable domain, when present in a bispecific antibody that has a second variable domain that binds an irrelevant antigen such as Tetanus Toxoid, binds PD-L1 with a $K_D$ of lower than or equal to 4.27 nM, preferably of lower than or equal to 1.31 nM, preferably of lower than or equal to 1.27 nM, as measured by surface plasmon resonance (SPR). Preferably, said PD-L1 specific variable domain, when present in a bispecific antibody that has a second variable domain that binds an irrelevant antigen such as Tetanus Toxoid, binds PD-L1 with a $K_D$ of 0.9-4.27 nM, preferably with a $K_D$ of 0.94-4.27 nM, or with a $K_D$ of 0.9-1.31 nM, preferably with a $K_D$ of 0.94-1.31 nM. An antibody or variant according to the invention that comprises a variable domain that can bind to an extracellular part of PD-1 and a variable domain that can bind to an extracellular part of PD-L1 or an extra-cellular part of PD-L2, is preferably an antibody or a variant thereof that comprises a variable domain that can bind to an extracellular part of PD-1 and blocks the binding of PD-1 to PD-L1. It is preferred that the variable domain that can bind to an extracellular part of PD-L1 or an extracellular part of PD-L2 is a variable domain that blocks the binding of PD-1 to PD-L1 or PD-L2, respectively. A variable domain that can bind PD-1 and that blocks the binding of PD-1 to PD-L1 is preferably a domain that also blocks the binding of PD-1 to PD-L2. A variable domain of the invention may be one that can bind PD-L1 and that blocks the binding of PD-L1 to PD-1 and/or PD-L1 to CD80. This provides the advantage that these antibodies are also able to counteract tumor resistance to treatment via the PD-1/PD-L2 pathway.

An antibody or variant thereof according to the invention preferably reduces the activity of the binding of the binding pair. Reducing the activity is typically achieved by blocking the capacity of the binding pair to bind to each other. The capacity can be blocked by blocking any one or preferably both of the member of the binding pair. When the binding pair is coinhibitory the inhibitory or coinhibitory activity is reduced by the blocking. When the binding pair is costimulatory the costimulatory activity is reduced by the blocking.

The preference for a member of the CD28 family and a member of the B7 family or TNFRSF14 is the same in Oligoclonics embodiments.

The invention also provides a method of engaging and/or activating T-cells comprising providing a system comprising a T-cell and a cell to which said T-cell is to be engaged or activated, and providing said system with one or more antibodies that each comprise a variable domain that can bind a member of the CD28 family and a variable domain that can bind to an extracellular part of a member of the B7 family or TNFRSF14 and incubating said system under conditions that are permissive for the T-cell to become engaged and/or activated. In some embodiments, said method is an in vitro method. Some embodiments provide a method of engaging and/or activating T-cells comprising providing a system comprising a T-cell and a cell to which said T-cell is to be engaged or activated, and providing said system with one or more antibodies that each comprise a variable domain that can bind an extracellular part of PD-1 and a variable domain that can bind to an extracellular part of PD-L1 and incubating said system under conditions that are permissive for the T-cell to become engaged and/or activated. The cell to which said T-cell is to be engaged or activated is preferably an immune cell, for example an antigen presenting cell, a macrophage, a neoplastic cell, a virus infected cell, or an intracellular parasite infected cell. Engaging and/or activating T-cells directs T-cells to a specific target. Activating a T-cell is activating the T-cell receptor of said T-cell. Engaging a T-cell typically is activating a T-cell. Engagement can also direct an already activated T-cell to a target specified by the antibody. Conditions that are permissive for said T-cell to become engaged and/or activated are typically culture conditions but can also be incubation in an animal and thus may cover, inter alia, methods of treatment. The conditions are typically such that the T-cell is not engaged in the absence of the antibody. If collections of T-cells are measured some of these can be already engaged or activated provided that the collection contains sufficient T-cells that are not engaged or activated.

An antibody of the invention can bring two cells together in close proximity that allows the interactions between the cells mediated by proteins other than the receptor-ligand pair bound by the antibody of the invention. One such interaction is an interaction of a T-cell receptor of one cell and MHC on the other cell.

An antibody or a variant thereof that comprises a variable domain that can bind to an extracellular part of PD-1 preferably comprises a heavy chain variable region with a CDR3 region that comprises the amino acid sequence of the CDR3 region of the variable heavy chain region of MF6076; MF6236; MF6256; MF6226; MF6930; MF6932; MF6935; MF6936; MF6972; MF6974; MF6982; MF6929; MF7699; MF7698; MF7687; MF7686; MF7685; or MF7684 (FIG. 3 and/or FIG. 13).

An antibody or variant thereof that comprises a variable domain that can bind to an extracellular part of PD-1 preferably comprises a heavy chain variable region with a CDR1, CDR2 and CDR3 region that comprises the amino acid sequence of the CDR1, CDR2 and CDR3 of a variable heavy chain region of one of the VH depicted for MF6076; MF6236; MF6256; MF6226; MF6930; MF6932; MF6935; MF6936; MF6972; MF6974; MF6982; MF6929; MF7699; MF7698; MF7687; MF7686; MF7685; or MF7684 (FIG. 3 and/or FIG. 13). The CDR1, CDR2 and CDR3 sequences are preferably selected from the same VH region.

An antibody or variant thereof that comprises a variable domain that can bind to an extra-cellular part of PD-1 preferably comprises the amino acid sequence of the variable heavy chain region of MF6076; MF6256; MF6226; MF6930; MF6932; MF6935; MF6936; MF6972; MF6974; MF6982; MF6929; MF7699; MF7698; MF7687; MF7686; MF7685; or MF7684 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the VH of MF (FIG. 3 and/or FIG. 13). The amino acid insertion(s), deletion(s), substitution(s) or a combination thereof, if any, are preferably not in the amino acid sequence of the CDR regions.

An antibody or variant thereof that comprises a variable domain that can bind to an extracellular part of PD-L1 preferably comprises a heavy chain variable region with a CDR3 region that comprises the amino acid sequence of the CDR3 region of the variable heavy chain region of MF5359; MF5361; MF5377; MF5382; MF5424; MF5426; MF5439; MF5442; MF5553; MF5557; MF5561; MF5576; MF5594; MF5708; MF5442; MF7691; MF7690; MF7689; MF7688; MF7700; MF7701; MF7703; MF7694; MF7693; MF7692; MF7697; MF7696; or MF7695 (FIG. 3 and/or FIG. 13).

An antibody or variant thereof that comprises a variable domain that can bind to an extracellular part of PD-L1 preferably comprises a heavy chain variable region with a CDR1, CDR2 and CDR3 region that comprises the amino acid sequence of the CDR1, CDR2 and CDR3 of a variable heavy chain region of one of the VH depicted for MF5359; MF5361; MF5377; MF5382; MF5424; MF5426; MF5439; MF5442; MF5553; MF5557; MF5561; MF5576; MF5594; MF5708; MF5442; MF7691; MF7690; MF7689; MF7688; MF7700; MF7701; MF7703; MF7694; MF7693; MF7692; MF7697; MF7696; or MF7695 (FIG. 3 and/or FIG. 13). The CDR1, CDR2 and CDR3 sequences are preferably selected from the same VH region.

An antibody or variant thereof that comprises a variable domain that can bind to an extracellular part of PD-L1 preferably comprises the amino acid sequence of the variable heavy chain region of MF5359; MF5361; MF5377; MF5382; MF5424; MF5426; MF5439; MF5442; MF5553; MF5557; MF5561; MF5576; MF5594; MF5708; MF5442; MF7691; MF7690; MF7689; MF7688; MF7700; MF7701; MF7703; MF7694; MF7693; MF7692; MF7697; MF7696; or MF7695 having at most, 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the indicated MF (FIG. 3 and/or FIG. 13). The amino acid insertion(s), deletion(s), substitution(s) or a combination thereof, if any, are preferably not in the amino acid sequence of the CDR regions.

An antibody or variant thereof preferably comprises a variable domain that can bind to an extracellular part of PD-1 that blocks the binding of PD-1 to PD-L1 and a variable domain that can bind to an extracellular part of PD-L1 that, blocks the binding of PD-1 to PD-L1. The variable domain that can bind PD-1 and that blocks the binding of PD-1 to PD-L1 preferably also blocks the binding of PD-1 to PD-L2. The variable domain that can bind PD-L1 and that blocks the binding of PD-1 to PD-L1 preferably also blocks the binding of PD-L1 to CD80. This provides the advantage that, immunosuppression by tumor cells through interactions between PD-1 and CD80 can also be counteracted.

An antibody of the present invention or a variant thereof, for example a bispecific antibody or variant thereof, preferably comprises a variable domain that can bind to an extracellular part of PD-1 and that blocks the interaction of PD-1 with PD-L1 and/or PD-L2 and comprises a variable domain that can bind to an extracellular part of PD-L1 and that blocks the interaction of PD-L1 with PD-1 and/or CD80. Preferably, such a molecule of the present invention is capable of blockade of the full PD-1 axis, including PD-1 with PD-L1 or PD-L2, and PD-L1 with PD-1 and CD80.

The variable domain that binds an extracellular part of PD-L1 in such antibodies or variants thereof preferably comprises a VH region with the amino acid sequence of the CDR3 or the amino acid sequence of the CDR1, CDR2 and CDR3 of one of the VH of MF5359; MF5377; MF5382; MF5424; MF5426; MF5439; MF5442; MF5553; MF5557; MF5561; MF5576; MF5594; MF5708; MF5442; MF7691; MF7690; MF7689; MF7688; MF7700; MF7701; MF7703; MF7694; MF7693; MF7692; MF7697; MF7696; or MF7695 (FIG. 3 and/or FIG. 13). In a preferred embodiment, the variable domain that binds an extracellular part of PD-L1 comprises a VH region with the amino acid sequence of a VH of MF5359; MF5377; MF5382; MF5424; MF5426; MF5439; MF5442; MF5553; MF5557; MF5561; MF5576; MF5594; MF5708; MF5442; MF7691; MF7690; MF7689; MF7688; MF7700; MF7701; MF7703; MF7694; MF7693; MF7692; MF7697; MF7696; or MF7695 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the indicated MF (FIG. 3 and/or FIG. 13).

The variable domain that binds an extracellular part of PD-1 in this antibody or variant thereof preferably comprises a VH region with the amino acid sequence of the CDR3 or the amino acid sequence of the CDR1, CDR2 and CDR3 of one of the VH of MF6076; MF6236; MF6256; MF6226; MF6930; MF6932; MF6935; MF6936; MF6972; MF6974; MF6982; MF6929; MF7699; MF7698; MF7687; MF7686; MF7685; or MF7684 (FIG. 3 and/or FIG. 13). In a preferred embodiment, the variable domain that binds an extracellular part of PD-1 comprises a VH region with the amino acid sequence of the VH of MF6076; MF6236; MF6256; MF6226; MF6930; MF6932; MF6935; MF6936; MF6972; MF6974; MF6982; MF6929; MF7699; MF7698; MF7687; MF7686; MF7685; or MF7684 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the amino acid sequence of the VH of the indicated MF (FIG. 3 and/or FIG. 13). The amino acid insertion(s), deletion(s), substitution(s) or a combination thereof, if any, are preferably not in the amino acid sequence of the CDR regions. A particularly preferred combination in this antibody or variant thereof is the combination of variable domains that comprise the indicated sequence or variant thereof of MF5382 and MF6256.

Some embodiments provide an antibody or variant according to the present invention, that comprises a variable domain that can bind to an extracellular part of PD-1 and a variable domain that can bind to an extracellular part of PD-L1, wherein said antibody or variant has a stronger CD4+ T cell activation potential in a *Staphylococcus* enterotoxin B (SEB) assay as compared to an equimolar mix of:
  bivalent monospecific antibodies that comprise two of said variable domains that bind PD-1, and
  bivalent monospecific antibodies that comprise two of said variable domains that bind PD-L1. In view of its stronger CD4+ T cell activation potential, an antibody or variant according to these embodiments is preferred over an equimolar mix of the parental antibodies.

Some embodiments provide an antibody or variant according to the present invention, that comprises a variable domain that can bind to an extracellular part of PD-1 and a variable domain that can bind to an extracellular part of PD-L1 and that is able to activate T cells in an antigen-specific CD4+ T cell assay more strongly than benchmark antibody 5C4, or benchmark antibody YW243.55.S70, or a combination of benchmark antibodies 5C4 and YW243.55.S70. In view of its stronger antigen-specific CD4+ T cell activation potential, an antibody or variant according to this embodiment is preferred over the anti PD-1 benchmark antibody Nivolumab and the anti PD-L1 benchmark antibody Atezolizumab. Of note, an antibody or variant according to these embodiments is even preferred over a combination of Nivolumab and Atezolizumab.

Some embodiments provide an antibody or variant according to the present invention, that comprises a variable domain that can bind to an extracellular part of PD-1 and a variable domain that can bind to an extracellular part of PD-L1 and that has a stronger CD4+ T cell activation potential in a mixed lymphocyte reaction (MLR) assay as compared to benchmark antibody 5C4, which is based on Nivolumab, or benchmark antibody YW243.55.S70, which is based on Atezolizumab. Of note, in view of its stronger CD4+ T cell activation potential, an antibody or variant according to these embodiments is preferred over Nivolumab and Atezolizumab.

Some embodiments provide an antibody or variant according to the present invention, that comprises a variable domain that can bind to an extracellular part of PD-1 and a variable domain that can bind to an extracellular part of PD-L1 and that is capable of enhancing the proliferation of CD4+ and/or CD8+ tumor-infiltrating T cells. In view of its tumor-infiltrating T cell activation potential, an antibody or variant, according to these embodiments is particularly suitable for inducing or increasing a T cell mediated anti-tumor response.

Some embodiments provide an antibody or variant according to the present invention, that comprises a variable domain that can bind to an extracellular part of PD-1 and a variable domain that can bind to an extracellular part of PD-L1 and that is capable of inducing a stronger T cell mediated anti-tumor response in vivo as compared to a combination of benchmark antibodies MK-3475, which is based on Pembrolizumab, and YW243.55.S70, which is based on Atezolizumab. An antibody or variant according to these embodiments is thus particularly suitable for inducing or increasing a T cell mediated anti tumor response in vivo. Of note, in view of its stronger T cell activation potential, an antibody or variant according to these embodiments is preferred over Pembrolizumab and Atezolizumab.

As shown in Table 4, bispecific antibodies demonstrating blocking of at least 60% in a PD-1/PD-L1 reporter assay bispecific antibodies were formed when PD-1 specific Fab arm 6076 was combined with PD-L1 specific Fab arm MF5553, MF5359, MF5424, MF5561, MF5442 or MF5382.

An antibody or a variant thereof as described herein preferably comprises
  a PD-1 binding variable domain that comprises a VH region with the amino acid sequence of the CDR3 or the amino acid sequence of the CDR1, CDR2 and CDR3 of the VH of MF6076; and
  a PD-L1 binding variable domain that comprises a VH region with the amino acid sequence of the CDR3 or the amino acid sequence of the CDR1, CDR2 and CDR3 of the VH of MF5553; MF5359; MF5424; MF5561; MF5442 or MF5382, preferably MF5359; MF5424; MF5561; MF5442 or MF5382, preferably MF5359; MF5424; MF5561 or MF5442, preferably MF5359; MF5424 or MF5442, preferably MF5359 or MF5442 preferably MF5442 (FIG. 3).

An antibody or a variant thereof preferably comprises
  a PD-1 binding variable domain that comprises a VH region with the amino acid sequence of the VH of MF6076 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the amino acid sequence of the VH of MF6076 and;
  a PD-L1 binding variable domain that, comprises a VH region with the amino acid sequence of the VH of MF5553; MF5359; MF5424; MF5561; MF5442 or MF5382, preferably MF5359; MF5424; MF5561; MF5442 or MF5382, preferably MF5359; MF5424; MF5561 or MF5442, preferably MF5359; MF5424 or MF5442, preferably MF5359 or MF5442 preferably MF5442 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF (FIG. 3).

As shown in Table 4, bispecific antibodies demonstrating blocking of at least GO % in a PD-1/PD-L1 reporter assay were formed when PD-1 specific Fab arm MF6236 was combined with PD-L1 specific Fab arm MF5561, MF5442 or MF5382. An antibody or a variant thereof as described herein preferably comprises
- a PD-1 binding variable domain that comprises a VH region with the amino acid sequence of the CDR3 or the amino acid sequence of the CDR1, CDR2 and CDR3 of the VH of MF6236 (FIG. 3); and
- a PD-L1 binding variable domain that comprises a VH region with the amino acid sequence of the CDR3 or the amino acid sequence of the CDR1, CDR2 and CDR3 of the VH of MF5561; MF5442 or MF5382, preferably MF5561 or MF5442, preferably MF5442 (FIG. 3).

An antibody or a variant thereof preferably comprises
- a PD-1 binding variable domain that comprises a VH region with the amino acid sequence of the VH of MFG236 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the amino acid sequence of the VH of MF6236 (FIG. 3) and;
- a PD-L1 binding variable domain that comprises a VH region with the amino acid sequence of the VH of MF5561; MF5442 or MF5382, preferably MF5561 or MF5442, preferably MF5442 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF (FIG. 3).

As shown in Table 4, bispecific antibodies demonstrating blocking of at least 60% in a PD-1/PD-L1 reporter assay were formed when PD-1 specific Fab arm MF6974 was combined with PD-L1 specific Fab arm MF5424; MF5561; MF5442 or MF5382. An antibody or a variant thereof as described herein preferably comprises
- a PD-1 binding variable domain that comprises a VH region with the amino acid sequence of the CDR3 or the amino acid sequence of the CDR1, CDR2 and CDR3 of the VH of MF6974 (FIG. 3); and
- a PD-L1 binding variable domain that comprises a VH region with the amino acid sequence of the CDR3 or the amino acid sequence of the CDR1, CDR2 and CDR3 of the VH of MF5424; MF5561; MF5442 or MF5382, preferably MF5424; MF5561 or MF5442, preferably MF5424 or MF5442, preferably MF5442 (FIG. 3).

An antibody or a variant thereof preferably comprises
- a PD-1 binding variable domain that comprises a VH region with the amino acid sequence of the VH of MF6974 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the amino acid sequence of the VH of MF6974 (FIG. 3) and;
- a PD-L1 binding variable domain that comprises a VH region with the amino acid sequence of the VH of MF5424; MF5561; MF5442 or MF5382, preferably MF5424; MF5561 or MF5442, preferably MF5424 or MF5442, preferably MF5442 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF (FIG. 3).

As shown in Table 4, bispecific antibodies demonstrating blocking of at least 60% in a PD-1/PD-L1 reporter assay were formed when PD-1 specific Fab arm MF6935 was combined with PD-L1 specific Fab arm MF5424, MF5561, MF5442 or MF5382. An antibody or a variant thereof as described herein preferably comprises
- a PD-1 binding variable domain that comprises a VH region with the amino acid sequence of the CDR3 or the amino acid sequence of the CDR1, CDR2 and CDR3 of the VH of MF6935 (FIG. 3); and
- a PD-L1 binding variable domain that comprises a VH region with the amino acid sequence of the CDR3 or the amino acid sequence of the CDR1, CDR2 and CDR3 of the VH of MF5424; MF5561; MF5442 or MF5382, preferably MF5561; MF5442 or MF5382, preferably MF5442 or MF5382, preferably MF5382 (FIG. 3).

An antibody or a variant thereof preferably comprises
- a PD-1 binding variable domain that comprises a VH region with the amino acid sequence of the VH of MF6935 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the amino acid sequence of the VH of MF6935 (FIG. 3) and;
- a PD-L1 binding variable domain that comprises a VH region with the amino acid sequence of the VH of MF5424; MF5561; MF5442 or MF5382, preferably MF5561; MF5442 or MF5382, preferably MF5442 or MF5382, preferably MF5382 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF (FIG. 3).

As shown in Table 4, bispecific antibodies demonstrating blocking of at least 60% in a PD-1/PD-L1 reporter assay were formed when PD-1 specific Fab arm MF6936 was combined with PD-L1 specific Fab arm MF5576, MF5424, MF5561, MF5557, MF5442 or MF5382. An antibody or a variant thereof as described herein preferably comprises
- a PD-1 binding variable domain that comprises a VH region with the amino acid sequence of the CDR3 or the amino acid sequence of the CDR1, CDR2 and CDR3 of the VH of MF6936 (FIG. 3); and
- a PD-L1 binding variable domain that comprises a VH region with the amino acid sequence of the CDR3 or the amino acid sequence of the CDR1, CDR2 and CDR3 of the VH of MF5576; MF5424; MF5561; MF5557; MF5442 or MF5382, preferably MF5424; MF5561; MF5557; MF5442 or MF5382, preferably MF5424; MF5561; MF5442 or MF5382, preferably MF5561; MF5442 or MF5382, preferably MF5442 or MF5382, preferably MF5382 (FIG. 3).

An antibody or a variant thereof preferably comprises
- a PD-1 binding variable domain that comprises a VH region with the amino acid sequence of the VH of MF6936 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the amino acid sequence of the VH of MF6936 (FIG. 3) and;

a PD-L1 binding variable domain that comprises a VH region with the amino acid sequence of the VlA of MF5576; MF5424; MF5561; MF5557; MF5442 or MF5382, preferably MF5424; MF5561; MF5557; MF5442 or MF5382, preferably MF5424; MF5561; MF5442 or MF5382, preferably MF5561; MF5442 or MF5382, preferably MF5442 or MF5382, preferably MF5382 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF (FIG. 3).

As shown in Table 4, bispecific antibodies demonstrating blocking of at least, 60% in a PD-1/PD-L1 reporter assay were formed when PD-1 specific Fab arm MF6256 was combined with PD-L1 specific Fab arm MF5576, MF5424, MF5561, MF5557, MF5439, MF5442 or MF5382. An antibody or a variant thereof as described herein preferably comprises a PD-1 binding variable domain that comprises a VH region with the amino acid sequence of the CDR3 or the amino acid sequence of the CDR1, CDR2 and CDR3 of the VH of MF6256 (FIG. 3); and a PD-L1 binding variable domain that comprises a VH region with the amino acid sequence of the CDR3 or the amino acid sequence of the CDR1, CDR2 and CDR3 of the VH of MF5576; MF5424; MF5561; MF5557; MF5439; MF5442 or MF5382, preferably MF5576; MF5424; MF5561; MF5557; MF5442 or MF5382, preferably MF5576; MF5561; MF5557; MF5442 or MF5382, preferably MF5576; MF5561; MF5442 or MF5382, preferably MF5576; MF5442 or MF5382, preferably MF5442 or MF5382, preferably MF5382 (FIG. 3).

An antibody or a variant thereof preferably comprises a PD-1 binding variable domain that comprises a VH region with the amino acid sequence of the VH of MF6256 having at, most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the VH of MF6256 (FIG. 3) and;

a PD-L1 binding variable domain that comprises a VH region with the amino acid sequence of the VH of MF5576; MF5424; MF5561; MF5557; MF5439; MF5442 or MF5382, preferably MF5576; MF5424; MF5561; MF5557; MF5442 or MF5382, preferably MF5576; MF5561; MF5557; MF5442 or MF5382, preferably MF5576; MF5561; MF5442 or MF5382, preferably MF5576; MF5442 or MF5382, preferably MF5442 or MF5382, preferably MF5382 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF (FIG. 3).

In some preferred embodiments, an antibody or a variant, thereof as described herein comprises;

a PD-1 binding variable domain that comprises a VH region with the amino acid sequence of the CDR3 or the amino acid sequence of the CDR1, CDR2 and CDR3 of the VH of MF6076; and a PD-L1 binding variable domain that comprises a VH region with the amino acid sequence of the CDR3 or the amino acid sequence of the CDR1, CDR2 and CDR3 of the VH of MF5442; MF7691; MF7690; MF7689; MF7688; MF7700; MF7701; MF7703; MF7694; MF7693; MF7692; MF7697; MF7696; or MF7695, preferably MF7703 or MF7689 (FIG. 3 and/or FIG. 13).

An antibody or a variant thereof preferably comprises a PD-1 binding variable domain that comprises a VH region with the amino acid sequence of the VH of MF6076 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the amino acid sequence of the VH of MF6076 and;

a PD-L1 binding variable domain that comprises a VH region with the amino acid sequence of the VH of MF5442; MF7691; MF7690; MF7689; MF7688; MF7700; MF7701; MF7703; MF7694; MF7693; MF7692; MF7697; MF7696; or MF7695, preferably MF7703 or MF7689 having at, most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF (FIG. 3 and/or FIG. 13).

In some preferred embodiments an antibody or a variant thereof as described herein comprises;

a PD-1 binding variable domain that comprises a VH region with the amino acid sequence of the CDR3 or the amino acid sequence of the CDR1, CDR2 and CDR3 of the VH of MF6974 (FIG. 3); and a PD-L1 binding variable domain that comprises a VH region with the amino acid sequence of the CDR3 or the amino acid sequence of the CDR1, CDR2 and CDR3 of the VH of MF7703 or MF7689, preferably MF7703 or MF7689, more preferably MF7689 (FIG. 3 and/or FIG. 13).

An antibody or a variant thereof preferably comprises:

a PD-1 binding variable domain that comprises a VH region with the amino acid sequence of the VH of MF6974 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the amino acid sequence of the VH of MF6974 (FIG. 3) and;

a PD-L1 binding variable domain that comprises a VH region with the amino acid sequence of the VH of MF7703 or MF7689, preferably MF7703 or MF7689, more preferably MF7689, having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF (FIG. 3 and/or FIG. 13).

In some preferred embodiments, an antibody or a variant thereof as described herein comprises:

a PD-1 binding variable domain that comprises a VH region with the amino acid sequence of the CDR3 or the amino acid sequence of the CDR1, CDR2 and CDR3 of the VH of MF7686 (FIG. 13); and a PD-L1 binding variable domain that, comprises a VH region with the amino acid sequence of the CDR3 or the amino acid sequence of the CDR1, CDR2 and CDR3 of the VH of MF5359, MF5361, MF5377, MF5382, MF5424, MF5426, MF5439, MF5442, MF5553, MF5557, MF5561, MF5576, MF5594, MF5708, MF7703 or MF7689, preferably MF7703 or MF7689, more preferably MF7703 (FIG. 3 and/or FIG. 13).

An antibody or a variant thereof preferably comprises:
a PD-1 binding variable domain that comprises a VH region with the amino acid sequence of the VH of MF7686 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the VH of MF7686 (FIG. 13) and;
a PD-L1 binding variable domain that comprises a VH region with the amino acid sequence of the VH of MF5359, MF5361, MF5377, MF5382, MF5424, MF5426, MF5439, MF5442, MF5553, MF5557, MF5561, MF5576, MF5594, MF5708, MF7703 or MF7689, preferably MF7703 or MF7689, more preferably MF7703, having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF (FIG. 3 and/or FIG. 13).

Some preferred embodiments provide an antibody or variant thereof according to the invention that comprises a variable domain that can bind to an extracellular part of PD-1 and wherein said variable domain that can bind to an extracellular part of PD-1 comprises:
a heavy chain CDR3 sequence that is identical to the heavy chain CDR3 sequence of a variable region selected from the group consisting of MF6974, MF6076 and MF7686; or
a heavy chain CDR3 sequence that deviates in no more than three, preferably no more than two, more preferably no more than one amino acid from the heavy chain CDR3 sequence of MF6974 or MF6076 or MF7686; or
heavy chain CDR1, CDR2 and CDR3 sequences that are identical to the heavy chain CDR1, CDR2 and CDR3 sequences of a variable region selected from the group consisting of MF6974, MF6076 and MF7686; or
heavy chain CDR1, CDR2 and CDR3 sequences that deviate in no more than three, preferably no more than two, more preferably no more than one amino acid from the heavy chain CDR1, CDR2 and CDR3 sequence of MF6974 or MF6076 or MF7686.

Some preferred embodiments provide an antibody or variant thereof according to the invention that comprises a variable domain that can bind to an extracellular part of PD-1 and wherein said variable domain that can bind to an extracellular part of PD-1 comprises:
a heavy chain variable region that comprises the amino acid sequence of MF6974 or MF6076 or MF7686, or
a heavy chain variable region having a sequence that is at least 80%, or at least 85%, or at least 90%, or at least 91%, or at least 92%, or at least 93%, or at least, 94%, or at least 95%, or at, least 96%, or at least, 97%, or at least 98%, or at, least 99%, identical to the amino acid sequence of MF6974 or MF6076 or MF7686.

Some preferred embodiments provide an antibody or variant thereof according to the invention that comprises a variable domain that can bind to an extracellular part of PD-L1 and wherein said variable domain that can bind to an extracellular part of PD-L1 comprises:
a heavy chain CDR3 sequence that is identical to the heavy chain CDR3 sequence of a variable region selected from the group consisting of MF7689 and MF7703; or
a heavy chain CDR3 sequence that deviates in no more than three, preferably no more than two, more preferably no more than one amino acid from the heavy chain CDR3 sequence of MF7689 or MF7703; or
heavy chain CDR1 and CDR2 and CDR3 sequences that are identical to the heavy chain CDR1 and CDR2 and CDR3 sequences of a variable region selected from the group consisting of MF7689 and MF7703; or
heavy chain CDR1 and CDR2 and CDR3 sequences that deviate in no more than three, preferably no more than two, more preferably no more than one amino acid from the heavy chain CDR1 and CDR2 and CDR3 sequences of MF7689 or MF7703.

Some preferred embodiments provide an antibody or variant thereof according to the invention that comprises a variable domain that can bind to an extracellular part of PD-L1 and wherein said variable domain that can bind to an extracellular part of PD-L1 comprises:
a heavy chain variable region that comprises the amino acid sequence of MF7689 or MF7703, or
a heavy chain variable region having a sequence that is at least 80%, or at least 85%, or at least 90%, or at least 91%, or at least 92%, or at least 93%, or at least 94%, or at least 95%, or at least 96%, or at least 97%, or at least 98%, or at least 99%, identical to the amino acid sequence of MF7689 or MF7703.

Some preferred embodiments provide an antibody or variant thereof according to the invention that comprises a variable domain that can bind to an extracellular part of PD-1 and a variable domain that can bind to an extracellular part of PD-L1, wherein said variable domain that can bind to an extracellular part of PD-1 comprises heavy chain CDR1, CDR2 and CDR3 sequences that are identical to the heavy chain CDR1, CDR2 and CDR3 sequences of a variable region selected from the group consisting of MF6974, MF6076 and MF7686, and wherein said variable domain that can bind to an extracellular part of PD-L1 comprises heavy chain CDR1 and CDR2 and CDR3 sequences that are identical to the heavy chain CDR1 and CDR2 and CDR3 sequences of a variable region selected from the group consisting of MF7689 and MF7703.

Some preferred embodiments provide an antibody or variant thereof according to the invention that comprises a variable domain that can bind to an extracellular part of PD-1 and a variable domain that can bind to an extracellular part of PD-L1, wherein said variable domain that can bind to an extracellular part of PD-1 comprises heavy chain CDR1, CDR2 and CDR3 sequences that are identical to the heavy chain CDR1, CDR2 and CDR3 sequences of MF6974, and wherein said variable domain that can bind to an extracellular part of PD-L1 comprises heavy chain CDR1 and CDR2 and CDR3 sequences that are identical to the heavy chain CDR1 and CDR2 and CDR3 sequences of MF7689. As shown in the Examples, an antibody or variant according to this embodiment has a good PD-1/PD-L1 blocking activity and a strong T cell activation potential.

Some embodiments provide an antibody or variant thereof according to the invention that comprises a variable domain that can bind to an extracellular part of PD-1 and a variable domain that can bind to an extracellular part of PD-L1, wherein said variable domain that can bind to an extracellular part of PD-1 comprises heavy chain CDR1, CDR2 and CDR3 sequences that are identical to the heavy chain CDR1, CDR2 and CDR3 sequences of MF7686, and wherein said variable domain that can bind to an extracellular part of PD-L1 comprises heavy chain CDR1 and CDR2 and CDR3 sequences that are identical to the heavy chain CDR1 and CDR2 and CDR3 sequences of MF7703. As shown in the Examples, an antibody or variant according to this embodiment has a good PD-1/PD-L1 blocking activity and a strong T cell activation potential.

In another embodiment an antibody or a variant thereof comprises a variable domain that can bind to an extracellular part of PD-L1 that does not block the binding of PD-1 to PD-L1. The variable domain that binds an extracellular part of PD-L1 in this antibody or a variant thereof preferably comprises the amino acid sequence of the CDR3 or the amino acid sequence of the CDR1, CDR2 and CDR3 of the VH of MF5361 (FIG. 3). In a preferred embodiment, the variable domain that binds an extracellular part of PD-L1 comprises the amino acid sequence of a VH of MF5361 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the indicated MF.

The mentioned at most 15, preferably 1, 2, 3, 4, 5, 6, 7, 8, 9 or 10 and preferably 1, 2, 3, 4 or 5 amino acid substitutions in the mentioned H, VH, L and VL regions are preferably conservative amino acid substitutions, the insertions, deletions, substitutions or a combination thereof are preferably not in the CDR3 region of the H, VH, L or VL chain, preferably not in the CDR1, CDR2 or CDR3 region of the VH or VL chain and preferably not in the FR4 region.

A method as described herein preferably uses an antibody or a variant thereof as described herein.

An antibody or variant thereof, for example a part, derivative, or analogue thereof according to the invention preferably comprises two variable domains as described. Such an antibody is preferably a bispecific antibody or a variant thereof. Two or more antibodies or variants thereof can be linked together. Various methods are known in the art. A suitable method is conjugation. In addition, the technology of making multi-specific antibodies has progressed to also include bispecific antibodies that have the same overall structure as a normal mono-specific antibody but wherein the two arms of the antibody each bind a different target. The bispecific antibody or variant thereof preferably has two heavy chains with compatible heterodimerization domains. The light chain is preferably a Gammon light chain. Some embodiments provide an antibody or variant according to the invention, wherein the antigen binding sites of said antibody or variant consist of one immunoglobulin variable domain that can bind an extracellular part of PD-1 and one immunoglobulin variable domain that can bind an extracellular part of PD-L1 or PD-L2. An antibody according to the invention is preferably a full length bispecific antibody that consists of two heavy chains with compatible heterodimerization domains. In some embodiments, an antibody according to the invention is an IgG, preferably IgG1 or IgG3 or IgG4, more preferably IgG1 or IgG4, most preferably IgG1. An IgG format typically provides the advantage of a longer half-life, and/or a reduced immunogenicity, as compared to other formats.

In some embodiments, an antibody or variant according to the invention is monovalent for PD-1 and monovalent for PD-L1.

The light chain of an antibody or variant according to the invention is preferably a common light chain.

As used herein, the term "conjugate" refers to two or more molecules that have been covalently joined, optionally by a linking region. For example, in some embodiments, a conjugate is a first, protein or non-protein moiety joined to a second protein or non-protein moiety by a linking region. For example, in some embodiments of a binding molecule of the invention it comprises or consists of two or more antibodies that have been covalently joined. A conjugate is not limited to a first and second moiety but in some embodiments may also have a third, fourth or more moieties joined by further linking regions. As described elsewhere in this application, examples of protein moieties include, but are not limited to: a polypeptide, a peptidomimetic or an antibody (or antibody part, derivative, or analogue, as described elsewhere in the application). Examples of non-protein moieties include, hut are not limited to aptamers. Numerous types of linker can be used, and the linker will be selected to be appropriate according to the molecule types in the conjugate and on the desired properties of the linker (length, flexibility, resistance to protease activity and other similar characteristics). Such linkers may comprise nucleotides, polypeptides, or a suitable synthetic material. For example, a linker may be a flexible peptide linker. In certain embodiments, the linker may be a cleavable linker, allowing the parts of the conjugate to be separated from each other. In other embodiments, a peptide linker might be a helical linker. Various examples and kits for linking proteins and other molecules are well known in the art. As used herein, the term "fusion protein" refers to a protein that comprises two or more polypeptides or proteins that have been joined at the DNA level by recombination and are expressed together as a single polypeptide. A fusion protein may also comprise a peptide linking region also encoded by the DNA and expressed together with the fusion protein. A peptide linker that is part of a fusion protein may be designed to have particular characteristics such as flexibility, hydrophilicity, protease-resistance, cleavability etc. All these properties can be designed within the DNA sequence and methods for designing linkers are well known in the art. For example, antibodies can be linked together by methods well-known in the art, and as described herein, to form bispecific or multi-targeting antibodies. Furthermore, bispecific, antibodies can be constructed by various methods known in the art, for example, by using technology such as Biclonics® (see for instance WO2013/157954). A bispecific monoclonal antibody (BsMAb, BsAb) typically comprises binding domains of two different monoclonal antibodies and consequently binds to two different epitopes. Biclonics® molecules, but also other full length IgG bispecific antibodies have two different, antigen binding specificities encoded by two different variable regions of a full length IgG molecule of a Fab of a scFv. Biclonics® can be produced by co-transfection of individual cells with genetic constructs encoding two different common light chain (cLC) antibodies as detailed elsewhere herein. CH3 engineering ensures efficient hetero-dimerization and formation of essentially pure bispecific antibodies.

An antibody of the present invention is preferably a bispecific antibody. Antibodies typically bind their target via the so-called antigen binding site. An unmodified antigen-binding site is typically formed by and present in a variable domain of the antibody. A variable domain contains the antigen-binding site. A variable domain that can bind an antigen is a variable domain comprising an antigen-binding site that can bind to an antigen.

An antibody variable domain typically comprises a heavy chain variable region (VH) and a light chain variable region (VL). The antigen-binding site can be present in the combined VH/VL variable domain, or in only the VH region or only the VL region. When the antigen-binding site is present in one of the two regions of the variable domain, the counterpart variable region can contribute to the folding and/or stability of the binding variable region, but does not significantly contribute to the binding of the antigen itself.

As used herein, antigen-binding refers to the typical binding capacity of an antibody to its antigen. Binding of an antibody to an antigen can be assessed in various ways. One way is to incubate the antibody with the antigen (preferably cells expressing the antigen), removing unbound antibody (preferably by a wash step) and detecting bound antibody by means of a labeled antibody that binds to the bound antibody.

Antigen binding by an antibody is typically mediated through the complementarity determining regions (CDR) of the antibody and the specific three-dimensional structure of both the antigen and the variable domain allowing these two structures to bind together with precision (an interaction similar to a lock and key), as opposed to random, non-specific sticking of proteins. As an antibody typically recognizes part of an antigen called the epitope of an antigen, and as such epitope may be present in other compounds as well, antibodies according to the present invention may recognize other proteins as well, if such other compounds contain the same epitope. Hence, the term "binding" does not exclude binding of the antibodies to another protein or protein(s) that contain the same epitope. Such other protein(s) is preferably not a human protein.

An antibody typically does not bind to other proteins than the specified target protein on the membrane of cells in a post-natal, preferably adult human.

A variable domain in an antibody or a variant thereof of the invention that can bind an extracellular part of a member of the CD28 family binds to specified member and, under otherwise identical conditions, at least 100-fold lower to the extracellular part of another member of the CD28 family of the same species. For instance, a variable domain of an antibody or a variant thereof that binds PD-1 binds to PD-1 and, under otherwise identical conditions, at least a 100-fold lower to the CD28, CTLA4, ICOS, BTLA, NKp30 and TMIGD2 of the same species. Of course, when an antibody or a variant thereof is designed to bind to two or more members of the family, the binding to the two or more members can be essentially the same. In the present invention it is preferred that respective antibodies each bind to only one member of a CD28 family member. Considering that the CD28-family is a family of cell surface molecules, the binding is typically assessed on cells that express a member on a cell surface.

A variable domain in an antibody or a variant thereof of the invention that can bind an extracellular part of a member of the B7 family or TNFRSF14 binds to specified molecule and, under otherwise identical conditions, at least 100-fold lower to the extracellular part of another member of the B7 family or TNFRSF14 of the same species. For instance, a variable domain of an antibody or a variant thereof that binds PD-L1 binds to PD-L1 and, under otherwise identical conditions, at least a 100-fold lower to the CD80, CD86, ICOSL, PD-L2, B7-H3, B7-H4, B7-HG and B7-117 of the same species. Of course, when an antibody or a variant thereof is designed to bind to two or more members of the family, the binding to the two or more members can be essentially the same. In the present invention it is preferred that respective antibodies each bind to only one member of a B7 family member or TNFRSF14. Considering that the B7-family is a family of cell surface molecules, the binding is typically assessed on cells that, express a member on a cell surface.

A CD28 family member binding variable domain of an antibody or variant thereof as described herein and that blocks the binding of the member to one or more of its binding partners; inhibits a biological activity that would otherwise be exhibited by a cell comprising the member when bound to the mentioned binding partner. An antibody comprising said variable domain possesses the same activity in kind, not necessarily in amount.

A B7 family member or TNFRSF14 binding variable domain of an antibody or variant thereof as described herein and that blocks the binding of the member or TNFRSF14 to one or more of its binding partners; typically inhibits a biological activity that would otherwise be exhibited by a cell comprising the member or TNFRSF14 when bound to the mentioned binding partner. An antibody comprising said variable domain possesses the same activity in kind, not, necessarily in amount.

An antibody comprising a variable domain that can bind an extracellular part of a CD28 family member and a variable domain that can bind a binding partner thereof selected from the B7 family or TNFRSF14 and wherein both variable domains do not block the binding of the CD28 family member to said binding partner; typically does not inhibit a biological activity that would otherwise be exhibited by a cell comprising the CD28 family member or the B7 family member or TNFRSF14 when bound to the mentioned binding partner.

The term "antibody" as used herein means a proteinaceous molecule, preferably belonging to the immunoglobulin class of proteins, containing one or more variable domains that bind an epitope on an antigen, where such domains are derived from or share sequence homology with the variable domain of an antibody. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is specifically bound by the binding domain. The affinity is a measure for the strength of binding to a particular antigen or epitope. Antibodies such as the bispecific antibodies of the present invention typically comprise the constant domains (Fe part) of a natural antibody, which may be engineered as described elsewhere herein, for instance to reduce ADCC and/or CDC activity. An antibody of the invention is typically a bispecific full length antibody, preferably of the human IgG subclass.

The terms 'variable domain', 'VH/VL pair', 'VH/VL' are used herein interchangeably. A variable domain is composed of the variable region of a heavy chain and a variable region of a light chain. The variable region of a heavy chain is typically formed by a rearranged VDJ region. A variable region of a light chain is typically formed by a rearranged VJ region. The VDJ/VJ regions can now also be artificially produced using for instance the large body of sequence information that is available of functional antibodies.

An antibody of the invention is preferably a "fill length" antibody. The term 'full length' according to the invention is defined as comprising an essentially complete antibody, without one or more artificially added moieties which a size of larger than 20 amino acid residues, such as for instance additional antigen binding sites or additional activation sites or additional ligands or additional ligand-binding moieties. A full length antibody, however, does not necessarily have all functions of an intact antibody. For the avoidance of doubt, a full length antibody contains two heavy and two light chains. Each chain contains constant (C) and variable (V) regions, which can be broken down into domains designated CH1, CH2, CH3, VH for the heavy chain, and CL, VL for the light chain. The domains of the heavy chains are preferably present in the order of a natural antibody (VH-CH1-CH2-CH3, meaning that the VH domain is adjacent to the CH1 domain, followed by a CH2 domain and subsequently followed by a CH3 domain). The domains of the light chains are also preferably present in the order of a natural antibody (VL-CL: meaning that the VL domain is adjacent to the CL domain). An antibody binds to antigen via the variable domains contained in the Fab fragment portion. The antibody can interact with molecules and cells of the immune system through the constant domains, mostly through the Fc portion.

In some embodiments, an antibody of the invention is an IgG, preferably a full length IgG. Full length IgG antibodies are preferred because of their typically favorable half-life and the desire to stay as close to fully autologous (human) molecules for reasons of immunogenicity. In some embodiments, an antibody of the invention is a full length IgG1, a full length IgG2, a full length IgG3 or a full length IgG4 antibody.

Full length antibodies according to the invention encompass antibodies wherein mutations may be present that provide desired characteristics or are just alternatives to the ones in the original chain. Such mutations should not be deletions of substantial portions of any of the regions. However, antibodies wherein one or several amino acid residues are acid inserted, deleted, substituted or a combination thereof, without essentially altering the antigen binding characteristics of the resulting antibody are embraced within the term "full length antibody". For instance, an IgG antibody can have 1-20 amino acid residue insertions, substitutions, deletions or a combination thereof in the constant region.

An antibody or a variant thereof of the invention is preferably a bispecific antibody or a variant thereof. In a preferred embodiment it is a bispecific IgG antibody with reduced effector function. In a preferred embodiment an antibody of the invention is a bispecific full length antibody. An antibody of the invention is preferably a bispecific full length IgG antibody, preferably mutated in the CH2/lower hinge region to reduce effector function. IgG1 which is mutated in the CH2/lower hinge region to reduce effector function is favored based on its long circulatory half-life in man. In order to prevent any immunogenicity in humans it is preferred that the bispecific antibody according to the invention is a human antibody.

The term 'bispecific' (bs) means that one part of the antibody (as defined above) binds to one epitope on an antigen whereas a second part binds to a different epitope on either the same antigen, or a different antigen. The different epitopes are typically present on different antigens. The different epitopes can, however, also be present on the same antigen. According to the present invention, said first and second antigens are in fact two different proteins. A preferred bispecific antibody is an antibody that comprises parts of two different, monoclonal antibodies and consequently can bind to two different epitopes, preferably on two different antigens. Dependent on the expression level, (sub-) cellular localization and stoichiometry of the two antigens recognized by a bispecific antibody, both Fab arms of the antibody may or may not simultaneously bind their epitope. One arm of the bispecific antibody typically contains the variable domain of one antibody and the other arm contains the variable domain of another antibody (i.e. one arm of the bispecific antibody is formed by one heavy chain paired with one light chain whereas the other arm is formed by a different heavy chain paired with a light chain). The heavy chain variable regions of the bispecific antibody of the invention are typically different from each other, whereas the light chain variable regions are preferably the same in the bispecific antibodies of the invention. A bispecific antibody wherein the different heavy chain variable regions are associated with the same or a common, light chain variable region is also referred to as a bispecific antibody with a common light chain variable region (cLcv). It, is preferred that, the light chain constant region is also the same. Such bispecific antibodies are referred to as having a common light chain (cLc). Further provided is therefore a bispecific antibody according to the invention, wherein both arms comprise a common light chain.

Bispecific antibodies as described herein preferably comprise a common light chain variable domain, preferably a common light chain. The term 'common light chain' according to the invention refers to light chains which may be identical or have some amino acid sequence differences while the binding specificity of the full length antibody is not affected. It is for instance possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms 'common light chain', 'common LC', 'cLC', 'single light chain' with or without the addition of the term 'rearranged' are all used herein interchangeably. The terms 'common light chain variable region', 'common VL', 'common LCv', 'cLCv', 'single VL' with or without the addition of the term 'rearranged' are all used herein interchangeably. It is a preferred aspect of the present invention that a bispecific antibody has a common light chain (variable region) that can combine with at least two, and preferably a plurality of heavy chains (variable regions) of different binding specificity to form antibodies with functional antigen binding domains (WO2004/009618, WO2009/157771, Merchant et al. 1998 and Nissim et al. 1994). The common light chain (variable region) is preferably a human light chain (variable region). A common light chain (variable region) preferably has a germline sequence. A preferred germline sequence is a light chain variable region that is frequently used in the human repertoire and has good thermodynamic stability, yield and solubility. A preferred germline light chain is O12. A common light chain is preferably the rearranged germline human kappa light chain IgVκ1-39*01/IGJκ1*01 (FIG. 1A). The common light chain variable region is preferably the variable region of the rearranged germline human kappa light chain IgVκ1-39*01/IGJκ1*01. A common light chain preferably comprises a light chain variable region as depicted in FIG. 1B, or 1D with 0-5 amino acid insertions, deletions, substitutions, additions or a combination thereof. The common light preferably further comprises a light chain constant region, preferably a kappa light chain constant region. A nucleic acid that encodes the common light chain can be codon optimized for the cell system used to express the common light chain protein. The encoding nucleic acid can deviate from a germ-line nucleic acid sequence.

In a preferred embodiment the light chain comprises a light chain region comprising the amino acid sequence of an O12/IgVκ1-3901 gene segment as depicted in FIG. 1A with 0-10, preferably 0-5 amino acid insertions, deletions, substitutions, additions or a combination thereof. The phrase "O12 light chain" will be used throughout the specification as short for "a light chain comprising a light chain variable region comprising the amino acid sequence of an O12/IgVκ1-3901 gene segment as depicted in FIG. 1A with 0-10, preferably 0-5 amino acid insertions, deletions, substitutions, additions or a combination thereof. IgVκ1-39 is short for Immunoglobulin Variable Kappa 1-39 Gene. The gene is also known as Immunoglobulin Kappa Variable 1-39; IGKV139; IGKV1-39; O12a or O12. External Ids for the gene are HGNC: 5740; Entrez Gene: 28930; Ensembl: ENSG00000242371. A preferred amino acid sequence for IgVκ1-39 is given in FIG. 1E. This lists the sequence of the V-region. The V-region can be combined with one of five J-regions. FIGS. 1B and 1D describe two preferred sequences for IgVκ1-39 in combination with a J-region. The joined sequences are indicated as IGKV1-39/jk1 and IGKV1-39/jk5; alternative names are IgVκ1-39*01/IGJκ1*01 or IgVκ1-39*01/IGJκ5*01 (nomenclature according to the IMGT database worldwide web at imgt.org).

It is preferred that the O12/IgVκ1-39*01 comprising light chain variable region is a germline sequence. It is further preferred that the IGJκ1*01 or /IGJκ5*01 comprising light chain variable region is a germline sequence. In a preferred embodiment, the IGKV1-39/jk1 or IGKV1-39/jk5 light chain variable regions are germline sequences.

In a preferred embodiment the light chain variable region comprises a germline O12/IgVκ1-39*01. In a preferred embodiment the light chain variable region comprises the kappa light chain IgVκ1-39*01/IGJκ1*01 or IgVκ1-39*01/IGJκ5*01. In a preferred embodiment a IgVκ1-39*01/IGJκ1*01. The light chain variable region preferably comprises a germline kappa light chain IgVκ1-39*01/IGJκ1*01 or germline kappa light chain IgVκ1-39*01/IGJκ5*01, preferably a germline IgVκ1-39*01/IGJκ1*01.

Mature B-cells that produce an antibody with an O12 light chain often produce a light chain that has undergone one or more mutations with respect to the germline sequence, i.e. the normal sequence in non-lymphoid cells of the organism. The process that is responsible for these mutations is often referred to as somatic (hyper)mutation. The resulting light chain is referred to as an affinity matured light chain. Such light chains, when derived from an O12 germline sequence are O12-derived light chains. In this specification, the phrase "O12 light chains" will include O12-derived light chains. The mutations that are introduced by somatic hypermutation can of course also be introduced artificially in the lab. In the lab also other mutations can be introduced without affecting the properties of the light chain in kind, not necessarily in amount. A light chain is at least an O12 light chain if it comprises a sequence as depicted in FIG. 1A, FIG. 1B; FIG. 1D or FIG. 1E with 0-10, preferably 0-5 amino acid insertions, deletions, substitutions, additions or a combination thereof. In a preferred embodiment the O12 light chain is a light chain comprising a sequence as depicted in FIG. 1A; 1B; 1D or 1E with 0-9, 0-8, 0-7, 0-6, 0-5, 0-4 amino acid insertions, deletions, substitutions, additions or a combination thereof. In a preferred embodiment the O12 light chain is a light chain comprising a sequence as depicted in FIG. 1A, FIG. 1B; FIG. 1D or FIG. 1E with 0-5, preferably 0-4, more preferably 0-3 amino acid insertions, deletions, substitutions, additions or a combination thereof. In a preferred embodiment the O12 light chain is a light chain comprising a sequence as depicted in FIG. 1A, FIG. 1B; FIG. 1D or FIG. 1E with 0-2, more preferably 0-1, most preferably 0 amino acid insertions, deletions, substitutions, additions or a combination thereof. In a preferred embodiment the O12 light chain is a light chain comprising a sequence as depicted in FIG. 1A or FIG. 1B with the mentioned amino acid insertions, deletions, substitutions, additions or a combination thereof. In a preferred embodiment the light chain comprises the sequence of FIG. 1A. In a preferred embodiment the light chain variable region comprises the sequence of FIG. 1B.

The common light chain (variable region) can be a lambda light chain and this is therefore also provided in the context of the invention, however a kappa light chain is preferred. The constant part of a common light chain of the invention can be a constant region of a kappa or a lambda light chain. It is preferably a constant region of a kappa light chain, preferably wherein said common light chain is a germline light chain, preferably a rearranged germline human kappa light chain comprising the $IgV_\kappa I$-39 gene segment, most preferably the rearranged germline human kappa light chain $IgV_\kappa I$-39*01/$IGJ_\kappa I$*01 (FIG. 1). The terms rearranged germline human kappa light chain IgVκ1-39*01/IGJκ1*01, IGKV1-39/$IG_\kappa J1$, huVκ1-39 light chain or in short huVκ1-39, or simply 1-39 are used interchangeably throughout the application. Those of skill in the art will recognize that "common" also refers to functional equivalents of the light chain of which the amino acid sequence is not identical. Many variants of said light chain exist wherein mutations (deletions, substitutions, additions) are present that do not influence the formation of functional binding regions.

IgVκ1-39 is short for Immunoglobulin Variable Kappa 1-39 Gene. The gene is also known as Immunoglobulin Kappa Variable 1-39; IGKV139; IGKV1-39; O12a or O12. External Ids for the gene are HGNC: 5740; Entrez Gene: 28930; Ensembl: ENSG00000242371. A preferred amino acid sequence for IgVκ1-39 is given in FIG. 1. This lists the sequence of the V-region. The V-region can be combined with one of five J-regions. FIG. 1 describes two preferred sequences for IgVκ1-39 in combination with a J-region. The joined sequences are indicated as IGKV1-39/jk1 and IGKV1-39/jk5; alternative names are IgVκ1-39*01/IGJκ1*01 or IgVκ1-39*01/IGJκ5*01 (nomenclature according to the IMGT database worldwide web at imgt.org).

A common light chain variable region is preferably linked to a kappa light chain constant region. In a preferred embodiment the light chain variable region comprises the kappa light chain IgVκ1-39*01/IGJκ1*01 or IgVκ1-39*01/IGJκ5*01. In a preferred embodiment a IgVκ-39*01/IGJκ1*01.

A cell that produces a common light chain can produce for instance rearranged germline human kappa light chain IgVκ1-39*01/1GJκ1*01 and a light chain comprising the variable region of the mentioned light chain fused to a lambda constant region. Where herein reference is made to a germ-line sequence it is preferred that the variable region is a germ-line sequence.

Bispecific antibodies or variants thereof as described herein preferably have one heavy chain variable region/light chain variable region (VH/VL) combination that binds an extracellular part of a member of the CD28 family and a second VH/VL combination that binds an extracellular part of a member of the B7 family or TNFRSF14. In a preferred embodiment the VL in said first VH/VL combination is similar to the VL in said second VH/VL combination. In a more preferred embodiment, the VLs in the first and second VH/VL combinations are identical. In a preferred embodiment, the bispecific antibody is a full length antibody which has one heavy/light (H/L) chain combination that binds an extracellular part of a member of the CD28 family and one H/L chain combination that binds an extracellular part of a member of the B7 family or TNFRSF14. In a preferred embodiment the light chain in said first H/L chain combination is similar to the light, chain in said second H/L chain combination. In a more preferred embodiment, the light chains in the first and second H/L chain combinations are identical.

Several methods have been published to favor the production of the bispecific antibody or vice versa, the monospecific antibodies. In the present invention it is preferred that the cell favors the production of the bispecific antibody over the production of the respective monospecific antibodies. Such is typically achieved by modifying the constant region of the heavy chains such that they favor heterodimerization (i.e. dimerization with the heavy chain of the other heavy/light chain combination) over homodimerization. In a preferred embodiment the bispecific antibody of the invention comprises two different immunoglobulin heavy chains with compatible heterodimerization domains. Various compatible heterodimerization domains have been described in the art. The compatible heterodimerization domains are preferably compatible immunoglobulin heavy chain CH3 heterodimerization domains. When wildtype CH3 domains are used, co-expression of two different heavy chains (A and B) and a common light chain will result in three different antibody species, AA, AB and BB. AA and BB are designations for the two mono-specific, bivalent antibodies, and AB is a designation for the bispecific antibody. To increase the percentage of the desired bispecific product (AB) CH3 engineering can be employed, or in other words, one can use heavy chains with compatible heterodimerization domains, as defined hereunder. The art describes various ways in which such hetero-dimerization of heavy chains can be achieved. One way is to generate 'knob into hole' bispecific antibodies. See WO1998/050431 (Arathoon et al.).

The term 'compatible hetero-dimerization domains' as used herein refers to protein domains that are engineered such that engineered domain A' will preferentially form heterodimers with engineered domain B' and vice versa, homodimerization between A'-A' and B'-B' is diminished.

In U.S. Ser. No. 13/866,747 (now issued as U.S. Pat. No. 9,248,181), U.S. Ser. No. 14/081,848 (now issued as U.S. Pat. No. 9,358,286); WO2013/157953 and PCT/NL2013/050294 (published as WO2013/157954); incorporated herein by reference) methods and means are disclosed for producing bispecific antibodies using compatible heterodimerization domains. These means and methods can also be favorably employed in the present, invention. Specifically, a bispecific antibody of the invention preferably comprises mutations to produce essentially only bispecific full length IgG molecules. Preferred mutations are the amino acid substitutions L351K and T366K (EU numbering) in the first CH3 domain (the 'KK-variant' heavy chain) and the amino acid substitutions L351D and L368E in the second domain (the 'DE-variant' heavy chain), or vice versa. It was previously demonstrated in our U.S. Pat. Nos. 9,248,181 and 9,358,286 patents as well as the WO2013/157954 PCT application that the DE-variant and KR-variant preferentially pair to form heterodimers (so-called 'DEKK' bispecific molecules). Homodimerization of DE-variant heavy chains (DEDE homodimers) hardly occurs due to repulsion between the charged residues in the CH3-CH3 interface between identical heavy chains.

Bispecific antibodies can be generated by (transient) transfection of aplasmid encoding a light chain and two different heavy chains that are CH3 engineered to ensure efficient hetero-dimerization and formation of the bispecific antibodies. The production of these chains in a single cell leads to the favored formation of bispecific antibodies over the formation of monospecific antibodies.

Further provided is therefore a method for producing an antibody or variant according to the invention from a single cell, wherein said antibody or variant thereof comprises two CH3 domains that are capable of forming an interface, said method comprising providing:

a cell having a) a first nucleic acid molecule encoding a IgG heavy chain that specifically recognizes an extracellular part of PD-1, and that contains a 1st CH3 domain, and b) a second nucleic acid sequence encoding a IgG heavy chain that specifically recognizes an extracellular part of PD-L1, and that contains a 2nd CH3 domain, wherein said nucleic acid sequences are provided with mutations for preferential pairing of said 1st and 2nd CH3 domains, said method further comprising the step of culturing said cell and allowing for expression of said nucleic acid sequences and harvesting said antibody or variant thereof from the culture. In some preferred embodiments, said cell has a third nucleic acid sequence encoding a common light chain, preferably the rearranged germline human kappa light chain IgVκ1-39*01/IGJκ1*01.

Preferred mutations to produce essentially only bispecific full length IgG1 molecules are amino acid substitutions at positions 351 and 366, e.g. L351K and T366K (numbering according to EU numbering) in the first CH3 domain (the 'KK-variant' heavy chain) and amino acid substitutions at positions 351 and 368, e.g. L351D and L368E in the second CH3 domain (the 'DE-variant' heavy chain), or vice versa. Further provided is therefore a method according to the invention for producing an antibody or variant according to the invention from a single cell, wherein said first CH3 domain comprises the amino acid substitutions L351K and T366 K (numbering according to the EU numbering) and wherein said second CH3 domain comprises the amino acid substitutions L351D and L368E (numbering according to the EU numbering), said method further comprising the step of culturing said cell and allowing for expression of said nucleic acid sequences and harvesting said antibody or variant thereof from the culture.

In one embodiment the heavy chain/light chain combination that comprises the variable domain that binds PD-1, comprises a DE variant of the heavy chain. In this embodiment the heavy chain/light chain combination that comprises the variable domain that can bind to an antigen other than PD-1 comprises a KK variant of the heavy chain.

The Fc region mediates effector functions of an antibody, such as complement-dependent cytotoxicity (CDC), antibody-dependent cellular cytotoxicity (ADCC) and antibody-dependent cell phagocytosis (ADCP). Depending on the therapeutic antibody or Fc fusion protein application, it may be desired to either reduce or increase the effector function. Reduced effector functions are preferred in the present invention. Reduced effector function can be desired when an immune response is to be activated, enhanced or stimulated as in some of the embodiments of the invention. Antibodies with reduced effector functions can be used to target cell-surface molecules of immune cells, among others.

Binding of IgG to the FcγRs or C1q was found to require residues located in the hinge region and the CH2 domain. Two regions of the CH2 domain (FIG. 2D) are relevant for FcγRs and C1q binding. Substitutions into human IgG1 of IgG2 residues at positions 233-236 and IgG4 residues at positions 327, 330 and 331 were shown to greatly reduce ADCC and CDC (Armour et al., 1999. Eur J Immunol. 29(8):2613-24; Shields et al., 2001. J Biol Chem. 276(9): 6591-604). Furthermore, Idusogie et al. demonstrated that alanine substitution at different positions, including K322, significantly reduced complement activation (Idusogie et al., 2000. J Immunol. 164(8):4178-84).

Due to their reduced effector functions, IgG4 antibodies represent an IgG subclass for receptor blocking without cell depletion. IgG4 molecules can exchange half-molecules in a dynamic process termed Fab-arm exchange. This phenomenon can occur between therapeutic antibodies and endogenous IgG4. The S228P mutation is an example of a mutation that ensures reduced capacity to Fab-arm exchange. (Labrijn. et al., 2009. Nat Biotechnol. 27(8):767-71).

Antibodies with reduced effector functions are preferably IgG antibodies comprising a modified CH2/lower hinge region, for instance to reduce Fc-receptor interaction or to reduce C1q binding. In some embodiments the antibody of the invention is an IgG antibody with a mutant CH2 and/or lower hinge domain such that interaction of the bispecific IgG antibody to a Fc-gamma receptor is reduced. An antibody comprising a mutant CH2 region is preferably an IgG1 antibody. Such a mutant IgG1 CH2 and/or lower hinge domain preferably comprise an amino substitution at position 235 and/or 236 (EU numbering), preferably an L235G and/or G236R substitution (FIG. 2E).

A variant of an antibody or bispecific antibody as described herein may comprise a functional part, derivative and/or analogue of the antibody or bispecific antibody. A variant typically maintains the binding specificity of the antibody, such as a bispecific antibody. A variant typically maintain the binding specificity of the antibody, such as a bispecific antibody. A variant is preferably a functional part or derivative of an antibody or bispecific antibody as described herein. It is preferably a functional part.

Binding specificity is defined by capacity to bind an extracellular part of a member of the CD28 family and an extracellular part, of a member of the B7 family, or TNFRSF14, wherein the members are binding partners (i.e. a receptor-ligand pair).

A functional part of an antibody, or preferably a functional part of a bispecific antibody as described herein is a part comprising a variable domain that binds an extracellular part of a member of the CD28 family, preferably PD-1, and a variable domain that binds an extracellular part of a member of the B7 family, or TNFRSF14, preferably PD-L1. A suitable part is for instance an F(ab')$_2$ fragment as created by digestion of a bispecific antibody with pepsin. Other parts comprising said variable domains are included in the present invention.

A functional derivative of an antibody, or preferably a functional derivative of a bispecific antibody as described herein is a protein comprising a variable domain that binds an extracellular part of a member of the CD28 family, preferably PD-1, and a variable domain that, binds an extracellular part of a member of the B7 family or TNFRSF14, preferably PD-L1, that are linked by a linking region. The variable domains may be variable domains as such, or Fab fragments or variable domain like molecules such as single chain Fv fragments comprising a VH and a VL linked together via a linker. Other examples of variable domain like molecules are so-called single domain antibody fragment. A single-domain antibody fragment (sdAb) is an antibody fragment with a single monomeric variable antibody region. Like a whole antibody, it is able to bind selectively to a specific antigen. With a molecular weight of only 12-15 kDa, single-domain antibody fragments are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable regions, one from a light and one from a heavy chain). Single-domain antibodies by themselves are not much smaller than normal antibodies (being typically 90-100 kDa). Single-domain antibody fragments are mostly engineered from heavy-chain antibodies found in camelids; these are called VHH fragments (Nanobodies®) . Some fishes also have heavy-chain only antibodies (IgNAR, 'immunoglobulin new antigen receptor'), from which single-domain antibody fragments called VNAR fragments can be obtained. An alternative approach is to split the dimeric variable domains from common immunoglobulin G (IgG) from humans or mice into monomers. Although most research into single-domain antibodies is currently based on heavy chain variable domains, nanobodies derived from light chains have also been shown to bind specifically to target epitopes. Other non-limiting examples of variable domain-like molecules are VHH, Human Domain Antibodies (dAbs) and Unibodies. Preferred functional parts are parts that comprise variable domains comprising a heavy chain variable region and a light chain variable region. Non-limiting examples of such variable domains are F(ab)-fragments and Single chain Fv fragments. Bispecific formats for variable domain(-like) linkage are for instance human Serum Albumine (HSA) bound to two different scFv; bispecific mini-antibodies comprising two different scFv bound together via a dimerization motifs or self-associating secondary structures such as helix bundles or coiled coils to bring about dimerization of the scFv fragments (Morrison (2007) Nat. Biotechnol 25:1233-34). Examples of suitable HSA linkers and method for coupling scFv to the linker are described in WO2009/126920.

A functional analogue of an antibody, or preferably a functional analogue of a bispecific antibody as described herein is a molecule that comprises a binding site for an extracellular part of a member of the CD28 family, preferably PD-1, and binding site for an extracellular part of a member of the B7 family or TNFRSF14, preferably PD-L1. A functional derivative can be an antibody mimetic, a polypeptide, an aptamer or a combination thereof. These proteins or aptamers typically bind to one target. The protein of the invention binds to two or more targets. It is to be understood that any combination of these antibodies, antibody mimetics, polypeptides and aptamers can be linked together by methods known in the art. For example, in some embodiments the binding molecule of the invention is a conjugate or a fusion protein. For antibodies the technology of making multi-specific antibodies has progressed to also include bispecific antibodies that have the same overall structure as a normal mono-specific antibody hut wherein the two arms of the antibody each bind a different target.

An antibody mimetic is a polypeptide that, like antibodies, can specifically bind antigen, but that is not structurally related to antibodies. Antibody mimetics are usually artificial peptides or proteins with a molar mass of about 3 to 20 kDa. Common advantages over antibodies are better solubility, tissue penetration, stability towards heat and enzymes, and comparatively low production costs. Non-limiting examples of antibody mimetics are affibody molecules (typically based on the Z domain of Protein A); affilins (typically based on Gamma-B crystalline or Ubiquitin); affimers (typically based on Cystatin); affitins (typically based on Sac7d from *Sulfolobus acidocaldarius*); alphabodies (typically based on Triple helix coiled coil); anticalins (typically based on Lipocalins); avimers (typically based on A domains of various membrane receptors); DARPins (typically based on ankyrin repeat motif); fynomers (typically based on SH3 domain of Fyn 7); kunitz domain peptides (typically based on Kunitz domains of various protease inhibitors); and monobodies (typically based on type III domain of fibronectin).

Monobodies are synthetic binding proteins that are constructed using a fibronectin type III domain (FN3) as a molecular scaffold. Monobodies are simple and robust alternative to antibodies for creating target-binding proteins. The term "monobody" was coined in 1998 by the Koide group who published the first paper demonstrating the monobody concept using the tenth FN3 domain of human fibronectin.

Monobodies and other antibody mimetics are typically generated from combinatorial libraries in which portions of the scaffold are diversified using molecular display and directed evolution technologies such as phage display, mRNA display and yeast surface display. A large number of antibody mimetics have high affinity and high specificity to their respective targets.

Aptamers are oligonucleotide or peptide molecules that bind to a specific target molecule. Aptamers are usually created by selecting them from a large random sequence pool, but natural aptamers also exist in riboswitches. Aptamers can be used for both basic research and clinical purposes as macromolecules.

As used herein, the term "conjugate" refers to two or more molecules that have been covalently joined, optionally by a linking region also referred as a linker. For example, in some embodiments, a conjugate is a first protein or non-protein moiety joined to a second protein or non-protein moiety by a linking region. For example, in some embodiments of a binding molecule of the invention it comprises or consists of two or more antibodies that have been covalently joined. A conjugate is not limited to a first and second moiety but in some embodiments may also have a third, fourth or more moieties joined by further linking regions. As described elsewhere in this application, examples of protein moieties include, but are not limited to: a polypeptide, a peptidomimetic or an antibody (or antibody part, derivative, or analogue, as described elsewhere in the application). Examples of non-protein moieties include, but are not limited to aptamers. Numerous types of linker can be used, and the linker will be selected to be appropriate according to the molecule types in the conjugate and on the desired properties of the linker (length, flexibility, resistance to protease activity and other similar characteristics). Such linkers may comprise nucleotides, polypeptides, or a suitable synthetic material. For example, a linker may be a flexible peptide linker. In certain embodiments, the linker may be a cleavable linker, allowing the parts of the conjugate to be separated from each other. In other embodiments, a peptide linker might be a helical linker. Various examples and kits for linking proteins and other molecules are known in the art. As used herein, the term "fusion protein" refers to a protein that comprises two or more polypeptides or proteins that have been joined at the DNA level by recombination and are expressed together as a single polypeptide. A fusion protein may also comprise a peptide linking region also encoded by the DNA and expressed together with the fusion protein. A peptide linker that is part of a fusion protein may be designed to have particular characteristics such as flexibility, hydrophilicity, protease-resistance, cleavability etc. All these properties can be designed within the DNA sequence and methods for designing linkers are well known in the art. For example, antibodies can be linked together by methods well-known in the art, and as described herein, to form bispecific or multi-targeting antibodies. Furthermore, bispecific antibodies can be constructed by various methods known in the art, for example, by using technology such as BiClonics®. A bispecific monoclonal antibody (BsMAb, BsAb) typically comprises binding domains of two different monoclonal antibodies and consequently binds to two different epitopes. Biclonics® molecules, but, also other full length IgG bispecific antibodies have two different antigen binding specificities encoded by two different variable regions of a full length IgG molecule of a Fab of a scFv. Biclonics® can be produced by co-transfection of individual cells with genetic constructs encoding two different common light chain (cLC) antibodies as detailed elsewhere herein. CH3 engineering ensures efficient hetero-dimerization and formation of essentially pure bispecific antibodies.

The invention also provides an antibody or variant according to the invention for use as a medicament. Further provided is an antibody or variant according to the invention for use in a method for the treatment of cancer or an infection with a pathogen, such as a virus or parasite.

The invention also provides a method for the treatment of an individual that has a cancer, the method comprising administering an antibody of the invention, such as a bispecific antibody, or a variant thereof, such as a variant, to the individual in need thereof. The individual is preferably an individual that has a cancer. In some embodiments, the cancer is a cancer that comprises cancer cells that express said second membrane protein. In a preferred embodiment the cancer is a cancer that comprises cancer cells that express a member of the B7 family or TNFRSF14. The cancer is preferably an adenocarcinoma. Preferred cancers are colorectal cancer; pancreatic cancer; lung cancer; breast cancer; liver cancer; prostate cancer; ovarian cancer; cervical cancer; endometrial cancer; head and neck cancer; melanoma; testis cancer; urothelial cancer; renal cancer; stomach cancer; or carcinoid cancer. In a preferred embodiment the cancer is colorectal cancer; pancreatic cancer; lung cancer; breast cancer; liver cancer; prostate cancer; ovarian cancer; cervical cancer; endometrial cancer; head and neck cancer; or melanoma. In a particularly preferred embodiment the cancer is colorectal cancer; pancreatic cancer; lung cancer; breast cancer; or liver cancer. In a particularly preferred embodiment the cancer is a gastrointestinal cancer. In a preferred embodiment the cancer is colorectal cancer. In this embodiment the antibody or variant thereof is preferably an antibody with a variable domain that can bind PD-1 and a variable domain that can bind PD-L1. The variable domains preferably each block the binding of PD-1 to PD-L1.

Further provided is an ex vivo system comprising an antibody or a variant according to the invention, and a first cell and a second cell. The first and second cell preferably express respectively said first and said second membrane protein on the cell membrane. The system is preferably a cell system suitable for the maintenance and/or the growth of said first cell. The cell system is preferably suitable for the maintenance and/or the growth of said second cell. Such as system is for instance suitable to raise and/or multiply immune cells that are directed towards aberrant cells. Such immune cells can subsequently be administered to an individual in need thereof, for instance a cancer patient. The immune cells preferably comprise a T-cell or NK-cell, preferably a cytotoxic T-cell. The immune cells are preferably autologous to the individual in need thereof.

Further provided is a method for inducing and/or stimulating an immune response in an individual against an aberrant cell in said individual, the method comprising providing said individual with an antibody or a variant thereof of the invention. The aberrant cell is preferably a cancer cell, a virus-infected cell, a parasite or a parasite infected cell. In a preferred embodiment the cell is a cancer cell or a neoplastic cell. In this embodiment the antibody or variant thereof is preferably an antibody with a variable domain that can bind PD-1 and a variable domain that can bind PD-L1. The variable domains preferably each block the binding of PD-1 to PD-L1.

A neoplasm is an abnormal growth of tissue and when it also forms a mass is commonly referred to as a tumor. A neoplasm in the present invention typically forms a mass. A neoplastic cell is a cell from a neoplasm that has formed a mass. The World Health Organization (WHO) classifies neoplasms into four main groups: benign neoplasms, in situ neoplasms, malignant neoplasms, and neoplasms of uncertain or unknown behavior. Malignant neoplasms are also simply known as cancers.

Inducing and/or stimulating an immune response encompasses inducing an immune response and enhancing an already existing immune response. The immune response in an individual can be measured by measuring where applicable; the tumor load of the individual; the virus load of the individual; the parasite load of the individual.

Said virus-infected cell is preferably a cell infected with an immune-deficiency virus, a herpes virus, preferably a herpes simplex virus, a varicella-zostervirus, a cytomegalovirus or an Epstein-Barr virus, a papilloma virus, a hepatis virus, preferably a hepatitis A, B or C virus, a measles virus or an adenoviruses. The virus is preferably a virus known to be able to persist in an individual. Persistent infections are characterized as those in which the virus is not cleared but remains in specific cells of infected individuals. Persistent infections may involve stages of both silent and productive infection without rapidly killing or even producing excessive damage of the host cells. Persistent virus-host interaction may be a latent, a chronic and/or a slow infection.

A parasite-infected cell is a cell that is infected with an intracellular parasite. Such parasites are parasitic microorganisms that are capable of growing and reproducing inside the cells of a host. Some intracellular parasites can also live outside a cell. Such parasites are so-called facultative intracellular parasites. Non-limiting examples are *Listeria monocytogenes, Legionella*, certain species of *mycobacterium* and *Cryptococcus neoformans*. Preferred intracellular parasites are parasites that cannot grow outside host cells, preferred examples are *Chlamydia*, and closely related species, certain species of *mycobacterium* such as *Mycobacterium leprae*, certain protozoa, including: Apicomplexans (*Plasmodium* spp., *Toxoplasma gondii* and *Cryptosporidium parvum* and trypanosomatids.

An antibody or variant thereof or preferably a bispecific antibody or variant thereof of the present invention is preferably used in humans. To this end an antibody or variant thereof of the invention is preferably a human or humanized antibody. Tolerance of a human to a polypeptide is governed by many different aspects. Immunity, be it T-cell mediated, B-cell mediated or other is one of the variables that are encompassed in tolerance of the human for a polypeptide. The constant region of a bispecific antibody of the present invention preferably comprises a human heavy chain constant region, preferably comprising a sequence as depicted in FIG. 2; and a human light chain constant region, preferably comprising a sequence as depicted in FIG. 1C. The constant region may contain one or more, preferably not more than 10, preferably not more than 5 amino-acid differences with the constant region of a naturally occurring human antibody. It is preferred that the constant part is entirely derived from a naturally occurring human antibody. Various antibodies produced herein are derived from common light chain mice immunized with the respective target as described in WO2009/157771. Various antibodies produced herein are derived from a human antibody variable domain library. As such these variable domains are human. The unique CDR regions may be derived from humans, be synthetic or derived from another organism. The variable region is at least a human variable region when it has, with the exception of the CDR regions, an amino acid sequence that is identical to an amino acid sequence of the variable region of a naturally occurring human antibody. In such embodiments, the VH of a variable domain of an antibody that binds a CD28 family member or membrane associated member of the B7 family or TNFRSF14, or a light chain in an antibody of the invention may contain one or more, preferably not more than 10, preferably not more than 5 amino-acid differences with the variable region of a naturally occurring human antibody, not counting possible differences in the amino acid sequence of the CDR regions. Such mutations also occur in nature in the context of somatic hypermutation.

Antibodies may be derived from various animal species, at least with regard to the heavy chain variable region. It is common practice to humanize such e.g. murine heavy chain variable regions. There are various ways in which this can be achieved among which there are CDR-grafting into a human heavy chain variable region with a 3D-structure that matches the 3-D structure of the murine heavy chain variable region; de-immunization of the murine heavy chain variable region, preferably done by removing known or suspected T- or B-cell epitopes from the murine heavy chain variable region. The removal is typically by substituting one or more of the amino acids in the epitope for another (typically conservative) amino acid, such that the sequence of the epitope is modified such that it is no longer a T- or B-cell epitope.

De-immunized murine heavy chain variable regions are less immunogenic in humans than the original murine heavy chain variable region. Preferably a variable region or domain of the invention is further humanized, such as for instance veneered. By using veneering techniques, exterior residues which are readily encountered by the immune system are selectively replaced with human residues to provide a hybrid molecule that comprises either a weakly immunogenic or substantially non-immunogenic veneered surface. An animal as used in the invention is preferably a mammal, more preferably a primate, most preferably a human.

An antibody or bispecific antibody or variant thereof according to the invention preferably comprises a constant region of a human antibody. According to differences in their heavy chain constant domains, antibodies are grouped into five classes, or isotypes: IgG, IgA, IgM, IgD, and IgE. These classes or isotypes comprise at least one of said heavy chains that is named with a corresponding Greek letter. In a preferred embodiment the invention provides an antibody according to the invention wherein said constant region is selected from the group of IgG constant regions, i.e. selected from the group consisting of IgG1, IgG2, IgG3 and IgG4. Preferably said constant region is an IgG4 or IgG1 constant region (FIG. 2), more preferably a mutated IgG1 constant region. Some variation in the constant region of IgG1 occurs in nature and/or is allowed without changing the immunological properties of the resulting antibody. Typically between about 1-10 amino acid insertions, deletions, substitutions or a combination thereof are allowed in the constant region. The constant region may be mutated as indicated herein for enabling efficient heterodimerization, for reducing effector function or for other reasons including half-life, stability and the like.

Rational methods have evolved toward minimizing the content of non-human residues in the human context. Various methods are available to successfully graft the antigen-binding property of an antibody onto another antibody. The binding properties of antibodies may rest predominantly in the exact sequence of the CDR3 region, often supported by the sequence of the CDR1 and CDR2 regions in the variable domain combined with the appropriate structure of the variable domain as a whole. Various methods are presently available to graft CDR regions onto a suitable variable domain of another antibody. Some of these methods are reviewed in J. C. Almagrol and J. Fransson (2008) Frontiers in Bioscience 13, 1619-1633, which is included by reference herein.

The light chain variable region of a variable domain comprising a variable heavy chain sequence as depicted in FIG. 3 and/or FIG. 13 is preferably a germline light chain of or based on O12, preferably the rearranged germline human kappa light chain IgVκ1-39*01/IGJκ1*01 or a fragment or a functional derivative thereof (nomenclature according to the IMGT database worldwide web at imgt.org). The terms rearranged germline human kappa light chain IgVκ1-39*01/IGJκ1*01, IGKV1-39/IGKJ1, huVκ1-39 light chain or in short huVκ1-39 are used. The light chain can have 1, 2, 3, 4 or 5 amino acid insertions, deletions, substitutions or combination thereof. The mentioned 1, 2, 3, 4 or 5 amino acid substitutions are preferably conservative amino acid substitutions, the insertions, deletions, substitutions or combination thereof are preferably not in the CDR3 region of the VL chain, preferably not in the CDR1, CDR2 or CDR3 region or FR4 region of the VL chain. A preferred sequence for the common light chain is depicted in FIG. 1.

Various methods are available to produce bispecific antibodies. One method involves the expression of two different heavy chains and two different light chains in a cell and collecting antibody that is produced by the cell. Antibody produced in this way will typically contain a collection of antibodies with different combinations of heavy and light chains, some of which are the desired bispecific antibody. The bispecific antibody can subsequently be purified from the collection. The ratio of bispecific to other antibodies that are produced by the cell can be increased in various ways. In a preferred embodiment of the invention, the ratio is increased by expressing not two different light chains but two essentially identical light chains in the cell. The two essentially identical light chains can be light chains with essentially the same light chain variable regions and different light chain constant regions or, preferably, two essentially identical light chain constant regions. This concept is in the art also referred to as the "common light chain" method. When the essentially identical light chains work together with the two different heavy chains allowing the formation of variable domains with different antigen-binding sites and concomitant different binding properties, the ratio of bispecific antibody to other antibody that is produced by the cell is significantly improved over the expression of two essentially different light chains. The ratio of bispecific antibody that is produced by the cell can be further improved by stimulating the pairing of two different heavy chains with each other over the pairing of two identical heavy chains. The art describes various ways in which such hetero-dimerization of heavy chains can be achieved. A preferred method is described in U.S. provisional application 61/635,935, which has been followed up by U.S. regular application Ser. No. 13/866,747 and PCT application No. PCT/NL2013/050294 (WO 2013/157954 A1), which are incorporated herein by reference. Methods and means are disclosed for producing bispecific antibodies (from a single cell), whereby means are provided that favor the formation of bispecific antibodies over the formation of monospecific antibodies. These methods can also be favorably employed in the present invention. Thus the invention provides a method for producing a bispecific antibody according to the invention (from a single cell), wherein said bispecific antibody comprises two CH3 domains that, are capable of forming an interface, said method comprising providing in said cell a) a first nucleic acid molecule encoding a 1st CH3 domain comprising heavy chain, b) a second nucleic acid molecule encoding a 2nd CH3 domain comprising heavy chain, wherein said nucleic acid molecules are provided with means for preferential pairing of said 1st and 2nd CH3 domain comprising heavy chains, said method further comprising the step of culturing said host cell and allowing for expression of said two nucleic acid molecules and harvesting said bispecific antibody from the culture. Said first and second nucleic acid molecules may be part of the same nucleic acid molecule, vector or gene delivery vehicle and may be integrated at the same site of the host cell's genome. Alternatively, said first and second nucleic acid molecules are separately provided to said cell. The host cell comprises at least one light chain, and preferably a common light chain.

A preferred embodiment provides a method for producing a bispecific antibody according to the invention from a single cell, wherein said bispecific antibody comprises two CH3 domains that are capable of forming an interface, said method comprising providing:

a cell having a) a first nucleic acid molecule encoding a heavy chain comprising an antigen binding site that can bind to an extracellular part of a membrane associated member of the CD28 family and that, contains a 1st CH3 domain, and b) a second nucleic acid molecule encoding a heavy chain comprising an antigen-binding site that can bind to an extracellular part of a membrane associated member of the B7 family or TNFRSF14 and that contains a 2nd CH3 domain, wherein said nucleic acid molecules are provided with means for preferential pairing of said 1st and 2nd CH3 domains, said method further comprising the step of culturing said cell and allowing for expression of the proteins encoded by said two nucleic acid molecules and harvesting said bispecific IgG antibody from the culture. In a particularly preferred embodiment, said cell also has a third nucleic acid molecule encoding a common light chain. Said first, second and third nucleic acid molecule may be part of the same nucleic acid molecule, vector or gene delivery vehicle and may be integrated at the same site of the host cell's genome. Alternatively, said first, second and third nucleic acid molecules are separately provided to said cell. A preferred common light chain is based on O12, preferably it, is the rearranged germline human kappa light chain IgVκ1 39*01/IGJκ1*01, as described above. Means for preferential pairing of said 1st and said 2nd CH3 domain are preferably the corresponding mutations in the CH3 domain of the heavy chain coding regions. The preferred mutations to produce essentially only bispecific antibodies are the amino acid substitutions L351K and T366K (numbering according to EU numbering) in the first CH3 domain and the amino acid substitutions L351D and L368E in the second CH3 domain, or vice versa (FIG. 2). Further provided is therefore a method according to the invention for producing a bispecific antibody, wherein said first CH3 domain comprises the amino acid substitutions L351K and T366K (numbering according to EU numbering) and wherein said second CH3 domain comprises the amino acid substitutions L351D and L368E, said method further comprising the step of culturing said cell and allowing for expression of proteins encoded by said nucleic acid molecules and harvesting said bispecific antibody from the culture. Also provided is a method according to the invention for producing a bispecific antibody, wherein said first CH3 domain comprises the amino acid substitutions L351D and L368E (numbering according to EU numbering) and wherein said second CH3 domain comprises the amino acid substitutions L351K and T366K, said method further comprising the step of culturing said cell and allowing for expression of said nucleic acid molecules and harvesting said bispecific antibody from the culture. Antibodies that can be produced by these methods are also part of the present invention. The CH3 hetero-dimerization domains are preferably IgG1 hetero-dimerization domains. The heavy chain constant regions comprising the CH3 hetero-dimerization domains are preferably IgG1 constant regions.

The invention also provides a nucleic acid molecule that encodes at least part of an antibody heavy chain variable region according to the invention. Provided herein is a nucleic acid molecule with a length of at least 15 nucleotides, encoding at least one CDR region of an antibody or variant according to the invention. Further provided is a nucleic acid molecule encoding at least a heavy chain variable region of an antibody or variant according to the invention.

The nucleic acid molecule (typically an in vitro, isolated or recombinant nucleic acid molecule) preferably encodes any one of the heavy chain variable regions as depicted in FIG. 3 and/or FIG. 13, or a heavy chain variable region as depicted in FIG. 3 and/or FIG. 13 having 1, 2, 3, 4 or 5 amino acid insertions, deletions, substitutions or combination thereof. Some embodiments provide a nucleic acid molecule encoding an antibody or variant according to the invention. The nucleic acid molecule preferably uses codons that are optimized for expression in the antibody producing cell that is to be used. Preferably the nucleic acid encoding a heavy chain variable region as depicted in FIG. 3 and/or FIG. 13, or a heavy chain variable region as depicted in FIG. 3 and/or FIG. 13 having 1, 2, 3, 4 or 5 amino acid insertions, deletions, substitutions or combination thereof is codon optimized for expression in a human cell, preferably Per.C6™; or a Chinese hamster cell, preferably CHO. The invention further provides a nucleic acid molecule that codes for the mentioned heavy chain variable region together with a heavy chain constant region of FIG. 2.

A nucleic acid molecule as used in the invention is typically but not exclusively a ribonucleic acid (RNA) or a deoxyribonucleic acid (DNA). Alternative nucleic acids, such as for instance locked nucleic acid (INA) and peptide nucleic acid (PNA), are available for a person skilled in the art.

Further provided is a vector comprising a nucleic acid molecule according to the invention.

A nucleic acid molecule according to the invention is for instance comprised in a cell. When said nucleic acid molecule is expressed in said cell, said cell can produce an antibody or variant according to the invention. Therefore, the invention in one embodiment provides a cell comprising an antibody or variant according to the invention and/or a nucleic acid molecule according to the invention and/or a vector according to the invention. An antibody is produced when said cell produces a heavy chain and a light chain. Provided is a cell that can produce an antibody of the invention. The cell preferably comprises a nucleic acid molecule that encodes an antibody heavy chain that comprises an antibody heavy chain variable region that, when combined with a common light chain, can bind said first membrane protein. Said cell preferably further comprises a nucleic acid molecule that encodes an antibody heavy chain that comprises an antibody heavy chain variable region that, when combined with a common light chain, can bind said second membrane protein. Said cell preferably further comprises a nucleic acid molecule that codes for a common light chain. Said cell is preferably an animal cell, more preferably a mammal cell, more preferably a primate cell, most preferably a human cell. For the purposes of the invention a suitable cell is any cell capable of comprising and preferably of producing an antibody according to the invention and/or a nucleic acid according to the invention.

The invention further provides a cell comprising an antibody according to the invention. Also provided is a cell that comprises one or more nucleic acid molecules that alone or together encode an antibody of the invention. The one or more nucleic acid molecules are expressible nucleic acid molecules meaning that they contain the in cis required signals for RNA transcription and translation of protein coding domains. Preferably said cell (typically an in vitro, isolated or recombinant cell) produces said antibody. In a preferred embodiment said cell is a hybridoma cell, a Chinese hamster ovary (CHO) cell, an NS0 cell or a PER-C6™ cell. In a particularly preferred embodiment said cell is a CHO cell. Further provided is a cell culture that comprises a cell according to the invention. Various institutions and companies have developed cell lines for the large scale production of antibodies, for instance for clinical use. Non-limiting examples of such cell lines are CHO cells, NS0 cells or PER.C6™ cells. These cells are also used for other purposes such as the production of proteins. Cell lines developed for industrial scale production of proteins and antibodies are herein further referred to as industrial cell lines. Thus in a preferred embodiment the invention provides the use of a cell line developed for the large scale production of antibody for the production of an antibody of the invention. The invention further provides a cell for producing an antibody comprising a nucleic acid molecule that codes for a VH, a VL, and/or a heavy chain as depicted in FIGS. 3, 13, 1 and/or 2. Preferably said nucleic acid molecule comprises a sequence as depicted in FIGS. 1 and 2.

The invention further provides a method for producing an antibody comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

A cell of the invention is for instance a hybridoma cell line, a CHO cell, a 293F cell, an NS0 cell or any other cell type known in the art for its suitability for antibody production for clinical purposes, in particular for the production of antibodies used for administration in humans. In a particularly preferred embodiment said cell is a human cell, preferably a cell that is transformed by an adenovirus E1 region or a functional equivalent thereof. A preferred example of such a cell line is the PER.C6™ cell line or equivalent thereof. In a particularly preferred embodiment said cell is a CHO cell or a variant thereof, preferably a variant that makes use of a Glutamine synthetase (GS) vector system for expression of an antibody.

An antibody or variant according to the invention can also be produced in non-human animals. Further provided is therefore a non-human animal comprising an antibody according to the invention, and/or a nucleic acid molecule according to the invention, and/or a vector according to the invention. In some embodiments, said non-human animal comprises a rodent or a rabbit, preferably a mouse or a rat.

The invention further provides a composition or kit of parts comprising at least one antibody or variant according to the invention. The invention further provides a pharmaceutical composition comprising one or more antibodies or variants thereof according to the invention. The pharmaceutical composition preferably comprises a pharmaceutically acceptable excipient, diluent or carrier.

An antibody or a variant thereof of the invention may further comprise a label, preferably a label for in vivo imaging. Such a label is typically not necessary for therapeutic applications. In for instance a diagnostic setting, a label can be helpful. For instance in visualizing target cells in the body. Various labels are suited and many are well known in the art. In a preferred embodiment the label is a radioactive label for detection. In another preferred embodiment, the label is an infrared label. Preferably the infrared label is suited for in vivo imaging. Various infrared labels are available to the person skilled in the art. Preferred infrared labels are for instance, IRDye 800; IRDye 680RD; IRDye 680LT; IRDye 750; IRDye 700DX; IRDye 800RS IRDye 650; IRDye 700 phosphoramidite; IRDye 800 phosphoramidite (LI-COR USA; 4647 Superior Street; Lincoln, Nebr.).

The amount of antibody according to the invention to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. An antibody according to the invention exerting sufficient therapeutic effects at low dosage is, therefore, preferred. The dosage can be in range of the dosing regimen of Nivolumab. The dosage can also be lower.

An antibody or variant thereof and in particular a bispecific antibody or a variant thereof according to the invention may have fewer side effects than a combination of bivalent monospecific antibodies with the variable domains. Combinations of antibodies that block inhibitory and/or costimulatory molecules benefit patients that do not respond to existing immunotherapies. However, dual blockade of immuno-modulatory receptors (iMODs) has been shown to increase immune-related toxicity. An antibody or variant thereof and in particular a bispecific antibody or a variant thereof according to the invention is suited to address dual blockade of iMODs, as they can exert functional activities that cannot be reproduced by monoclonal antibody combinations, and can more selectively target specific cell populations, which reduces safety liabilities in patients.

The antibodies were produced as bispecific antibodies by cloning them into complementary expression vectors that contain mutations in the CH3 region that drives heterodimerization of heavy chains. Many bispecific antibodies were produced at small scale and tested in binding and functional assays on cancer cell lines. An antibody of the invention, particularly a bispecific antibody of the invention can combine low toxicity profiles with high efficacy. An antibody of the invention can be useful in various types and lines of immune targeted therapies. An antibody of the invention can have an increased therapeutic, window when compared to an antibody that binds the same antigen(s) with both arms.

Further provided is a use of a bispecific antibody according to the invention or a variant thereof, for the preparation of a medicament for the treatment or prevention of aberrant cells, cancerous cells, a tumor and/or the formation of metastases. The tumor from which said metastases originate is preferably a tumor that is positive for a member of the B7 family or TNFRSF14.

Antibodies of the invention can be produced at levels >50 mg/L after transient transfection in suspension 293F cells. The bispecific antibodies can be purified to greater than 98% purity with yields >70%. Analytical characterization studies show bispecific IgG1 antibody profiles that are comparable to bivalent monospecific IgG1.

The invention also provides a bispecific antibody or a variant thereof that can bind to an extracellular part of a membrane associated member of the CD28 family and an extracellular part of a membrane associated member of the B7 or TNFRSF14.

Also provided is a method for the treatment of an individual that has a cancer or an infection with a pathogen, the method comprising administering a therapeutically effective amount of an antibody or variant according to the invention, or a composition according to the invention, or a nucleic acid molecule according to the invention, or a vector according to the invention, to the individual in need thereof.

The invention further provides a protein of the invention or a bispecific antibody of the invention, for use in the treatment of an individual that has cancer.

Further provided is a cell system comprising an antibody or a bispecific antibody or a variant thereof of the invention, and a first cell that expresses a membrane associated member of the CD28 family and a second cell that expresses a membrane associated member of the B7 family or TNFRSF14.

The invention also provides a bivalent antibody or a variant thereof comprising variable domains that bind PD-L1 wherein the VH chain of the variable domains comprises the amino acid sequence of VH chain MF5708 as depicted in FIG. 3A having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5708 as depicted in FIG. 3A. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF5594 as depicted in FIG. 3B having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5594 as depicted in FIG. 3B. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF5576 as depicted in FIG. 3C having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5576 as depicted in FIG. 3C. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF5561 as depicted in FIG. 3D having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5561 as depicted in FIG. 3D. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF5557 as depicted in FIG. 3E having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5557 as depicted in FIG. 3E. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF5553 as depicted in FIG. 3F having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5553 as depicted in FIG. 3F. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF5442 as depicted in FIG. 3G having at most 15, preferably 0, 1, 2, 3, 4, 5, (3, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5442 as depicted in FIG. 3G. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF5439 as depicted in FIG. 3H having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5439 as depicted in FIG. 3H. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF5426 as depicted in FIG. 3I having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5426 as depicted in FIG. 3I. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF5424 as depicted in FIG. 3J having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5424 as depicted in FIG. 3J. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF5382 as depicted in FIG. 3K having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5382 as depicted in FIG. 3K. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF5377 as depicted in FIG. 3L having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5377 as depicted in FIG. 3L. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF5359 as depicted in FIG. 3M having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5359 as depicted in FIG. 3M. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF5361 as depicted in FIG. 3N having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5361 as depicted in FIG. 3N. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF5442 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF5442 as depicted in FIG. 13. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF7691 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7691 as depicted in FIG. 13. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF7690 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7690 as depicted in FIG. 13. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF7689 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7689 as depicted in FIG. 13. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF7688 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7688 as depicted in FIG. 13. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF7700 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7700 as depicted in FIG. 13. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF7701 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7701 as depicted in FIG. 13. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF7703 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7703 as depicted in FIG. 13. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF7694 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7694 as depicted in FIG. 13. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF7693 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7693 as depicted in FIG. 13. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF7692 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7692 as depicted in FIG. 13. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF7697 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7697 as depicted in FIG. 13. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF7696 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7696 as depicted in FIG. 13. In a preferred embodiment of this antibody the antibody is monospecific.

The invention also provides a bivalent antibody or a variant thereof comprising variable domains that bind PD-L1 wherein the VH chain of the variable domains comprises the amino acid sequence of VH chain MF7695 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7695 as depicted in FIG. 13. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF6982 as depicted in FIG. 3O having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF6982 as depicted in FIG. 3O. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF6974 as depicted in FIG. 3P having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF6974 as depicted in FIG. 3P. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF6972 as depicted in FIG. 3Q having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF6972 as depicted in FIG. 3Q. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF6936 as depicted in FIG. 3R having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF6936 as depicted in FIG. 3R. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF6935 as depicted in FIG. 3S having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF6935 as depicted in FIG. 3S. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF6932 as depicted in FIG. 3T having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF6932 as depicted in FIG. 3T. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF6076 as depicted in FIG. 3U having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF6076 as depicted in FIG. 3U. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF6236 as depicted in FIG. 3V having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF6236 as depicted in FIG. 3V. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF6256 as depicted in FIG. 3W having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF6256 as depicted in FIG. 3W. In a preferred embodiment of this antibody the antibody is monospecific.

The invention also provides a bivalent antibody or a variant, thereof comprising variable domains that bind PD-1 wherein the VH chain of the variable domains comprises the amino acid sequence of VH chain MF6226 as depicted in FIG. 3Y having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF6226 as depicted in FIG. 3W. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF6930 as depicted in FIG. 3X having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF6930 as depicted in FIG. 3W. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF6929 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF6929 as depicted in FIG. 13. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF7699 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7699 as depicted in FIG. 13. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF7698 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7698 as depicted in FIG. 13. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF7687 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7687 as depicted in FIG. 13. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF7686 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7686 as depicted in FIG. 13. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF7685 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7685 as depicted in FIG. 13. In a preferred embodiment of this antibody the antibody is monospecific.

The invention also provides a bivalent antibody or a variant thereof comprising variable domains that bind PD-1 wherein the VH chain of the variable domains comprises the amino acid sequence of VH chain MF7684 as depicted in FIG. 13 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect said VH. In a preferred embodiment said VH chain comprises the amino acid sequence of MF7684 as depicted in FIG. 13. In a preferred embodiment of this antibody the antibody is monospecific.

A monospecific antibody as used herein is an antibody that can bind to one epitope only. As a result only one kind of antigen is bound. A bivalent antibody as used herein comprises two variable domains that can bind the same epitope. A monospecific bivalent antibody is typically referred to as monoclonal antibody. Such a monospecific bivalent antibody has two variable domains that each has a heavy chain variable region that comprises the amino acid sequence of indicated MF and a common light chain as defined herein.

A bispecific antibody or variant thereof comprises two variable domains that bind different epitopes. The two different epitopes are typically present on two different antigens or proteins. A bispecific antibody is monovalent for the capacity to bind to a specific epitope. It is bivalent in the sense that it has the potential for two binding interactions.

The invention is further explained in the following examples. These examples do not limit the scope of the invention, but merely serve to clarify the invention.

BRIEF DESCRIPTION OF THE DRAWINGS

FIG. 1: Common light chain used in mono- and bispecific IgG

FIG. 1A: Common light chain amino acid sequence. FIG. 1B: Common light chain variable domain DNA sequence and translation (IGKV1-39/jk1). FIG. 1C: Common light chain constant region DNA sequence and translation. FIG. 1D: IGKV1-39/jk5 common light chain variable domain translation. FIG. 1E: V-region IGKV1-39A.

FIG. 2: IgG heavy chains for the generation of bispecific molecules. FIG. 2A: VH is nucleic acid encoding the amino acid sequence for an MF depicted in FIG. 3. FIG. 2B: CH1 region. FIG. 2C: hinge region. FIG. 2D: CH2 region. FIG. 2E: CH2 containing L235G and G238R silencing substitutions. FIG. 2F: CH3 domain containing substitutions L351K and T366K (KK). FIG. 2G; CH3 domain containing substitutions L351D and L368E (DE)

FIG. 3: Amino acid sequence of heavy chain variable regions: The notation MF refers to a fab containing a heavy chain variable region as depicted and a common light chain. The amino acid sequence of the light chain is indicated in FIG. 1A. The underlined sequences indicate per amino acid sequence respectively the CDR1, the CDR2 and the CDR3 region.

FIG. 10: PD-1/PD-L1 blocking assay. Assessment of the capacity of the anti-PD-L1 and anti-PD-1 antibody panel to block the interaction of PD-L1 to coated PD-1 at a concentration of 10 μg/ml bispecific IgG. Data are normalized to data obtained with the bivalent benchmark PD-L1 antibody MPDL3280A at a concentration of 10 μg/ml (100% blocking). A representative example is shown of the PD-L1 (top graph) and PD-1 (bottom graph) panel. Maximum binding (normalized to 0% blocking) was established by incubation with a non-PD-1/PD-L1 specific human isotype antibody. All PD-1 and PD-L1 variable domains comprising MF sequences depicted in FIG. 3 and not represented here block the PD-1/PD-L1 interaction >70%.

FIG. 12: SEB-induced IL-2 production in PBMC is enhanced by PD-1×PD-L1 antibodies in a dose dependent way. PB composition is listed in Table 5. IL-2 productions are shown as stimulation index in relation to the negative control antibody (Ctrl Ab).

FIG. 13: Amino acid sequence of heavy chain variable regions: The notation MF refers to a fab containing a heavy chain variable region as depicted and a common light chain. The amino acid sequence of the light chain is indicated in FIG. 1A. The underlined sequences indicate per amino acid sequence respectively the CDR1, the CDR2 and the CDR3 region.

FIG. 14: Binding to PD-1. All bispecific IgGs bind to PD-1 in ELISA.

FIG. 16: FACS assay confirms binding to antigen expressed by CHO cells. Upper Panel, binding to CHO-PD-L1 cells; Lower panel right binding to CHO-PD1 cells FIG. 17: FACS assay confirms binding of lead candidate PD-1×PD-L1 bispecific IgGs to antigen on activated T cells.

FIG. 20: PD-1×PD-L1 antibodies enhance SEB-induced IL-2 production by PBMCs relative to an equimolar mix of their parental bivalent monospecific antibodies. Data represent mean IL-2 production by PBMCs from 4 independent donors in the presence of increasing concentrations of antibody. PG codes indicate the respective parental bivalent antibodies for each of the two bispecific antibodies (indicated by PB). IL-2 production is shown as relative light units (RLU) measured in AlphaLISA.

EXAMPLES

As used herein "MFXXXX" wherein X is independently a numeral 0-9, refers to a Fab comprising a variable domain wherein the VH has the amino acid sequence identified by the 4 digits. Unless otherwise indicated the light chain variable region of the variable domain typically has a sequence of FIG. 1A, typically 1B, "MFXXXX VH" refers to the amino acid sequence of the VH identified by the 4 digits. The MF further comprises a constant region of a light chain and a constant region of a heavy chain that normally interacts with a constant region of a light chain. PG refers to a monospecific antibody comprising identical heavy and light chains. PB refers to a bispecific antibody with two different heavy chains. The variable region of the heavy chains differs and typically also the CH3 region, wherein one of the heavy chains has a KK mutation of its CH3 domain and the other has the complementing DE mutation of its CH3 domain (see for reference PCT/NL2013/050294 (published as WO2013/157954).

Example: 1

Generation of Materials for Selection and Screening
Culturing of Cell Lines

Figure 4:
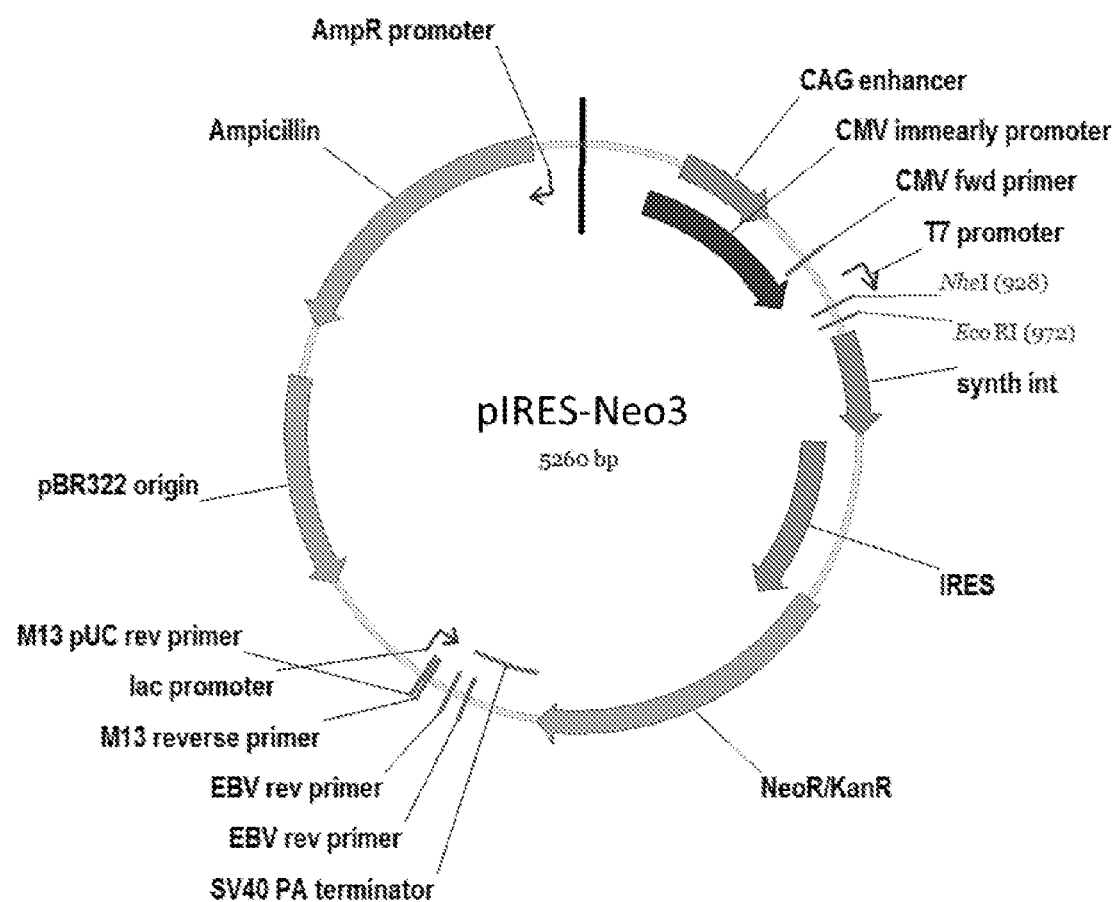
FIG. 4: Vector map and features of pIRES-Neo3 (MV1363).
Figure 5:
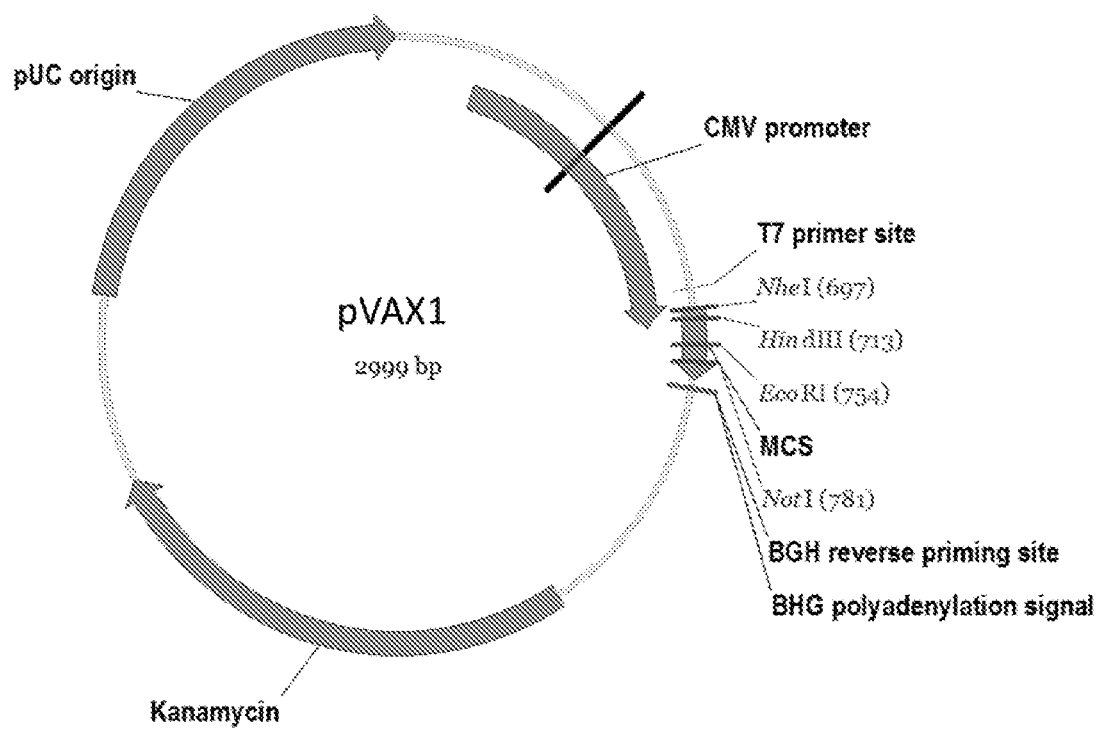
FIG. 5: Vector map and features of pVAX1.

Human ES-2 cells (cat. no. CRL-1978) were purchased from ATCC and routinely maintained in McCoy's 5A (Gibco) supplemented with 10% FBS (Lonza). Freestyle 293F cells (cat. no. p/n51-0029) were obtained from Invitrogen and routinely maintained in 293 FreeStyle medium. HEK293T (cat. no. ATCC-CRL-11268), CHO-K1 (cat. no. DSMZ ACC110) cell lines were purchased from ATCC and routinely maintained in DMEM/F12 (Gibco) supplemented with L-Glutamine (Gibco) and FBS (Lonza), and CHO-S (cat. no. 11619-012) cell lines were purchased from Gibco and routinely maintained in Freestyle CHO expression medium (Invitrogen) supplemented with L-glutamine
Generation of PD-1 and PD-L1 Expression Vectors for Immunization, and for Generation of Stable Cell Lines Full length cDNA of each target including unique restriction sites for cloning and kozak consensus sequence for efficient translation was either synthetized, or obtained via PCR amplification on a commercially available expression construct, containing the target cDNA, with specific primers that introduced unique restriction sites for cloning and kozak consensus sequence for efficient translation. The cDNA of each target was cloned into a eukaryotic expression construct such as pIRES-Neo3 (Clontech; FIG. 4) or pVAX1 (Thermo Fisher Scientific; FIG. 5) via NheI/EcoRI, resulting in pIRES-Neo3_[TARGET_NAME] and pVAX1_[TARGET_NAME], respectively. The insert sequences were verified by comparison with NCBI Reference amino acid sequences. The pIRES-Neo3 constructs were used for generation of stable cell lines. The pVAX1 constructs were used for immunization purposes. See TABLE 1 for an overview of the names of the resulting constructs.

```
Amino acid sequence full length huPD-1 insert (both
in pIRES-Neo3 and pVAX1) for expression on the
cell surface (Identical to Gen Bank: NP_005009.2):
MQIPQAPWPVVWAVLQLGWRPGWFLDSPDRPWNPPTFSPALLVVTEGDNAT

FTCSFSNTSESFVLNWYRMSPSNQTDKLAAFPEDRSQPGQDCRFRVTQLPN

GRDFHMSVVRARRNDSGTYLCGAISLAPKAQIKESLRAELRVTERRAEVPT

AHPSPSPRPAGQFQTLVVGVVGGLLGSLVLLVWVLAVICSRAARGTIGARR

TGQPLKEDPSAVPVFSVDYGELDFQWREKTPEPPVPCVPEQTEYATIVFPS

GMGTSSPARRGSADGPRSAQPLRPEDGHCSWPL

Of which:
MQIPQAPWPVVWAVLQLGWR: signal peptide.

PGWFLDSPDRPWNPPTFSPALLVVTEGDNATFTCSFSNTSESFVLNWYRMS

PSNQTDKLAAFPEDRSQPGQDCRFRVTQLPNGRDFHMSVVRARRNDSGTYL

CGAISLAPKAQIRESLRAELRVTERRAEVPTAHPSPSPRPAGQFQTLV:

ECD of huPD-1.

VGVVGGLLGSLVLLVWVLAVI: Predicted TM region.

CSRAARGTIGARRTGQPLKEDPSAVPVFSVDYGELDFQWREKTPEPPVPCV

PEQTEYATIVFPSGMGTSSPARRGSADGPRSAQPLRPEDGHCSWPL:

Intracellular tail.

Amino acid sequence full length macaque (macaca
fascicularis)PD-1 insert(both in pIRES-Neo3 and
pVAX1)for expression on the cell surface
(Identical to GenBank: ABR15751.1):
MQIPQAPWPVVWAVLQLGWRPGWFLESPDRPWNAPTFSPALLLVTEGDNAT

FTCSFSNASESFVLNWYRMSPSNQTDKLAAFPEDRSQPGQDCRFRVTRLPN

GRDFHMSVVRARRNDSGTYLCGAISLAPKAQIKESLRAELRVTERRAEVPT

AHPSPSPRPAGQFQALVVGVVGGLLGSLVLLVWVLAVICSRAAQGTIEARR

TGQPLKEDPSAVPVFSVDYGELDFQWREKTPEPPAPCVPEQTEYATIVFPS

GLGTSSPARRGSADGPRSPRPLRPEDGHCSWPL

Of which:
MQIPQAPWPVVWAVLQLGWR: signal peptide.

PGWFLESPDRPWNAPTFSPALLLVTEGDNATFTCSFSNASESFVLNWYRMS

PSNQTDKLAAFPEDRSQPGQDCRFRVTRLPNGRDFHMSVVRARRNDSGTYL

CGAISLAPKAQIKESLRAELRVTERRAEVPTAHPSPSPRPAGQFQALV:

ECD of maPD-1.

VGVVGGLLGSLVLLVWVLAVI: Predicted TM region.

CSRAAQGTIEARRTGQPLKEDPSAVPVFSVDYGELDFQWREKTPEPPAPCV

PEQTEYATIVFPSGLGTSSPARRGSADGPRSPRPLRPEDGHCSWPL:

Intracellular tail.

Amino acid sequence full length huPD-L1 insert
(both
in pIRES-Neo3 and pVAX1)for expression on the
cell surface (Identical to GenBank: AAI13735.1):
MRIFAVFIFMTYWHLLNAFTVTVPKDLYVVEYGSNMTIECKFPVEKQLDLA

ALIVYWEMEDKNIIQFVHGEEDLKVQHSSYRQRARLLKDQLSLGNAALQIT

DVKLQDAGVYRCMISYGGADYKRITVKVNAPYNKINQRILVVDPVTSEHEL

TCQAEGYPKAEVIWTSSDIIQVLSGKTTTTNSKREEKLFNVTSTLRINTTT

NEIFYCTFRRLDPEENHTAELVIPELPLAHPPNERTHLVILGAILLCLGVA

LTFIFRLRKGRMMDVKKCGIQDTNSKKQSDTHLEET

Of which:
MRIFAVFIFMTYWHLLNA: signal peptide.

FTVTVPKDLYVVEYGSNMTIECKFPVEKQLDLAALIVYWEMEDKNIIQFVI

IGEEDLKVQHSSYRQRARLLKDQLSLGNAALQITDVKLQDAGVYRCMISYG
```

-continued

GADYKRITVKYNAPYNKINQRILVVDPVTSEHELTCQAEGYPKAEVIWTSS

DHQVLSGKTTTTNSKREEKLFNVTSTLRINTTTNEIFYCTFRRLDPEENHT

AELVIPELPLAHPPNER: ECD of huPD-L1.

THLVILGAILLCLGVALTFIF: Predicted TM region.

RLRKGRMMDVKKCGIQDTNSKKQSDTHLEET: Intracellular tail.

Amino acid sequence full length macaque (macaca
mulatta) PD-L1 insert (both in pIRES-Neo3 and
pVAX1) for expression on the cell surface
(Identical to GenBank: ABO33161.1): MRIFAVFIFTIYWHL

LNAFTVTVPKDLYVVEYGSNMTIECRFPVEKQLGLTSLIVYWEMEDKNIIQ

FVIIGEEDLKVQIISNYRQRAQLLKDQLSLGNAALRITDVKLQDAGVYRCM

ISYGGADYKRITVKVNAPYNKINQRILVVDPVTSEHELTCQAEGYPKAEVI

WTSSDHQVLSGKTTTTNSKREEKLLNVTSTLRINTTANEIFYCIFRRLGPE

ENHTAELVIPELPLALPPNERTHLVILGAIFLLLGVALTFIFYLRKGRMMD

MKKSGIRVTNSKKQRDTQLEET

Of which:
MRIFAVFIFTIYWHLLNA: signal peptide.

FTVTVPKDLYVVEYGSNMTIECRFPVEKQLGLTSLIVYWEMEDKNIIQFVH

GEEDLKVQHSNYRQRAQLLKDQLSLGNAALRITDVKLQDAGVYRCMISYGG

ADYKRITVKVNAPYNKINQRILVVDPVTSEHELTCQAEGYPKAEVIWTSSD

HQVLSGKTTTTNSKREEKLLNVTSTLRINTTANEIFYCIFRRLGPEENIIT

AELVIPELPLALPPNER: ECD of maPD-L1.

THLVILGAIFLLLGVALTFIF: Predicted TM region.

YLRKGRMMDMKKSGIRVTNSKKQRDTQLEET: Intracellular tail.

Generation of Stable Cell Lines Expressing PD-1 or PD-L1 pIRES-Neo3_[TARGET_NAME] expression constructs (TABLE 1) were used to generate CHO-S or CHO-K1 clones stably expressing the respective proteins. Constructs were transiently transfected in CHO-K1 cells using lipofectamine transfection, or using PEI transfection for CHO-S cells and screened by FACS using antibodies reacting with the respective proteins. After confirmation of expression, transiently transfected cells were seeded in limiting dilution and cultured under selection pressure relevant for the used expression construct to obtain stable cell clones. After 2-3 weeks of selection, clones were screened by FACS. The selected clones were expanded by serial passage, retested in FACS and frozen to −150° C. The names of clones that stably express the heterologous proteins are CHO-K1_[TARGET_NAME] cells or CHO-S_[TARGET_NAME] cells. See TABLE 1 for an overview of the constructs used to generate the stable cell lines and their resulting name.

Example 2

Immunization, Selection and Screening
Mice Used for Immunizations

For generation of human antibodies binding to huPD-1 and huPD-L1, mice transgenic for the human VK1-39 light chain (common light chain mice, see WO2009/157771) and for a human heavy chain (HC) minilocus (comprising a selection of human V gene segments, all human Ds and all human Js) were immunized with either recombinant protein or DNA encoding the proteins as briefly described below. These mice are referred to as 'MeMo®' mice.
Protein Immunizations 'MeMo®' mice were immunized by subcutaneous injections with recombinant protein and Gerbu adjuvant MM (Gerbu Biotechnik c #3001). Recombinant huPD-L1-His (SinoBiological; cat. no. 10084-H08H) and huPD-1-Fc (R&D; cat. no. 1086-PD) proteins were used for immunizations. Mice were immunized with 40 µg recombinant protein in PBS mixed with 40 µl of adjuvant in a total volume of 100 µl. Subsequently mice were boosted on day 14 and 28 with 20 µg of recombinant protein in PBS together with 20 µl of adjuvant in a total volume of 50 Mouse serum was collected at day 35 to determine serum titers. Mice with low serum titers received additional cycles of booster immunizations and serum analyses. Each cycle consisted of two weekly immunizations using 20 µg of recombinant protein in 50 µl PBS followed one week later by serum collection for titer analysis. Mice showing high serum titers against human but not the macaque homologue received booster immunizations with macaque antigen protein. Mice showing high serum titers against the human and macaque target received a final boost immunization consisting of daily injections with 20 µg of recombinant protein in 50 µl PBS on three consecutive days. One day after the final injection mice lymphoid tissue was collected.
DNA Immunizations MeMo®' mice were immunized by DNA tattooing using a micropigmentation device. DNA tattoo immunizations were performed with 20 µg plasmid DNA encoding the target antigen (pVAX1_[TARGET_NAME], TABLE 1). Mice were immunized with DNA encoding the human target only (PD-1, PD-L1). For PD-L1 immunizations, Treg cells were depleted four days prior to the start of immunization by injection of mice with 0.5 mg anti-CD25 antibody PC61.5 (Bioceros) to break tolerance. Mice were immunized at day 0, 3, 6, 14, 17, 28 and 31. Mouse serum was collected at day 35 to determine serum titers. Mice with low serum reactivity received additional cycles of booster immunizations and serum analyses. Each cycle consisted of two weekly immunizations followed one week later by serum collection for titer analysis. Mice showing strong serum reactivity against cells expressing the human and macaque target received a final boost immunization followed after 3 days by collection of lymphoid tissue.
Determination of Serum Titers Serum titers were determined by FACS analysis using cell lines expressing the human and macaque target antigens (Table 1).
Generation of 'Immune' Phage Fab Libraries by RT-PCR from Tissues of Immunized Mice Spleen and draining lymph nodes were removed from mice for which a significant humoral response was observed against the respective target proteins.

Single cell suspensions were generated from both spleen and inguinal lymph nodes and subsequently these tissues were lysed in Trizol LS Reagent (Thermo Scientific c #10296028) and stored at −80° C. until use.

Figure 6:
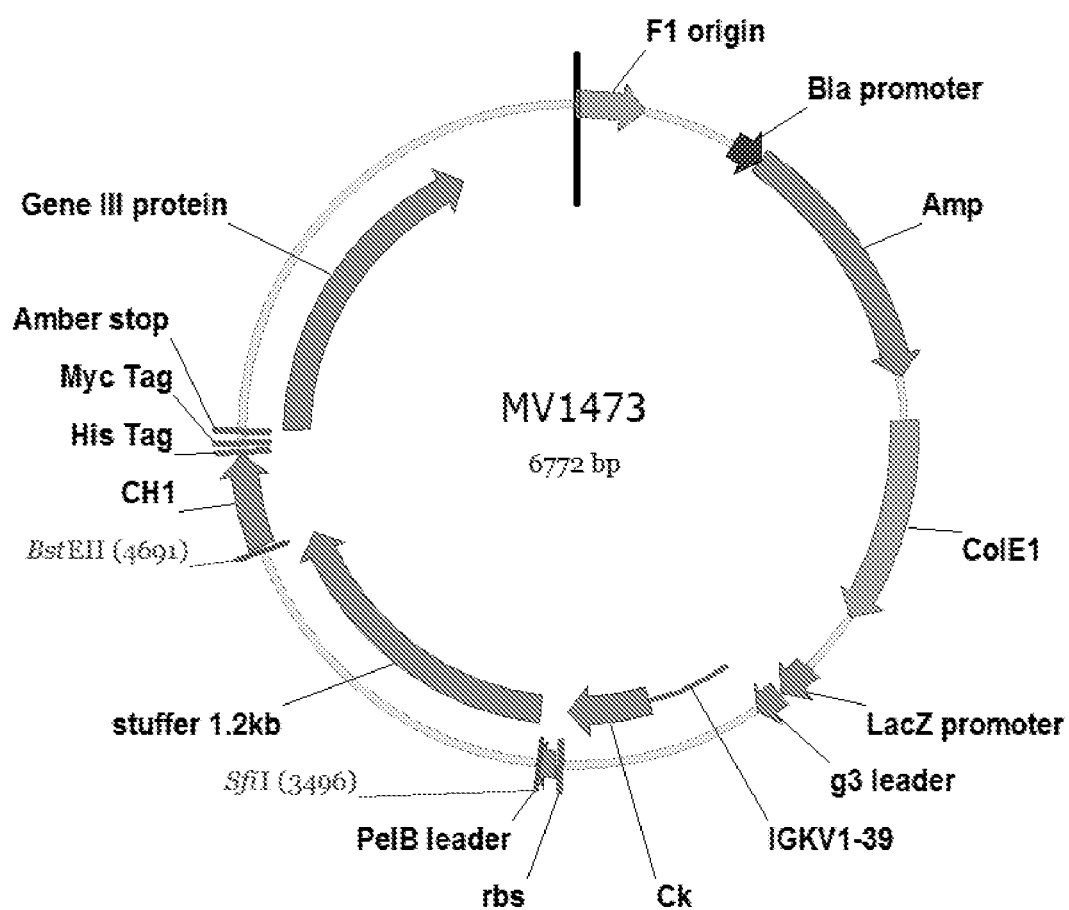
FIG. 6: Vector map and features of the phagemid vector MV1473 used to generate 'immune' phage display libraries.

From successfully immunized mice, the inguinal lymph nodes were used for the construction of 'immune' phage antibody repertoires. RNA was extracted from the single cell suspensions of the lymphoid tissue. 1 µg of total RNA was used in a RT reaction using an IgG-CH1 specific primer. The resulting cDNA was then used to amplify the polyclonal pool of VH-encoding cDNA using in-house adapted VHspecific primers essentially as described in Marks et al. (J Mol Biol. 1991 Dec. 5; 222(3):581-97). The resulting PCR product was then cloned in a phagemid vector (FIG. 6) for the display of Fab fragments on phage, as described in de Haard et al. (J Biol Chem. 1999 Jun. 25; 274(26):18218-30) with the exception that the light chain (FIGS. 1A and 1B) was the same for every antibody and was encoded by the vector. After ligation, the phagemids were used to transform *E. coli* TG1 bacteria and transformed bacteria were plated onto LB-agar plates containing ampicillin and glucose. All phage libraries contained >4×10$^5$ transformants and had an insert frequency of >90%. Bacteria were harvested after overnight growth and used to prepare phage according to established protocols (de Haard et al., J Biol Chem. 1999 Jun. 25; 274(26):18218-30).

Selection of Phage Carrying Fab Fragments Specifically Binding to Human Target Protein from 'Immune' Phage Fab Libraries Using Recombinant Proteins The phage Fab libraries that were generated were used to select target specific Fabs using phage display on directly coated recombinant proteins. For PD-L1, huPD-L1-His (Sinobiological; cat. no. 10084-H08H), huPD-L1-Fc (R&D; cat. no. 156-B7) and maPD-L1-His (Sinobiological; cat. no. 90251-C08H) were used. For PD-1, huPD-1-Fc (R&D; cat. no. 1086-PD) and huPD-1 biotin (BPS bioscience; cat. no. 71109) were used.

For selections with non-biotinylated recombinant protein ('panning selections'), proteins were coated onto the wells of a MAXISORP™ ELISA plate. The MAXISORP™ ELISA plates were blocked with 4% dried skimmed milk (Marvel) in PBS. Phage Fab libraries were also blocked with 4% Marvel and, when Fc tagged recombinant protein was used, also with excess of human IgG to deplete for Fc region binders prior to the addition of the phage library to the coated antigen. Incubation of the phage library with the coated protein was performed for 1.5 hrs at room temperature under shaking conditions. Plates or tubes were then washed fifteen times with 0.05% Tween-20 in PBS followed by 5 times washing with PBS. Bound phage were eluted for 20 minutes using trypsin, after which trypsin was neutralized with AEBSF trypsin inhibitor (Sigma).

For selections with biotinylated protein ('in-solution selections'), neutravidin was coated onto the well of a MAXISORP™ ELISA plate. The MAXISORP™ ELISA plates were blocked with 1% casein in PBS. In parallel, biotinylated protein and phage Fab libraries were blocked for 30 minutes in 0.5% casein in PBS, containing an excess of human IgG, in separate Eppendorf tubes. Thereafter, the blocked phage and biotinylated protein were mixed and incubated for 2 hours at room temperature. The mixture was thereafter added to the neutravidin coated wells for 20 minutes to capture the phage Fab particles that were bound to biotinylated protein. Plates were then washed fifteen times with 0.05% Tween-20 in PBS followed by 5 times washing with PBS. Bound phage were eluted for 20 minutes using trypsin, after which trypsin was neutralized with AEBSF trypsin inhibitor (Sigma).

The eluates of both selection strategies ('panning and in-solution') were added to *E. coli* TG-1 and incubated at 37° C. for phage infection. Subsequently infected bacteria were plated on agar plates containing Ampicillin and glucose, and incubated at 37° C. overnight. Single clones from the selection outputs were screened for target binding in ELISA or FACS depending on the target.

Selection of Phage Carrying Fab Fragments Specifically Binding to Human Target from 'Immune' Phage Fab Libraries Using Cells Stably Expressing the Target Protein Phage Fab libraries that were generated from target immunized mice were selected using phage display on cells expressing the respective target. The stable cell lines expressing PD-1 or PD-L1 (Table 1) were used for 1$^{st}$ round selections. Cells were blocked with 10% FBS in PBS. After blocking, the rescued phage were incubated with blocked cells. Cells plus phage were incubated for 1 hr at 4° C. Washing the cells (5 times) was performed using 1 ml of 10% FBS in PBS. Bound phage were eluted using trypsin for 20 minutes, after which trypsin was neutralized with AEBSF trypsin inhibitor (Sigma). The eluate was added to *E. coli* TG-1 and incubated at 37° C. for phage infection. Subsequently, phage-infected bacteria were plated on agar plates containing ampicillin and glucose, and incubated at 37° C. overnight.

For PD-L1, second round selections with ES-2 cells endogenously expressing huPD-L1 were performed with the same protocol as was used for the 1st round selection. After selection, single clones were screened for target binding in FACS.

Screening for Target Specific Fab Clones in ELISA

Of single clones, soluble Fab were prepared as described (J Mol Biol. 1991 Dec. 5; 222(3):581-97; J Biol Chem. 1999 Jun. 25; 274(26):18218-30). These were diluted 1:5 in 4% dried skimmed milk (Marvel) in PBS (blockbuffer) and tested for binding in ELISA to wells coated with the same antigen as was used for selection. Bound Fabs were detected by staining with an anti-myc antibody (Roche; cat. no. 11667203001) diluted 1:1000 in blockbuffer, followed by a HRP-conjugated anti-mouse IgG antibody (Jackson Immunoresearch; cat. no. 715-035-150) diluted 1:5000 in blockbuffer. After each antibody staining, wells were washed with PBS-T (PBS-0.05% v/v Tween 20). Bound secondary antibody was visualized by TMB/H$_2$O$_2$ staining and staining was quantified by means of OD$_{450\,nm}$ measurement. Clones were considered to bind the target when the OD450 nm was at least three times above the background signal obtained with a negative control Fab.

The VH-encoding cDNA's of all target-specific clones were sequenced. A selection of unique clones based on sequence identity and cluster analysis was then analyzed in FACS on binding to PD-L1 expressed on cells as described below for the clones obtained from the cell selection outputs.

Screening for Target Specific Fab Clones in FACS

Of single clones, selected on cells expressing the respective target, soluble Fab were prepared as described (J Mol Biol. 1991 Dec. 5; 222(3):581-97; J Biol Chem. 1999 Jun. 25; 274(26):18218-30). These were tested for binding in FACS to cells expressing the human and macaque target (Table 1) by incubation with a mix of 1:5 diluted Fab sample with 1:1000 diluted anti-myc antibody (centaur; cat. no. 04-CMYC-9E10) in FACS buffer (0.5% HI-FBS in PBS). Bound Fab/anti-myc complexes were detected by incubation with an APC-conjugated goat anti-mouse IgG antibody (BD Bioscience; cat. no. 550826) diluted 1:500 in FACS buffer. After each antibody incubation, wells were washed three times with FACS buffer. Stained cells were analysed using a FACS Accuri C6 instrument (Becton and Dickinson). Clones were considered positive when the mean fluorescence intensity was at least three times above the background signal obtained with a negative control Fab.

Example 3

Figures 7, 8:
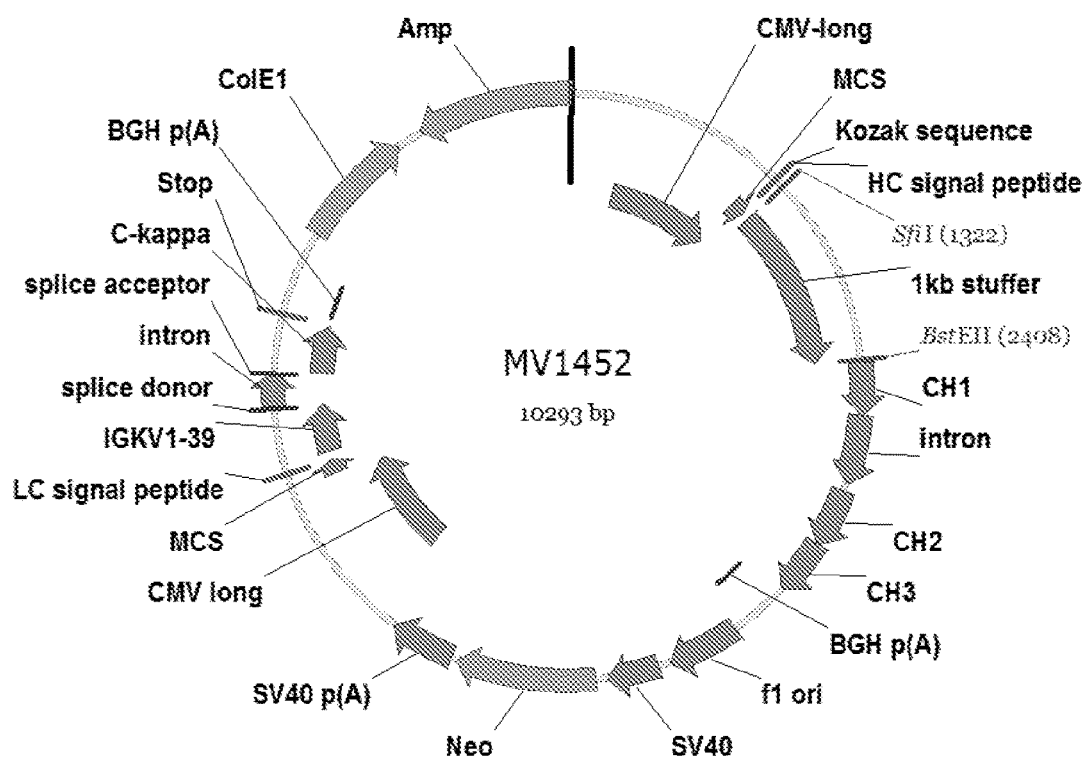
FIG. 7: Vector map and features of the IgG expression vector MV1452, that was used for expression of the PD-1 and PD-L1 specific Fab arms in the KK-variant heavy chain for bispecific IgG generation.
FIG. 8: Amino acid sequence of the VH gene that is tetanus toxin specific when combined with the common light chain as MF1337, and that is present in the DE-variant heavy chain that was used to generate PD-L1×TT and PD-1×TT bispecific IgG molecules. The underlined sequences indicate per amino acid sequence respectively the CDR1, the CDR2 and the CDR3 region.

Characterization huPD-L1 and huPD-1 Specific Fab Clones in IgG Format Recloning Human PD-L1 and PD-1 Specific Fab to IgG Format A selection of unique clones, based on CDR3 sequence and VH germline differences, that bound human and macaque target protein expressed on cells, was then re-cloned to an IgG expression plasmid such as MV1452 (FIG. 7), which contained the common light chain (FIG. 1), using SfiI-BstEII digestion and ligation of the pool of digested cDNA's according to standardized molecular biological techniques.

Expression of Bispecific IgG Containing a Human PD-L1 or Human PD-1 Specific Fab and a Tetanus Toxin Specific Fab Bispecific antibodies were generated by transient co-transfection of two plasmids encoding IgG with different VH domains, using a proprietary CH3 engineering technology to ensure efficient hetero-dimerisation and formation of bispecific antibodies. The common light chain present on both plasmids containing the heavy chain is also co-transfected in the same cell. In our co-pending applications (e.g. WO2013/157954 and WO2013/157953; incorporated herein by reference) we have disclosed methods and means for producing bispecific antibodies from a single cell, whereby means are provided that favor the formation of bispecific antibodies over the formation of monospecific antibodies. These methods can also be favorably employed in the present invention. Specifically, preferred mutations to produce essentially only bispecific full length IgG molecules are amino acid substitutions at positions 351 and 366, e.g. L351K and T366K (numbering according to EU numbering) in the first CH3 domain (the 'KK-variant' heavy chain) and amino acid substitutions at positions 351 and 368, e.g. L351D and L368E in the second CH3 domain (the 'DE-variant' heavy chain), or vice versa (FIG. 2). It was previously demonstrated in our co-pending applications that the negatively charged DE-variant heavy chain and positively charged KK-variant heavy chain preferentially pair to form heterodimers (so-called 'DEKK' bispecific molecules). Homodimerization of DE-variant heavy chains (DE-DE homodimers) or KK-variant heavy chains (KK-KK homodimers) hardly occurs due to strong repulsion between the charged residues in the CH3-CH3 interface between identical heavy chains.

Figure 9:
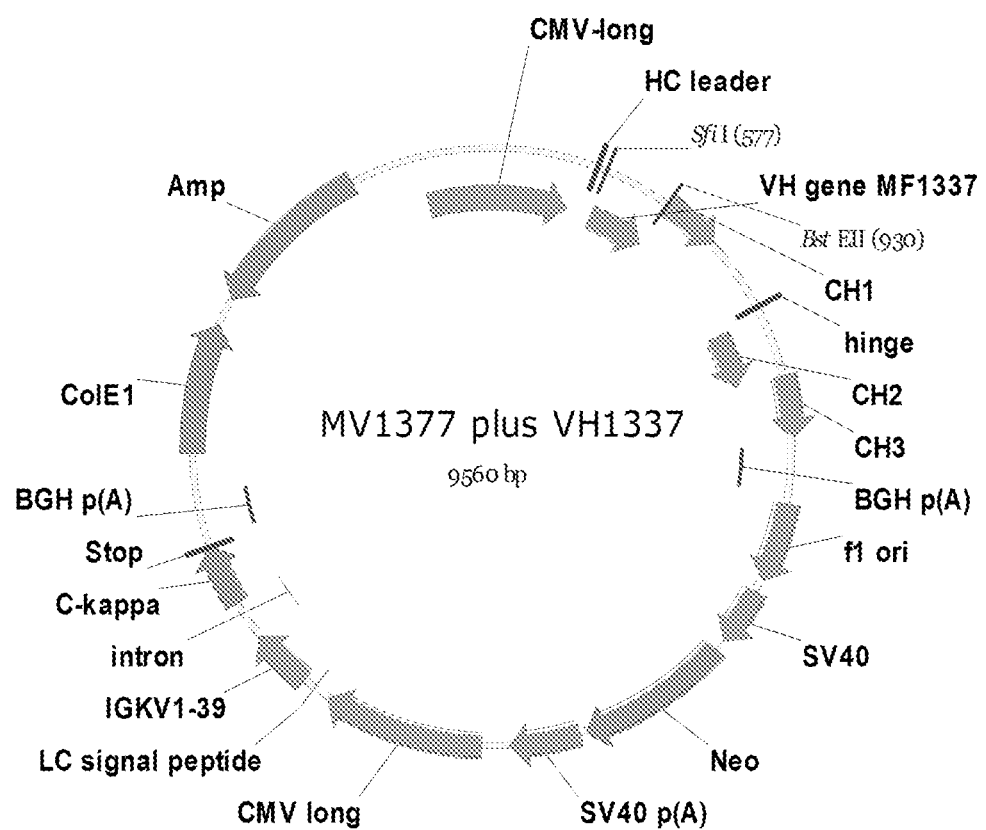
FIG. 9: Vector map and features of the IgG expression vector MV1377, that was used for expression of the TT specific Fab arm MF1337 in the DE-variant heavy chain for bispecific IgG generation.

VH genes encoding the antibodies binding human PD-L1 and PD-1 described above were cloned into the MV1452 IgG expression vector encoding the positively charged CH3 domain. A tetanus toxin (TT) targeting antibody (FIG. 8) was cloned into the MV1377 IgG expression vector (FIG. 9) encoding the negatively charged CH3 domain. Suspension growth-adapted 293F Freestyle cells were cultivated in T125 flasks on a shaker plateau until a density of $3.0 \times 10^6$ cells/mi. Cells were seeded at a density of $0.3$-$0.5 \times 10^6$ viable cells/ml in each well of a 24-deep well plate. The cells were transiently transfected with a mix of two plasmids encoding different antibodies, cloned into the proprietary vector system. Seven days after transfection, the cellular supernatant was harvested and filtered through a 0.22 µM filter (Sartorius). The sterile supernatant was stored at 4° C. until purification of the antibodies.

Purification of Bispecific IgG

Purification of IgG was performed on a small scale (<500 µg), using protein-A affinity chromatography. Small scale purifications were performed under sterile conditions in 24 well filter plates using filtration. First, the pH of the medium was adjusted to pH 8.0 and subsequently, IgG-containing supernatants were incubated with protein A Sepharose CL-4B beads (50% v/v) (Pierce) for 2 hrs at 25° C. on a shaking platform at 600 rpm. Next, the beads were harvested by filtration. Beads were washed twice with PBS pH 7.4. Bound IgG was then eluted at pH 3.0 with 0.1 M citrate buffer and the eluate was immediately neutralized using Tris pH 8.0. Buffer exchange was performed by centrifugation using multiscreen Ultracel 10 multiplates (Millipore). The samples were finally harvested in PBS pH7.4. The IgG concentration was measured using Octet. Protein samples were stored at 4° C.

IgG Quantification Using Octet

To determine the amount of IgG purified, the concentration of antibody was determined by means of Octet analysis using protein-A biosensors (Forte-Bio, according to the supplier's recommendations) using total human IgG (Sigma Aldrich, cat. nr. 14506) as standard.

Specificity Analysis huPD-L1×TT and huPD-1×TT Bispecific IgG

The bispecific antibodies were tested for binding in FACS to the stable cell lines expressing the relevant human and macaque orthologs (Table 1) and the wt cells. Therefore, cells were harvested and diluted to $10^6$ cells/ml in FACS buffer (PBS/0.5% BSA/0.5 mM EDTA). $1$-$2 \times 10^5$ cells were added to each well in a U-bottom 96 well plate. Cells were centrifuged for 2 minutes at 300 g at 4° C. Supernatant was discarded by inverting the plate(s). 50 µl of each IgG sample at a concentration of 10 µg/ml was added and incubated for 1H on ice. Cells were centrifuged once, supernatant was removed and cells were washed twice with 150 µl of FACS buffer. 50 µl diluted 1:400 goat anti human IgG PE (Invitrogen) was added and incubated for 30 minutes on ice in the dark. After adding FACS buffer, cells were centrifuged once, supernatant was removed and cells were washed twice with FACS buffer. Cells were analyzed on a FACSCanto Flow cytometer (Becton and Dickinson) in a HTS setting. Binding of the antibodies to cells was assessed by measuring the mean fluorescence intensity (MFI) of the stained cell population. Antibodies were considered to bind their target when the MFI was at least five-fold that of the same cell population stained with a (negative control) non-binding antibody (directed to tetanus toxoid).

Binning huPD-L1 and huPD-1 Specific Fab Arms Present in the PD-L1×TT and PD-1×TT Bispecific IgG on Ligand Blocking Ability huPD-L1 and huPD-1 binding clones were tested for their ability to block the interaction of PD-L1 with PD-1. For the PD-L1 Fab arms, the ability to block the interaction between PD-L1 and CD80 was also assessed. Therefore PD1-Fc (R&D systems; cat. no. 1086-PD) or CD80-Fc (R&D systems; cat. no. 140-B1) was coated to a maxisorp plate at 1 and 3 µg/ml, respectively. Coated wells were blocked with 4% BSA in PBS. Thereafter, 0.55 µg/ml biotinylated PD-L1 (BPS bioscience; cat. no. 71105) was added in the presence or absence of IgG in the range of 0.15 to 20 µg/ml. Bound biotinylated PD-L1 was detected with HRP-conjugated streptavidin (BD bioscience: cat. no. 554066) diluted 1:2000 in block buffer. After each incubation step, the ELISA plate was washed three times with PBS-T (PBS-0.05% v/v Tween 20). Bound streptavidin was visualized by TMB/$H_2O_2$ staining and staining was quantified by means of $OD_{450\ nm}$ measurement. Clones were considered to block the interaction of PD-1 with PD-L1 when the ELISA signal was reduced more than 70% at an IgG (PD-L1×TT or PD-1×TT) concentration of 10 µg/ml, compared to a control in which a TT specific competition antibody was added. See FIG. 10 for the results obtained with a representative selection of the PD-1 and PD-L1 antibody panel tested as PD-1×TT or PD-L1×TT bispecific molecules.

Affinity Ranking huPD-L1 and huPD-1 Specific Fab Arms Present in the PD-L1×TT and PD-1×TT Bispecific IgG Bispecific antibodies that were shown to bind the respective human and macaque orthologs in FACS were ranked on apparent affinity for both orthologs in FACS. Therefore, the stable cell lines expressing the respective orthologs (Table 1) were harvested and diluted to $10^6$ cells/ml in FACS buffer (PBS/0.5% BSA/0.5 mM EDTA). Cells were centrifuged for 2 minutes at 300 g at 4° C. Supernatant was discarded by inverting the plate(s). 50 µl of each IgG sample, in a 11-step, 2-fold dilution series ranging from 10 to 0.01 µg/ml, was added and incubated for 1H on ice. Cells were centrifuged once, supernatant was removed and cells were washed twice with 150 µl of FACS buffer. 50 µl diluted 1:400 goat anti human IgG PE (Invitrogen) was added and incubated for 30 minutes on ice in the dark. After adding FACS buffer, cells were centrifuged once, supernatant was removed and cells were washed twice with FACS buffer. Cells were analyzed on a FACSCanto Flow cytometer (Becton and Dickinson) in a HTS setting. Binding of the antibodies to cells was assessed by measuring the mean fluorescence intensity (MFI) of the stained cell population. Antibodies were considered to bind their target when the MFI was at least five-fold that of the same cell population stained with a (negative control) non-binding antibody (directed to tetanus toxoid).

PBMC Isolation

Human whole blood was obtained from buffy coats (Sanquin) and was diluted 1:1 with PBS. Leucosep tubes (Greiner Bio-One cat. no. 227 290) were filled with 17.5 m Ficoll-Paque Plus (Amersham Biosciences cat. no. 17-1440-02) warmed at room temperature (RT). Ficoll-Paque Plus was spun down for 30 seconds at 1000×g at RT. 30 ml of diluted whole blood was poured on top. The tubes were spun at 1000×g for 10 minutes at RT and the mononuclear PBMC interface was harvested, washed twice in PBS and resuspended in 250 µl PBS. The PBMCs were counted and readjusted to 1×106/ml in tissue culture medium (DMEM with 10% FCS) and frozen down by adding an equal volume of ice-cold freeze medium (80% culture medium/20% DMSO). Cells were stored in 1 ml aliquots at −150° C. until further use.

SEB Assay

The functional activity of the bispecific antibodies was determined by using PBMCs stimulated by *Staphylococcus* enterotoxin B (SEB). SEB specifically activates T cells expressing the Vβ3, 12, 14, 15, 17 and 20T cell receptor chain. PBMCs from 3 donors were thawed, washed, counted and resuspended in culture medium (RPMI1640 plus 10% heat inactivated FBS) to a concentration of 2×106 cells/ml. Cells were seeded in flat bottom 96-well plates (2×105 cells/well) in the presence of SEB (2000 or 125 ng/ml). Antibody serial dilutions starting at 20 µg/ml were added. Each plate contained a serial dilution of negative (TT specific PG1337) and positive control antibody (ipilumumab, nivolumab (PD-1×PD-L1), LAG3.5 (LAG-3×PD-1) that served as reference controls. Cells were stimulated for 3 days at 37° C., 5% CO2 in 95% relative humidity prior to being tested for cytokine secretion and/or cell surface expression of antigens.

Cytokine Assays

ELISA: After stimulation of T-cells or PBMCs at various times, plates were centrifuged and media was removed. Cytokine levels were detected by AlphaLISA in accordance with the manufacturer's instructions (Perkin Elmer). Concentrations were calculated based on the standard curve.

Luminex assay: Another method used to determine cytokine production in vitro was using multiplex analysis developed by eBioscience. Levels of IFN-γ, IL-2, and TNF-α were measured in culture supernatants following manufacturer's instructions. Results were analyzed by eBioscience analysis software.

Reference Antibodies

Antibodies that inhibit the function of PD-1 and PD-L1 are known in the art. Monoclonal bivalent antibodies were constructed according to published information and expressed in CHO-S cells. The anti-PD-1 antibody Nivolumab was generated based on the information disclosed in CA 02607147. The anti-PD-L1 antibody MPDL3280A was based on the information disclosed WO2010077634A1 Genentech Inc).

PD-1/PD-L1 Blockade Reporter Assay

The PD-1/PD-L1 blockade reporter assays used were developed by Promega and are based on a two cell system; CHO cells expressing PD-L1, and a T cell activator and a Jurkat/NFAT-RE Reporter Cell Line overexpressing PD-1. The PD-1/PD-L1 blockade reporter assays were performed using the thaw and use format of Promega. PD-L1 expressing cells (cat. no. 0187103) were thawed in 14.5 ml Cell Recovery Medium (DMEM/F12 containing 10% FBS). Next, 50 µl cell suspension was added to the inner wells of a 96 well half area plate (Corning, cat. no. 3688). Plates were incubated overnight at 37° C., 5% CO, in 95% relative humidity. Next day, culture medium was removed and 20 µl test antibody in assay medium (RPMI 1640 containing 4% FRS) in a serial dilution (starting concentration 10 µg/ml) was added to each well. Each plate contained a serial dilution of negative (TT specific PG1337) and positive control antibody (one control based on Nivolumab, referred to herein as 5C4, and one control based on Atezolizumab, referred to herein as MPDL3280A or YW243.55.S70) that served as reference controls. PD-1 effector cells (cat no. C187105) were thawed in 5.9 ml Assay medium and 20 µl cell suspension was added to each well. Plates were incubated for 6 H or overnight at 37° C., 5% CO, in 95% relative humidity. 40 µl of luciferase (Bio-Glo Luciferase Assay System, cat. no. G794L) was added the next day and the amount of luciferase activity was measured using aBioTek Synergy 2 Multi-Mode Microplate Reader. Potency was measured as luciferase activity in comparison to the negative control antibody.

Example 4

Screening of the PD1×PD-L1 Antibody Panel

VH from the PD-1 and PD-L1 antibody panel were recloned into the charged engineered Fc-silenced vectors such that upon expression of the antibody heavy chains hetero dimerisation of heavy chains is forced resulting in the generation of bispecific antibodies after transfection. The PD-1 Fab arms were cloned in the MV1625 vector whereas the PD-L1 Fab arms were recloned in the MV1624 vector. PD-1 and PD-L1 antibodies were combined with MF1337 a TT targeting Fab arm to generated bispecific antibodies targeting PD-1 or PD-L1 in a monovalent manner. Bispecific antibodies were tested in a semi log serial titration (starting concentration 10 µg/ml) in the PD-1/PD-L1 blockade reporter assay to rank the antibodies for blocking potency. The panel of PD-L1 antibodies in monovalent format could be ranked, whereas the panel of PD-1 antibodies in monovalent format showed insufficient blocking capacity for a ranking in the PD-1/PD-L1 blockade reporter assay. Therefore, PD-1 antibodies were produced in a bivalent format and retested in the PD-1/PD-L1 blockade reporter assay. Based on the activity data antibodies were selected from the PD-1 or PD-L1 antibody panel for the subsequent PD1×PD-L1 bispecific screen. The activity of the selected candidates in the reporter assay is shown in Table 2 and 3 respectively.

The PD-1 Fab panel was composed of functional activity variants within three antibody clusters i.e. A, B and C, and the non-functional variant D whereas the PD-L1 Fab panel was composed of antibodies derived from eleven antibody clusters. Both the PD-1 and PD-L1 antibody panel included one functionally inactive antibody.

Figure 11:
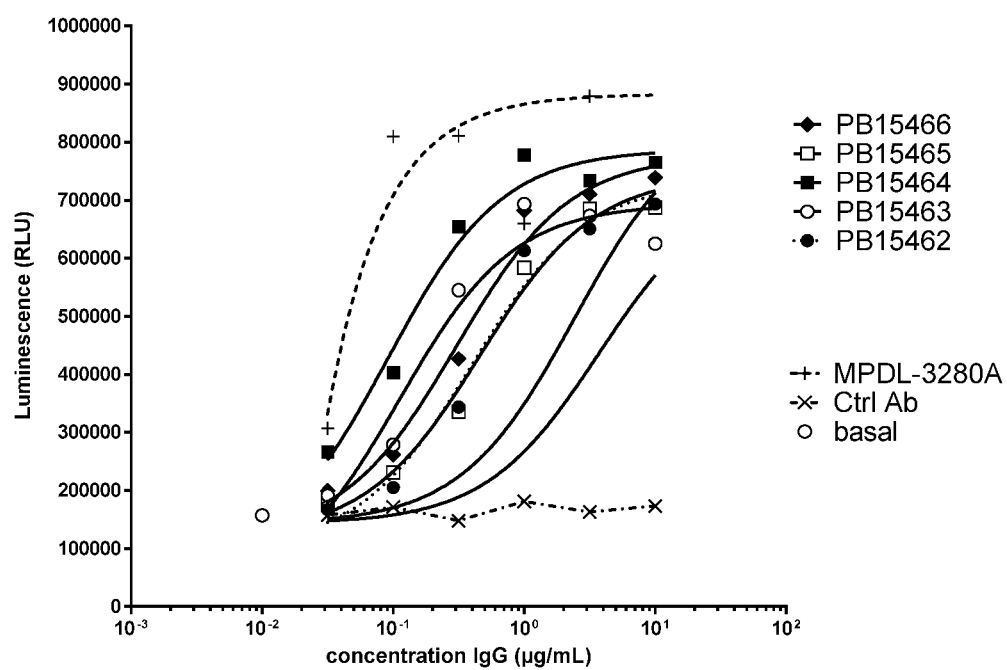
FIG. 11: PD-1/PD-L1 functional activity of a panel of antibodies in a dose titration in the in the PD-1/PD-L1-luc reporter system.

A total of 120 PD-1×PD-L1 bispecific antibodies comprising 10 different PD-1 Fab arms and 12 different PD-L1 Fab arms were produced in 24-well format and IgG purified. All antibodies were tested for their capacity to induce dose dependent luciferase expression in a serial titration in the PD-1/PD-L1-luc reporter system. Nivolumab or MPDL3280A were included as reference antibodies. FIG. 11, shows the luciferase induction of a selection of the bispecific antibodies showing a wide variety of responses.

Table 4 shows the percentage activity of the bispecific antibodies in comparison to MPDL3280A. PD-1×PD-L1 combinations containing one non-functional Fab arm were least effective. Furthermore, a combination of the most potent PD-L1 Fab with the most potent PD-1 Fab did not result in the most potent bispecific PD-1×PD-L1 antibody. Some PD-L1 Fab arms such as the MF5561, MF5442 and MF5382 were highly potent with various PD-1 Fab arms, whereas for example MF5359 was not. The PD-1 Fab arms with the highest activity induced a potent activity with several PD-L1 Fab arms.

The most potent PD-1×PD-L1 bispecific antibodies were tested in a serial titration in a SEB assay. FIG. 12, shows a representative experiment of a SEB assay performed on three donors stimulated with 2 µg/ml SEB. All PD-1×PD-L1 combinations tested showed a dose related induction of IL-2 and γ-IFN (not shown). Maximum induced IL-2 levels obtained were in the range of 50-100 ng/ml. Most of the PD-1×PD-L1 bispecific antibodies showed a higher potency in comparison to nivolumab. Below the 10 µg/ml the majority of PD-1×PD-L1 bispecific antibodies were more potent in comparison to ipilumumab. Thus, PD-1×PD-L1 antibodies are very effective in stimulating T cell responses.

Example 5

Cloning and Expression of PD-1×PD-L1 Fab Variants

A total of 15 PD-1 and 25 PD-L1 Fab arms were combined, to generate 65 bispecific antibodies. The sequences of the Fab arms are depicted in FIGS. 3 and 13.

The 65 VH regions from the PD-L1 and PD-1 Fab panel were recloned into engineered expression vectors such that expression of the antibody forces hetero-dimerization of the heavy chains, resulting in the generation of bispecific antibodies after transfection. The VH regions of the PD-1 Fab arms were cloned into vector MV1625, and those of the PD-L1 Fab arms were cloned into vector MV1624. Both vectors harbor extra mutations in the CH2 and CH3-coding regions of the IgG protein: MV1625 and MV1624 both contain 1,235G and G236R substitutions that abrogate Fcγ receptor and C1q interactions of the resulting antibody. MV1625 also contain the amino acid substitutions L351D and L368E in the CH3 domain (the 'DE variant' heavy chain), while MV1624 contains the amino acid substitutions L351K and T366K in the CH3 domain (the 'KR variant' heavy chain).

Following cloning into the relevant vectors, DNA sequences were confirmed by PCR. Midiprep DNA was prepared for all constructs. Different pairs of vectors—one vector carrying an anti-PD-1 clone and the other carrying an anti-PD-L1 clone—were co-transfected into FreeStyle 293-F cells in duplo to produce bispecific proteins (65 in total). The IgGs produced in each well of the 24-well plates were then purified and buffer exchanged using Zeba desalting columns according to the manufacturer's instructions; protein yield was then quantified by OD280 using Nanodrop.

Overview PB Numbers and their MF Composition.

| PD-1 arm | PD-L1 arm | PB number | PD-1 arm | PD-L1 arm | PB number |
|---|---|---|---|---|---|
| MF6076 | MF5442 | PB15527p04 | MF7685 | MF5424 | PB16661p01 |
| MF6076 | MF7691 | PB16635p01 | MF7686 | MF5424 | PB16662p01 |
| MF6076 | MF7690 | PB16679p01 | MF7685 | MF5424 | PB16661p02 |
| MF6076 | MF7689 | PB16636p01 | MF7684 | MF5424 | PB16663p02 |
| MF6076 | MF7688 | PB16637p01 | MF7684 | MF5424 | PB16663p01 |
| MF6076 | MF7688 | PB16637p02 | MF7687 | MF7703 | PB16664p01 |
| MF7699 | MF7691 | PB16639p01 | MF7686 | MF7703 | PB16666p02 |
| MF7699 | MF7690 | PB16680p01 | MF7685 | MF7703 | PB16665p01 |
| MF7699 | MF7689 | PB16640p01 | MF7686 | MF7703 | PB16666p01 |
| MF7699 | MF7688 | PB16641p01 | MF7685 | MF7703 | PB16665p02 |
| MF7699 | MF7688 | PB16641p02 | MF7684 | MF7703 | PB16667p02 |
| MF7698 | MF7691 | PB16643p01 | MF7684 | MF7703 | PB16667p01 |
| MF7698 | MF7690 | PB16681p01 | MF6936 | MF5442 | PB15532p03 |
| MF7698 | MF7689 | PB16644p01 | MF6929 | MF7691 | PB16688p01 |
| MF7698 | MF7688 | PB16645p01 | MF6929 | MF7690 | PB16689p01 |
| MF7698 | MF7688 | PB16645p02 | MF6929 | MF7689 | PB16690p01 |
| MF6076 | MF5553 | PB15443p03 | MF6929 | MF7688 | PB16691p01 |
| MF6076 | MF7702 | PB16648p01 | MF6929 | MF7688 | PB16691p02 |
| MF6076 | MF7702 | PB16648p02 | MF6936 | MF5557 | PB15500p03 |
| MF7699 | MF7702 | PB16650p01 | MF6929 | MF7694 | PB16693p01 |
| MF7699 | MF7702 | PB16650p02 | MF6929 | MF7693 | PB16694p02 |
| MF7698 | MF7702 | PB16652p01 | MF6929 | MF7692 | PB16695p03 |
| MF7698 | MF7702 | PB16652p02 | MF6929 | MF7694 | PB16693p03 |
| MF6256 | MF5439 | PB15522p03 | MF6929 | MF7692 | PB16695p04 |
| MF6256 | MF7700 | PB16682p01 | MF6974 | MF5442 | PB15529p03 |
| MF6256 | MF7701 | PB16655p02 | MF6974 | MF7691 | PB16671p01 |
| MF6256 | MF7701 | PB16655p01 | MF6974 | MF7690 | PB16698p01 |
| MF6935 | MF5424 | PB15479p03 | MF6974 | MF7689 | PB16672p01 |
| MF6935 | MF5424 | PB15479p05 | MF6974 | MF7688 | PB16673p01 |
| MF6935 | MF7703 | PB16659p01 | MF6974 | MF7688 | PB16673p02 |
| MF7687 | MF5424 | PB16660p01 | MF6256 | MF7697 | PB16675p01 |
| MF7686 | MF5424 | PB16662p02 | MF6256 | MF7696 | PB16676p01 |
|  |  |  | MF6256 | MF7695 | PB16677p01 |

Example 6

Confirmation of Antigen Binding of PD-1 and PD-L1 Fabs by ELISA

Limiting Antigen ELISA for PD-1 or PD-L1

To confirm the binding of the PD-1 and PD-L1 Fabs present in the bispecific IgGs, antigen titration ELISAs were performed. In this ELISA, a serial dilution of PD-1 or PD-L1 antigen was coated to 96-well plates. Plates were then incubated with the test antibodies, which were detected using a secondary mouse anti-human antibody conjugated to horseradish peroxidase (HRP) that converts a colorless substrate to a dye that is readily visible. The negative TT specific control antibody PG1337 was included on all plates. The benchmark anti-huPD-1 antibody 5C4 (based on Nivolumab) was included as a positive control on all plates coated with PD-1 proteins, and benchmark anti-huPD-L1 antibody YW243.55.S70 (based on Atezolizumab) was included as a positive control on all plates coated with PD-L1 proteins.

To this end, 96-well Nunc Maxisorp plates were coated overnight at 4° C. with human PD-L1-Fc (R&D systems, cat. no. 156-B7) or human PD-1-Fe (R&D systems, cat. no. 1086-PD) in a 3-fold 7-step serial dilution from 10 μg/mL down to 0.014 μg/mL in PBS in each column of the plate. The next day, the ELISA plates were washed three times with 300 μL PBST, and blocked by filling wells with 2% BSA in PBS and incubating for 1 hour at, RT. Plates were emptied and PD-1×PD-L1 antibodies and control antibodies PG1337, 5C4 and YW243.55.S70 were added at 5 μg/mL in PBS-2% BSA (50 μL/well), one column per antibody. After incubation for 1 hr at room temperature, wells were washed three times with 300 μL PBST before the addition of 50 μL secondary antibody in the form of HRP-conjugated mouse anti-human IgG (BD, cat. no. 555788) diluted 1:2000 in PBS-2% BSA. After incubation for 1 hr at room temperature, wells were washed three times with 300 μL PBST before the addition of TMB peroxidase substrates A (BD, cat. no. 51-2506KC) and B (BD, cat. no. 51-2607KC) in a ratio of 1:1, 50 μL per well. After a maximum of 10 minutes, the reaction was stopped by adding a 1 M solution of $H_2SO_4$ at 50 μL/well. A ELx808 microplate reader then measured optical density (OD) at a wavelength of 450 nM.

Figure 15:
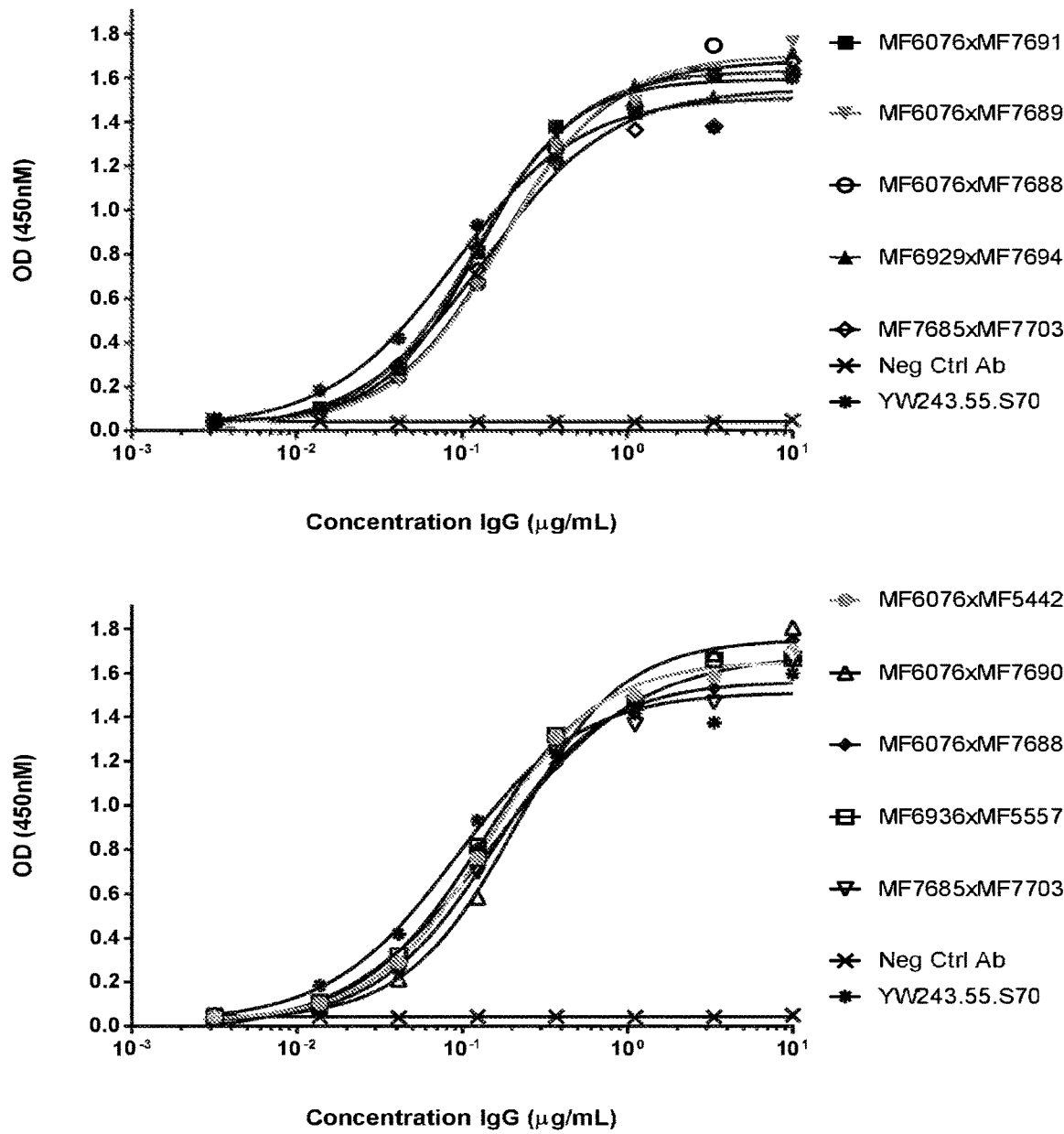
FIG. 15: Binding to PD-L1. All bispecific IgGs bind to PD-L1 in ELISA

The results of the limiting specific human IgG ELISA for PD-1 are shown in FIG. 14 and those for PD-L1 are shown in FIG. 15. Graphs show optical density (OD) at 450 nM as measured by microplate reader for increasing concentrations of coated antigen. All Fab arms tested bound well to PD-1 and PD-L1 and the level of binding was similar to that of the benchmark antibodies, making all Fab arms suitable for use in a bispecific PD-1×PD-L1 antibody.

Example 7

Activity of Antibodies in PD-1/PD-L1 Blockade Reporter Assay

The blocking activity of the generated bispecific PD-1× PD-L1 antibodies was tested in vitro in a physiologically relevant PD-1/PD-L1 blockade reporter assay developed by Promega Corporation, USA. The assay is based on a two-cell system in which CHO cells expressing PD-L1 and a T-cell receptor activator are co-cultured with a Jurkat/NFAT-RE reporter cell line overexpressing PD-1. The Jurkat T cells contain a luciferase reporter gene that can become activated through the NFAT (nuclear factor of activated T cells) pathway. Interaction of PD-1 with PD-L1 inhibits activation of this pathway. However, blocking the PD-1/PD-L1 interaction with antibodies against PD-1 or PD-L1 can activate the NFAT pathway. Therefore, the greater the degree of PD-1/PD-L1 blockade, the greater the activation of the luciferase reporter gene. To this end, serial dilutions of each antibody were added to PD-L1-expressing CHO cells before addition of Jurkat/NFAT-RE reporter cells overexpressing PD-1.

Methods

PD-1/PD-L1 Blockade Reporter Assay

The PD-1/PD-L1 blockade reporter assays used were developed by Promega and are based on a two cell system: CHO cells expressing PD-L1 and a T cell activator, and a Jurkat/NFAT-RE reporter cell line overexpressing PD-1. The PD-1/PD-L1 blockade reporter assays were performed using the thaw and use format of Promega. PD-L1-expressing cells (cat. no. C187103) were thawed in 14.5 mL Cell Recovery Medium (DMEM/F12 containing 10% FBS). Next, 50 μl, cell suspension was added to the inner wells of a 96-well half area plate (Corning, cat. no. 3688). Plates were incubated overnight at 37° C., 5% $CO_2$, in 95% relative humidity. Next day, culture medium was removed and 20 μL test antibody in assay medium (RPMI 1640 containing 4% FBS) in a serial dilution (starting concentration 10 μg/mL) was added to each well. Each plate contained a serial dilution of negative antibody, directed against Tetanus Toxoid (PG1337) and positive control anti-PD-L1 antibody (YW243.55.S70; based on Atezolizumab) that served as reference controls. PD-1 effector cells (cat no. C187105) were thawed in 5.9 ml Assay Medium and 20 μL cell suspension was added to each well. Plates were incubated for 24 hrs at 37° C., 5% $CO_2$, in 95% relative humidity. 40 μL of luciferase substrate (Bio-Glo Luciferase Assay System, cat. no. G794L) was added the next day and the amount of luciferase activity was measured using a BioTek Synergy 2 Multi-Mode Microplate Reader. Potency was measured as luciferase activity in comparison to the positive control antibody, YW243.55.S70

Results

The degree of blockade after 24 hours is shown in Table 6, where data show the relative induction of luciferase activity compared to the activity measured in wells to which no antibody was added. The percentage activity was calculated based on the Area Under the Curve (AUC) relative to the positive control anti-PD-L1 antibody YW243.55.S70. All tested bispecific PD-1×PD-L1 antibodies showed clear blocking activity.

Example 8

FACS Binding of PD-1×PD-L1 Bispecific IgGs to Antigen-Expressing Cells

Two PD-1×PD-L1 bispecific antibodies were tested for binding to PD-1 and PD-L1 on CHO cell lines that stably express each antigen. The cell lines used for this FACS were CHO-huPD-L1, CHO-S-huPD-1, and non-transfected CHO cells (negative cells). Briefly, these cell lines were stained with increasing concentrations of bispecific IgG, parental IgG or control IgG, followed by detection with goat anti-human IgG-PE. Positive controls were benchmark anti-huPD-1 antibody 5C1 (based on Nivolumab) and benchmark anti-huPD-L1 antibody YW243.55.S70 (based on Atezolizumab); the negative control was anti-tetanus toxin antibody PG1337.

To this end, stable CHO-huPD-L1 cells (MC0866) and CHO-S-huPD-1 cells (MC0617) were harvested and diluted to $10^6$ cells/mL in FACS buffer (PBS/0.5% BSA/2 mM EDTA). $0.5-2\times10^5$ cells were added to each well in a U-bottom plate (BD, cat. no. 353910). Cells were centrifuged for 3 minutes at 300 g at 4° C. Supernatant was discarded by inverting the plate. Cells were washed by adding 200 μL ice-cold FACS buffer. Cells were again centrifuged for 3 minutes at 300 g at 4° C. and the supernatant discarded as before. 40 μL of each IgG sample was added (3-fold 9-step serial dilution starting at 10 μg/mL) and the cells incubated for 30 min on ice in the dark. Cells were then washed twice starting with direct addition of 200 μL ice-cold FACS buffer, followed by centrifugation for 3 minutes at 300 g at 4° C. and removal of supernatant. Secondary antibody staining was performed by adding 40 μL goat anti-human IgG-PE (3 μg/mL; Invitrogen, cat. no. H10104), and incubating plates for 30 minutes on ice in the dark. Cells were again washed twice with 200 μL ice-cold FACS buffer and resuspended in 50-200 μL FACS buffer. Cells were analyzed on a FACSCanto Flow cytometer (Becton and Dickinson) in a high throughput sampler (HTS) setting. Binding of the antibodies to cells was assessed by measuring the mean fluorescence intensity (MFI) of the stained cell population. Antibodies were considered to bind their target when the MFI was at least five-fold that of the same cell population stained with the negative control antibody.

Results

The binding of the two bispecific IgGs to PD-L1 and PD-1 and that of the reference antibodies is shown in FIG. 16 Data show MFI detected by FACS on PD-L1 and PD-1-expressing CHO cells stained with increasing concentrations of bispecific IgG or control IgG. These results show that both bispecific IgGs recognized both targets when expressed on CHO cells and that the degree of binding was similar to or better than that of the reference antibodies.

Example 9

FACS Binding of PD-1×PD-L1 Bispecific IgGs to Activated T Cells
FACS Binding Assay Using Human Activated T Cells Two PD-1×PD-L1 bispecific antibodies were also tested for binding to PD-1 and PD-L1 on activated T cells. Briefly, 96-well plates were coated overnight with anti-CD3 antibody. Purified T cells from a single donor were then added and cultured for 3 days. After 3 days, activated T cells were harvested and pooled and used in a FACS assay to compare binding of the bispecific IgGs with that of their parental monospecific bivalent IgGs. Positive controls were benchmark anti-huPD-1 antibody 5C4, benchmark anti-huPD-L1 antibody YW243.55.S70; the negative control was anti-tetanus toxin antibody PG1337.

Methods

T Cell Purification

Peripheral blood mononuclear cells (PBMCs) from healthy donors were thawed and 9 volumes of culture medium (RPMI1640 with 10% heat-inactivated (hi) FBS) was added drop by drop. Cells were centrifuged for 10 minutes at 200 g at RT. The cell pellet was resuspended in 10 mL culture medium and cells were allowed to rest by incubating overnight at 37° C., 5% $CO_2$, in 95% relative humidity. Next day, T lymphocytes were isolated using the EasySep T cell enrichment (pan CD3) purification procedure as described by the manufacturer (Stem cell Technologies cat #19051). The EasySep procedure uses negative selection. Briefly, PBMCs were centrifuged for 10 minutes at 200 g at RT. The cell pellet was resuspended in EasySep buffer at a concentration of $5×10^7$ cells/mL. 50 µL of EasySep Human T Cell Enrichment cocktail was added to each mL of cell volume, mixed and allowed to incubate for 10 minutes at RT. Next, 50 µL of EasySep D Magnetic Particles were added to each mL of cell volume and allowed to incubate for 5 minutes at RT. The total volume was brought to 2.5 mL with EasySep buffer, and after mixing the cell suspension was transferred to a 5 µL round-bottomed Falcon tube (BD Biosciences, cat. no. 352235). Next, the tube was placed into the magnet allowing the undesired cell fraction to be bound to the magnet for 5 minutes at RT. Next, the tube was inverted and the purified T cell fraction was poured off into a new tube containing 7.5 mL culture medium. Cells were harvested by 10 minutes centrifugation at 200 g at RT and subsequently resuspended in at a concentration of $1×10^6$ cells/mL in culture medium.

FACS Binding Assay

One day before the start of the assay, 96-well flat-bottom plates (Cellstar, cat. no. 655180) were coated overnight at 4° C. with 5 µg/mL anti-CD3 (clone OKT3, eBioscience, cat. no. 16-0037-85). The next day, the culture plates were washed twice with PBS and 100 µL of T cell suspension was added to each well (100,000 cells/well). Plates were incubated at 37° C., 5% $CO_2$ for 3 days. The activated T cells were then harvested by gently pipetting up and down a few times using a multichannel pipette. Cells were pooled, mixed and transferred to U-bottom 96-well FACS assay plates (BD, cat. no. 353910) at $0.2$-$5×10^5$ cells per well.

For FACS analysis, cells were centrifuged for 3 minutes at 300 g at 4° C. Supernatant was discarded by inverting the plate. Cells were washed by adding 200 µL ice-cold FACS buffer. Cells were again centrifuged for 3 minutes at 300 g at 4° C. and the supernatant discarded as before. 40 µL of each bispecific IgG, parental IgG or control IgG sample was added (8-step semi-log titration starting at 20 µg/mL) and the cells incubated for 30 min on ice in the dark. Cells were then washed twice starting with direct addition of 200 µL ice-cold FACS buffer, followed by centrifugation for 3 minutes at 300 g at 4° C. and removal of supernatant. Secondary antibody staining was performed by adding 40 µL goat anti-human IgG-PE (3 µg/mL; Invitrogen, cat. no. H10104), and incubating plates for 30 minutes on ice in the dark. Cells were again washed twice with 200 µL ice-cold FACS buffer and resuspended in 50-200 µL FACS buffer. Cells were analyzed on a FACSCanto Flow cytometer (Becton and Dickinson) in a high throughput sampler (IITS) setting. Binding of the antibodies to cells was assessed by measuring the mean fluorescence intensity (MFI) of the stained cell population. Antibodies were considered to bind their target when the MFI was at least five-fold that of the same cell population stained with the negative control antibody.

Results

The results of the FACS binding assay are provided in FIG. 17. Data show MFI detected by FACS on human activated T cells stained with increasing concentrations of IgG. The graphs compare the binding of the two bispecific IgGs and their parental IgGs and show that all specific IgGs bound to activated T cells. The maximum level of binding for the bispecific IgGs was higher than that of both the parental monospecific bivalent IgGs and the positive control IgGs.

Example 10

Affinity Determination of Anti-PD-L1 Fab Arms for PD-L1 by Means of SPR

The affinity for PD-L1 of the anti-PD-L1 Fab arms was determined using surface plasmon resonance (SPR). To avoid avidity effects, affinity was measured in the context of a bispecific IgG that has just one arm specific for PD-L1, i.e. in monovalent format.

To determine the kinetics of binding of anti-PD-L1 Fab arms to the antigen, Surface plasmon resonance (SPR) using a BIAcore T100 was used. Recombinant, purified, Fc-tagged human PD-L1 (R&D Systems, cat. nr. 156-B7-100) was coupled to flow cell (FC) 2 of a CM5 sensor chip (FC1 served as blank for subtraction and was activated, then inactivated directly using ethanolamine) at to a level of approximately 200 resonance units (RU) using NHS/EDC chemistry at pH5.0 (NaAc buffer), 2 µg/ml antigen concentration and 10 µl/min flow rate. Bispecific IgG composed of an anti-PD-L1 Fab arm and an irrelevant Fab arm were then run over the surfaces of FC1 and 2 at different concentrations (100 nM and serial 2-fold dilutions in HBS, 6 dilutions) in a kinetic run at 30 µl/min. The irrelevant Fab arm is specific for PD-1. Regeneration was performed using a pulse of 50 mM HCl in water (15 µl at a flow rate of 10 µl/min). Obtained sensorgrams were evaluated using the BIAevaluation software and kinetic association- and dissociation rate constants were determined.

Several measurements were performed on different surfaces of different sizes on several days. Different measurements gave very similar results, underscoring their validity. All measurements were carried out at 25° C.

Results

The results of the affinity determination are provided in Table 7, which shows that all tested anti-PD-L1 Fab arms have a good affinity.

Example 11

PD-L2 Blockade Via PD-1×PD-L1 Antibodies

While therapeutic antibodies against PD-1 and PD-L1 are known to be effective in cancer treatment, the role of PD-L2 in anticancer immunity is currently unclear. PD-L1 blockade could potentially promote tumor resistance to treatment by upregulating PD-L2. Since PD-L1 and PD-L2 interact with largely overlapping regions of PD-1, it is expected that anti-PD-1 antibodies that block the interaction between PD-1 and PD-L1 will also block the interaction between PD-1 and PD-L2. It was therefore decided to determine whether several PD-1/PD-L1 bispecific antibodies could block the PD-1/PD-L2 pathway.

This blocking activity was tested in vitro in a physiologically relevant PD-1/PD-L2 blockade reporter assay developed by Promega based on a two-cell system: CHO cells expressing PD-L2 and a T-cell receptor activator, and a Jurkat/NFAT-RE reporter cell line overexpressing PD-1. The Jurkat T cells contain a luciferase reporter gene that can become activated through the NFAT (nuclear factor of activated T-cells) pathway. Interaction of PD-1 with PD-L2 inhibits activation of this pathway. However, blocking the PD-1/PD-L2 interaction with antibodies against PD-1 or PD-L2, but not PD-L1, can activate the NFAT pathway. This means that the greater the degree of PD-1/PD-L2 blockade, the greater the activation of the luciferase reporter gene.

The PD-1/PD-L2 blockade reporter assays were performed using Promega's thaw and use format. PD-L2 expressing cells (cat. no. CS187127) were thawed in 14.5 ml cell recovery medium (DMEM/F12 containing 10% FBS). Next, 100 µl cell suspension was added to the inner wells of two 96-well assay plates (Costar, cat. no. 3917). Plates were incubated overnight at 37° C., 5% $CO_2$, at 95% relative humidity. Next day, culture medium was removed and 40 µl test antibody in assay medium (RPMI 1640 containing 4% FBS) in a serial dilution (starting concentration 25 µg/ml) was added to each well. Each plate contained a serial dilution of negative control (RSV G specific antibody PG2708) and positive control (anti-PD-1 therapeutic antibody based on Nivolumab, referred to herein as 5C4) that served as reference controls. PD-1 effector cells (cat no. CS187105) were thawed in 5.9 ml assay medium and 40 µl cell suspension was added to each well. Plates were incubated for 6 hours at 37° C., 5% $CO_2$, at 95% relative humidity. 80 µl of Bio-Glo reagent (Bio-Glo™ Luciferase Assay System, cat. no. G7941, G7940) was then added and the amount of luciferase activity was measured using a BioTek Synergy 2 Multi-Mode Microplate Reader. Fold of induction was calculated as the luciferase activity after induction relative to that measured in wells with no antibody.

Results

Figure 18:
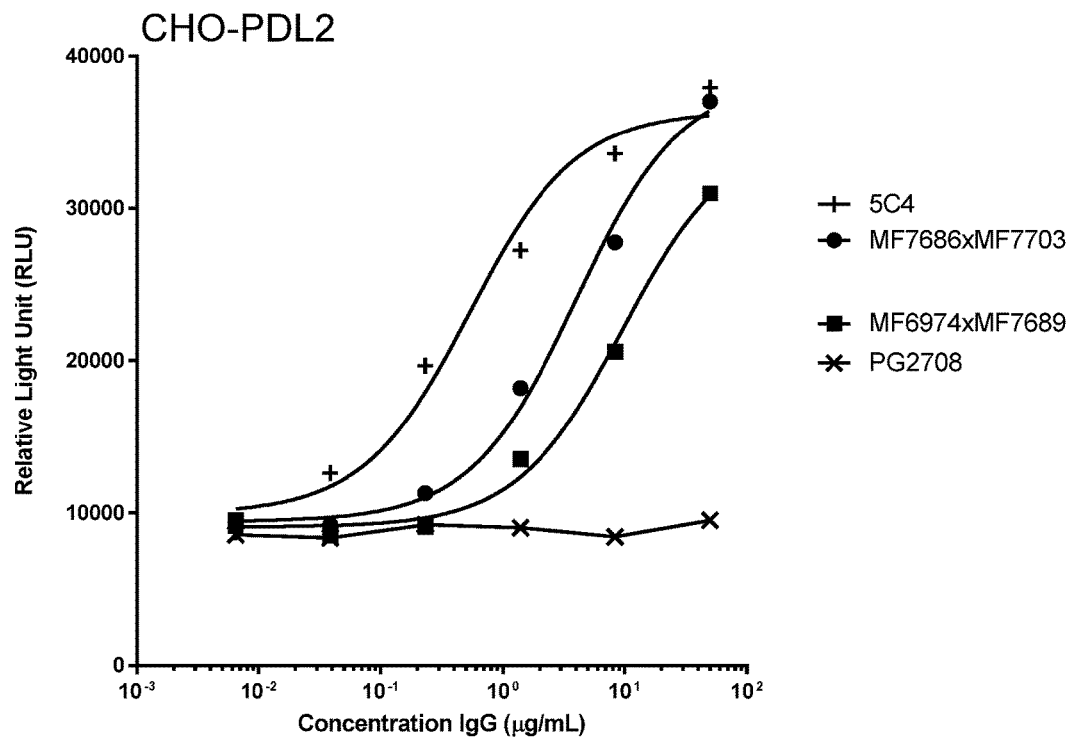
FIG. 18: PD-1/PD-L2 blocking assay. Assessment of the capacity of anti-PD-1/PD-L1 antibodies and their parental bivalent antibodies to block the interaction between PD-L2 and PD-1 in an in vitro blockade reporter assay.

The two PD-1×PD-L1 bispecific IgGs that were tested were able to diminish the interaction between PD-1 and PD-L2 (FIG. 18). This provides the advantage that tumor resistance to treatment via the PD-1/PD-L2 pathway is counteracted by these antibodies.

The negative control anti-RSV G antibody PG2708 was not able to prevent interaction between PD-1 and PD-L2.

Example 12

CD80 Blockade Via PD-1×PD-L1 Antibody

The immunosuppressive PD-1/PD-L1 pathway has been studied extensively in recent years and therapeutic antibodies blocking PD-1 or PD-L1 are effective treatments against cancer. Immunosuppression is also thought to be induced through interactions between PD-1 and its alternative ligand PD-L2, and through PD-L1 binding to CD80 (B7-1). As the CD80 binding site on PD-L1 appears to overlap with the PD-1 binding site, most commercial anti-PD-L1 antibodies have been shown to block the interaction of PD-L1 with both PD-1 and CD80. However, one prior art antibody (MIH3) appears to block the PD-1:PD-L1 interaction, but not the CD80:PD-L1 interaction (Butte et al, 2008). We therefore decided to test whether our bispecific antibodies were able to block the interaction of PD-L1 with PD-1 and CD80.

In the current Example the blocking activity of bispecific antibody MF7686×MF7703 was tested in a PD-L1 blocking ELISA that also included the parental anti-PD-1 (PG-7686) and anti-PD-L1 (PG7703) IgGs, as the bispecific antibody (MF7686×MF7703) cannot be tested directly due to its specificity for both PD-1 and PD-L1. The ability of these parental IgGs to block the interaction of PD-L1 with PD-1 or CD80 was compared with that of the anti-PD-1 benchmark antibody 5C4 (based on Nivolumab) and anti-PD-L1 benchmark antibody YW243.55.S70 (based on Atezolizumab). Anti-RSV G antibody PG2708 was used on each plate as a negative competition control.

For this ELISA, PD1-Fe (R&D systems; cat. no. 1086-PD) or CD80-Fc (R&D systems; cat. no. 140-B1) was coated to a maxisorp plate at 1 and 3 µg/ml, respectively. Coated wells were blocked with 4% BSA in PBS. Thereafter, 0.55 µg/ml biotinylated PD-L1 (BPS bioscience; cat. no. 71105) was added in the presence or absence of IgG in the range of 0.08 to 10 µg/ml (final concentration in plate), diluted in 2% BSA in PBS. Bound biotinylated PD-L1 was detected with HRP-conjugated streptavidin (BD bioscience: cat. no. 554066) diluted 1:2000 in 2% BSA in PBS. After each incubation step, the ELISA plate was washed three times with PBS-T (PBS-0.05% v/v Tween 20). Bound streptavidin was visualized by TMB/$H_2O_2$ staining, and staining was quantified by measuring optical density (OD) at 450 nm using a microplate reader.

Results

Figure 19:
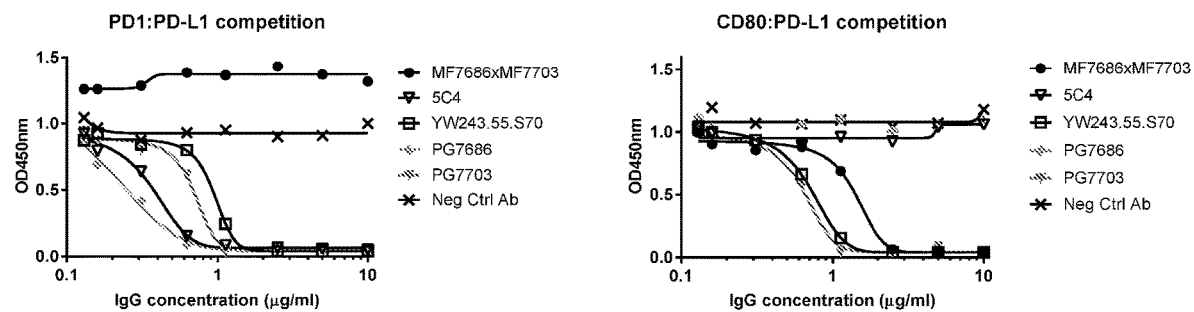
FIG. 19: PD-L1 blocking assay. Assessment of the capacity of an anti-PD-1/PD-L1 bispecific antibody and its parental bivalent antibodies to block the interaction of PD-L1 with coated PD-1 or CD80 in a PD-L1 blocking assay.

In the PD-1/PD-L1 competition assay it was not possible to determine the ability of the bispecific antibody to block the PD-L1:PD-1 interaction (FIG. 19, left-hand panel). However, both arms of the bispecific, antibody (MF7686 and MF7703) blocked the PD-L1:PD-1 interaction when tested in bivalent IgG format. The PD-L1 parental IgG PG7703 blocked the interaction more strongly than the benchmark PD-L1 antibody (YW243.55.S70). The anti-PD-1 IgGs inhibited the interaction to an even greater degree, with the PD-1 parental IgG PG7686 performing better than the PD-1 benchmark IgG (5C4).

In the CD80 competition assay, the tested bispecific antibody (MF7686×MF7703) blocked the interaction between CD80 and PD-L1. This provides the advantage that immunosuppression through interactions between PD-1 and CD80 is counteracted by this antibody.

PD-1 IgGs were not able to inhibit this interaction.

Example 13

SEB Assay: Bispecifics Compared to Mixed Parentals
Functional Comparison of PD-1×PD-L1 Bispecific IgGs with Equimolar Mix of Both Parental IgGs A SEB assay was performed in order to compare bispecific antibodies with a mixture of their parental IgGs. Peripheral blood mononuclear cells (PBMCs) were stimulated by *Staphylococcus* enterotoxin B (SEB). SEB specifically activates T cells expressing the Vβ 3, 12, 14, 15, 17 and 20 T cell receptor chain and the levels of IL-2 released by the cells are an indication of T cell activation.

In the current experiments, PBMCs from 2 donors were thawed, washed, counted and resuspended in culture medium (RPMI1640 plus 10% heat inactivated FBS) to a concentration of $2 \times 10^6$ cells/ml. Cells were seeded in flat-bottom 96-well plates ($2 \times 10^5$ cells/well) in the presence of SEB (2000 ml) followed by the addition of 6-step 10-fold serial dilutions of antibody, starting at 20 Cells were stimulated for 3 days at 37° C., 5% $CO_2$ at 95% relative humidity prior to collection of supernatant. Plates were centrifuged at 350 g for 5 min and 140 µl supernatant collected for TL-2 AlphaLISA (PerkinElmer cat. no. AL221C), which was performed according to the manufacturer's instructions. The following bispecific antibodies were tested: PB16666 (MF7686×MF7703) and PB16672 (MF6974×7689).

Results

The results in FIG. 20 show that the tested bispecific antibodies are capable of activating T cells. Of note, SEB-induced IL-2 production by PBMCs is higher when the cells are incubated with the PD-1/PD-L1 bispecific antibodies than when they are incubated with an equimolar mix of their parental bivalent monospecific antibodies. Hence, each of the tested bispecific antibodies has a stronger T cell activation potential as compared to an equimolar mix of their parental bivalent monospecific antibodies.

Example 14

PD-1×PD-L1 T-Cell Responses

In the SEB assay of the previous Example, all tested bispecific PD-1×PD-L1 antibodies were found to induce a stronger immune response (IL-2 production) than that of the parental IgGs, and even a stronger response than that of an equimolar mixture of the parental IgGs. These results suggest that in this assay blocking both PD-1 and PD-L1 simultaneously is more effective than blocking only one target in the PD-1/PD-L1 pathway. A subsequent step was to determine whether the bispecific antibodies were also more effective than existing PD-1 or PD-L1 therapeutic antibodies in an antigen-specific CD4+ T cell assay. In a SEB assay, T cells are strongly activated through cross-linking of the T cell receptor and MHC-II molecules present on antigen presenting cells. However, the number of T cells which specifically recognize a certain antigen is generally much lower than the number of T cells that respond to SEB. To more closely mimic activation of antigen-specific cells, an antigen-specific CD4+ T cell assay was used. In this assay PBMCs are stimulated with a mixture of antigens that the immune system of a donor individual commonly responds to. Activation of T cells is assessed by measuring production of IL-2 and IFNγ.

To this end, PBMCs from 3 healthy donors were separated by density gradient, and $2 \times 10^5$ cells per well were cultured in a 96-well plate and stimulated with mixed antigen (influenza and tetanus toxoid) in the presence or absence of test antibodies. Supernatant was harvested on day five and stored at −80° C. until analysis of cytokine production by Luminex assay. Antibodies were tested over a four-point dose response curve (10, 100, 1000 and 10000 ng/ml). For each donor, the effect of a bispecific PD-1×PD-L1 antibody (MF7686×MF7703) was compared with that of bivalent anti-PD-L1 antibody (YW243.55.S70, based on Atezolizumab) and bivalent anti-PD-1 antibody (5C4, based on Nivolumab) or a 1:1 mixture of these two control antibodies. The negative control was anti-RSV-G antibody PG2708p217.

Results

Figure 21:
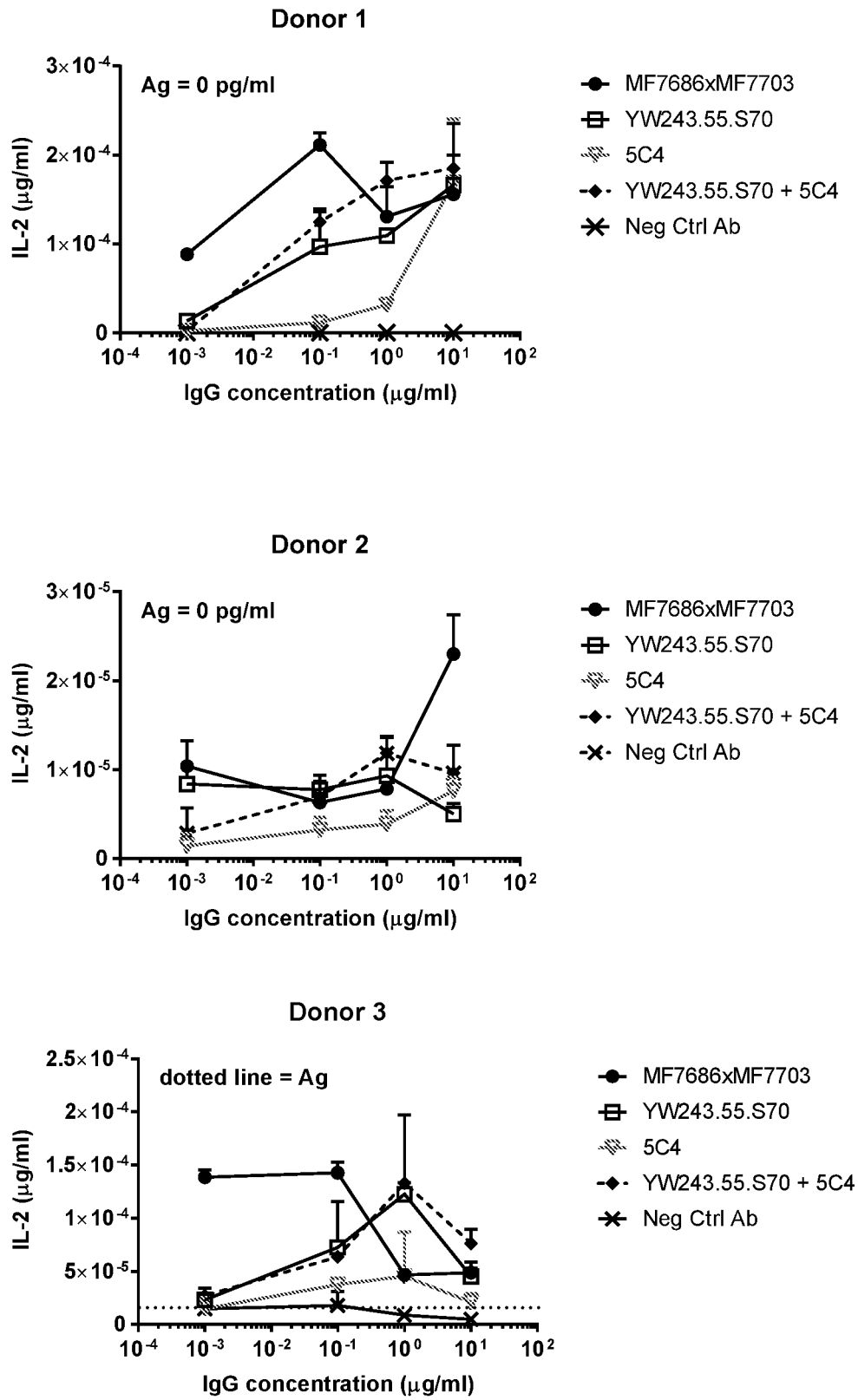
FIG. 21: In vitro enhancement by a bispecific PD-1×PD-L1 antibody of antigen-specific T cell IFNγ/IL-2 release. Graphs show levels of IL-2 (upper panel) or IFNγ (lower panel) present in the supernatant. All graphs show mean values from duplicate wells. Dotted lines indicate cytokine levels in the presence of antigen (Ag). Only in case the dotted lines are not shown, exact concentrations (Ag=pg/ml) are shown
Figure 21:
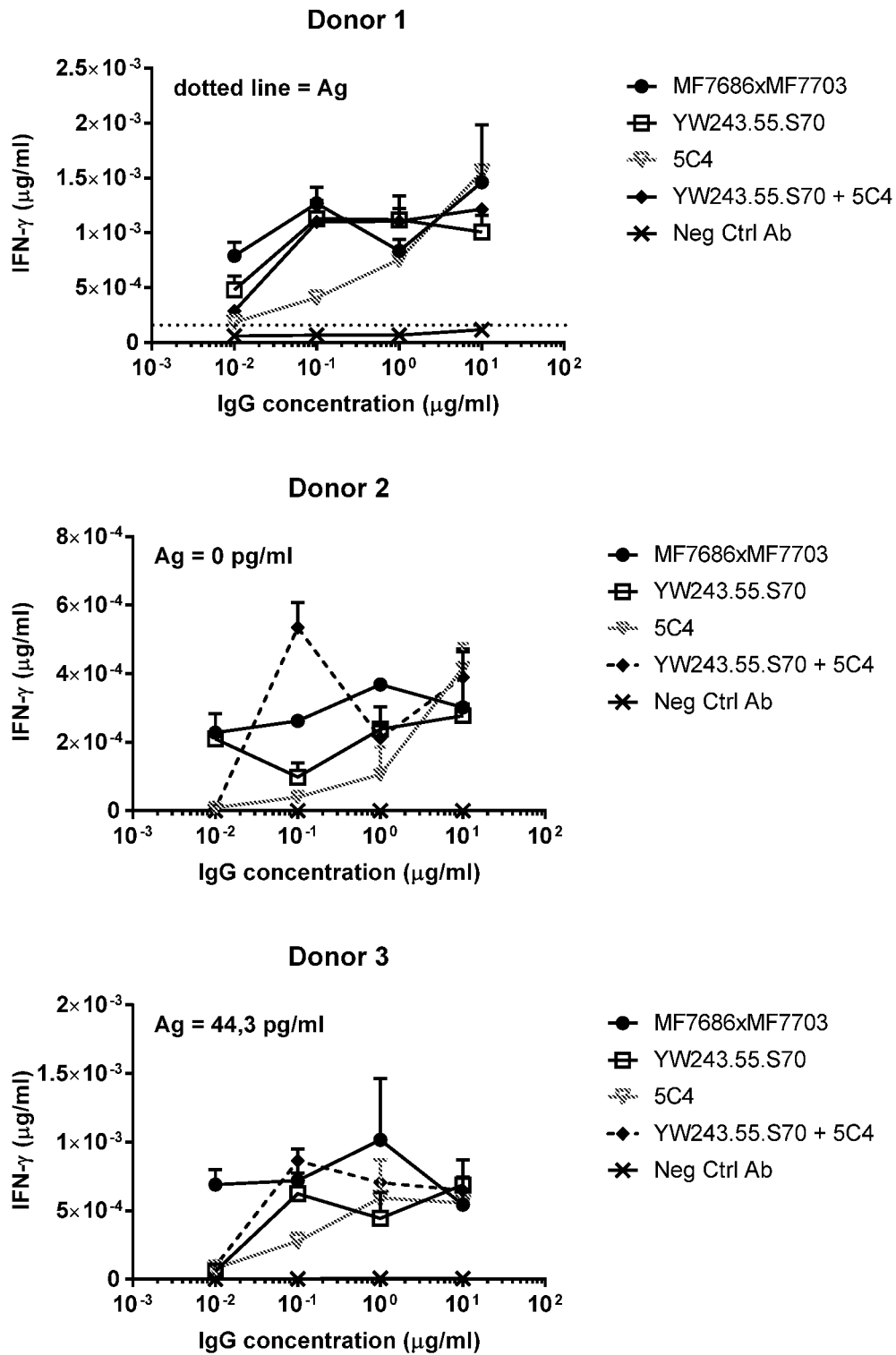

As illustrated in FIG. 21, the bispecific PD-1×PD-L1 antibody induced levels of IL-2 and IFNγ higher than those induced by the benchmark control antibodies. Of note, the bispecific antibody also induced higher IL-2 and IFNγ levels as compared to those levels induced by a combination of the two benchmark antibodies, particularly at lower concentrations. These results show that the bispecific PD-1×PD-L1 antibody is more effective than existing PD-1 or PD-L1 therapeutic antibodies, or mixtures thereof, in terms of enhancing antigen-driven cytokine release by CD4+ T cells.

Example 15

PD-1×PD-L1 Mixed Lymphocyte Reaction
Bispecific PD-1×PD-L1 Antibodies Enhance IFNγ Production by T Cells in a Mixed Lymphocyte Reaction Mixed lymphocyte reaction (MLR) assays are commonly used to understand the effects of antibodies on T-cell activation and proliferation. Such assays aid understanding of whether such compounds will affect the potential of T cells to mount such a response in the tumor microenvironment.

Here we used an allogeneic MLR protocol with immature DCs to determine the ability of bispecific PD-1×PD-L1 antibodies to enhance IFNγ production by T cells, compared with that of benchmark reference antibodies. The responsiveness of the T cells was quantified by measuring the levels of IFNγ in culture supernatant.

To this end, human peripheral blood mononuclear cells (PBMCs) from healthy donors were prepared from buffy coats. Immature monocyte-derived dendritic cells (Mo-DCs) were prepared by isolating CD14+ cells (EasySep Stemcell, lot no. 16C69672) using magnetic activated cell sorting (MACS) and culturing these in differentiation medium for seven days. Responder T cells derived from a different donor to that used for the Mo-DCs were prepared from cryopreserved PBMCs on the day required, using a T-cell isolation kit (EasySep Stemcell, lot no. 16D70573) to obtain untouched T cells. Six separate MLRs were performed to provide biological replication.

For the assay, $1 \times 10^4$ immature Mo-DCs were co-cultured with $1 \times 10^5$ T cells for 4 days, in the presence or absence of test antibody at an end concentration of 10 µg/mL. Cultures were performed in triplicate. Supernatants were collected at the end of the culture period and assessed for IFNγ by ELISA (R&D BioTechne, lot no. 342687) according to the manufacturer's instructions with plates read at 450 nm.

Results

Figure 22:
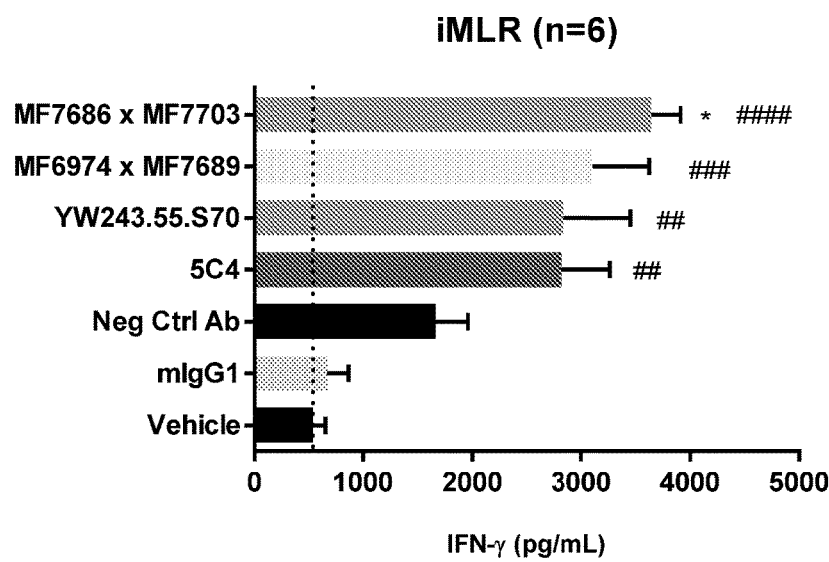
FIG. 22: Bispecific PD-1×PD-L1 antibodies enhance responsiveness of T cells in vitro. Bars show mean levels of IFNγ present in the supernatant collected from an allogeneic iMLR, with error bars indicating S.E.M. (n=6). A one-way ANOVA with Sidaks post-test analysis compared mean levels obtained with test antibodies with those obtained with isotype control antibody (*), or vehicle control (#).*P<0.05, **P<0.01, ## p<0.01, ### P<0.001, #### P<0.0001. Dotted line indicates mean IFNγ levels obtained with vehicle only. iMLR: immature mixed lymphocyte reaction.

FIG. 22 shows the results of this assay, illustrating the ability of the bispecific PD-1×PD-L1 antibodies to enhance IFNγ production by T cells compared with that of bivalent anti-PD-L1 antibody (YW243.55.S70) and bivalent anti- PD-1 antibody (5C4). This increase in responsiveness was also seen in the presence of the benchmark control antibodies but to a lesser extent. Hence, the tested bispecific antibodies have a stronger T cell activation potential as compared to the benchmark antibodies YW243.55.S70 (based on Atezolizumab) and 5C4 (based on Nivolumab). These results indicate that the bispecific antibodies will increase the potential of T cells to mount an immune response in the tumor microenvironment, and that the effect of the bispecific antibodies will be more pronounced as compared to the benchmark antibodies.

Example 16

Effect of Bispecific PD-1×PD-L1 Antibodies on the Proliferation of Tumor-Infiltrating T Cells To test our bispecific antibodies in a tumor-related setting, we made use of recently developed ex vivo assays based on T cells isolated from patient tumor material. Zhou et al. have developed a method of obtaining fresh tumor material from patients with hepatocellular carcinoma (HCC) and isolating tumor infiltrating cells (myeloid and lymphocytic cells), thereby providing a way of testing the effects of antibodies that target immune checkpoint inhibitors on the functions of tumor-infiltrating T cells (Zhou et al., 2017). Here we obtained material from patients with HCC to test whether the anti-PD-1×PD-L1 bispecific antibody MF7686× MF7703 could reactivate tumor-infiltrating CD4+ and CD8+ T cells derived from these patients.

To this end, fresh tumor material was obtained from five patients with HCC eligible for surgical resection of the tumor. None of the patients had received chemotherapy or immunosuppressive treatment at least three months before surgery. The method as described by Zhou et al. (2017) was the following: tumor-infiltrating myeloid and lymphocytic cells were isolated from fresh tissue by cutting it into small pieces followed by digestion for 20-30 minutes at 37° C. in 0.5 mg/mL collagenase IV (Sigma-Aldrich, St. Louis, Mo.) and 0.2 mg/mL DNAse I (Roche, Indianapolis, Ind.). The resulting cell suspension was filtered through 100-µm pore cell strainers (BD Biosciences, Erembodegem, Belgium), and mononuclear leukocytes were obtained by Ficoll density gradient centrifugation. Viability was determined by trypan blue exclusion. The cells were then labeled with 0.1 µM of the fluorescent dye carboxyfluorescein diacetate succinimidyl ester (CFSE, Invitrogen) and suspended in RPMI medium supplemented with 10% human AB serum, 2 mM L-glutamine, 50 mM HEPES buffer, 1% penicillin-streptomycin, 5 mM sodium pyruvate and 1% minimum essential medium non-essential amino acids (MEM NEAA). $1\times10^6$ cells in 100 µL were then transferred to each well of a 96-well round-bottom plate.

The tumor-infiltrating lymphocytes (TILS) were then stimulated to induce activation in the absence or presence of test antibody by adding 100 µL of the same medium containing test antibody and $10^3$ autologous CD40-activated B cell blasts that had been expanded and subsequently transfected with mRNA encoding the full-length tumor antigen glypican-3 (GPC3). These cells were co-incubated for six days.

After co-incubation, CFSE-labeled cells were harvested and stained with anti-CD8, anti-CD4, and anti-CD3 antibodies. Dead cells were excluded using 7-Aminoactinomycin D (7AAD; Invitrogen, Paisley UK), and T cell proliferation was determined based on CFSE dilution by flow cytometry analysis. Cells were measured by a FACSCanto II flow cytometer (BD Biosciences, San Diego, USA) and analyzed using FlowJo software.

The PD-1×PD-L1 bispecific antibody MF7686×MF7703 was compared with anti-PD-L1 reference antibody YW243.55.S70 (which is based on Atezolizumab), and negative control antibody PG2708 against an irrelevant antigen, namely respiratory syncytial virus G (RSV-G). Samples without antibody were included as controls and all conditions were tested in duplo at an IgG concentration of 10 µg/mL. Results were presented as the means±SEM. Differences were considered statistically significant if $P<0.05$.

Results

Figure 23:
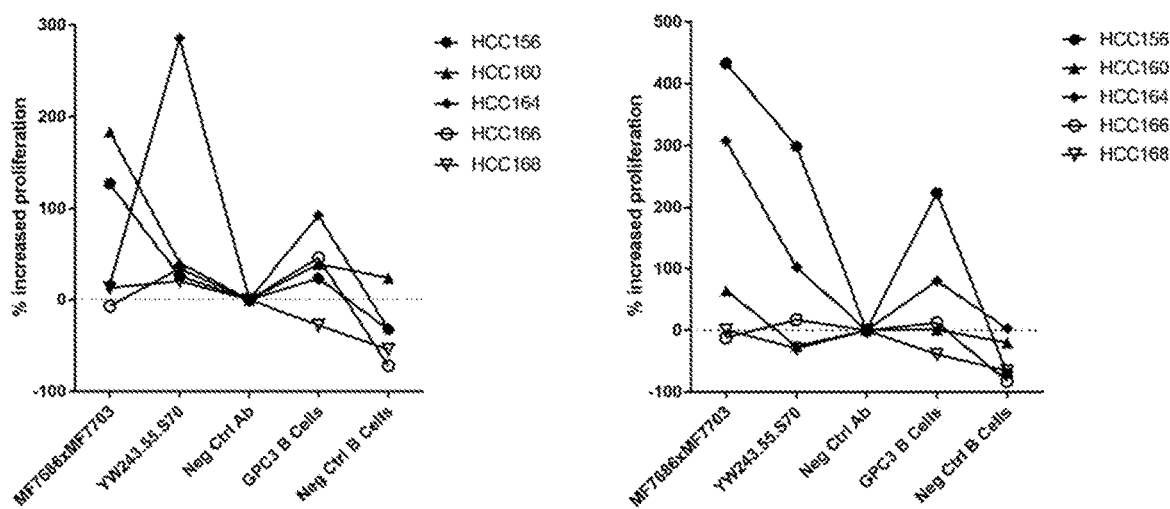
FIG. 23: Effect of PD-1×PD-L1 on the proliferation of tumor-infiltrating CD4+(left) and CD8+ T cells (right) derived from five patients with hepatic carcinoma (HCC).

The results are shown in FIG. 23. Proliferation of CD4+ TILs (left, panel) and CD8+ TILs (right panel) from each individual donor was determined by measuring the percentage of proliferating T cells (low levels of CFSE) in the presence of negative control antibody. Control wells containing GPC-expressing B cells but no antibody (GPC B cells) and non-transfected B cells (neg ctrl B cells) are also shown. Values are mean±SEM (n=5).

Blocking of the PD-1/PD-L1 pathway with our bispecific PD-1×PD-L1 antibody or with YW243.55.S70 does appear to enhance CD4+ and CD8+ TIL proliferation. Importantly, our tested PD-1×PD-L1 antibody activates TILs in other donors then YW243.55.S70. The proliferative GPC3-specific response to PD-1×PD-L1 observed in these TILs from HCC mimics the situation in patient tumors.

These experiments demonstrate the added value of using a PD-1×PD-L1 IgG in bispecific format and that a bispecific PD-1×PD-L1 antibody can enhance the proliferation of CD4+ and CD8+ TILs derived from patients with hepatocellular carcinoma.

Example 17

PD-1×PD-L1 In Vivo Efficacy Study huCD34-MDA-MB-231

In order to test the in vivo activity of our bispecific antibodies, the capacity of bispecific antibody MF7686× MF7703 to induce a T cell mediated anti-tumor response was studied in vivo in female immunodeficient NOD scid gamma (NSG) mice reconstituted with human CD34+ hematopoietic stem cells from umbilical cord blood (19 weeks of age; The Jackson Laboratory, Bar Harbor, Me.) inoculated subcutaneously with $3\times10^6$ MDA-MB-231 tumor cells (ATCC, cat. no. HTB-26), a triple-negative breast cancer (TNBC) cell line expressing PD-L1. These $3\times10^6$ cells were inoculated in an 1:1 suspension of 100 µl serum-free DMEM culture medium (Life technologies, cat. no. 10566-016) and matrigel membrane matrix (Fisher Scientific, cat. no. CB354248). Treatment of tumor-bearing mice was started 7 days after cell line inoculation, when tumor volume had reached 170-180 mm³. The mice were then treated intraperitoneally every 5 days with 0.5 or 5 mg/kg MF7686×MF7703 bispecific antibody. Control mice were left untreated or treated every 5 days with 5 mg/kg of a negative control antibody specific for RSV-G antigen (IgG1 harboring Fc-silencing mutations). Tumor volume was recorded twice a week using a study log system. Upon termination of the in vivo phase of the study on day 37, i.e. 30 days after start of treatment, tumor infiltrating lymphocytes (TILs) were analyzed by flow cytometric analysis. To this end, tumors were harvested, micro-dissected and digested using a Tumor Dissociation Kit (Miltenyi Biotec) according to the manufacturer's instructions. Following red blood cell lysis, cells were stained for FACS analysis using Viability dye and marker specific fluorochrome-conjugated antibodies. Cells were run using a BD LSR Fortessa flow cytometry analyzer and analyzed using the FlowJo software package. Alive TILs were identified as Viability dye negative cells and positively stained for CD45 and CD3 specific antibodies (BD Biosciences, cat. no. 564307). Subsequently the T cell fraction was characterized for expression of CD4 (BD Biosciences, cat. no. 557852) and CD8 (BD Biosciences, cat. no. 557834). Cells were run using a BD LSR Fortessa flow cytometry analyzer and analyzed using the FlowJo software package.

Results

Figure 24:
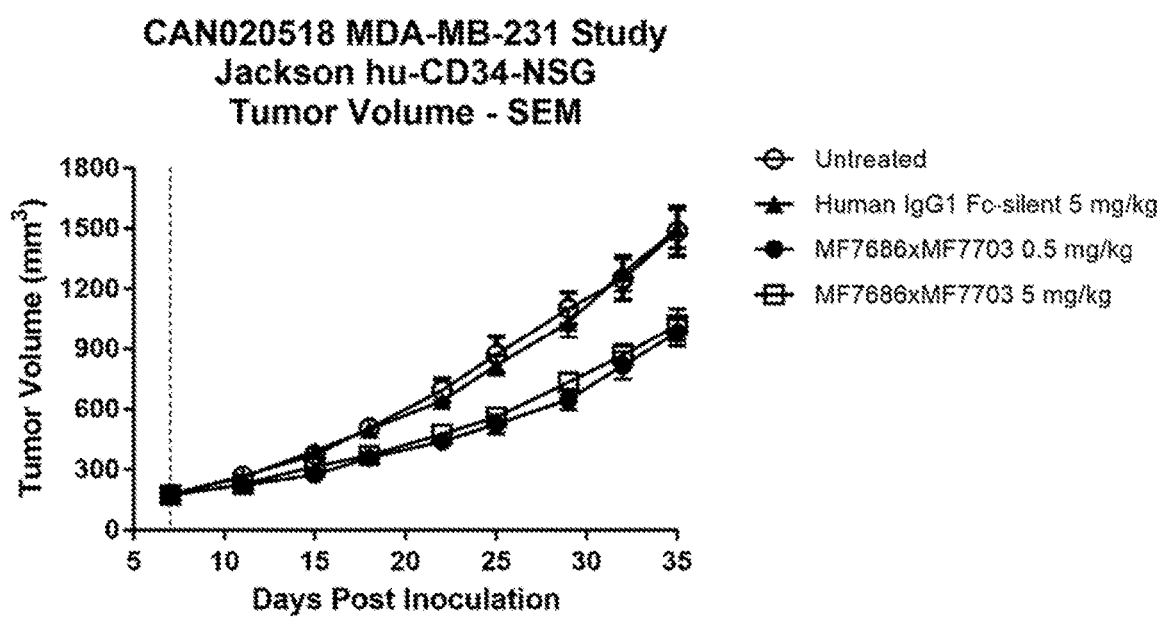
FIG. 24: MF7686×MF7703 induces an anti-tumor response
Figure 25:
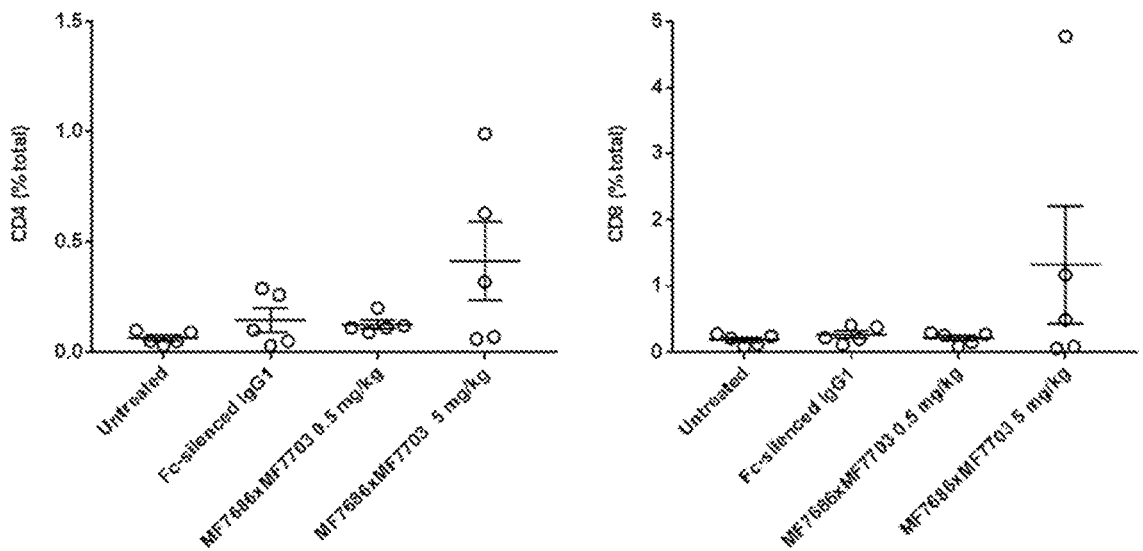
FIG. 25: MF7686×MF7703 enhances T cell numbers in tumors

MF7686×MF7703 bispecific antibody induced an anti-tumor response, even at the lower dose of just 0.5 mg/kg (FIG. 24), as tumor volume in both MF7686×MF7703 treatment groups was lower than that in the control mouse groups. Comparison of the TIL composition in the MF7686×MF7703-treated mice and control mice by flow cytometric analysis revealed that 5 mg/kg MF7686×MF7703 had the capacity to enhance both CD4 and CD8 T cell numbers (FIG. 25). Altogether these data show that in a CD34+ humanized mouse model with a PD-L1 positive tumor, our bispecific antibody MF7686×MF7703 has the capacity to enhance the number of TILs as well as to induce an anti-tumor response.

Example 18

PD-1×PD-L1 In Vitro and In Vivo Efficacy Study (A549)

The capacity of the MF7686×MF7703 bispecific antibody to enhance T cell-mediated cytotoxicity of tumor cells in the context of antigen-TCR-specific signaling was studied in vitro using A549-A2-ESO-1 tumor cells and NY-ESO-1-specific T cells. A549-A2-ESO tumor cells are derived from a non-small-cell lung carcinoma (NSCLC) cell line and express PD-L1 and the HLA-A2 restricted NY-ESO-1 peptide antigen, as described by Moon et al (2016). NY-ESO-1-specific T cells were prepared according to Moon et al (2016). The A549-A2-ESO-1 tumor cells (which overexpress luciferase) were co-cultured with NY-ESO-1-specific T cells in RPMI 1640 medium (Gibco, cat. no. 11875-085) supplemented with 10% heat inactivated fetal bovine serum (FBS) (HyClone, cat. no. SH30071.03). A549-NY-ESO-1 cells were added to 96-well flat-bottom plates, followed by NY-ESO-1 specific Ly95 T cells at different effector to target (E:T) ratios (1:1, 0.5:1, 0.25:1 and 0.125:1). Cells were co-cultured for 72 hrs at 37° C. with or without antibody treatment, whereby MF7686×MF7703 was compared with anti-PD-1 control antibody MK-3475 (based on Pembrolizumab), anti-PD-L1 control antibody YW243.55.S70 (based on Atezolizumab), or a combination of MK-3475+YW243.55.S70 (all antibodies at 10 µg/mL final concentration). After 72 hours, supernatants from co-cultures were collected and analyzed for IFNγ secretion using an IFNγ Quantikine ELISA Kit (R&D Systems, cat. no. DIF50) according to the manufacturer's instructions. The degree of cytotoxicity induced by NY-ESO-1-specific T cells was quantified by measuring the remaining luminescence on a SpectraMax Multimode Plate Reader using a Luciferase Assay System (Promega, cat. no. E1501).

Results

Figure 26:
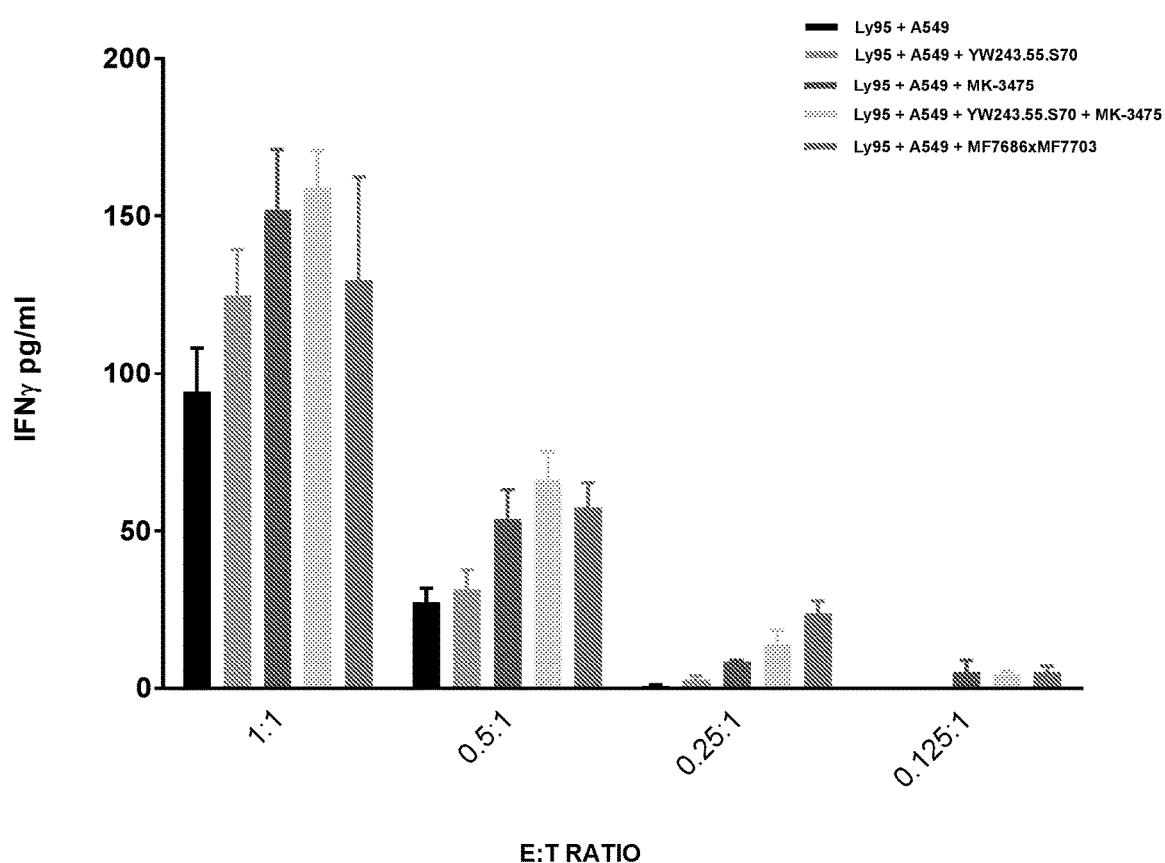
FIG. 26: MF7686×MF7703 enhances IFNγ release by tumor-specific T cells co-cultured with tumor cells
Figure 27:
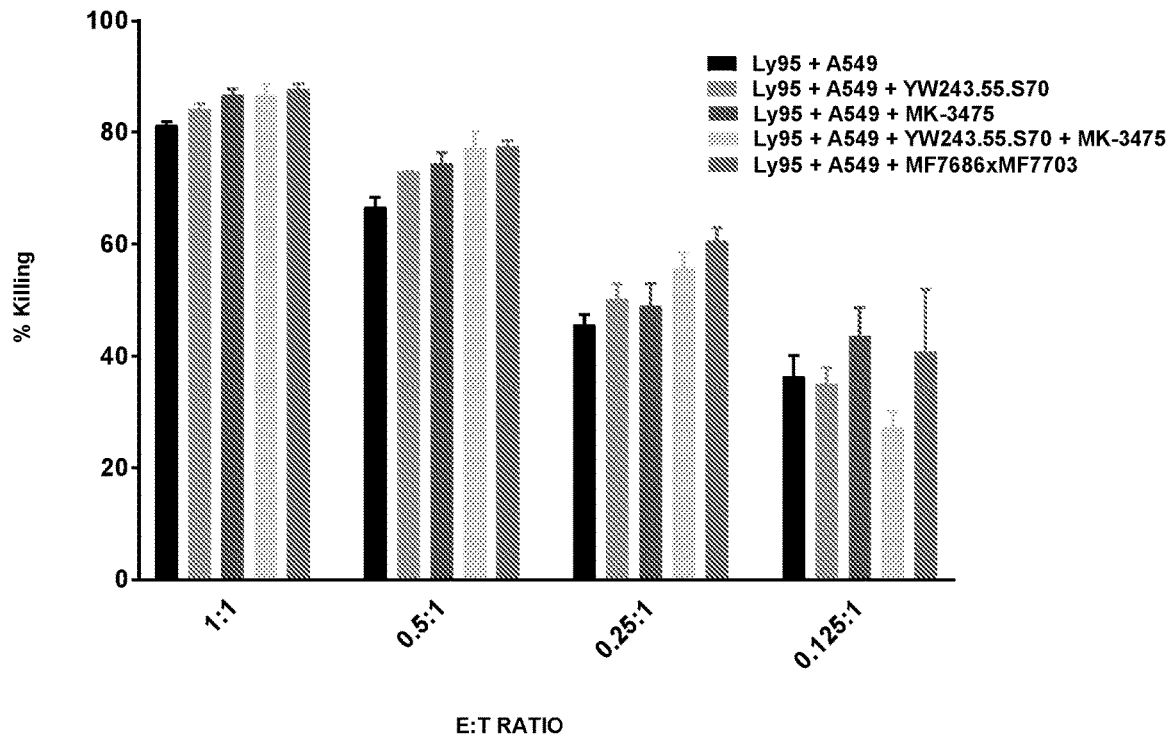
FIG. 27: MF7686×MF7703 enhances cytotoxicity of tumor-specific T cells co-cultured with tumor cells

Comparison of co-cultures treated with MF7686×MF7703 and control antibodies indicated that MF7686×MF7703 enhances both the fraction of functional T reflected by the increase in IFNγ release (FIG. 26), and the degree of T cell cytotoxicity towards A549-NY-ESO-1 tumor cells (FIG. 27), even at low E:T ratios. Of note, bispecific antibody MF7686×MF7703 resulted in a higher IFNγ release as compared to control antibody YW243.55.S70 at all E:T ratios. At lower E:T ratios, the IFNγ release induced by MF7686×MF7703 was comparable or even higher as compared to the IFNγ release that was induced by control antibody MK-3475 or by a combination of control antibodies YW243.55.S70 and MK-3475.

Next, the capacity of MF7686×MF7703 to enhance a T cell-mediated anti-tumor response was studied in vivo in immunodeficient NOD scid gamma (NSG) mice (13 weeks of age; The Jackson Laboratory, Bar Harbor, Me.). Mice were first inoculated subcutaneously with $5×10^6$ A549-A2-ESO tumor cells suspended in 100µl serum-free culture medium and matrigel membrane matrix (Corning) in equal volumes. After tumors were established (volume of 80-100 $mm^3$), the mice were randomized into six groups whereby one group received a single IV (tail-vein) injection of PBS alone, and five groups were injected with PBS containing $10×10^6$ NY-ESO1-reactive Ly95 TCR construct-expressing human T cells. The five groups that had undergone adoptive transfer with the tumor-specific transgenic Ly95 T cells were subsequently treated intraperitoneally every five days with PBS, MK-3475 (5 mg/kg), YW243.55.S70 (5 mg/kg), MF7686×MF7703 (5 mg/kg), or a combination of MK-3475 (5 mg/kg)+YW243.55.S70 (5 mg/kg). Over a period of four weeks, tumor volume was recorded twice a week using a study log system. Upon termination of the in vivo phase of the study on day 35, i.e. 28 days after start of treatment, tumor infiltrating lymphocytes (TILs) were analyzed by flow cytometric analysis. To this end, tumors were harvested, micro-dissected and digested using a Tumor Dissociation Kit (Miltenyi Biotec) according to the manufacturer's instructions. Following red blood cell lysis, cells were stained for FACS analysis using a viability dye and marker-specific fluorochrome-conjugated antibodies. Cells were measured using a BD LSR Fortessa flow cytometry analyzer and analyzed using the FlowJo software package. Living TILs were identified as staining negative for viability dye and positive for CD45 and CD3-specific antibodies (BD Biosciences, cat. no. 564307). Subsequently, the T cell fraction was characterized for expression of CD4 (BD Biosciences, cat. no. 557852), CD8 (BD Biosciences, cat. no. 557834), and GITR (eBiosciences, cat. no. 46-5875-42), as well as Vβ13.1 TCR chain (Miltenyi Biotec, cat. no. 130-108-742) to identify NY-ESO-1-specific T cells.

Results

Figure 28:
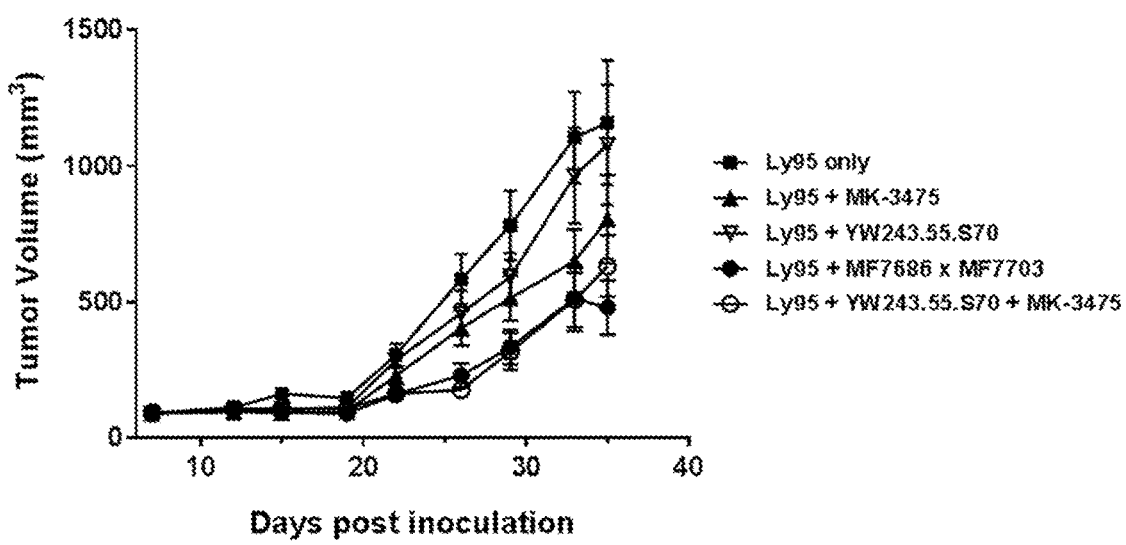
FIG. 28: MF7686×MF7703 induces an anti-tumor response

As shown in FIG. 28, the MF7686×MF7703 bispecific antibody induced an anti-tumor response, as tumor volume in the MF7686×MF7703 treatment group was lower than that in the control mouse groups. Of note, this MF7686×MF7703-induced anti-tumor response was greater than the response observed in mice treated with an equivalent dose of a single reference antibody (YW243.55.S70 or MK-347) and comparable to the response observed in mice given twice the equivalent dose of the combined reference antibodies (YW243.55.S70+MK-3475; FIG. 28). Hence, when bispecific antibody MF7686×MF7703 was used, the same reduction in tumor mass was obtained with only half the dosage as compared to a combination of YW243.55.S70 and MK-3475.

Figure 29:
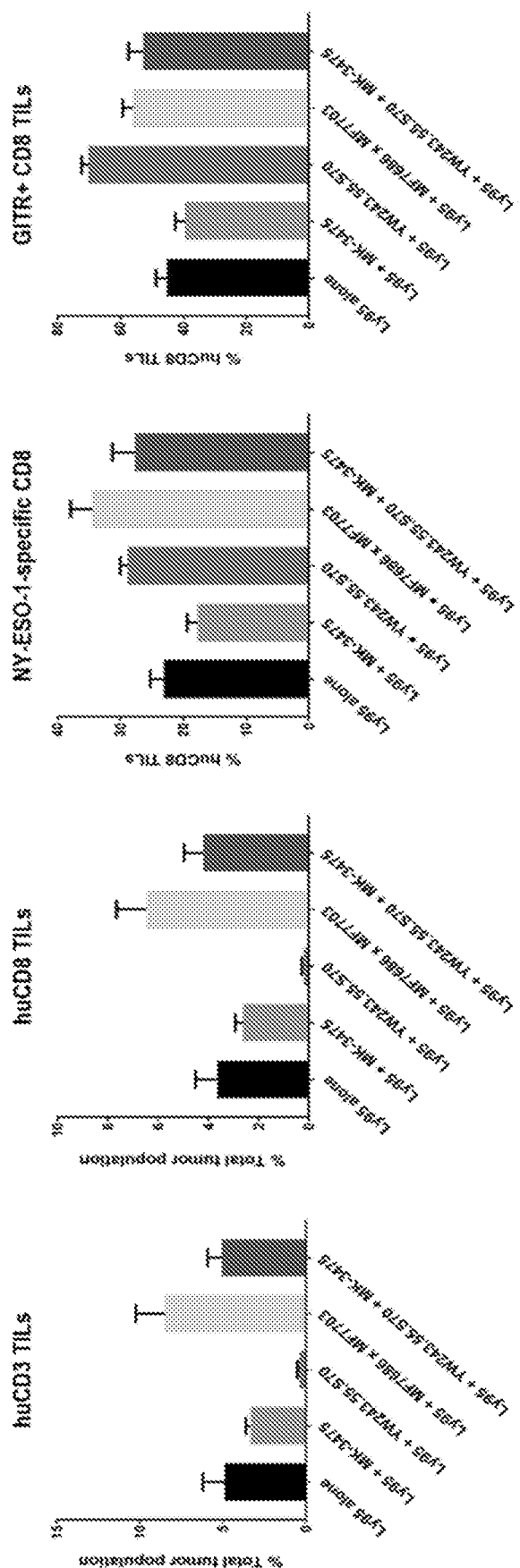
FIG. 29: MF7686×MF7703 enhances numbers of tumor-specific (NY-ESO-1-specific) CD8+ T cells in tumors

Analysis of the TILs by flow cytometric analysis indicated that, relative to the groups treated with reference antibody, MF7686×MF7703 enhances the total number of CD8 T cells (FIG. 29), the majority of which are activated, as reflected by the high percentage of GITR+ CD8 T cells. The tumors of mice treated with MF7686×MF7703 had not only the highest percentage of total CD8 T cells, but also the highest percentage of CD8-positive TILs specific for NY- ESO-1 antigen. Of note, the percentage of CD8-positive TILs was higher after treatment with bispecific antibody MF7686×MF7703 as compared to a treatment with a combination of PD-L1 specific control antibody YW243.55.S70 and PD-1 specific control antibody MK-3475.

Altogether these data show that MF7686×MF7703 enhances the activation of T cells, resulting in enhanced T cell-mediated cytotoxicity. In vivo, MF7G86×MF7703 induces higher numbers of TILs, as well as an anti-tumor response that is greater than the response seen for single treatment with the reference antibodies YW243.55.S70 or MK-3475, and comparable to the response seen for twice the equivalent dose of the combined reference antibodies YW243.55.S70 and MK-3475, indicating that a lower dosage of MF7G86×MF7703 is sufficient for achieving a comparable anti-tumor response.

Example 19

PD-1×PD-L1 Bispecific Antibodies Block PD-1/PD-L1 Signaling in a Co-Stimulation-Dependent Manner We tested the ability of the two PD-1×PD-L1 bispecific antibodies MF7686×MF7703 and MF6974×MF7689 to inhibit PD-L1/PD-1 engagement on activated T cell cytokine production. We used anti-CD3/anti-CD28 stimulation to activate T cells and co-stimulation was provided by co-culture with recombinant human PD-L1-Fc, which engages with PD-1 on the T cells. Since this PD-1/PD-L1 interaction inhibits cell activation, blocking the PD-1/PD-L1 interaction with antibodies against PD-1 or PD-L1 re-activates the cells, resulting in IL-2 production.

The ability of the bispecific antibodies to block the interaction of PD-L1 with PD-1 was compared with that of the parental anti-PD-1 and anti-PD-L1 antibodies, both alone and in combination, and with that of anti-PD-1 benchmark antibody (5C4, based on Nivolumab) and anti-PD-L1 benchmark antibody (YW243.55.S70, based on Atezolizumab), both alone and in combination. Anti-RSV antibody PG2708 was used on each plate as a negative control.

Methods

Co-Stimulation-Dependent T Cell Activation Assay

Peripheral blood mononuclear cells (PBMCs) from healthy donors were thawed and 9 volumes of culture medium (RPMI1640 with 10% heat-inactivated (hi) FBS) was added drop by drop. Cells were centrifuged for 10 minutes at 200 g at RT. The cell pellet was resuspended in 10 mL culture medium and cells were allowed to rest by incubating overnight at 37° C., 5% $CO_2$, in 95% relative humidity. Next day, T lymphocytes were isolated using the EasySep T cell enrichment (pan CD3) purification procedure as described by the manufacturer (Stem cell Technologies cat #19051). The EasySep procedure uses negative selection. Briefly, PBMCs were centrifuged for 10 minutes at 200 g at RT. The cell pellet was resuspended in EasySep buffer at a concentration of $5\times10^7$ cells/mL. 50 µL of EasySep Human T Cell Enrichment cocktail was added to each mL of cell volume, mixed and allowed to incubate for 10 minutes at RT. Next, 50 µL of EasySep D Magnetic Particles were added to each mL of cell volume and allowed to incubate for 5 minutes at RT. The total volume was brought to 2.5 mL with EasySep buffer, and after mixing the cell suspension was transferred to a 5 mL round-bottomed Falcon tube (BD Biosciences, cat. no. 352235). Next, the tube was placed into the magnet allowing the undesired cell fraction to be bound to the magnet for 5 minutes at RT. Next, the tube was inverted and the purified T cell fraction was poured off into a new tube containing 7.5 mL culture medium. Cells were harvested by 10 minutes centrifugation at 200 g at RT and subsequently resuspended at a concentration of $1\times10^6$ cells/mL in culture medium.

One day before the start of the assay, 96-well flat-bottomed plates (Cellstar, cat. no. 655180) were coated overnight at 4° C. with 4 µg/mL anti-CD3 antibody (clone OKT3, eBioscience, cat. no. 16-0037-85) and 8 µg/mL recombinant human PD-L1-Fc (R&D Systems, cat. no. 156-B7) in PBS, 50 µL per well. The next day, the assay plates were washed twice with PBS and the outer wells of the assay plates were filled with 100 µl PBS. Anti-CD28 antibody (clone 28.2, BD, cat. no. 555725) was added to the T cell suspension at a concentration of 2 µg/mL (final concentration 1 µg/mL). 50 µL of this T cell/anti-CD28 suspension was added to all inner wells of the assay plates (50,000 cells/well) followed by 50 µL of pre-prepared 5-step 10-fold serial dilutions of antibody in assay medium (RPMI1640+10% hiFBS), with a starting concentration of 20 µg/mL or 1 µg/mL). Plates were covered and incubated for 72 hours in an incubator at 37° C., 5% $CO_2$, 95% humidity. The concentration of IL-2 in the supernatant was determined by AlphaLISA (Perkin Elmer, cat. no. AL221F).

Expression of PD-1 and PD-L1 was determined by flow cytometry in a separate assay in which no IgG was added. Cells were harvested after 24, 48 and 72 hours and stained with anti-PD1 or anti-PD-L1 antibodies. The cells were then stained with a secondary antibody (anti-human IgG-PE) and analyzed by FACS.

Results

Figure 30:
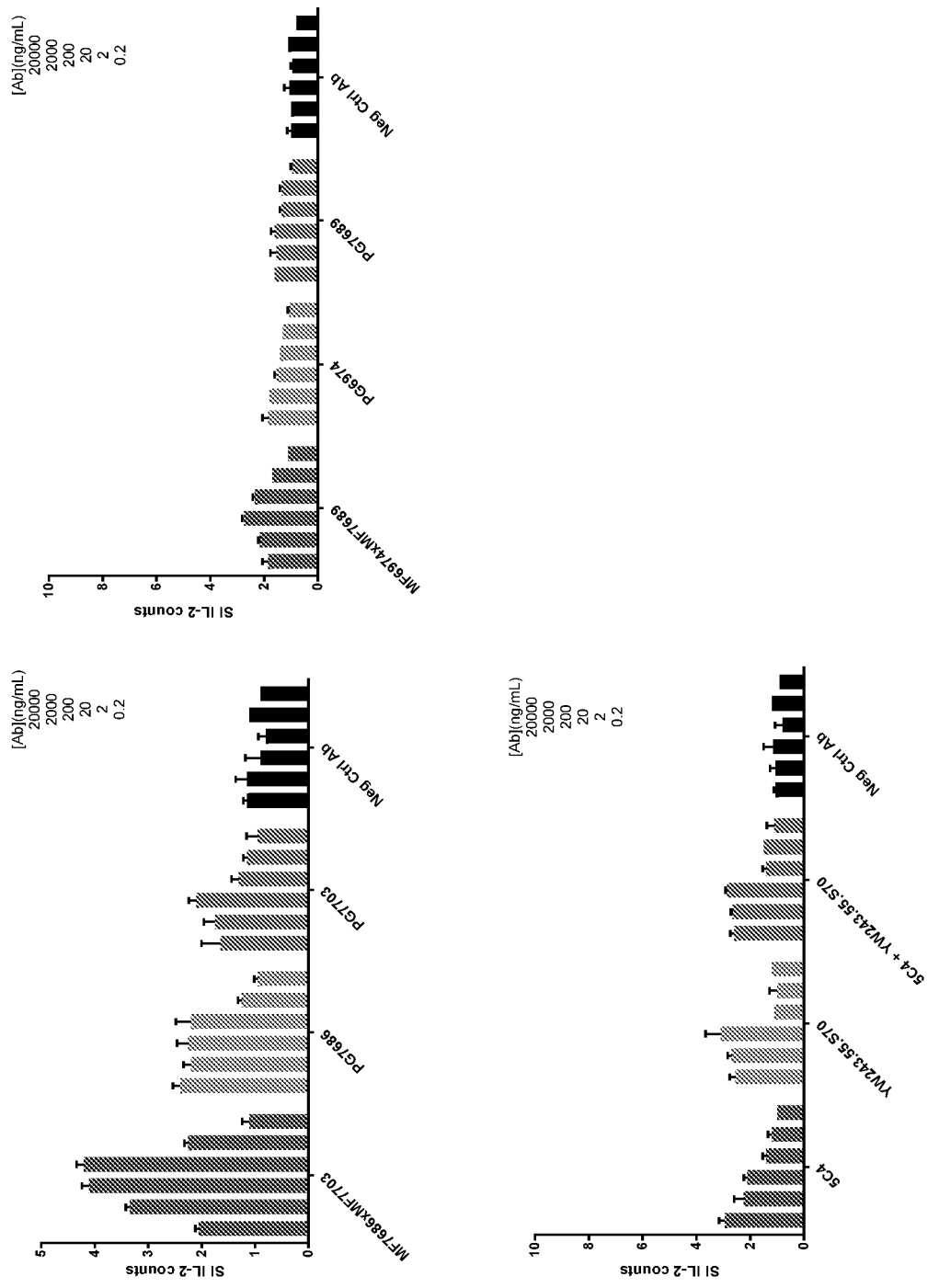
FIG. 30: PD-1×PD-L1 antibodies block the inhibitory effect of human recombinant PD-L1-Fe in a co-stimulation-dependent primary human T cell activation assay. Data represent the mean stimulation index (SI) of duplo cultures, performed in an experiment with a single PBMC donor (1058), for increasing concentrations of antibody as indicated (left to right). PG codes indicate the respective parental bivalent antibodies of the two bispecific antibodies.
Figure 31:
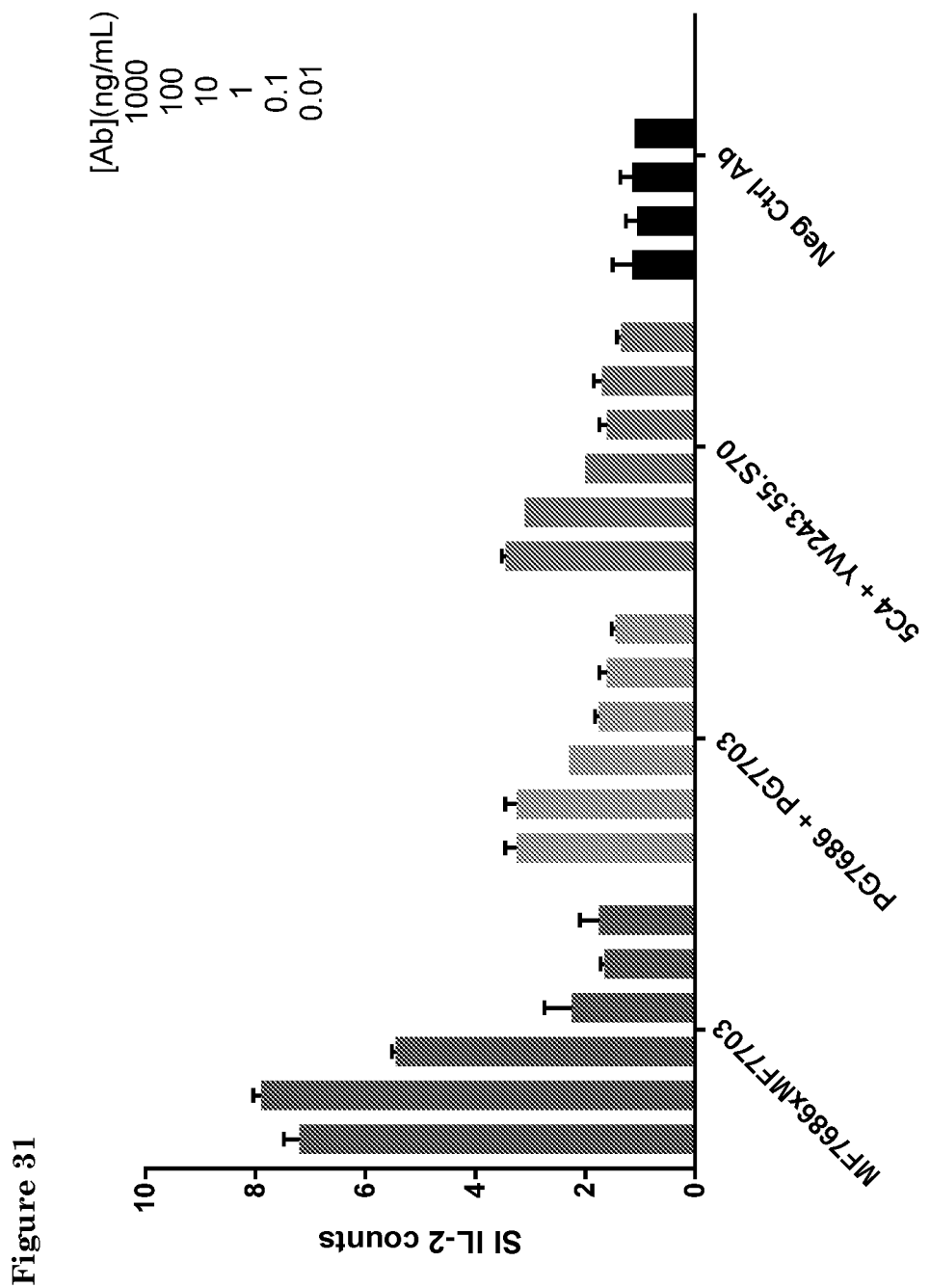
FIG. 31: Blocking effect of PD-1×PD-L1 bispecific antibodies in a co-stimulation-dependent primary human T cell activation assay is higher than that of the combination of parental antibodies or the combination of benchmark antibodies. Data represent the mean stimulation index (SI) of duplo cultures, performed in an experiment with a single PBMC donor (1058), for increasing concentrations of antibody as indicated (left to right). PG codes indicate the respective parental bivalent antibodies of the two bispecific antibodies.
Figure 31:
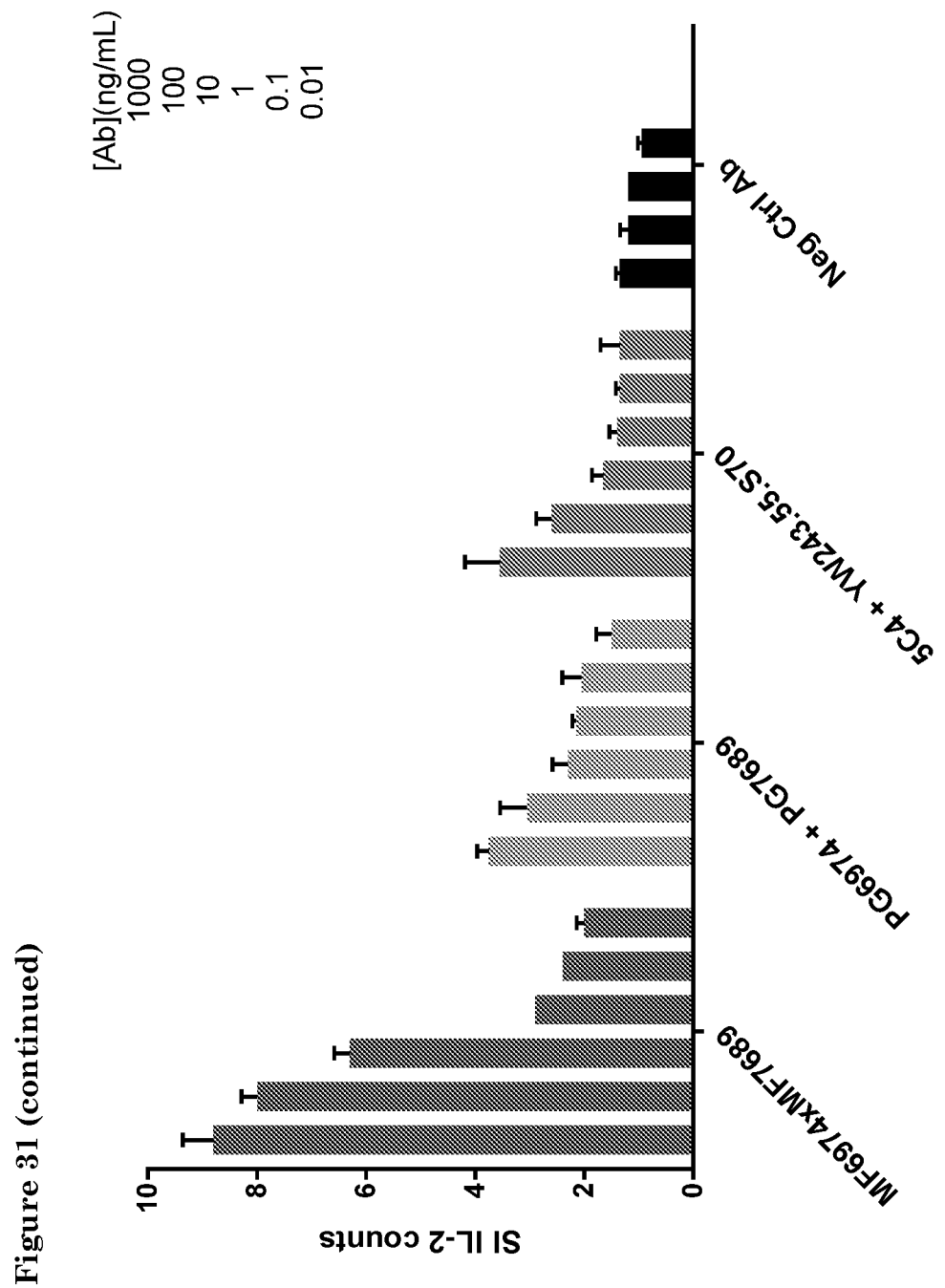

FIGS. 30 and 31 show the stimulation index (SI) which was calculated as the ratio of IL-2 counts measured in wells containing antibody to those in wells without antibody. The SI was higher in the presence of two PD-1×PD-L1 bispecific antibodies than when the cells were incubated with the negative control antibody PG2708 or with the parental bivalent antibodies, both alone (FIG. 30) and in combination (FIG. 31). Of note, the SI was also higher in the presence of the two PD-1×PD-L1 bispecific antibodies than when the cells were incubated with anti-PD-1 benchmark antibody (5C4) and anti-PD-L1 benchmark antibody (YW243.55.S70), both alone and in combination. This demonstrates that all tested bispecific antibodies have a stronger co-stimulation-dependent T cell activation activity as compared to the parental antibodies and as compared to the benchmark antibodies. The T cell activation induced by the bispecific antibodies was even stronger than the T cell activation induced by a mixture of the benchmark antibodies.

Figure 32:
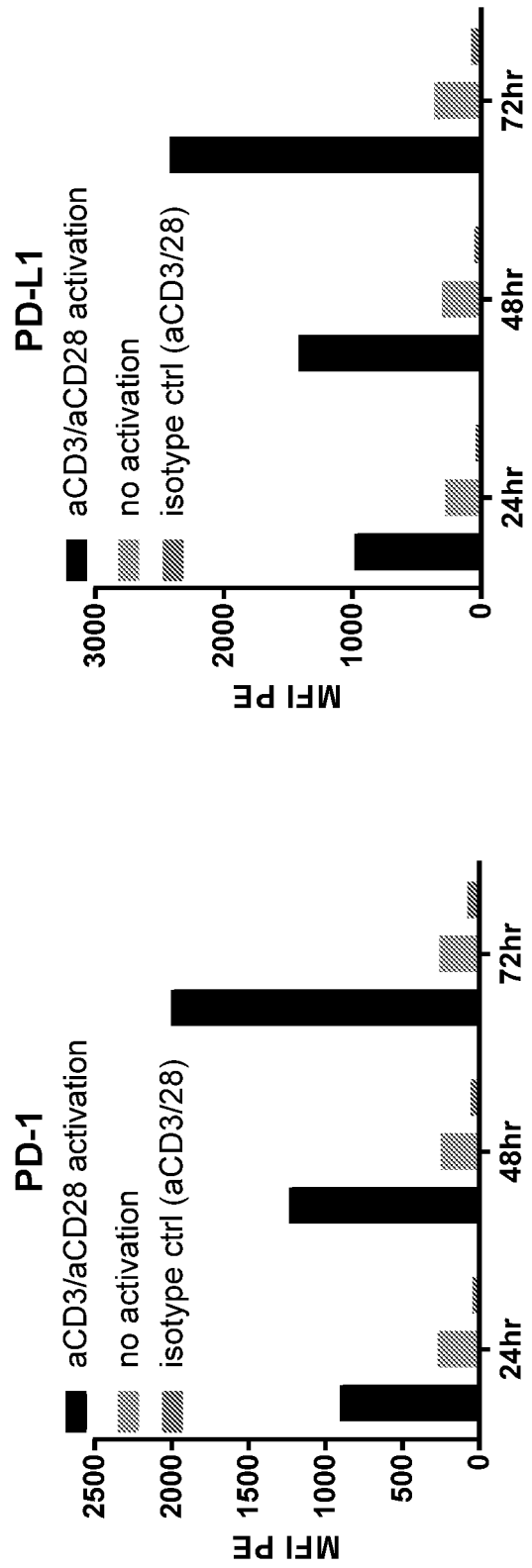
FIG. 32: T cells in the co-stimulation-dependent primary human T cell activation assay express increasing amounts of PD-1 and PD-L1 after activation with anti-CD3 and anti-CD28. The mean fluorescence index (MFI) represents the level of expression of PD-1 or PD-L1 on T cells harvested after 24, 48 and 72 hours of activation with anti-CD3 and anti-CD28 antibody.
Figure 33:
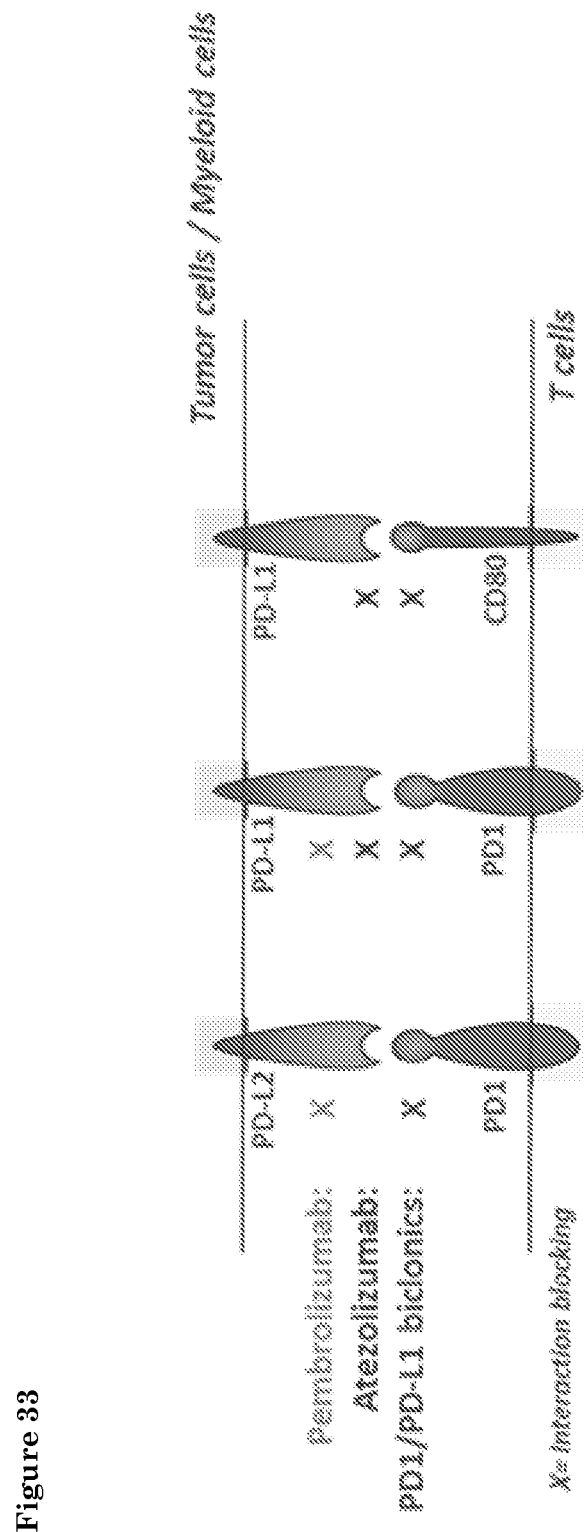
FIG. 33: A bispecific PD1×PDL1 antibody capable of entirely blocking the PD1 axis.

FIG. 32 shows the increase in PD-1 and PD-L1 expression over time on the T cells upon anti-CD3/anti-CD28 activation.

Tables:

TABLE 1

Expression constructs for each target that were used for DNA immunization (pVAX1 vector based) and for generation of stable CHO-S or CHO-K1 cell lines (pIRES-neo3 vector based or similar)

| Target | Vectors | Stable cell line |
|---|---|---|
| PD-1 | pVAX1_huPD-1 | NA |
|  | pIRES-neo3_huPD-1 | CHO-S_huPD-1 |
|  | pIRES-neo3_maPD-1 | CHO-S_maPD-1 |
| PD-L1 | pVAX1_huPD-L1 | NA |
|  | pIRES-neo3_huPD-L1 | CHO-K1_huPD-L1 |
|  | pIRES-neo3_maPD-L1 | CHO-K1_maPD-L1 | hu = human,
ma = macaque,
NA = not applicable

TABLE 2

Functional activity of PD-1 Fab arms as measured in the PD-1/PD-L1 blockade reporter assay as a bivalent antibody in comparison to the positive control Nivolumab. Variants of the same cluster (A, B and C) that displayed a range of PD-L1 blocking activity were tested.

| MF ID | Cluster | % activity of Nivolumab |
|---|---|---|
| MF6972 | A | 17.7 |
| MF6236 | A | 38.6 |
| MF6076 | A | 49.2 |
| MF6982 | B | 18.4 |
| MF6974 | B | 46.5 |
| MF6932 | C | 15.9 |
| MF6935 | C | 32.0 |
| MF6936 | C | 38.2 |
| MF6256 | C | 57.9 |

TABLE 3

Functional activity of PD-L1 Fab arms as measured in the PD-1/PD-L1 blockade reporter assay as a monovalent antibody expressed in area under the curve (AUC) Antibodies with an AUC > 2 showed PD-1 blocking activity in the assay. Antibody affinities were determined by Biacore analysis PD-L1 monovalent

| MF ID | AUC | Affinity nM |
|---|---|---|
| MF5594 | 4.8 | 0.6 |
| MF5553 | 4.5 | ND |
| MF5576 | 4.1 | 3.8 |
| MF5359 | 3.9 | 1.9 |
| MF5424 | 3.6 | 4.6 |
| MF5561 | 3.6 | 4.1 |
| MF5557 | 3.4 | ND |
| MF5708 | 3.3 | ND |
| MF5439 | 3.2 | 5.5 |
| MF5442 | 3.1 | 6.0 |
| MF5382 | 2.9 | 10.8 |
| MF5377 | 2.8 | 15.0 |
| MF5361 | NA | 19.4 |

TABLE 4

Overview screening PD-1xPD-L1 antibodies in the PD-1/PD-L1 reporter assay.
On display percentage activity in comparison to Ctrl MPDL-3280A. (DE) indicates the DE side of the DEKK bispecific .KK indicates the KK side of the DEKK bispecific. Blocking activity of individual PD-1 Fab arms is indicated in −, +/−, ++, and +++. Blocking activity of PD-L1 Fab arm is arranged from top to bottom with the topantibody (MF5594) being the strongest blocker and the MF5361 being incapable of blocking. Antibody combinations that are bolded showed activity above 60% and were selected for subsequent testing.

Blocking activity PD1 Fab arm (DE)

|  |  | +/− | + | ++ | +/− | ++ | +/− | + | ++ | +++ | − |
|---|---|---|---|---|---|---|---|---|---|---|---|
|  |  | MF6972 | MF6236 | MF6076 | MF6982 | MF6974 | MF6932 | MF6935 | MF6936 | MF6256 | MF6176 |
| Blocking | MF5594 | 44.6 | 53.2 | 57.2 | 49.9 | 53.2 | 36.2 | 42.4 | 53.9 | 56.7 | 27.4 |
| activity | MF5553 | 48.2 | 54.8 | 62.7 | 52.7 | 56.6 | 40.4 | 49.0 | 54.2 | 57.8 | 25.1 |
| PD-L1 | MF5576 | 47.2 | 56.6 | 58.5 | 45.1 | 53.0 | 50.9 | 58.6 | 65.8 | 73.2 | 29.4 |
| Fab arm | MF5359 | 47.2 | 59.4 | 76.2 | 48.0 | 57.4 | 33.5 | 42.5 | 52.3 | 56.4 | 22.7 |
| (KK) | MF5424 | 49.3 | 60.1 | 72.1 | 54.7 | 69.5 | 40.4 | 61.2 | 66.1 | 70.2 | 24.8 |
|  | MF5561 | 52.6 | 73.1 | 70.0 | 59.6 | 65.7 | 43.3 | 62.2 | 70.1 | 72.0 | 28.2 |
|  | MF5557 | 41.1 | 55.3 | 58.9 | 40.8 | 53.4 | 42.5 | 58.3 | 65.9 | 70.2 | 14.6 |
|  | MF5708 | 20.6 | 36.7 | 40.1 | 19.7 | 39.7 | 9.4 | 24.9 | 34.1 | 41.9 | −1.2 |
|  | MF5439 | 40.0 | 48.4 | 54.2 | 42.0 | 53.2 | 32.4 | 52.2 | 57.5 | 62.5 | 17.4 |
|  | MF5442 | 42.1 | 74.1 | 76.7 | 53.6 | 70.1 | 50.8 | 69.4 | 73.3 | 77.8 | 29.2 |
|  | MF5382 | 45.3 | 71.9 | 68.2 | 48.7 | 63.3 | 56.1 | 80.9 | 97.6 | 104.9 | 31.7 |
|  | MF5377 | 27.3 | 39.3 | 39.5 | 30.6 | 42.3 | 20.1 | 33.6 | 36.1 | 45.1 | 8.3 |
|  | MF5361 | 6.4 | 13.1 | 12.4 | 5.7 | 8.5 | 5.7 | 20.3 | 17.0 | 15.4 | −1.9 |

TABLE 5

| Overview PB numbers and their MF composition | | |
|---|---|---|
| PB | PD1 MF ID | PD-L1 MF ID |
| PB15443 | MF6076 | MF5553 |
| PB15459 | MF6936 | MF5576 |
| PB15460 | MF6256 | MF5576 |
| PB15464 | MF6076 | MF5359 |
| PB15474 | MF6076 | MF5424 |
| PB15476 | MF6974 | MF5424 |
| PB15479 | MF6935 | MF5424 |
| PB15480 | MF6936 | MF5424 |
| PB15481 | MF6256 | MF5424 |
| PB15484 | MF6236 | MF5561 |
| PB15485 | MF6076 | MF5561 |
| PB15487 | MF6974 | MF5561 |
| PB15490 | MF6936 | MF5561 |
| PB15491 | MF6256 | MF5561 |
| PB15500 | MF6936 | MF5557 |
| PB15522 | MF6256 | MF5439 |
| PB15527 | MF6076 | MF5442 |
| PB15529 | MF6974 | MF5442 |
| PB15532 | MF6936 | MF5442 |
| PB15536 | MF6236 | MF5382 |
| PB15537 | MF6076 | MF5382 |
| PB15539 | MF6974 | MF5382 |
| PB15542 | MF6936 | MF5382 |
| PB15466 | MF6974 | MF5359 |
| PB15465 | MF6982 | MF5359 |
| PB15463 | MF6236 | MF5359 |
| PB15462 | MF6972 | MF5359 |

| PD-1 arm | PD-L1 arm | PB number | PD-1 arm | PD-L1 arm | PB number |
|---|---|---|---|---|---|
| MF6076 | MF5442 | PB15527p04 | MF7685 | MF5424 | PB16661p01 |
| MF6076 | MF7691 | PB16635p01 | MF7686 | MF5424 | PB16662p01 |
| MF6076 | MF7690 | PB16679p01 | MF7685 | MF5424 | PB16661p02 |
| MF6076 | MF7689 | PB16636p01 | MF7684 | MF5424 | PB16663p02 |
| MF6076 | MF7688 | PB16637p01 | MF7684 | MF5424 | PB16663p01 |
| MF6076 | MF7688 | PB16637p02 | MF7687 | MF7703 | PB16664p01 |
| MF7699 | MF7691 | PB16639p01 | MF7686 | MF7703 | PB16666p02 |
| MF7699 | MF7690 | PB16680p01 | MF7685 | MF7703 | PB16665p01 |
| MF7699 | MF7689 | PB16640p01 | MF7686 | MF7703 | PB16666p01 |
| MF7699 | MF7688 | PB16641p01 | MF7685 | MF7703 | PB16665p02 |
| MF7699 | MF7688 | PB16641p02 | MF7684 | MF7703 | PB16667p02 |
| MF7698 | MF7691 | PB16643p01 | MF7684 | MF7703 | PB16667p01 |
| MF7698 | MF7690 | PB16681p01 | MF6936 | MF5442 | PB15532p03 |
| MF7698 | MF7689 | PB16644p01 | MF6929 | MF7691 | PB1688p01 |
| MF7698 | MF7688 | PB16645p01 | MF6929 | MF7690 | PB16689p01 |
| MF7698 | MF7688 | PB16645p02 | MF6929 | MF7689 | PB16690p01 |
| MF6076 | MF5553 | PB15443p03 | MF6929 | MF7688 | PB16691p01 |
| MF6256 | MF5439 | PB15522p03 | MF6929 | MF7688 | PB16691p02 |
| MF6256 | MF7700 | PB16682p01 | MF6936 | MF5557 | PB15500p03 |
| MF6256 | MF7701 | PB16655p02 | MF6929 | MF7694 | PB16693p01 |
| MF6256 | MF7701 | PB16655p01 | MF6929 | MF7693 | PB16694p02 |
| MF6935 | MF5424 | PB15479p03 | MF6929 | MF7692 | PB16695p03 |
| MF6935 | MF5424 | PB15479pp05 | MF6929 | MF7694 | PB16693p03 |
| MF6935 | MF7703 | PB16659p01 | MF6929 | MF7692 | PB16695p04 |
| MF7687 | MF5424 | PB16660p01 | MF6974 | MF5442 | PB15529p03 |
| MF7686 | MF5424 | PB16662p02 | MF6974 | MF7691 | PB16671p01 |
| | | | MF6974 | MF7690 | PB16698p01 |
| | | | MF6974 | MF7689 | PB16672p01 |
| | | | MF6974 | MF7688 | PB16673p01 |
| | | | MF6974 | MF7688 | PB16673p02 |
| | | | MF6256 | MF7697 | PB16675p01 |
| | | | MF6256 | MF7696 | PB16676p01 |
| | | | MF6256 | MF7695 | PB16677p01 |

TABLE 6

Bispecific anti-PD-1xPD-L1 antibodies block the interaction between PD-L1 and PD-1 in an in vitro blockade reporter assay

| MG1 | MG2 | % effectivity | MG1 | MG2 | % effectivity |
|---|---|---|---|---|---|
| MG7687 | MG5424 | 98.4 | MG6935 | MG7703 | 73.5 |
| MG7687 | MG7703 | 95.4 | MG6076 | MG7690 | 73.4 |
| MG7685 | MG7703 | 94.8 | MG6935 | MG5424 | 72.5 |
| MG7684 | MG7703 | 94.3 | MG6974 | MG5442 | 72.1 |
| MG7685 | MG7703 | 93.2 | MG6974 | MG7688 | 71.5 |
| MG7684 | MG5424 | 91.5 | MG7699 | MG7689 | 71.2 |
| MG6076 | MG7689 | 85.3 | MG6974 | MG7691 | 70.8 |
| MG7686 | MG7703 | 94.5 | MG7699 | MG7690 | 70.4 |
| MG6256 | MG5439 | 84.2 | MG6936 | MG5442 | 68.9 |
| MG7685 | MG5424 | 83.3 | MG7698 | MG7688 | 68.2 |
| MG6256 | MG7701 | 81.1 | MG6929 | MG7694 | 68.2 |
| MG6929 | MG7691 | 81.0 | MG6076 | MG5442 | 67.9 |
| MG6076 | MG7688 | 80.8 | MG7698 | MG7702 | 67.7 |
| MG7684 | MG5424 | 80.8 | MG6974 | MG5442 | 65.9 |
| MG6076 | MG7691 | 80.3 | MG6256 | MG7700 | 65.3 |
| MG6076 | MG7688 | 79.8 | MG6929 | MG7690 | 65.0 |
| MG7686 | MG5424 | 78.9 | MG7698 | MG7689 | 64.9 |
| MG7698 | MG7702 | 78.7 | MG7699 | MG7702 | 64.4 |
| MG6076 | MG5553 | 78.5 | MG6935 | MG5424 | 63.7 |
| MG6936 | MG5557 | 77.4 | MG7698 | MG7688 | 63.5 |
| MG7684 | MG7703 | 76.9 | MG6076 | MG7702 | 63.3 |
| MG7699 | MG7688 | 75.7 | MG6929 | MG7688 | 61.6 |
| MG7699 | MG7691 | 75.5 | MG6929 | MG7689 | 61.4 |
| MG6076 | MG7702 | 75.4 | MG6974 | MG7689 | 59.7 |
| MG7685 | MG5424 | 75.4 | MG7698 | MG7690 | 58.9 |
| MG7698 | MG7691 | 75.2 | MG6974 | MG7688 | 56.7 |
| MG6929 | MG7688 | 74.9 | MG6935 | MG5414 | 55.9 |
| MG7699 | MG7688 | 74.6 | MG6256 | MG7701 | 55.8 |
| | | | MG6974 | MG7690 | 55.5 |
| | | | MG6256 | MG7697 | 54.9 |
| | | | MG6256 | MG7696 | 45.3 |
| | | | MG6256 | MG7695 | 43.1 |

TABLE 7

Binding affinity for the two tested PD-L1 arms for PD-L as determined using surface plasmon resonance (SPR). Antibodies were tested in monovalent format. For the anti-PD-L1 Fab arms, measurements are shown from three separate runs. koff: off-rate constant, kon: on-rate constant; KD: dissociation constant (koff/kon).

| Antibody | Date of run | kon | koff | KD (nM) |
|---|---|---|---|---|
| FAB7703 | 24 Nov. 2017 | 1.96exp6 | 2.4exp-3 | 1.25 |
| | 24 Nov. 2017 | 1.76exp6 | 2.3exp-3 | 1.31 |
| | 24 Nov. 2017 | 1.82exp6 | 2.3exo-3 | 1.25 |
| FAB7689 | 24 Nov. 2017 | 6.7exp5 | 2.8exp-3 | 4.27 |
| | 24 Nov. 2017 | 7.17exp5 | 2.7exp-3 | 3.81 |
| | 24 Nov. 2017 | 8.2exp5 | 3.1exp-3 | 3.76 |

REFERENCES

J. C. Almagrol and J. Fransson (2008) Frontiers in Bioscience 13, 1619-1633

Armour et al., 1999. Eur J Immunol. 29(8):2613-24; Shields et al., 2001. J Biol Chem. 276(9):6591-604

Butte M J, Peña-Cruz V, Kim M J, Freeman G J, Sharpe A H. Interaction of human PD-L1 and B7-1. Mol Immunol. 2008 August; 45(13):3567-72. doi: 10.1016/j.molimm.2008.05.014. Epub 2008 Jun. 27

Idusogie et al., 2000. J Immunol. 164(8):4178-84

Labrijn. et al., 2009. Nat Biotechnol. 27(8):767-71

Moon et al. Blockade of Programmed Death 1 Augments the Ability of Human T cells Engineered to Target NY-ESO-1 to Control Tumor Growth after Adoptive Transfer. Clinical Cancer Research 2016, 22(2): 436-447. doi: 10.1158/1078-0432.CCR-15-1070

Zhou et al. Antibodies Against Immune Checkpoint Molecules Restore Functions of Tumor-infiltrating T cells in Hepatocellular Carcinomas. Gastroenterology 2017 doi: 10.1053/j.gastro.2017.06.017.

The invention claimed is:

1. An antibody that comprises
a variable domain that can bind to an extracellular part of PD-1, comprising a heavy chain variable region with a CDR1, CDR2 and CDR3 region that comprises the amino acid sequence of the CDR1, CDR2 and CDR3 of a variable heavy chain region of one of SEQ ID NOs: 38-48 and 50-56; and
a variable domain that can bind to an extracellular part of PD-L1, comprising a heavy chain variable region with a CDR1, CDR2 and CDR3 region that comprises the amino acid sequence of the CDR1, CDR2 and CDR3 of a variable heavy chain region of one of SEQ ID NOs: 24-37 and 58-69;
wherein the variable domain that binds to an extracellular part of PD-1 and the variable domain that binds to an extracellular part of PD-L1 comprise a light chain comprising a CDR1 comprising the sequence QSISSY (SEQ ID NO:70), a CDR2 comprising the sequence AAS, and a CDR3 comprising the sequence QQSYSTPPT (SEQ ID NO:71).

2. The antibody of claim 1, wherein the binding of the antibody reduces an inhibitory activity of the binding of PD-1 to PD-L1.

3. The antibody of claim 1, wherein the binding of the variable domain that binds PD-1 blocks the binding of PD-1 to PD-L1 and/or the binding of the variable domain that binds PD-L1 blocks the binding of PD-L1 to PD-1.

4. The antibody of claim 1, wherein the binding of the variable domain that binds PD-1 blocks the binding of PD-1 to PD-L1 or PD-L2.

5. The antibody of claim 1, wherein the binding of the variable domain that binds PD-L1 blocks the binding of PD-L1 to PD-1 or CD80.

6. The antibody of claim 1, wherein the antibody has a stronger CD4+ T cell activation potential in a *Staphylococcus* enterotoxin B (SEB) assay as compared to an equimolar mix of:
bivalent monospecific antibodies that comprise two of said variable domains that bind PD-1, and
bivalent monospecific antibodies that comprise two of said variable domains that bind PD-L1;
and/or is able to activate T cells in an antigen-specific CD4+ T cell assay more strongly than benchmark antibody 5C4 or benchmark antibody YW243.55.570 or a combination of benchmark antibodies 5C4 and YW243.55.570;
and/or has a stronger CD4+ T cell activation potential in a mixed lymphocyte reaction (MLR) assay as compared to benchmark antibody 5C4 or benchmark antibody YW243.55.570.

7. The antibody or variant thereof of claim 1, wherein the variable domain that binds an extracellular part of PD-L1 has a binding affinity with an equilibrium dissociation constant ($K_D$) of lower than or equal to 4.27 nM as measured by SPR.

8. The antibody of claim 1, that comprises a variable domain that can bind to an extracellular part of PD-1 and a variable domain that can bind to an extracellular part of PD-L1 and that is capable of enhancing the proliferation of CD4+ and/or CD8+ tumor-infiltrating T cells;
or that comprises a variable domain that can bind to an extracellular part of PD-1 and a variable domain that can bind to an extracellular part of PD-L1 and that is capable of inducing a stronger T cell mediated anti-tumor response in vivo as compared to a combination of benchmark antibodies MK-3475 and YW243.55.S70.

9. The antibody of claim 1, wherein the variable domain that binds an extracellular part of PD-1 is defined as a variable domain that when in a bivalent monospecific antibody format that comprises two of said variable domains that bind PD-1, inhibits PD-1/PD-L1 mediated inhibition of T cell receptor mediated activation of a Jurkat cell in a range of 20-150% when compared to the inhibition obtained with the antibody Nivolumab on a Jurkat cell;
and/or wherein the variable domain that binds an extracellular part of PD-L1 is defined as a variable domain that when in a bispecific antibody that has a second variable domain that binds an irrelevant antigen such as Tetanus Toxoid, provides the bispecific antibody with a Kd of 0.1-14 nM for PD-L1 binding (as measured by biacore).

10. The antibody of claim 1, wherein the variable domain that can bind to an extracellular part of PD-1 comprises a heavy chain variable region that comprises the amino acid sequence of the variable heavy chain any one of SEQ ID NOs: 38-48 and 50-56, having at most 15 amino acid insertions, deletions, substitutions or a combination thereof, with respect the amino acid sequence of the heavy chain variable region, wherein said insertions, deletions, substitutions or a combination thereof are not in the CDR1, CDR2 or CDR3 of the variable heavy chain region.

11. The antibody of claim 1, wherein the variable domain that can bind to an extra cellular part of PD-L1 comprises a heavy chain variable region that comprises the amino acid sequence of any one of SEQ ID NOs: 24-37 and 58-69, having at most 15 amino acid insertions, deletions, substitutions or a combination thereof, with respect the amino acid sequence of the heavy chain variable region, wherein said insertions, deletions, substitutions or a combination thereof are not in the CDR1, CDR2 or CDR3 of the variable heavy chain variable region.

12. The antibody of claim 1, wherein the antibody comprises a light chain variable region having a sequence that is at least 80% identical to the amino acid sequence according to SEQ ID NO: 6, comprising light chain variable region CDR1 comprising sequence QSISSY (SEQ ID NO:70), CDR2 comprising sequence AAS, and CDR3 comprising sequence QQSYSTPPT (SEQ ID NO:71).

13. The antibody of claim 1, wherein said antibody is a full length bispecific antibody.

14. A composition or kit of parts comprising at least one antibody according to claim 1.

15. A pharmaceutical composition comprising at least one antibody of claim 1 and a pharmaceutically acceptable carrier, diluent or excipient.

16. A method for treating a cancer or an infection with a pathogen comprising administering to a subject in need thereof a therapeutically effective amount of the antibody of claim 1.

17. The antibody of claim 1, wherein the variable domain that can bind to an extracellular part of PD-1 comprises:
a heavy chain variable region with a CDR1, CDR2 and CDR3 region that comprises the amino acid sequence of the CDR1, CDR2 and CDR3 of a variable heavy chain region according to SEQ ID NO: 39, SEQ ID NO: 44 or SEQ ID NO: 53; and
a light chain variable region CDR1 comprising sequence QSISSY (SEQ ID NO:70), CDR2 comprising sequence AAS and CDR3 comprising sequence QQSYSTPPT (SEQ ID NO:71).

18. The antibody of claim 1, wherein the variable domain that can bind to an extracellular part of PD-1 comprises a heavy chain variable region having a sequence that is at least 90% identical to the amino acid sequence of SEQ ID NO: 39, SEQ ID NO: 44 or SEQ ID NO: 53, and comprises the CDR1, CDR2, and CDR3 sequences of the heavy chain variable region of SEQ ID NO: 39, SEQ ID NO: 44 or SEQ ID NO: 53.

19. The antibody of claim 1, wherein the variable domain that can bind to an extracellular part of PD-L1 comprises:
a heavy chain variable region with a CDR1, CDR2 and CDR3 region that comprises the amino acid sequence of the CDR1, CDR2 and CDR3 of a variable region according to SEQ ID NO: 59 or SEQ ID NO: 63; and
a light chain variable region CDR1 comprising sequence QSISSY (SEQ ID NO:70), CDR2 comprising sequence AAS and CDR3 comprising sequence QQSYSTPPT (SEQ ID NO:71).

20. The antibody of claim 1, wherein the variable domain that can bind to an extracellular part of PD-L1 comprises a heavy chain variable region having a sequence that is at least 90% identical to the amino acid sequence of SEQ ID NO: 59 or SEQ ID NO: 63, and comprises the CDR1, CDR2, and CDR3 sequences of the heavy chain variable region of SEQ ID NO: 59 or SEQ ID NO: 63.

21. The antibody of claim 1, wherein
the variable domain that can bind to an extracellular part of PD-L1 comprises a heavy chain variable region that comprises the amino acid sequence of SEQ ID NO: 59 having at most 15 amino acid insertions, deletions, substitutions or a combination thereof, with respect to the amino acid sequence of SEQ ID NO: 59, wherein said insertions, deletions, or substitutions or a combination thereof are not in the CDR1, CDR2 or CDR3 of the variable heavy chain region;
the variable domain that can bind to an extracellular part of PD-1 comprises a heavy chain variable region that comprises the amino acid sequence of SEQ ID NO: 39 having at most 15 amino acid insertions, deletions, substitutions or a combination thereof, with respect to the amino acid sequence of SEQ ID NO: 39, wherein said insertions, deletions, or substitutions or a combination thereof are not in the CDR1, CDR2 or CDR3 of the variable heavy chain region, and
wherein the antibody comprises a light chain variable region CDR1 comprising sequence QSISSY (SEQ ID NO:70), CDR2 comprising sequence AAS, and CDR3 comprising sequence QQSYSTPPT (SEQ ID NO:71).

22. The antibody of claim 1, wherein
the variable domain that can bind to an extracellular part of PD-L1 comprises a heavy chain variable region that comprises the amino acid sequence of SEQ ID NO: 59 having at most 15 amino acid insertions, deletions, substitutions or a combination thereof, with respect to the amino acid sequence of SEQ ID NO: 59, wherein said insertions, deletions, or substitutions or a combination thereof are not in the CDR1, CDR2 or CDR3 of the variable heavy chain region;
the variable domain that can bind to an extracellular part of PD-1 comprises a heavy chain variable region that comprises the amino acid sequence of SEQ ID NO: 44 having at most 15 amino acid insertions, deletions, substitutions or a combination thereof, with respect to the amino acid sequence of SEQ ID NO: 44, wherein said insertions, deletions, or substitutions or a combination thereof are not in the CDR1, CDR2 or CDR3 of the variable heavy chain region, and
wherein the antibody comprises a light chain variable region CDR1 comprising sequence QSISSY (SEQ ID NO:70), CDR2 comprising sequence AAS, and CDR3 comprising sequence QQSYSTPPT (SEQ ID NO:71).

23. The antibody of claim 1, wherein
the variable domain that can bind to an extracellular part of PD-L1 comprises a heavy chain variable region that comprises the amino acid sequence of SEQ ID NO: 59 having at most 15 amino acid insertions, deletions, substitutions or a combination thereof, with respect to the amino acid sequence of SEQ ID NO: 59, wherein said insertions, deletions, or substitutions or a combination thereof are not in the CDR1, CDR2 or CDR3 of the variable heavy chain region;
the variable domain that can bind to an extracellular part of PD-1 comprises a heavy chain variable region that comprises the amino acid sequence of SEQ ID NO: 53 having at most 15 amino acid insertions, deletions, substitutions or a combination thereof, with respect to the amino acid sequence of SEQ ID NO: 53, wherein said insertions, deletions, or substitutions or a combination thereof are not in the CDR1, CDR2 or CDR3 of the variable heavy chain region, and
wherein the antibody comprises a light chain variable region CDR1 comprising sequence QSISSY (SEQ ID NO:70), CDR2 comprising sequence AAS, and CDR3 comprising sequence QQSYSTPPT (SEQ ID NO:71).

24. The antibody of claim 1, wherein
the variable domain that can bind to an extracellular part of PD-L1 comprises a heavy chain variable region that comprises the amino acid sequence of SEQ ID NO: 63 having at most 15 amino acid insertions, deletions, substitutions or a combination thereof, with respect to the amino acid sequence of SEQ ID NO: 63, wherein said insertions, deletions, or substitutions or a combination thereof are not in the CDR1, CDR2 or CDR3 of the variable heavy chain region;
the variable domain that can bind to an extracellular part of PD-1 comprises a heavy chain variable region that comprises the amino acid sequence of SEQ ID NO: 39 having at most 15 amino acid insertions, deletions, substitutions or a combination thereof, with respect to the amino acid sequence of SEQ ID NO: 39, wherein said insertions, deletions, or substitutions or a combination thereof are not in the CDR1, CDR2 or CDR3 of the variable heavy chain region, and
wherein the antibody comprises a light chain variable region CDR1 comprising sequence QSISSY (SEQ ID NO:70), CDR2 comprising sequence AAS, and CDR3 comprising sequence QQSYSTPPT (SEQ ID NO:71).

25. The antibody of claim 1, wherein
the variable domain that can bind to an extracellular part of PD-L1 comprises a heavy chain variable region that comprises the amino acid sequence of SEQ ID NO: 63 having at most 15 amino acid insertions, deletions, substitutions or a combination thereof, with respect to the amino acid sequence of SEQ ID NO: 63, wherein said insertions, deletions, or substitutions or a combination thereof are not in the CDR1, CDR2 or CDR3 of the variable heavy chain region;
the variable domain that can bind to an extracellular part of PD-1 comprises a heavy chain variable region that comprises the amino acid sequence of SEQ ID NO: 44 having at most 15 amino acid insertions, deletions, substitutions or a combination thereof, with respect to the amino acid sequence of SEQ ID NO:44, wherein said insertions, deletions, or substitutions or a combination thereof are not in the CDR1, CDR2 or CDR3 of the variable heavy chain region, and
wherein the antibody comprises a light chain variable region CDR1 comprising sequence QSISSY (SEQ ID NO:70), CDR2 comprising sequence AAS, and CDR3 comprising sequence QQSYSTPPT (SEQ ID NO:71).

26. The antibody of claim 1, wherein
the variable domain that can bind to an extracellular part of PD-L1 comprises a heavy chain variable region that comprises the amino acid sequence of SEQ ID NO: 63 having at most 15 amino acid insertions, deletions, substitutions or a combination thereof, with respect to the amino acid sequence of SEQ ID NO: 63, wherein said insertions, deletions, or substitutions or a combination thereof are not in the CDR1, CDR2 or CDR3 of the variable heavy chain region;
the variable domain that can bind to an extracellular part of PD-1 comprises a heavy chain variable region that comprises the amino acid sequence of SEQ ID NO: 53 having at most 15 amino acid insertions, deletions, substitutions or a combination thereof, with respect to the amino acid sequence of SEQ ID NO: 53, wherein said insertions, deletions, or substitutions or a combination thereof are not in the CDR1, CDR2 or CDR3 of the variable heavy chain region, and
wherein the antibody comprises a light chain variable region CDR1 comprising sequence QSISSY (SEQ ID NO:70), CDR2 comprising sequence AAS, and CDR3 comprising sequence QQSYSTPPT (SEQ ID NO:71).

27. The method of claim 16, wherein the binding of the antibody reduces an inhibitory activity of the binding of PD-1 to PD-L1.

28. The method of claim 16, wherein the binding of the variable domain that binds PD-1 blocks the binding of PD-1 to PD-L1 and/or the binding of the variable domain that binds PD-L1 blocks the binding of PD-L1 to PD-1.

29. The method of claim 16, wherein the binding of the variable domain that binds PD-1 blocks the binding of PD-1 to PD-L1 or PD-L2.

30. The method of claim 16, wherein the binding of the variable domain that binds PD-L1 blocks the binding of PD-L1 to PD-1 or CD80.

31. The method of claim 16, wherein the antibody has a stronger CD4+T cell activation potential in a Staphylococcus enterotoxin B (SEB) assay as compared to an equimolar mix of:
bivalent monospecific antibodies that comprise two of said variable domains that bind PD-1, and
bivalent monospecific antibodies that comprise two of said variable domains that bind PD-L2;
and/or is able to activate T cells in an antigen-specific CD4+ T cell assay more strongly than benchmark antibody 5C4 or benchmark antibody YW243.55.570 or a combination of benchmark antibodies 5C4 and YW243.55.570;
and/or has a stronger CD4+ T cell activation potential in a mixed lymphocyte reaction (MLR) assay as compared to benchmark antibody 5C4 or benchmark antibody YW243.55.570.

32. The method of claim 16, wherein the variable domain that binds an extracellular part of PD-L1 has a binding affinity with an equilibrium dissociation constant (KD) of lower than or equal to 4.27 nM as measured by SPR.

33. The method of claim 16, that comprises a variable domain that can bind to an extracellular part of PD-1 and a variable domain that can bind to an extracellular part of PD-L1 and that is capable of enhancing the proliferation of CD4+ and/or CD8+ tumor-infiltrating T cells;
or that comprises a variable domain that can bind to an extracellular part of PD-1 and a variable domain that can bind to an extracellular part of PD-L1 and that is capable of inducing a stronger T cell mediated anti-tumor response in vivo as compared to a combination of benchmark antibodies MK-3475 and YW243.55.S70.

34. The method of claim 16, wherein the variable domain that binds an extracellular part of PD-1 is defined as a variable domain that when in a bivalent monospecific antibody format that comprises two of said variable domains that bind PD-1, inhibits PD-1/PD-L1 mediated inhibition of T cell receptor mediated activation of a Jurkat cell in a range of 20-150% when compared to the inhibition obtained with the antibody Nivolumab on a Jurkat cell;
and/or wherein the variable domain that binds an extracellular part of PD-L1 is defined as a variable domain that when in a bispecific antibody that has a second variable domain that binds an irrelevant antigen such as Tetanus Toxoid, provides the bispecific antibody with a Kd of 0.1-14 nM for PD-L1 binding (as measured by Biacore).

35. The method of claim 16, wherein the variable domain that can bind to an extracellular part of PD-1 comprises a heavy chain variable region that comprises the amino acid sequence of any one of SEQ ID NOs: 38-48 and 50-56, having at most 15 amino acid insertions, deletions, substitutions or a combination thereof, with respect the amino acid sequence of the heavy chain variable region, wherein said insertions, deletions, substitutions or a combination thereof are not in the CDR1, CDR2 or CDR3 of the variable heavy chain region.

36. The method of claim 16, wherein the variable domain that can bind to an extra cellular part of PD-L1 comprises a heavy chain variable region that comprises the amino acid sequence of any one of SEQ ID NOs: 24-37 and 58-69, having at most 15 amino acid insertions, deletions, substitutions or a combination thereof, with respect the amino acid sequence of the heavy chain variable region, wherein said insertions, deletions, substitutions or a combination thereof are not in the CDR1, CDR2 or CDR3 of the variable heavy chain variable region.

37. The method of claim 16, wherein the antibody comprises a light chain variable region having a sequence that is at least 80% identical to the amino acid sequence according to SEQ ID NO: 6, comprising light chain variable region CDR1 comprising sequence QSISSY (SEQ ID NO:70), CDR2 comprising sequence AAS, and CDR3 comprising sequence QQSYSTPPT (SEQ ID NO:71).

38. The method of claim 16, wherein said antibody is a full length bispecific antibody.

39. The method of claim 16, wherein the variable domain that can bind to an extracellular part of PD-1 comprises:
a heavy chain variable region with a CDR1, CDR2 and CDR3 region that comprises the amino acid sequence of the CDR1, CDR2 and CDR3 of a variable heavy chain region according to SEQ ID NO: 39, SEQ ID NO: 44 or SEQ ID NO: 53; and
a light chain variable region CDR1 comprising sequence QSISSY (SEQ ID NO:70), CDR2 comprising sequence AAS and CDR3 comprising sequence QQSYSTPPT (SEQ ID NO:71).

40. The method of claim 16, wherein the variable domain that can bind to an extracellular part of PD-1 comprises a heavy chain variable region having a sequence that is at least 90% identical to the amino acid sequence of SEQ ID NO: 39, SEQ ID NO: 44 or SEQ ID NO: 53, and comprises the CDR1, CDR2, and CDR3 sequences of the heavy chain variable region of SEQ ID NO: 39, SEQ ID NO: 44 or SEQ ID NO: 53.

41. The method of claim 16, wherein the variable domain that can bind to an extracellular part of PD-L1 comprises:
a heavy chain variable region with a CDR1, CDR2 and CDR3 region that comprises the amino acid sequence of the CDR1, CDR2 and CDR3 of a variable region according to SEQ ID NO: 59 or SEQ ID NO: 63; and
a light chain variable region CDR1 comprising sequence QSISSY (SEQ ID NO:70), CDR2 comprising sequence AAS and CDR3 comprising sequence QQSYSTPPT (SEQ ID NO:71).

42. The method of claim 16, wherein the variable domain that can bind to an extracellular part of PD-L1 comprises a heavy chain variable region having a sequence that is at least 90% identical to the amino acid sequence of SEQ ID NO: 59 or SEQ ID NO: 63, and comprises the CDR1, CDR2, and CDR3 sequences of the heavy chain variable region of SEQ ID NO: 59 or SEQ ID NO: 63.

43. The method of claim 16, wherein
the variable domain that can bind to an extracellular part of PD-L1 comprises a heavy chain variable region that comprises the amino acid sequence of SEQ ID NO: 59 having at most 15 amino acid insertions, deletions, substitutions or a combination thereof, with respect to the amino acid sequence of SEQ ID NO: 59, wherein said insertions, deletions, or substitutions or a combination thereof are not in the CDR1, CDR2 or CDR3 of the variable heavy chain region;
the variable domain that can bind to an extracellular part of PD-1 comprises a heavy chain variable region that comprises the amino acid sequence of SEQ ID NO: 39 having at most 15 amino acid insertions, deletions, substitutions or a combination thereof, with respect to the amino acid sequence of SEQ ID NO: 39, wherein said insertions, deletions, or substitutions or a combination thereof are not in the CDR1, CDR2 or CDR3 of the variable heavy chain region, and
wherein the antibody comprises a light chain variable region CDR1 comprising sequence QSISSY (SEQ ID NO:70), CDR2 comprising sequence AAS, and CDR3 comprising sequence QQSYSTPPT (SEQ ID NO:71).

44. The method of claim 16, wherein
the variable domain that can bind to an extracellular part of PD-L1 comprises a heavy chain variable region that comprises the amino acid sequence of SEQ ID NO: 59 having at most 15 amino acid insertions, deletions, substitutions or a combination thereof, with respect to the amino acid sequence of SEQ ID NO: 59, wherein said insertions, deletions, or substitutions or a combination thereof are not in the CDR1, CDR2 or CDR3 of the variable heavy chain region;
the variable domain that can bind to an extracellular part of PD-1 comprises a heavy chain variable region that comprises the amino acid sequence of SEQ ID NO: 44 having at most 15 amino acid insertions, deletions, substitutions or a combination thereof, with respect to the amino acid sequence of SEQ ID NO: 44, wherein said insertions, deletions, or substitutions or a combination thereof are not in the CDR1, CDR2 or CDR3 of the variable heavy chain region, and
wherein the antibody comprises a light chain variable region CDR1 comprising sequence QSISSY (SEQ ID NO:70), CDR2 comprising sequence AAS, and CDR3 comprising sequence QQSYSTPPT (SEQ ID NO:71).

45. The method of claim 16, wherein
the variable domain that can bind to an extracellular part of PD-L1 comprises a heavy chain variable region that comprises the amino acid sequence of SEQ ID NO: 59 having at most 15 amino acid insertions, deletions, substitutions or a combination thereof, with respect to the amino acid sequence of SEQ ID NO: 59, wherein said insertions, deletions, or substitutions or a combination thereof are not in the CDR1, CDR2 or CDR3 of the variable heavy chain region;
the variable domain that can bind to an extracellular part of PD-1 comprises a heavy chain variable region that comprises the amino acid sequence of SEQ ID NO: 53 having at most 15 amino acid insertions, deletions, substitutions or a combination thereof, with respect to the amino acid sequence of SEQ ID NO: 53, wherein said insertions, deletions, or substitutions or a combination thereof are not in the CDR1, CDR2 or CDR3 of the variable heavy chain region, and
wherein the antibody comprises a light chain variable region CDR1 comprising sequence QSISSY (SEQ ID NO:70), CDR2 comprising sequence AAS, and CDR3 comprising sequence QQSYSTPPT (SEQ ID NO:71).

46. The method of claim 16, wherein
the variable domain that can bind to an extracellular part of PD-L1 comprises a heavy chain variable region that comprises the amino acid sequence of SEQ ID NO: 63 having at most 15 amino acid insertions, deletions, substitutions or a combination thereof, with respect to the amino acid sequence of SEQ ID NO: 63, wherein said insertions, deletions, or substitutions or a combination thereof are not in the CDR1, CDR2 or CDR3 of the variable heavy chain region;
the variable domain that can bind to an extracellular part of PD-1 comprises a heavy chain variable region that comprises the amino acid sequence of SEQ ID NO: 39 having at most 15 amino acid insertions, deletions, substitutions or a combination thereof, with respect to the amino acid sequence of SEQ ID NO: 39, wherein said insertions, deletions, or substitutions or a combination thereof are not in the CDR1, CDR2 or CDR3 of the variable heavy chain region, and
wherein the antibody comprises a light chain variable region CDR1 comprising sequence QSISSY (SEQ ID NO:70), CDR2 comprising sequence AAS, and CDR3 comprising sequence QQSYSTPPT (SEQ ID NO:71).

47. The method of claim 16, wherein
the variable domain that can bind to an extracellular part of PD-L1 comprises a heavy chain variable region that comprises the amino acid sequence of SEQ ID NO: 63 having at most 15 amino acid insertions, deletions, substitutions or a combination thereof, with respect to the amino acid sequence of SEQ ID NO: 63, wherein said insertions, deletions, or substitutions or a combination thereof are not in the CDR1, CDR2 or CDR3 of the variable heavy chain region;
the variable domain that can bind to an extracellular part of PD-1 comprises a heavy chain variable region that comprises the amino acid sequence of SEQ ID NO: 44 having at most 15 amino acid insertions, deletions, substitutions or a combination thereof, with respect to the amino acid sequence of SEQ ID NO:44, wherein said insertions, deletions, or substitutions or a combination thereof are not in the CDR1, CDR2 or CDR3 of the variable heavy chain region, and wherein the antibody comprises a light chain variable region CDR1 comprising sequence QSISSY (SEQ ID NO:70), CDR2 comprising sequence AAS, and CDR3 comprising sequence QQSYSTPPT (SEQ ID NO:71).

48. The method of claim 16, wherein the variable domain that can bind to an extracellular part of PD-L1 comprises a heavy chain variable region that comprises the amino acid sequence of SEQ ID NO: 63 having at most 15 amino acid insertions, deletions, substitutions or a combination thereof, with respect to the amino acid sequence of SEQ ID NO: 63, wherein said insertions, deletions, or substitutions or a combination thereof are not in the CDR1, CDR2 or CDR3 of the variable heavy chain region;

the variable domain that can bind to an extracellular part of PD-1 comprises a heavy chain variable region that comprises the amino acid sequence of SEQ ID NO: 53 having at most 15 amino acid insertions, deletions, substitutions or a combination thereof, with respect to the amino acid sequence of SEQ ID NO: 53, wherein said insertions, deletions, or substitutions or a combination thereof are not in the CDR1, CDR2 or CDR3 of the variable heavy chain region, and wherein the antibody comprises a light chain variable region CDR1 comprising sequence QSISSY (SEQ ID NO:70), CDR2 comprising sequence AAS, and CDR3 comprising sequence QQSYSTPPT (SEQ ID NO:71).

\* \* \* \* \*

UNITED STATES PATENT AND TRADEMARK OFFICE
CERTIFICATE OF CORRECTION

| | |
|---|---|
| PATENT NO. | : 11,667,714 B2 |
| APPLICATION NO. | : 16/628547 |
| DATED | : June 6, 2023 |
| INVENTOR(S) | : Geuijen et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 288 days.

Signed and Sealed this
First Day of July, 2025

Coke Morgan Stewart
*Acting Director of the United States Patent and Trademark Office*